United States Patent
Eichhorn et al.

(10) Patent No.: US 12,416,027 B2
(45) Date of Patent: Sep. 16, 2025

(54) SQUALENE HOPENE CYCLASE (SHC) VARIANTS

(71) Applicant: Givaudan SA, Vernier (CH)

(72) Inventors: Eric Eichhorn, Zürich (CH); Christophe Ullmann, Nimes (FR)

(73) Assignee: GIVAUDAN SA, Vernier (CH)

( * ) Notice: Subject to any disclaimer, the term of this patent is extended or adjusted under 35 U.S.C. 154(b) by 362 days.

(21) Appl. No.: 17/776,686

(22) PCT Filed: Dec. 3, 2020

(86) PCT No.: PCT/EP2020/084491
§ 371 (c)(1),
(2) Date: May 13, 2022

(87) PCT Pub. No.: WO2021/110848
PCT Pub. Date: Jun. 10, 2021

(65) Prior Publication Data
US 2023/0021613 A1 Jan. 26, 2023

(30) Foreign Application Priority Data
Dec. 4, 2019 (GB) ..................................... 1917688

(51) Int. Cl.
*C12P 17/02* (2006.01)
*C12N 9/90* (2006.01)

(52) U.S. Cl.
CPC ................. *C12P 17/02* (2013.01); *C12N 9/90* (2013.01); *C12Y 504/99017* (2013.01)

(58) Field of Classification Search
CPC ........................ C12P 17/02; C12N 9/90; C12Y 504/99017; C07D 307/92; C07D 3011/92; C07D 313/00
See application file for complete search history.

(56) References Cited

U.S. PATENT DOCUMENTS

| 10,472,655 | B2 * | 11/2019 | Eichhorn | ................. | C12N 9/90 |
| 11,965,195 | B2 * | 4/2024 | Eichhorn | ....... | C12Y 504/99017 |
| 2012/0135477 | A1 | 5/2012 | Breuer et al. | | |

FOREIGN PATENT DOCUMENTS

| JP | 2009060799 A | 3/2009 |
| WO | 2012066059 A2 | 5/2012 |
| WO | 2016170099 A1 | 10/2016 |
| WO | 2016170106 A1 | 10/2016 |
| WO | 2017182542 A1 | 10/2017 |
| WO | 2018157021 A1 | 8/2018 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Hoshino et al., Squalene-hopene cyclase: catalytic mechanism and substrate recognition. Chem. Commun., 2002: 291-301 (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Siedenburg et al., Squalene-Hopene Cyclases. Appl. Environ. Microbiol., 2011, vol. 77(12): 3905-3915. (Year: 2011).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report for App. No. PCT/EP2020/084491 dated Feb. 24, 2021.
Written Opinion for App. No. PCT/EP2020/084491 dated Feb. 24, 2021.
Great Britain Search Report for App. No. 1917699.2 dated Jun. 3, 2020.
Shaoxiang Yang, et al., One-pot synthesis of (-)-Ambrox, Scientific Reports, Sep. 1, 2016, pp. 1-6, vol. 6.
Database Uniprot, Uniparc, May 31, 2019, retrieved from: www.uniprot.org/uniparc/UPI000BB5C353.
Stefan Neumann, et al., Purification, Partial Characterization and Substrate Specificity of a Squalene Cyclase from Bacillus acidocaldarius, Biological Chemistry Hoppe-Seyler, Aug. 1986, pp. 723-729, vol. 367, Walter de Gruyter & Co., Berlin, New York.
Ina G. Reipen, et al., Zymomonas mobilis squalene-hopene cyclase gene (shc): cloning, DNA sequence analysis, and expression in *Escherichia coli*, Microbiology, 1995, pp. 155-161, vol. 141, Great Britain.
Seckler, et al., Characterization and partial purification of squalene-hopene cyclase from Bacillus acidocaldarius, Biochimica et Biophysica Acta (BBA)—General Subjects, May 2, 1986, pp. 356-363, vol. 881, Issue 3.
D Ochs, et al., Cloning, expression, and sequencing of squalene-hopene cyclase, a key enzyme in triterpenoid metabolism, Journal of Bacteriology, Jan. 1992, pp. 298-302, vol. 174, Issue 1, American Society for Microbiology.
Miriam Seitz, et al., Substrate specificity of a novel squalene-hopene cyclase from Zymomonas mobilis, Journal of Molecular Catalysis B: Enzymatic, Feb. 25, 2012, pp. 72-77, Issue 84, Elsevier.
Miriam Seitz, Characterization of the substrate specificity of squalene-hopene cyclases (SHCs), PhD Dissertation, Feb. 6, 2013.

* cited by examiner

*Primary Examiner* — Ganapathirama Raghu
(74) *Attorney, Agent, or Firm* — Curatolo Sidoti & Trillis Co., LPA; Floyd Trillis, III; Salvatore A. Sidoti

(57) ABSTRACT

Squalene Hopene Cyclase (SHC) enzymes and variants thereof and their uses for making (-)-Ambrox from homofarnesol and Ambra oxide from bishomofarnesol.

13 Claims, 13 Drawing Sheets
Specification includes a Sequence Listing.

SEQUENCE LISTING

<160> NUMBER OF SEQ ID NOS: 30

<210> SEQ ID NO 1
<211> LENGTH: 631
<212> TYPE: PRT
<213> ORGANISM: Alicyclobacillus acidocaldarius

<400> SEQUENCE: 1

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365
```

Asn Val Tyr Tyr Pro Asp Val Asp Asp Thr Ala Val Val Trp Ala
370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
                500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
                580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
610                 615                 620

Lys Gln Ala Ile Glu Arg Arg
625                 630

<210> SEQ ID NO 2
<211> LENGTH: 631
<212> TYPE: PRT
<213> ORGANISM: Artificial Sequence
<220> FEATURE:
<223> OTHER INFORMATION: SHC/HAC enzyme variant #49

<400> SEQUENCE: 2

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

```
Ala Leu Lys Tyr Ile Gly Met Ser Arg Asp Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
    370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn Leu Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510
```

```
Glu Pro Tyr Ile Gln Lys Ala Leu Asp Trp Val Gln His Gln Asn
            515                 520                 525

Pro Asp Gly Gly Trp Gly Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
            610                 615                 620

Lys Gln Ala Ile Glu Arg Arg
625                 630

<210> SEQ ID NO 3
<211> LENGTH: 631
<212> TYPE: PRT
<213> ORGANISM: Artificial Sequence
<220> FEATURE:
<223> OTHER INFORMATION: SHC/HAC enzyme variant #65

<400> SEQUENCE: 3

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
            35                  40                  45

Leu Cys His Ile Leu Asp Arg Val Asp Arg Asp Arg Met Glu Lys Ile
        50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
                100                 105                 110

Ala Leu Arg Phe Ile Gln Ser Gln Gly Gly Ile Glu Ser Ser Arg Val
            115                 120                 125

Phe Thr Arg Arg Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Ala Ala
225                 230                 235                 240
```

Glu Ile Arg Ala Leu Asp Trp Leu Glu Arg Gln Ala Gly Asp Gly
            245                 250                 255

Ser Trp Gly Gly Ile Gln Pro Pro Trp Phe Tyr Ala Leu Ile Ala Leu
        260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
    370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg Arg
625                 630

<210> SEQ ID NO 4
<211> LENGTH: 631

```
<212> TYPE: PRT
<213> ORGANISM: Artificial Sequence
<220> FEATURE:
<223> OTHER INFORMATION: SHC/HAC enzyme variant #66

<400> SEQUENCE: 4
```

| | | | | | | | | | | | | | | |
|---|---|---|---|---|---|---|---|---|---|---|---|---|---|---|
| Met | Ala | Glu | Gln | Leu | Val | Glu | Ala | Pro | Ala | Tyr | Ala | Arg | Thr | Leu | Asp |
| 1 | | | | 5 | | | | | 10 | | | | | 15 | |
| Arg | Ala | Val | Glu | Tyr | Leu | Leu | Ser | Cys | Gln | Lys | Asp | Glu | Gly | Tyr | Trp |
| | | | 20 | | | | | 25 | | | | | 30 | | |
| Trp | Gly | Pro | Leu | Leu | Ser | Asn | Val | Thr | Met | Glu | Ala | Glu | Tyr | Val | Leu |
| | | 35 | | | | | 40 | | | | | 45 | | | |
| Leu | Cys | His | Ile | Leu | Asp | Arg | Val | Asp | Arg | Asp | Met | Glu | Lys | Ile |
| | 50 | | | | | 55 | | | | | 60 | | | | |
| Arg | Arg | Tyr | Leu | Leu | His | Glu | Gln | Arg | Glu | Asp | Gly | Thr | Trp | Ala | Leu |
| 65 | | | | | 70 | | | | | 75 | | | | | 80 |
| His | Pro | Gly | Gly | Pro | Pro | Asp | Leu | Asp | Thr | Thr | Ile | Glu | Ala | Tyr | Val |
| | | | | 85 | | | | | 90 | | | | | 95 | |
| Ala | Leu | Lys | Tyr | Ile | Gly | Met | Ser | Arg | Asp | Glu | Pro | Met | Gln | Lys |
| | | | 100 | | | | | 105 | | | | | 110 | | |
| Ala | Leu | Arg | Phe | Ile | Gln | Ser | Gln | Gly | Gly | Ile | Glu | Ser | Ser | Arg | Val |
| | | 115 | | | | | 120 | | | | | 125 | | | |
| Phe | Thr | Arg | Arg | Trp | Leu | Ala | Leu | Val | Gly | Glu | Tyr | Pro | Trp | Glu | Lys |
| 130 | | | | | 135 | | | | | 140 | | | | | |
| Val | Pro | Met | Val | Pro | Glu | Ile | Met | Phe | Leu | Gly | Lys | Arg | Met | Pro |
| 145 | | | | 150 | | | | | 155 | | | | | 160 | |
| Leu | Asn | Ile | Tyr | Glu | Phe | Gly | Ser | Trp | Ala | Arg | Ala | Thr | Val | Val | Ala |
| | | | | 165 | | | | | 170 | | | | | 175 | |
| Leu | Ser | Ile | Val | Met | Ser | Arg | Gln | Pro | Val | Phe | Pro | Leu | Pro | Glu | Arg |
| | | | 180 | | | | | 185 | | | | | 190 | | |
| Ala | Arg | Val | Pro | Glu | Leu | Tyr | Glu | Thr | Asp | Val | Pro | Pro | Arg | Arg |
| | | 195 | | | | | 200 | | | | | 205 | | | |
| Gly | Ala | Lys | Gly | Gly | Gly | Gly | Trp | Ile | Phe | Asp | Ala | Leu | Asp | Arg | Val |
| | 210 | | | | | 215 | | | | | 220 | | | | |
| Leu | His | Gly | Tyr | Gln | Lys | Leu | Ser | Val | His | Pro | Phe | Arg | Arg | Ala | Ala |
| 225 | | | | | 230 | | | | | 235 | | | | | 240 |
| Glu | Ile | Arg | Ala | Leu | Asp | Trp | Leu | Leu | Glu | Arg | Gln | Ala | Gly | Asp | Gly |
| | | | | 245 | | | | | 250 | | | | | 255 | |
| Ser | Trp | Gly | Gly | Ile | Gln | Pro | Pro | Trp | Phe | Tyr | Ala | Leu | Ile | Ala | Leu |
| | | | 260 | | | | | 265 | | | | | 270 | | |
| Lys | Ile | Leu | Asp | Met | Thr | Gln | His | Pro | Ala | Phe | Ile | Lys | Gly | Trp | Glu |
| | 275 | | | | | 280 | | | | | 285 | | | | |
| Gly | Leu | Glu | Leu | Tyr | Gly | Val | Glu | Leu | Asp | Tyr | Gly | Gly | Trp | Met | Phe |
| | 290 | | | | | 295 | | | | | 300 | | | | |
| Gln | Ala | Ser | Ile | Ser | Pro | Val | Trp | Asp | Thr | Gly | Leu | Ala | Val | Leu | Ala |
| 305 | | | | | 310 | | | | | 315 | | | | | 320 |
| Leu | Arg | Ala | Ala | Gly | Leu | Pro | Ala | Asp | His | Asp | Arg | Leu | Val | Lys | Ala |
| | | | | 325 | | | | | 330 | | | | | 335 | |
| Gly | Glu | Trp | Leu | Leu | Asp | Arg | Gln | Ile | Thr | Val | Pro | Gly | Asp | Trp | Ala |
| | | | 340 | | | | | 345 | | | | | 350 | | |
| Val | Lys | Arg | Pro | Asn | Leu | Lys | Pro | Gly | Gly | Phe | Ala | Phe | Gln | Phe | Asp |
| | | 355 | | | | | 360 | | | | | 365 | | | |
| Asn | Val | Tyr | Tyr | Pro | Asp | Val | Asp | Asp | Thr | Ala | Val | Val | Val | Trp | Ala |
| | | 370 | | | | | 375 | | | | | 380 | | | |

```
Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
                420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
        450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
                500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
        530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
                580                 585                 590

Glu Pro Tyr Tyr Thr Gly Thr Gly Phe Pro Gly Asp Phe Tyr Leu Gly
            595                 600                 605

Tyr Thr Met Tyr Ser His Val Phe Pro Thr Leu Ala Leu Gly Arg Tyr
        610                 615                 620

Lys Gln Ala Ile Glu Arg Arg
625                 630

<210> SEQ ID NO 5
<211> LENGTH: 631
<212> TYPE: PRT
<213> ORGANISM: Artificial Sequence
<220> FEATURE:
<223> OTHER INFORMATION: SHC/HAC enzyme variant #110B8

<400> SEQUENCE: 5

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
            35                  40                  45

Leu Cys His Ile Leu Asp Arg Val Asp Arg Asp Arg Met Glu Lys Ile
        50                  55                  60

Arg Arg Tyr Leu Leu His Glu Gln Arg Glu Asp Gly Thr Trp Ala Leu
65                  70                  75                  80

His Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
                100                 105                 110
```

```
Ala Leu Arg Phe Ile Gln Ser Gln Gly Gly Ile Glu Ser Ser Arg Val
            115                 120                 125

Phe Thr Arg Arg Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
            165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Arg Arg Arg
            195                 200                 205

Gly Ala Lys Gly Gly Gly Trp Ile Phe Asp Ala Leu Asp Arg Val
210                 215                 220

Leu His Gly Tyr Gln Lys Leu Ser Val His Pro Phe Arg Ala Ala
225                 230                 235                 240

Glu Ile Arg Ala Leu Asp Trp Leu Leu Glu Arg Gln Ala Gly Asp Gly
            245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
275                 280                 285

Gly Leu Glu Leu Tyr Gly Val Glu Leu Asp Tyr Gly Gly Trp Met Phe
            290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn Leu Thr
            420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
            450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
            515                 520                 525
```

```
Pro Asp Gly Gly Trp Gly Glu Asp Cys Arg Ser Tyr Glu Asp Pro Ala
        530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
            565                 570                 575

Gly Val Gln Tyr Leu Val Glu Thr Gln Arg Pro Asp Gly Gly Trp Asp
        580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
        610                 615                 620

Lys Gln Ala Ile Glu Arg Arg
625                 630
```

<210> SEQ ID NO 6
<211> LENGTH: 1896
<212> TYPE: DNA
<213> ORGANISM: Artificial Sequence
<220> FEATURE:
<223> OTHER INFORMATION: SHC/HAC enzyme variant #49

<400> SEQUENCE: 6

| | | |
|---|---|---|
| atggctgagc agttggtgga agctccggcc tacgcgcgga cgctggatcg cgcggtggag | 60 |
| tatctcctct cctgccaaaa ggacgaaggc tactggtggg gccgcttct gagcaacgtc | 120 |
| acgatggaag cggagtacgt cctcttgtgc acattctcg atcgcgtcga tcgggatcgc | 180 |
| atggagaaga tccggcggta cctgttgcac gagcagcgcg aggacggcac gtgggccctg | 240 |
| tacccgggtg gccgccgga cctcgacacg accatcgagg cgtacgtcgc gctcaagtat | 300 |
| atcggcatgt cgcgcgacga ggagccgatg cagaaggcgc tccggttcat tcagagccag | 360 |
| ggcgggatcg agtcgtcgcg cgtgttcacg cggaggtggc tggcgctggt gggagaatat | 420 |
| ccgtgggaga aggtgcccat ggtcccgccg gagatcatgt tcctcggcaa cgcatgccg | 480 |
| ctcaacatct cgagtttggg ctcgtgggct cgggcgaccg tcgtggcgct tcgattgtg | 540 |
| atgagccgcc agccggtgtt cccgctgccc gagcgggcgc gcgtgcccga gctgtacgag | 600 |
| accgacgtgc tccgcgccg gcgcggtgcc aaggagaggg gtgggtggat cttcgacgcg | 660 |
| ctcgaccggg tgctgcacgg gtatcagaag ctgtcggtgc acccgttccg ccgcgcggcc | 720 |
| gagatccgcg ccttggactg gttgctcgag cgccaggccg agacggcag ctggggcggg | 780 |
| attcagccgc cttggtttta cgcgctcatc gcgctcaaga ttctcgacat gacgcagcat | 840 |
| ccggcgttca tcaagggctg ggaaggtcta gagctgtacg gcgtggagct ggattacgga | 900 |
| ggatggatgt tcaggcttc catctcgccg gtgtgggaca cgggcctcgc cgtgctcgcg | 960 |
| ctgcgcgctg cggggcttcc ggccgatcac gaccgcttgg tcaaggcggg cgagtggctg | 1020 |
| ttggaccggc agatcacggt tccgggcgac tgggcggtga gcgcccgaa cctcaagccg | 1080 |
| ggcgggttcg cgttccagtt cgacaacgtg tactacccgg acgtggacga cacggccgtc | 1140 |
| gtggtgtggg cgctcaacac cctgcgcttg ccggacgagc gccgcaggcg ggacgccatg | 1200 |
| acgaagggat tccgctggat tgtcggcatg cagagctcga acggcggttg gggcgcctac | 1260 |
| gacgtcgaca cacgagcga tctcccgaac ctcaccccgt tctgcgactt cggcgaagtg | 1320 |
| accgatccgc cgtcagagga cgtcaccgcc acgtgctcg agtgtttcgg cagcttcggg | 1380 |
| tacgatgacg cctggaaggt catccggcgc gcggtggaat atctcaagcg ggagcagaag | 1440 |

```
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacgac ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg atttctacct cggctacacc atgtaccgcc acgtgtttcc gacgctcgcg    1860
ctcggccgct acaagcaagc catcgagcgc aggtga                             1896

<210> SEQ ID NO 7
<211> LENGTH: 1896
<212> TYPE: DNA
<213> ORGANISM: Artificial Sequence
<220> FEATURE:
<223> OTHER INFORMATION: SHC/HAC enzyme variant #65

<400> SEQUENCE: 7
atggctgagc agttggtgga agctccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc cacattctcg atcgcgtcga tcggatcgc     180 atggagaaga tccggcggta cctgttgcac gagcagcgcg aggacggcac gtgggccctg     240
tacccgggtg ggccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggaggtggc tggcgctggt gggagaatat     420
ccgtgggaga aggtgcccat ggtcccgccg gagatcatgt tcctcggcaa gcgcatgccg     480
ctcaacatct cgagtttgg ctcgtgggct cgggcgaccg tcgtggcgct ctcgattgtg     540
atgagccgcc agccggtgtt cccgctgccc gagcgggcg gcgtgcccga gctgtacgag     600
accgacgtgc ctccgcgccg gcgcggtgcc aagggagggg gtgggtggat cttcgacgcg     660
ctcgaccggg tgctgcacgg gtatcagaag ctgtcggtgc acccgttccg ccgcgcggcc     720
gagatccgcg ccttggactg gttgctcgag cgccaggccg gagacggcag ctggggcggg     780
attcagccgc cttggtttta cgcgctcatc gcgctcaaga ttctcgacat gacgcagcat     840
ccggcgttca tcaagggctg ggaaggtcta gagctgtacg gcgtggagct ggattacgga     900
ggatggatgt tcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccgga gatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat tccgctggat tgtcggcatg cagagctcga acggcggttg gggcgcctac    1260
gacgtcgaca cacgagcga tctcccgaac cacaccccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
```

```
gactgggtcg agcagcatca gaacccggac ggcggctggg gcgaggactg ccgctcgtac    1620
gaggatccgg cgtacgcggg taagggcgcg agcaccccgt cgcagacgac ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg atttctacct cggctacacc atgtacagcc acgtgtttcc gacgctcgcg    1860
ctcggccgct acaagcaagc catcgagcgc aggtga                              1896

<210> SEQ ID NO 8
<211> LENGTH: 1896
<212> TYPE: DNA
<213> ORGANISM: Artificial Sequence
<220> FEATURE:
<223> OTHER INFORMATION: SHC/HAC enzyme variant #66

<400> SEQUENCE: 8
atggctgagc agttggtgga agctccggcc tacgcgcgga cgctggatcg cgcggtggag      60
tatctcctct cctgccaaaa ggacgaaggc tactggtggg gccgcttct gagcaacgtc     120 acgatggaag cggagtacgt cctcttgtgc cacattctcg atcgcgtcga tcgggatcgc     180
atggagaaga tccggcggta cctgttgcac gagcagcgcg aggacggcac gtgggccctg     240
cacccgggtg gccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggaggtggc tggcgctggt gggagaatat     420
ccgtgggaga aggtgcccat ggtcccgccg agatcatgt tcctcggcaa cgcatgccg     480 ctcaacatct acgagtttgg ctcgtgggct cgggcgaccg tcgtggcgct ctcgattgtg     540
atgagccgcc agcggtgtt cccgctgccc gagcgggcgc gcgtgcccga gctgtacgag     600
accgacgtgc ctccgcgccg gcgcggtgcc aagggagggg gtgggtggat cttcgacgcg     660
ctcgaccggg tgctgcacgg gtatcagaag ctgtcggtgc acccgttccg ccgcgcggcc     720
gagatccgcg ccttggactg gttgctcgag cgccaggccg agacggcag ctggggcggg     780 attcagccgc cttggtttta cgcgctcatc gcgctcaaga ttctcgacat gacgcagcat     840
ccggcgttca tcaagggctg ggaaggtcta gagctgtacg gcgtggagct ggattacgga     900
ggatggatgt ttcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat tccgctggat tgtcggcatg cagagctcga acggcggttg ggcgcctac    1260 gacgtcgaca cacgagcga tctcccgaac cacaccccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttgggc gtcaattacc tctacggcac gggcgcggtg    1500
gtgtcggcgc tgaaggcggt cggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacgac ctgggcgctg    1680
atggcgctca tcgcgggcgg cagggcggag tccgaggccg cgcgccgcgg cgtgcaatac    1740
```

```
ctcgtggaga cgcagcgccc ggacggcggc tgggatgagc cgtactacac cggcacgggc     1800
ttcccagggg atttctacct cggctacacc atgtacagcc acgtgtttcc gacgctcgcg     1860
ctcggccgct acaagcaagc catcgagcgc aggtga                               1896
```

<210> SEQ ID NO 9
<211> LENGTH: 1896
<212> TYPE: DNA
<213> ORGANISM: Artificial Sequence
<220> FEATURE:
<223> OTHER INFORMATION: SHC/HAC enzyme variant #110B8

<400> SEQUENCE: 9

```
atggctgagc agttggtgga agctccggcc tacgcgcgga cgctggatcg cgcggtggag       60
tatctcctct cctgccaaaa ggacgaaggc tactggtggg gccgcttct gagcaacgtc      120 acgatggaag cggagtacgt cctcttgtgc acattctcg atcgcgtcga tcgggatcgc      180
atggagaaga tccggcggta cctgttgcac gagcagcgcg aggacggcac gtgggccctg     240
cacccgggtg gccgccgga cctcgacacg accatcgagg cgtacgtcgc gctcaagtat      300
atcggcatgt cgcgcgacga ggagccgatg cagaaggcgc tccggttcat tcagagccag     360
ggcgggatcg agtcgtcgcg cgtgttcacg cggaggtggc tggcgctggt gggagaatat    420
ccgtgggaga aggtgcccat ggtcccgccg gagatcatgt cctcggcaa gcgcatgccg      480 ctcaacatct acgagtttgg ctcgtgggct cgggcgaccg tcgtggcgct ctcgattgtg     540
atgagccgcc agccggtgtt cccgctgccc gagcgggcgc gcgtgcccga gctgtacgag     600
accgacgtgc ctccgcgccg gcgcggtgcc aaggaggg gtggtggat cttcgacgcg       660 ctcgaccggg tgctgcacgg gtatcagaag ctgtcggtgc acccgttccg ccgcgcggcc    720
gagatccgcg ccttggactg gttgctcgag cgccaggccg agacggcag ctggggcggg     780 attcagccgc cttggtttta cgcgctcatc gcgctcaaga ttctcgacat gacgcagcat    840
ccggcgttca tcaagggctg ggaaggtcta gagctgtacg cgtggagct ggattacgga    900 ggatggatgt tcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg    1200
acgaagggat ccgctggat tgtcggcatg cagagctcga acgcggttg gggcgcctac    1260 gacgtcgaca acacgagcga tctcccgaac ctcacccgt tctgcgactt cggcgaagtg    1320
accgatccgc cgtcagagga cgtcaccgcc cacgtgctcg agtgtttcgg cagcttcggg   1380
tacgatgacg cctggaaggt catccggcgc gcggtggaat atctcaagcg ggagcagaag   1440
ccggacggca gctggttcgg tcgttgggc gtcaattacc tctacggcac gggcgcggtg    1500 gtgtcgcgc tgaaggcggt cgggatcgac acgcgcgagc cgtacattca aaaggcgctc    1560
gactgggtcg agcagcatca gaacccggac ggcggctggg gcgaggactg ccgctcgtac   1620
gaggatccgc cgtacgcggg taagggcgcg agcaccccgt cgcagacgac ctgggcgctg    1680
atggcgctca tcgcgggcgg cagggcgag tccgaggccg cgccgcgg cgtgcaatac      1740 ctcgtggaga cgcagcgccc ggacggcggc tgggatgagc cgtactacac cggcacgggc    1800
```

```
ttcccagggg atttctacct cggctacacc atgtaccgcc acgtgtttcc gacgctcgcg    1860
ctcggccgct acaagcaagc catcgagcgc aggtga                              1896
```

<210> SEQ ID NO 10
<211> LENGTH: 631
<212> TYPE: PRT
<213> ORGANISM: Artificial Sequence
<220> FEATURE:
<223> OTHER INFORMATION: 215G2 SHC/HAC enzyme variant

<400> SEQUENCE: 10

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335
```

```
Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
            370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
            405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
            450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
            485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
            530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
            565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
            610                 615                 620

Lys Gln Ala Ile Glu Arg Arg
625                 630

<210> SEQ ID NO 11
<211> LENGTH: 608
<212> TYPE: PRT
<213> ORGANISM: Zymomonas mobilis

<400> SEQUENCE: 11

Met Gly Ile Asp Arg Met Asn Ser Leu Ser Arg Leu Leu Met Lys Lys
1               5                   10                  15

Ile Phe Gly Ala Glu Lys Thr Ser Tyr Lys Pro Ala Ser Asp Thr Ile
            20                  25                  30

Ile Gly Thr Asp Thr Leu Lys Arg Pro Asn Arg Arg Pro Glu Pro Thr
            35                  40                  45

Ala Lys Val Asp Lys Thr Ile Phe Lys Thr Met Gly Asn Ser Leu Asn
            50                  55                  60
```

```
Asn Thr Leu Val Ser Ala Cys Asp Trp Leu Ile Gly Gln Gln Lys Pro
 65                  70                  75                  80

Asp Gly His Trp Val Gly Ala Val Glu Ser Asn Ala Ser Met Glu Ala
             85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
            115                 120                 125

Ser Trp Gly Val Tyr Phe Gly Ala Gly Asn Gly Asp Ile Asn Ala Thr
            130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Ala Trp Ile Ala Glu Lys Gly Gly Leu
                165                 170                 175

Lys Asn Ile Arg Val Phe Thr Arg Tyr Trp Leu Ala Leu Ile Gly Glu
            180                 185                 190

Trp Pro Trp Glu Lys Thr Pro Asn Leu Pro Pro Glu Ile Ile Trp Phe
            195                 200                 205

Pro Asp Asn Phe Val Phe Ser Ile Tyr Asn Phe Ala Gln Trp Ala Arg
            210                 215                 220

Ala Thr Met Val Pro Ile Ala Ile Leu Ser Ala Arg Arg Pro Ser Arg
225                 230                 235                 240

Pro Leu Arg Pro Gln Asp Arg Leu Asp Glu Leu Phe Pro Glu Gly Arg
                245                 250                 255

Ala Arg Phe Asp Tyr Glu Leu Pro Lys Lys Glu Gly Ile Asp Leu Trp
            260                 265                 270

Ser Gln Phe Phe Arg Thr Thr Asp Arg Gly Leu His Trp Val Gln Ser
            275                 280                 285

Asn Leu Leu Lys Arg Asn Ser Leu Arg Glu Ala Ala Ile Arg His Val
            290                 295                 300

Leu Glu Trp Ile Ile Arg His Gln Asp Ala Asp Gly Gly Trp Gly Gly
305                 310                 315                 320

Ile Gln Pro Pro Trp Val Tyr Gly Leu Met Ala Leu His Gly Glu Gly
                325                 330                 335

Tyr Gln Leu Tyr His Pro Val Met Ala Lys Ala Leu Ser Ala Leu Asp
            340                 345                 350

Asp Pro Gly Trp Arg His Asp Arg Gly Glu Ser Ser Trp Ile Gln Ala
            355                 360                 365

Thr Asn Ser Pro Val Trp Asp Thr Met Leu Ala Leu Met Ala Leu Lys
            370                 375                 380

Asp Ala Lys Ala Glu Asp Arg Phe Thr Pro Glu Met Asp Lys Ala Ala
385                 390                 395                 400

Asp Trp Leu Leu Ala Arg Gln Val Lys Val Lys Gly Asp Trp Ser Ile
                405                 410                 415

Lys Leu Pro Asp Val Glu Pro Gly Gly Trp Ala Phe Glu Tyr Ala Asn
            420                 425                 430

Asp Arg Tyr Pro Asp Thr Asp Thr Ala Val Ala Leu Ile Ala Leu
            435                 440                 445

Ser Ser Tyr Arg Asp Lys Glu Glu Trp Gln Lys Lys Gly Val Glu Asp
            450                 455                 460

Ala Ile Thr Arg Gly Val Asn Trp Leu Ile Ala Met Gln Ser Glu Cys
465                 470                 475                 480
```

```
Gly Gly Trp Gly Ala Phe Asp Lys Asp Asn Asn Arg Ser Ile Leu Ser
                485                 490                 495

Lys Ile Pro Phe Cys Asp Phe Gly Glu Ser Ile Asp Pro Pro Ser Val
            500                 505                 510

Asp Val Thr Ala His Val Leu Glu Ala Phe Gly Thr Leu Gly Leu Ser
            515                 520                 525

Arg Asp Met Pro Val Ile Gln Lys Ala Ile Asp Tyr Val Arg Ser Glu
530                 535                 540

Gln Glu Ala Glu Gly Ala Trp Phe Gly Arg Trp Gly Val Asn Tyr Ile
545                 550                 555                 560

Tyr Gly Thr Gly Ala Val Leu Pro Ala Leu Ala Ala Ile Gly Glu Asp
                565                 570                 575

Met Thr Gln Pro Tyr Ile Thr Lys Ala Cys Asp Trp Leu Val Ala His
            580                 585                 590

Gln Gln Glu Asp Gly Gly Trp Gly Glu Ser Cys Ser Ser Tyr Met Glu
            595                 600                 605

<210> SEQ ID NO 12
<211> LENGTH: 658
<212> TYPE: PRT
<213> ORGANISM: Zymomonas mobilis

<400> SEQUENCE: 12

Met Thr Val Ser Thr Ser Ser Ala Phe His His Ser Pro Leu Ser Asp
1               5                   10                  15

Asp Val Glu Pro Ile Ile Gln Lys Ala Thr Arg Ala Leu Leu Glu Lys
            20                  25                  30

Gln Gln Gln Asp Gly His Trp Val Phe Glu Leu Glu Ala Asp Ala Thr
        35                  40                  45

Ile Pro Ala Glu Tyr Ile Leu Leu Lys His Tyr Leu Gly Glu Pro Glu
    50                  55                  60

Asp Leu Glu Ile Glu Ala Lys Ile Gly Arg Tyr Leu Arg Arg Ile Gln
65                  70                  75                  80

Gly Glu His Gly Gly Trp Ser Leu Phe Tyr Gly Gly Asp Leu Asp Leu
                85                  90                  95

Ser Ala Thr Val Lys Ala Tyr Phe Ala Leu Lys Met Ile Gly Asp Ser
            100                 105                 110

Pro Asp Ala Pro His Met Leu Arg Ala Arg Asn Glu Ile Leu Ala Arg
        115                 120                 125

Gly Gly Ala Met Arg Ala Asn Val Phe Thr Arg Ile Gln Leu Ala Leu
    130                 135                 140

Phe Gly Ala Met Ser Trp Glu His Val Pro Gln Met Pro Val Glu Leu
145                 150                 155                 160

Met Leu Met Pro Glu Trp Phe Pro Val His Ile Asn Lys Met Ala Tyr
                165                 170                 175

Trp Ala Arg Thr Val Leu Val Pro Leu Leu Val Leu Gln Ala Leu Lys
            180                 185                 190

Pro Val Ala Arg Asn Arg Arg Gly Ile Leu Val Asp Glu Leu Phe Val
        195                 200                 205

Pro Asp Val Leu Pro Thr Leu Gln Glu Ser Gly Asp Pro Ile Trp Arg
    210                 215                 220

Arg Phe Phe Ser Ala Leu Asp Lys Val Leu His Lys Val Glu Pro Tyr
225                 230                 235                 240

Trp Pro Lys Asn Met Arg Ala Lys Ala Ile His Ser Cys Val His Phe
                245                 250                 255
```

```
Val Thr Glu Arg Leu Asn Gly Glu Asp Gly Leu Gly Ala Ile Tyr Pro
            260                 265                 270

Ala Ile Ala Asn Ser Val Met Met Tyr Asp Ala Leu Gly Tyr Pro Glu
            275                 280                 285

Asn His Pro Glu Arg Ala Ile Ala Arg Arg Ala Val Glu Lys Leu Met
            290                 295                 300

Val Leu Asp Gly Thr Glu Asp Gln Gly Asp Lys Glu Val Tyr Cys Gln
305                 310                 315                 320

Pro Cys Leu Ser Pro Ile Trp Asp Thr Ala Leu Val Ala His Ala Met
                325                 330                 335

Leu Glu Val Gly Gly Asp Glu Ala Glu Lys Ser Ala Ile Ser Ala Leu
            340                 345                 350

Ser Trp Leu Lys Pro Gln Gln Ile Leu Asp Val Lys Gly Asp Trp Ala
            355                 360                 365

Trp Arg Arg Pro Asp Leu Arg Pro Gly Gly Trp Ala Phe Gln Tyr Arg
            370                 375                 380

Asn Asp Tyr Tyr Pro Asp Val Asp Asp Thr Ala Val Val Thr Met Ala
385                 390                 395                 400

Met Asp Arg Ala Ala Lys Leu Ser Asp Leu His Asp Asp Phe Glu Glu
            405                 410                 415

Ser Lys Ala Arg Ala Met Glu Trp Thr Ile Gly Met Gln Ser Asp Asn
            420                 425                 430

Gly Gly Trp Gly Ala Phe Asp Ala Asn Asn Ser Tyr Thr Tyr Leu Asn
            435                 440                 445

Asn Ile Pro Phe Ala Asp His Gly Ala Leu Leu Asp Pro Pro Thr Val
            450                 455                 460

Asp Val Ser Ala Arg Cys Val Ser Met Met Ala Gln Ala Gly Ile Ser
465                 470                 475                 480

Ile Thr Asp Pro Lys Met Lys Ala Ala Val Asp Tyr Leu Leu Lys Glu
            485                 490                 495

Gln Glu Glu Asp Gly Ser Trp Phe Gly Arg Trp Gly Val Asn Tyr Ile
            500                 505                 510

Tyr Gly Thr Trp Ser Ala Leu Cys Ala Leu Asn Val Ala Ala Leu Pro
            515                 520                 525

His Asp His Leu Ala Val Gln Lys Ala Val Ala Trp Leu Lys Thr Ile
            530                 535                 540

Gln Asn Glu Asp Gly Gly Trp Gly Glu Asn Cys Asp Ser Tyr Ala Leu
545                 550                 555                 560

Asp Tyr Ser Gly Tyr Glu Pro Met Asp Ser Thr Ala Ser Gln Thr Ala
                565                 570                 575

Trp Ala Leu Leu Gly Leu Met Ala Val Gly Glu Ala Asn Ser Glu Ala
            580                 585                 590

Val Thr Lys Gly Ile Asn Trp Leu Ala Gln Asn Gln Asp Glu Glu Gly
            595                 600                 605

Leu Trp Lys Glu Asp Tyr Tyr Ser Gly Gly Phe Pro Arg Val Phe
            610                 615                 620

Tyr Leu Arg Tyr His Gly Tyr Ser Lys Tyr Phe Pro Leu Trp Ala Leu
625                 630                 635                 640

Ala Arg Tyr Arg Asn Leu Lys Lys Ala Asn Gln Pro Ile Val His Tyr
            645                 650                 655

Gly Met
```

<210> SEQ ID NO 13
<211> LENGTH: 684
<212> TYPE: PRT
<213> ORGANISM: Bradyrhizobium japonicum

<400> SEQUENCE: 13

```
Met Thr Val Thr Ser Ser Ala Ser Ala Arg Thr Arg Asp Pro Gly
1               5                   10                  15

Asn Tyr Gln Thr Ala Leu Gln Ser Thr Val Arg Ala Ala Asp Trp
            20                  25                  30

Leu Ile Ala Asn Gln Lys Pro Asp Gly His Trp Val Gly Arg Ala Glu
        35                  40                  45

Ser Asn Ala Cys Met Glu Ala Gln Trp Cys Leu Ala Leu Trp Phe Met
50                  55                  60

Gly Leu Glu Asp His Pro Leu Arg Lys Arg Leu Gly Gln Ser Leu Leu
65                  70                  75                  80

Asp Ser Gln Arg Pro Asp Gly Ala Trp Gln Val Tyr Phe Gly Ala Pro
                85                  90                  95

Asn Gly Asp Ile Asn Ala Thr Val Glu Ala Tyr Ala Ala Leu Arg Ser
            100                 105                 110

Leu Gly Phe Arg Asp Asp Glu Pro Ala Val Arg Arg Ala Arg Glu Trp
        115                 120                 125

Ile Glu Ala Lys Gly Gly Leu Arg Asn Ile Arg Val Phe Thr Arg Tyr
130                 135                 140

Trp Leu Ala Leu Ile Gly Glu Trp Pro Trp Glu Lys Thr Pro Asn Ile
145                 150                 155                 160

Pro Pro Glu Val Ile Trp Phe Pro Leu Trp Phe Pro Ser Ile Tyr
                165                 170                 175

Asn Phe Ala Gln Trp Ala Arg Ala Thr Leu Met Pro Ile Ala Val Leu
            180                 185                 190

Ser Ala Arg Arg Pro Ser Arg Pro Leu Pro Pro Glu Asn Arg Leu Asp
        195                 200                 205

Ala Leu Phe Pro His Gly Arg Lys Ala Phe Asp Tyr Glu Leu Pro Val
210                 215                 220

Lys Ala Gly Ala Gly Gly Trp Asp Arg Phe Phe Arg Gly Ala Asp Lys
225                 230                 235                 240

Val Leu His Lys Leu Gln Asn Leu Gly Asn Arg Leu Asn Leu Gly Leu
                245                 250                 255

Phe Arg Pro Ala Ala Thr Ser Arg Val Leu Glu Trp Met Ile Arg His
            260                 265                 270

Gln Asp Phe Asp Gly Ala Trp Gly Gly Ile Gln Pro Trp Ile Tyr
        275                 280                 285

Gly Leu Met Ala Leu Tyr Ala Glu Gly Tyr Pro Leu Asn His Pro Val
290                 295                 300

Leu Ala Lys Gly Leu Asp Ala Leu Asn Asp Pro Gly Trp Arg Val Asp
305                 310                 315                 320

Val Gly Asp Ala Thr Tyr Ile Gln Ala Thr Asn Ser Pro Val Trp Asp
                325                 330                 335

Thr Ile Leu Thr Leu Leu Ala Phe Asp Asp Ala Gly Val Leu Gly Asp
            340                 345                 350

Tyr Pro Glu Ala Val Asp Lys Ala Val Asp Trp Val Leu Gln Arg Gln
        355                 360                 365

Val Arg Val Pro Gly Asp Trp Ser Met Lys Leu Pro His Val Lys Pro
370                 375                 380
```

```
Gly Gly Trp Ala Phe Glu Tyr Ala Asn Asn Tyr Tyr Pro Asp Thr Asp
385                 390                 395                 400

Asp Thr Ala Val Ala Leu Ile Ala Leu Ala Pro Leu Arg His Asp Pro
                405                 410                 415

Lys Trp Lys Ala Lys Gly Ile Asp Glu Ala Ile Gln Leu Gly Val Asp
            420                 425                 430

Trp Leu Ile Gly Met Gln Ser Gln Gly Gly Trp Gly Ala Phe Asp
        435                 440                 445

Lys Asp Asn Asn Gln Lys Ile Leu Thr Lys Ile Pro Phe Cys Asp Tyr
450                 455                 460

Gly Glu Ala Leu Asp Pro Pro Ser Val Asp Val Thr Ala His Ile Ile
465                 470                 475                 480

Glu Ala Phe Gly Lys Leu Gly Ile Ser Arg Asn His Pro Ser Met Val
                485                 490                 495

Gln Ala Leu Asp Tyr Ile Arg Arg Glu Gln Glu Pro Ser Gly Pro Trp
            500                 505                 510

Phe Gly Arg Trp Gly Val Asn Tyr Val Tyr Gly Thr Gly Ala Val Leu
        515                 520                 525

Pro Ala Leu Ala Ala Ile Gly Glu Asp Met Thr Gln Pro Tyr Ile Gly
530                 535                 540

Arg Ala Cys Asp Trp Leu Val Ala His Gln Gln Ala Asp Gly Gly Trp
545                 550                 555                 560

Gly Glu Ser Cys Ala Ser Tyr Met Asp Val Ser Ala Val Gly Arg Gly
                565                 570                 575

Thr Thr Thr Ala Ser Gln Thr Ala Trp Ala Leu Met Ala Leu Leu Ala
            580                 585                 590

Ala Asn Arg Pro Gln Asp Lys Asp Ala Ile Glu Arg Gly Cys Met Trp
        595                 600                 605

Leu Val Glu Arg Gln Ser Ala Gly Thr Trp Asp Glu Pro Glu Phe Thr
610                 615                 620

Gly Thr Gly Phe Pro Gly Tyr Gly Val Gly Gln Thr Ile Lys Leu Asn
625                 630                 635                 640

Asp Pro Ala Leu Ser Gln Arg Leu Met Gln Gly Pro Glu Leu Ser Arg
                645                 650                 655

Ala Phe Met Leu Arg Tyr Gly Met Tyr Arg His Tyr Phe Pro Leu Met
            660                 665                 670

Ala Leu Gly Arg Ala Leu Arg Pro Gln Ser His Ser
        675                 680

<210> SEQ ID NO 14
<211> LENGTH: 685
<212> TYPE: PRT
<213> ORGANISM: Gluconobacter morbifer

<400> SEQUENCE: 14

Met Ser Pro Ala Asp Ile Ser Thr Lys Ser Ser Phe Gln Arg Leu
1               5                   10                  15

Asp Asn Met Leu Pro Glu Ala Val Ser Ser Ala Cys Asp Trp Leu Ile
                20                  25                  30

Asp Gln Gln Lys Pro Asp Gly His Trp Val Gly Pro Val Glu Ser Asn
            35                  40                  45

Ala Cys Met Glu Ala Gln Trp Cys Leu Ala Leu Trp Phe Leu Gly Gln
        50                  55                  60

Glu Asp His Pro Leu Arg Pro Arg Leu Ala Gln Ala Leu Leu Glu Met
65                  70                  75                  80
```

```
Gln Arg Glu Asp Gly Ser Trp Gly Ile Tyr Val Gly Ala Asp His Gly
                85                  90                  95

Asp Ile Asn Thr Thr Val Glu Ala Tyr Ala Ala Leu Arg Ser Met Gly
            100                 105                 110

Tyr Ala Ala Asp Met Pro Ile Met Ala Lys Ser Ala Ala Trp Ile Gln
        115                 120                 125

Gln Lys Gly Gly Leu Arg Asn Val Arg Val Phe Thr Arg Tyr Trp Leu
    130                 135                 140

Ala Leu Ile Gly Glu Trp Pro Trp Asp Lys Thr Pro Asn Leu Pro Pro
145                 150                 155                 160

Glu Ile Ile Trp Leu Pro Asp Asn Phe Ile Phe Ser Ile Tyr Asn Phe
                165                 170                 175

Ala Gln Trp Ala Arg Ala Thr Met Met Pro Leu Thr Ile Leu Ser Ala
            180                 185                 190

Arg Arg Pro Ser Arg Pro Leu Leu Pro Glu Asn Arg Leu Asp Gly Leu
        195                 200                 205

Phe Pro Glu Gly Arg Glu Asn Phe Asp Tyr Glu Leu Pro Val Lys Gly
    210                 215                 220

Glu Glu Asp Leu Trp Gly Arg Phe Phe Arg Ala Ala Asp Lys Gly Leu
225                 230                 235                 240

His Ser Leu Gln Ser Phe Pro Val Arg Arg Phe Val Pro Arg Glu Ala
                245                 250                 255

Ala Ile Arg His Val Ile Glu Trp Ile Ile Arg His Gln Asp Ala Asp
            260                 265                 270

Gly Gly Trp Gly Gly Ile Gln Pro Pro Trp Ile Tyr Gly Leu Met Ala
        275                 280                 285

Leu Ser Val Glu Gly Tyr Pro Leu His His Pro Val Leu Ala Lys Ala
    290                 295                 300

Met Asp Ala Leu Asn Asp Pro Gly Trp Arg Arg Asp Lys Gly Asp Ala
305                 310                 315                 320

Ser Trp Ile Gln Ala Thr Asn Ser Pro Val Trp Asp Thr Met Leu Ala
                325                 330                 335

Val Leu Ala Leu His Asp Ala Gly Ala Glu Asp Arg Tyr Ser Pro Gln
            340                 345                 350

Met Asp Lys Ala Ile Gly Trp Leu Leu Asp Arg Gln Val Arg Val Lys
        355                 360                 365

Gly Asp Trp Ser Ile Lys Leu Pro Asp Thr Glu Pro Gly Gly Trp Ala
    370                 375                 380

Phe Glu Tyr Ala Asn Asp Lys Tyr Pro Asp Thr Asp Asp Thr Ala Val
385                 390                 395                 400

Ala Leu Ile Ala Leu Ala Gly Cys Arg His Arg Pro Glu Trp Arg Glu
                405                 410                 415

Arg Asp Ile Glu Gly Ala Ile Ser Arg Gly Val Asn Trp Leu Leu Ala
            420                 425                 430

Met Gln Ser Ser Ser Gly Gly Trp Gly Ala Phe Asp Lys Asp Asn Asn
        435                 440                 445

Arg Ser Ile Leu Thr Lys Ile Pro Phe Cys Asp Phe Gly Glu Ala Leu
    450                 455                 460

Asp Pro Pro Ser Val Asp Val Thr Ala His Val Leu Glu Ala Phe Gly
465                 470                 475                 480

Leu Leu Gly Ile Ser Arg Asn His Pro Ser Val Gln Lys Ala Leu Ala
                485                 490                 495
```

```
Tyr Ile Arg Ser Glu Gln Glu Arg Asn Gly Ala Trp Phe Gly Arg Trp
            500                 505                 510

Gly Val Asn Tyr Val Tyr Gly Thr Gly Ala Val Leu Pro Ala Leu Ala
        515                 520                 525

Ala Ile Gly Glu Asp Met Thr Gln Pro Tyr Ile Val Arg Ala Cys Asp
    530                 535                 540

Trp Leu Met Ser Val Gln Gln Glu Asn Gly Gly Trp Gly Glu Ser Cys
545                 550                 555                 560

Ala Ser Tyr Met Asp Ile Asn Ala Val Gly His Gly Val Ala Thr Ala
                565                 570                 575

Ser Gln Thr Ala Trp Ala Leu Ile Gly Leu Leu Ala Ala Lys Arg Pro
            580                 585                 590

Lys Asp Arg Glu Ala Ile Ala Arg Gly Cys Gln Phe Leu Ile Glu Arg
        595                 600                 605

Gln Glu Asp Gly Ser Trp Thr Glu Glu Tyr Thr Gly Thr Gly Phe
    610                 615                 620

Pro Gly Tyr Gly Val Gly Gln Ala Ile Lys Leu Asp Asp Pro Ser Leu
625                 630                 635                 640

Pro Asp Arg Leu Leu Gln Gly Ala Glu Leu Ser Arg Ala Phe Met Leu
                645                 650                 655

Arg Tyr Asp Leu Tyr Arg Gln Tyr Phe Pro Val Met Ala Leu Ser Arg
            660                 665                 670

Ala Arg Arg Met Met Lys Glu Asp Ala Ser Ala Ala Ala
        675                 680                 685

<210> SEQ ID NO 15
<211> LENGTH: 1896
<212> TYPE: DNA
<213> ORGANISM: Alicyclobacillus acidocaldarius

<400> SEQUENCE: 15
atggctgagc agttggtgga agcgccggcc tacgcgcgga cgctggatcg cgcggtggag      60
tatctcctct cctgccaaaa ggacgaaggc tactggtggg gccgcttct gagcaacgtc     120 acgatggaag cggagtacgt cctcttgtgc acattctcg atcgcgtcga tcgggatcgc     180
atggagaaga tccggcggta cctgttgcac gagcagcgcg aggacggcac gtgggccctg     240
tacccgggtg gccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggatgtggc tggcgctggt gggagaatat     420
ccgtgggaga aggtgcccat ggtcccgccg gagatcatgt tcctcggcaa cgcatgccg     480 ctcaacatct cgagtttgg ctcgtgggct cgggcgaccg tcgtggcgct tcgattgtg     540 atgagccgcc agccggtgtt cccgctgccc gagcgggcgc gcgtgcccga gctgtacgag     600
accgacgtgc ctccgcgccg cgcggtgcc aaggaggggt gtggtggat cttcgacgcg     660 ctcgaccggg cgctgcacgg gtatcagaag ctgtcggtgc acccgttccg ccgcgcggcc     720
gagatccgcg ccttggactg gttgctcgag cgccaggccg agacggcag ctggggcggg     780 attcagccgc cttggttta cgcgctcatc gcgctcaaga ttctcgacat gacgcagcat     840
ccggcgttca tcaagggctg ggaaggtcta gagctgtacg gcgtggagct ggattacgga     900
ggatggatgt ttcaggcttc catctcgccg gtgtgggaca cgggcctcgc cgtgctcgcg     960
ctgcgcgctg cggggcttcc ggccgatcac gaccgcttgg tcaaggcggg cgagtggctc    1020
ttggaccggc agatcacggt tccgggcgac tgggcggtga agcgcccgaa cctcaagccg    1080
```

```
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg   1200
acgaagggat tccgctggat tgtcggcatg cagagctcga acggcggttg gggcgcctac   1260
gacgtcgaca cacgagcga  tctcccgaac cacatcccgt tctgcgactt cggcgaagtg   1320
accgatccgc cgtcagagga cgtcaccgcc cacgtgctcg agtgtttcgg cagcttcggg   1380
tacgatgacg cctggaaggt catccggcgc gcggtggaat atctcaagcg ggagcagaag   1440
ccggacggca gctggttcgg tcgttgggc  gtcaattacc tctacggcac gggcgcggtg   1500
gtgtcggcgc tgaaggcggt cgggatcgac acgcgcgagc cgtacattca aaaggcgctc   1560
gactgggtcg agcagcatca gaacccggac ggcggctggg gcgaggactg ccgctcgtac   1620
gaggatccgg cgtacgcggg taagggcgcg agcaccccgt cgcagacggc ctgggcgctg   1680
atggcgctca tcgcgggcgg cagggcggag tccgaggccg cgccgcgg   cgtgcaatac   1740 ctcgtggaga cgcagcgccc ggacggcggc tgggatgagc cgtactacac cggcacgggc   1800
ttcccagggg atttctacct cggctacacc atgtaccgcc acgtgtttcc gacgctcgcg   1860
ctcggccgct acaagcaagc catcgagcgc aggtga                             1896

<210> SEQ ID NO 16
<211> LENGTH: 1896
<212> TYPE: DNA
<213> ORGANISM: Artificial Sequence
<220> FEATURE:
<223> OTHER INFORMATION: 215G2 SHC/HAC enzyme variant

<400> SEQUENCE: 16
atggctgagc agttggtgga agctccggcc tacgcgcgga cgctggatcg cgcggtggag     60
tatctcctct cctgccaaaa ggacgaaggc tactggtggg ggccgcttct gagcaacgtc    120
acgatggaag cggagtacgt cctcttgtgc cacattctcg atcgcgtcga tcgggatcgc    180
atggagaaga tccggcggta cctgttgcac gagcagcgcg aggacggcac gtgggccctg    240
tacccgggtg gccgccgga  cctcgacacg accatcgagg cgtacgtcgc gctcaagtat    300
atcggcatgt cgcgcgacga ggagccgatg cagaaggcgc tccggttcat tcagagccag    360
ggcgggatcg agtcgtcgcg cgtgttcacg cggaggtggc tggcgctggt gggagaatat    420
ccgtgggaga aggtgcccat ggtcccgccg gagatcatgt tcctcggcaa gcgcatgccg    480
ctcaacatct acgagtttgg ctcgtgggct cgggcgaccg tcgtggcgct ctcgattgtg    540
atgagccgcc agcggtgtt  cccgctgccc gagcgggcgc gcgtgcccga gctgtacgag    600
accgacgtgc ctccgcgccg gcgcggtgcc aagggagggg gtgggtggat cttcgacgcg    660
ctcgaccggg tgctgcacgg gtatcagaag ctgtcggtgc acccgttccg ccgcgcggcc    720
gagatccgcg ccttggactg gttgctcgag cgccaggccg agacggcag  ctggggcggg    780 attcagccgc cttggtttta cgcgctcatc gcgctcaaga ttctcgacat gacgcagcat    840
ccggcgttca tcaagggctg ggaaggtcta gagctgtacg gcgtggagct ggattacgga    900
ggatggatgt ttcaggcttc catctcgccg gtgtgggaca cgggcctcgc cgtgctcgcg    960
ctgcgcgctg cggggcttcc ggccgatcac gaccgcttgg tcaaggcggg cgagtggctg   1020
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg   1200
```

```
acgaagggat tccgctggat tgtcggcatg cagagctcga acggcggttg gggcgcctac    1260
gacgtcgaca acacgagcga tctcccgaac cacaccccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg cgaggactg ccgctcgtac    1620 gaggatccgg cgtacgcggg taagggcgcg agcaccccgt cgcagacggc ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg atttctacct cggctacacc atgtaccgcc acgtgtttcc gacgctcgcg    1860
ctcggccgct acaagcaagc catcgagcgc aggtga                              1896
```

<210> SEQ ID NO 17
<211> LENGTH: 631
<212> TYPE: PRT
<213> ORGANISM: Artificial Sequence
<220> FEATURE:
<223> OTHER INFORMATION: SHC/HAC enzyme variant #90C7

<400> SEQUENCE: 17

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Ala Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240
```

```
Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
    370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg Arg
625                 630

<210> SEQ ID NO 18
<211> LENGTH: 631
<212> TYPE: PRT
```

<213> ORGANISM: Artificial Sequence
<220> FEATURE:
<223> OTHER INFORMATION: SHC/HAC enzyme variant #115A7

<400> SEQUENCE: 18

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Thr Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Lys Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
370                 375                 380
```

```
Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 19
<211> LENGTH: 642
<212> TYPE: PRT
<213> ORGANISM: Thermosynechococcus elongatus

<400> SEQUENCE: 19

Met Pro Thr Ser Leu Ala Thr Ala Ile Asp Pro Lys Gln Leu Gln Gln
1               5                   10                  15

Ala Ile Arg Ala Ser Gln Asp Phe Leu Phe Ser Gln Gln Tyr Ala Glu
                20                  25                  30

Gly Tyr Trp Trp Ala Glu Leu Glu Ser Asn Val Thr Met Thr Ala Glu
            35                  40                  45

Val Ile Leu Leu His Lys Ile Trp Gly Thr Glu Gln Arg Leu Pro Leu
        50                  55                  60

Ala Lys Ala Glu Gln Tyr Leu Arg Asn His Gln Arg Asp His Gly Gly
65                  70                  75                  80

Trp Glu Leu Phe Tyr Gly Asp Gly Gly Asp Leu Ser Thr Ser Val Glu
                85                  90                  95

Ala Tyr Met Gly Leu Arg Leu Leu Gly Val Pro Glu Thr Asp Pro Ala
            100                 105                 110
```

```
Leu Val Lys Ala Arg Gln Phe Ile Leu Ala Arg Gly Gly Ile Ser Lys
            115                 120                 125

Thr Arg Ile Phe Thr Lys Leu His Leu Ala Leu Ile Gly Cys Tyr Asp
        130                 135                 140

Trp Arg Gly Ile Pro Ser Leu Pro Pro Trp Ile Met Leu Leu Pro Glu
145                 150                 155                 160

Gly Ser Pro Phe Thr Ile Tyr Glu Met Ser Ser Trp Ala Arg Ser Ser
                165                 170                 175

Thr Val Pro Leu Leu Ile Val Met Asp Arg Lys Pro Val Tyr Gly Met
            180                 185                 190

Asp Pro Pro Ile Thr Leu Asp Glu Leu Tyr Ser Glu Gly Arg Ala Asn
        195                 200                 205

Val Val Trp Glu Leu Pro Arg Gln Gly Asp Trp Arg Asp Val Phe Ile
210                 215                 220

Gly Leu Asp Arg Val Phe Lys Leu Phe Glu Thr Leu Asn Ile His Pro
225                 230                 235                 240

Leu Arg Glu Gln Gly Leu Lys Ala Ala Glu Glu Trp Val Leu Glu Arg
                245                 250                 255

Gln Glu Ala Ser Gly Asp Trp Gly Ile Ile Pro Ala Met Leu Asn
            260                 265                 270

Ser Leu Leu Ala Leu Arg Ala Leu Asp Tyr Ala Val Asp Asp Pro Ile
        275                 280                 285

Val Gln Arg Gly Met Ala Ala Val Asp Arg Phe Ala Ile Glu Thr Glu
290                 295                 300

Thr Glu Tyr Arg Val Gln Pro Cys Val Ser Pro Val Trp Asp Thr Ala
305                 310                 315                 320

Leu Val Met Arg Ala Met Val Asp Ser Gly Val Ala Pro Asp His Pro
                325                 330                 335

Ala Leu Val Lys Ala Gly Glu Trp Leu Leu Ser Lys Gln Ile Leu Asp
            340                 345                 350

Tyr Gly Asp Trp His Ile Lys Asn Lys Lys Gly Arg Pro Gly Gly Trp
        355                 360                 365

Ala Phe Glu Phe Glu Asn Arg Phe Tyr Pro Asp Val Asp Asp Thr Ala
370                 375                 380

Val Val Val Met Ala Leu His Ala Val Thr Leu Pro Asn Glu Asn Leu
385                 390                 395                 400

Lys Arg Arg Ala Ile Glu Arg Ala Val Ala Trp Ile Ala Ser Met Gln
                405                 410                 415

Cys Arg Pro Gly Gly Trp Ala Ala Phe Asp Val Asp Asn Asp Gln Asp
            420                 425                 430

Trp Leu Asn Gly Ile Pro Tyr Gly Asp Leu Lys Ala Met Ile Asp Pro
        435                 440                 445

Asn Thr Ala Asp Val Thr Ala Arg Val Leu Glu Met Val Gly Arg Cys
450                 455                 460

Gln Leu Ala Phe Asp Arg Val Ala Leu Asp Arg Ala Leu Ala Tyr Leu
465                 470                 475                 480

Arg Asn Glu Gln Glu Pro Glu Gly Cys Trp Phe Gly Arg Trp Gly Val
                485                 490                 495

Asn Tyr Leu Tyr Gly Thr Ser Gly Val Leu Thr Ala Leu Ser Leu Val
            500                 505                 510

Ala Pro Arg Tyr Asp Arg Trp Arg Ile Arg Arg Ala Ala Glu Trp Leu
        515                 520                 525
```

```
Met Gln Cys Gln Asn Ala Asp Gly Gly Trp Gly Glu Thr Cys Trp Ser
    530                 535                 540
Tyr His Asp Pro Ser Leu Lys Gly Lys Gly Asp Ser Thr Ala Ser Gln
545                 550                 555                 560
Thr Ala Trp Ala Ile Ile Gly Leu Leu Ala Ala Gly Asp Ala Thr Gly
                565                 570                 575
Asp Tyr Ala Thr Glu Ala Ile Glu Arg Gly Ile Ala Tyr Leu Leu Glu
            580                 585                 590
Thr Gln Arg Pro Asp Gly Thr Trp His Glu Asp Tyr Phe Thr Gly Thr
        595                 600                 605
Gly Phe Pro Cys His Phe Tyr Leu Lys Tyr His Tyr Tyr Gln Gln His
    610                 615                 620
Phe Pro Leu Thr Ala Leu Gly Arg Tyr Ala Arg Trp Arg Asn Leu Leu
625                 630                 635                 640
Ala Thr

<210> SEQ ID NO 20
<211> LENGTH: 720
<212> TYPE: PRT
<213> ORGANISM: Acetobacter pasteurianus

<400> SEQUENCE: 20

Met Asn Met Ala Ser Arg Phe Ser Leu Lys Lys Ile Leu Arg Ser Gly
1               5                   10                  15
Ser Asp Thr Gln Gly Thr Asn Val Asn Thr Leu Ile Gln Ser Gly Thr
            20                  25                  30
Ser Asp Ile Val Arg Gln Lys Pro Ala Pro Gln Glu Pro Ala Asp Leu
        35                  40                  45
Ser Ala Leu Lys Ala Met Gly Asn Ser Leu Thr His Thr Leu Ser Ser
    50                  55                  60
Ala Cys Glu Trp Leu Met Lys Gln Gln Lys Pro Asp Gly His Trp Val
65                  70                  75                  80
Gly Ser Val Gly Ser Asn Ala Ser Met Glu Ala Glu Trp Cys Leu Ala
                85                  90                  95
Leu Trp Phe Leu Gly Leu Glu Asp His Pro Leu Arg Pro Arg Leu Gly
            100                 105                 110
Lys Ala Leu Leu Glu Met Gln Arg Pro Asp Gly Ser Trp Gly Thr Tyr
        115                 120                 125
Tyr Gly Ala Gly Ser Gly Asp Ile Asn Ala Thr Val Glu Ser Tyr Ala
    130                 135                 140
Ala Leu Arg Ser Leu Gly Tyr Ala Glu Asp Pro Ala Val Ser Lys
145                 150                 155                 160
Ala Ala Ala Trp Ile Ile Ser Lys Gly Gly Leu Lys Asn Val Arg Val
                165                 170                 175
Phe Thr Arg Tyr Trp Leu Ala Leu Ile Gly Glu Trp Pro Trp Glu Lys
            180                 185                 190
Thr Pro Asn Leu Pro Pro Glu Ile Ile Trp Phe Pro Asp Asn Phe Val
        195                 200                 205
Phe Ser Ile Tyr Asn Phe Ala Gln Trp Ala Arg Ala Thr Met Met Pro
    210                 215                 220
Leu Ala Ile Leu Ser Ala Arg Arg Pro Ser Arg Pro Leu Arg Pro Gln
225                 230                 235                 240
Asp Arg Leu Asp Ala Leu Phe Pro Gly Gly Arg Ala Asn Phe Asp Tyr
                245                 250                 255
```

-continued

```
Glu Leu Pro Thr Lys Glu Gly Arg Asp Val Ile Ala Asp Phe Phe Arg
            260                 265                 270
Leu Ala Asp Lys Gly Leu His Trp Leu Gln Ser Ser Phe Leu Lys Arg
            275                 280                 285
Ala Pro Ser Arg Glu Ala Ile Lys Tyr Val Leu Glu Trp Ile Ile
290                 295                 300
Trp His Gln Asp Ala Asp Gly Gly Trp Gly Gly Ile Gln Pro Pro Trp
305                 310                 315                 320
Val Tyr Gly Leu Met Ala Leu His Gly Glu Gly Tyr Gln Phe His His
                325                 330                 335
Pro Val Met Ala Lys Ala Leu Asp Ala Leu Asn Asp Pro Gly Trp Arg
                340                 345                 350
His Asp Lys Gly Asp Ala Ser Trp Ile Gln Ala Thr Asn Ser Pro Val
                355                 360                 365
Trp Asp Thr Met Leu Ser Leu Met Ala Leu His Asp Ala Asn Ala Glu
370                 375                 380
Glu Arg Phe Thr Pro Glu Met Asp Lys Ala Leu Asp Trp Leu Leu Ser
385                 390                 395                 400
Arg Gln Val Arg Val Lys Gly Asp Trp Ser Val Lys Leu Pro Asn Thr
                405                 410                 415
Glu Pro Gly Gly Trp Ala Phe Glu Tyr Ala Asn Asp Arg Tyr Pro Asp
                420                 425                 430
Thr Asp Thr Ala Val Ala Leu Ile Ala Ile Ala Ser Cys Arg Asn
                435                 440                 445
Arg Pro Glu Trp Gln Ala Lys Gly Val Glu Glu Ala Ile Gly Arg Gly
                450                 455                 460
Val Arg Trp Leu Val Ala Met Gln Ser Ser Cys Gly Gly Trp Gly Ala
465                 470                 475                 480
Phe Asp Lys Asp Asn Asn Lys Ser Ile Leu Ala Lys Ile Pro Phe Cys
                485                 490                 495
Asp Phe Gly Glu Ala Leu Asp Pro Pro Ser Val Asp Val Thr Ala His
                500                 505                 510
Val Leu Glu Ala Phe Gly Leu Leu Gly Leu Pro Arg Asp Leu Pro Cys
            515                 520                 525
Ile Gln Arg Gly Leu Ala Tyr Ile Arg Lys Glu Gln Asp Pro Thr Gly
            530                 535                 540
Pro Trp Phe Gly Arg Trp Gly Val Asn Tyr Leu Tyr Gly Thr Gly Ala
545                 550                 555                 560
Val Leu Pro Ala Leu Ala Ala Leu Gly Glu Asp Met Thr Gln Pro Tyr
                565                 570                 575
Ile Ser Lys Ala Cys Asp Trp Leu Ile Asn Cys Gln Gln Glu Asn Gly
                580                 585                 590
Gly Trp Gly Glu Ser Cys Ala Ser Tyr Met Glu Val Ser Ser Ile Gly
                595                 600                 605
His Gly Ala Thr Thr Pro Ser Gln Thr Ala Trp Ala Leu Met Gly Leu
            610                 615                 620
Ile Ala Ala Asn Arg Pro Gln Asp Tyr Glu Ala Ile Ala Lys Gly Cys
625                 630                 635                 640
Arg Tyr Leu Ile Asp Leu Gln Glu Glu Asp Gly Ser Trp Asn Glu Glu
                645                 650                 655
Glu Phe Thr Gly Thr Gly Phe Pro Gly Tyr Gly Val Gly Gln Thr Ile
                660                 665                 670
```

```
Lys Leu Asp Asp Pro Ala Ile Ser Lys Arg Leu Met Gln Gly Ala Glu
        675                 680                 685

Leu Ser Arg Ala Phe Met Leu Arg Tyr Asp Leu Tyr Arg Gln Leu Phe
690                 695                 700

Pro Ile Ile Ala Leu Ser Arg Ala Ser Arg Leu Ile Lys Leu Gly Asn
705                 710                 715                 720

<210> SEQ ID NO 21
<211> LENGTH: 685
<212> TYPE: PRT
<213> ORGANISM: Artificial Sequence
<220> FEATURE:
<223> OTHER INFORMATION: GmoSHC variant

<400> SEQUENCE: 21

Met Ser Pro Ala Asp Ile Ser Thr Lys Ser Ser Phe Gln Arg Leu
1               5                   10                  15

Asp Asn Met Leu Pro Glu Ala Val Ser Ser Ala Cys Asp Trp Leu Ile
                20                  25                  30

Asp Gln Gln Lys Pro Asp Gly His Trp Val Gly Pro Leu Glu Ser Asn
        35                  40                  45

Ala Cys Met Glu Ala Glu Trp Cys Leu Ala Leu Trp Phe Leu Gly Gln
50                  55                  60

Glu Asp His Pro Leu Arg Pro Arg Leu Ala Gln Ala Leu Leu Glu Met
65                  70                  75                  80

Gln Arg Glu Asp Gly Ser Trp Gly Ile Tyr Val Gly Ala Asp His Gly
                85                  90                  95

Asp Ile Asn Thr Thr Val Glu Ala Tyr Ala Ala Leu Arg Ser Met Gly
            100                 105                 110

Tyr Ala Ala Asp Met Pro Ile Met Ala Lys Ser Ala Ala Trp Ile Gln
        115                 120                 125

Gln Lys Gly Gly Leu Arg Asn Val Arg Val Phe Thr Arg Tyr Trp Leu
    130                 135                 140

Ala Leu Ile Gly Glu Trp Pro Trp Asp Lys Thr Pro Asn Leu Pro Pro
145                 150                 155                 160

Glu Ile Ile Trp Leu Pro Asp Asn Phe Ile Phe Ser Ile Tyr Asn Phe
                165                 170                 175

Ala Gln Trp Ala Arg Ala Thr Ile Met Pro Leu Thr Ile Leu Ser Ala
            180                 185                 190

Arg Arg Pro Ser Arg Pro Leu Leu Pro Glu Asn Arg Leu Asp Gly Leu
        195                 200                 205

Phe Pro Glu Gly Arg Glu Asn Phe Asp Tyr Glu Leu Pro Val Lys Gly
    210                 215                 220

Glu Glu Asp Leu Trp Gly Arg Phe Phe Arg Ala Ala Asp Lys Gly Leu
225                 230                 235                 240

His Ser Leu Gln Ser Phe Pro Val Arg Arg Phe Val Pro Arg Glu Ala
                245                 250                 255

Ala Ile Arg His Val Ile Glu Trp Ile Ile Arg His Gln Asp Ala Asp
            260                 265                 270

Gly Gly Trp Gly Gly Ile Gln Pro Pro Trp Ile Tyr Gly Leu Met Ala
        275                 280                 285

Leu Ser Val Glu Gly Tyr Pro Leu His His Pro Val Leu Ala Lys Ala
    290                 295                 300

Met Asp Ala Leu Asn Asp Pro Gly Trp Arg Arg Asp Lys Gly Asp Ala
305                 310                 315                 320
```

-continued

Ser Trp Ile Gln Ala Ser Asn Ser Pro Val Trp Asp Thr Met Leu Ala
                325                 330                 335

Val Leu Ala Leu His Asp Ala Gly Glu Asp Arg Tyr Ser Pro Gln
            340                 345                 350

Met Asp Lys Ala Ile Gly Trp Leu Leu Asp Arg Gln Val Arg Val Lys
            355                 360                 365

Gly Asp Trp Ser Ile Lys Leu Pro Asp Thr Glu Pro Gly Gly Trp Ala
        370                 375                 380

Phe Glu Tyr Ala Asn Asp Lys Tyr Pro Asp Thr Asp Thr Ala Val
385                 390                 395                 400

Ala Leu Ile Ala Leu Ala Gly Cys Arg His Arg Pro Glu Trp Arg Glu
                405                 410                 415

Arg Asp Ile Glu Gly Ala Ile Ser Arg Gly Val Asn Trp Leu Leu Ala
            420                 425                 430

Met Gln Ser Ser Ser Gly Gly Trp Gly Ala Phe Asp Lys Asp Asn Asn
            435                 440                 445

Arg Ser Ile Leu Thr Lys Ile Pro Phe Cys Asp Phe Gly Glu Ala Leu
        450                 455                 460

Asp Pro Pro Ser Val Asp Val Thr Ala His Val Leu Glu Ala Phe Gly
465                 470                 475                 480

Leu Leu Gly Ile Ser Arg Asn His Pro Ser Val Gln Lys Ala Leu Ala
                485                 490                 495

Tyr Ile Arg Ser Glu Gln Glu Arg Asn Gly Ala Trp Phe Gly Arg Trp
            500                 505                 510

Gly Val Asn Tyr Val Tyr Gly Thr Gly Ala Val Leu Pro Ala Leu Ala
        515                 520                 525

Ala Ile Gly Glu Asp Met Thr Gln Pro Tyr Ile Val Arg Ala Cys Asp
        530                 535                 540

Trp Leu Met Ser Val Gln Gln Glu Asn Gly Gly Trp Gly Glu Ser Cys
545                 550                 555                 560

Ala Ser Tyr Met Asp Ile Asn Ala Val Gly His Gly Val Ala Thr Ala
                565                 570                 575

Ser Gln Thr Ala Trp Ala Leu Ile Gly Leu Leu Ala Ala Lys Arg Pro
            580                 585                 590

Lys Asp Arg Glu Ala Ile Ala Arg Gly Cys Gln Phe Leu Ile Glu Arg
        595                 600                 605

Gln Glu Asp Gly Ser Trp Thr Glu Glu Tyr Thr Gly Thr Gly Tyr
        610                 615                 620

Pro Gly Tyr Gly Val Gly Gln Ala Ile Lys Leu Asp Asp Pro Ser Leu
625                 630                 635                 640

Pro Asp Arg Leu Leu Gln Gly Ala Glu Leu Ser Arg Ala Phe Met Leu
            645                 650                 655

Arg Tyr Asp Leu Tyr Arg Gln Tyr Phe Pro Val Met Ala Leu Ser Arg
            660                 665                 670

Ala Arg Arg Met Met Lys Glu Asp Ala Ser Ala Ala
        675                 680                 685

<210> SEQ ID NO 22
<211> LENGTH: 1896
<212> TYPE: DNA
<213> ORGANISM: Artificial Sequence
<220> FEATURE:
<223> OTHER INFORMATION: SHC/HAC enzyme variant #90C7

<400> SEQUENCE: 22

```
atggctgagc agttggtgga agctccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc acattctcg atcgcgtcga tcgggatcgc      180
atggagaaga tccggcggta cctgttgcac gagcagcgcg aggacggcac gtgggccctg     240
tacccgggtg ggccgccgga cctcgacgcg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggaggtggc tggcgctggt gggagaatat     420
ccgtgggaga aggtgcccat ggtcccgccg gagatcatgt tcctcggcaa gcgcatgccg     480
ctcaacatct cgagtttgg ctcgtgggct cgggcgaccg tcgtggcgct ctcgattgtg      540
atgagccgcc agccggtgtt cccgctgccc gagcgggcgc gcgtgcccga gctgtacgag     600
accgacgtgc ctccgcgccg gcgcggtgcc aagggagggg gtgggtggat cttcgacgcg     660
ctcgaccggg tgctgcacgg gtatcagaag ctgtcggtgc acccgttccg ccgcgcggcc     720
gagatccgcg ccttggactg gttgctcgag cgccaggccg agacggcag ctggggcggg     780
attcagccgc cttggtttta cgcgctcatc gcgctcaaga ttctcgacat gacgcagcat     840
ccggcgttca tcaagggctg ggaaggtcta gagctgtacg gcgtggagct ggattacgga     900
ggatggatgt ttcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat ccgctggat tgtcggcatg cagagctcga acggcggttg gcgcgcctac    1260
gacgtcgaca cacgagcga tctcccgaac cacaccccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacggc ctgggcgctg    1680
atggcgctca tcgcgggcgg cagggcggag tccgaggccg cgccgcgcgg cgtgcaatac    1740
ctcgtggaga cgcagcgccc ggacggcggc tgggatgagc cgtactacac cggcacgggc    1800
ttcccagggg atttctacct cggctacacc atgtacagcc acgtgtttcc gacgctcgcg    1860
ctcggccgct acaagcaagc catcgagcgc aggtga                              1896
```

<210> SEQ ID NO 23
<211> LENGTH: 1896
<212> TYPE: DNA
<213> ORGANISM: Artificial Sequence
<220> FEATURE:
<223> OTHER INFORMATION: SHC/HAC enzyme variant #115A7

<400> SEQUENCE: 23

```
atggctgagc agttggtgga agctccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc acattctcg atcgcgtcga tcgggatcgc     180
atggagaaga tccggcggta cctgttgcac gagcagcgcg aggacggcac gtgggccctg     240
tacccgggtg ggccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggaggtggc tggcgctggt gggagaatat     420
ccgtgggaga aggtgcccat ggtcccgccg gagatcatgt tcctcggcaa gcgcatgccg     480
ctcaacatct cgagtttgg ctcgtgggct cggacgaccg tcgtggcgct ctcgattgtg     540
atgagccgcc agccggtgtt cccgctgccc gagcgggcgc gcgtgcccga gctgtacgag     600
accgacgtgc ctccgcgccg cgcggtgcc aaggagggg gtgggtggat cttcgacgcg     660
ctcgaccggg tgctgcacgg gtatcagaag ctgtcggtgc acccgttccg ccgcgcggcc     720
gagatccgcg ccttggactg gttgctcgag cgccaggccg gagacggcag ctggggcggg     780
attcagccgc cttggtttta cgcgctcatc gcgctcaaga ttctcgacaa gacgcagcat     840
ccggcgttca tcaagggctg ggaaggtcta agctgtacg gcgtggagct ggattacgga     900
ggatggatgt ttcaggcttc catctcgccg gtgtgggaca cgggcctcgc cgtgctcgcg     960
ctgcgcgctg cgggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat tccgctggat tgtcggcatg cagagctcga cggcggttg gggcgcctac    1260
gacgtcgaca cacgagcga tctcccgaac cacaccccgt tctgcgactt cggcgaagtg    1320
accgatccgc cgtcagagga cgtcaccgcc cacgtgctcg agtgtttcgg cagcttcggg    1380
tacgatacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgc cgtacgcggg taagggcgcg agcaccccgt cgcagacggc ctgggcgctg    1680
atggcgctca tcgcgggcgg cagggcggag tccgaggccg cgccgcgcg cgtgcaatac    1740
ctcgtggaga cgcagcgccc ggacggcggc tgggatgagc cgtactacac cggcacgggc    1800
ttcccagggg atttctacct cggctacacc atgtaccgcc acgtgtttcc gacgctcgcg    1860
ctcggccgct acaagcaagc catcgagcgc aggtga                              1896
```

<210> SEQ ID NO 24
<211> LENGTH: 631
<212> TYPE: PRT
<213> ORGANISM: Artificial Sequence
<220> FEATURE:
<223> OTHER INFORMATION: 215G2 SHC/HAC enzyme variant + L37Q mutation

<400> SEQUENCE: 24

```
Met Ala Glu Gln Leu Val Glu Ala Pro Ala Tyr Ala Arg Thr Leu Asp
1               5                   10                  15
```

```
Arg Ala Val Glu Tyr Leu Leu Ser Cys Gln Lys Asp Glu Gly Tyr Trp
            20                  25                  30

Trp Gly Pro Leu Gln Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
130                 135                 140

Val Pro Met Val Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
            165                 170                 175

Leu Ser Ile Val Met Ser Arg Gln Pro Val Phe Pro Leu Pro Glu Arg
        180                 185                 190

Ala Arg Val Pro Glu Leu Tyr Glu Thr Asp Val Pro Arg Arg Arg
        195                 200                 205

Gly Ala Lys Gly Gly Gly Trp Ile Phe Asp Ala Leu Asp Arg Val
        210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
            245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
        290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
            325                 330                 335

Gly Glu Trp Leu Leu Asp Arg Gln Ile Thr Val Pro Gly Asp Trp Ala
        340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
        370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
            405                 410                 415

Trp Gly Ala Tyr Asp Val Asp Asn Thr Ser Asp Leu Pro Asn His Thr
        420                 425                 430
```

```
Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
        450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 25
<211> LENGTH: 631
<212> TYPE: PRT
<213> ORGANISM: Artificial Sequence
<220> FEATURE:
<223> OTHER INFORMATION: 215G2 SHC/HAC enzyme variant + V174I mutation

<400> SEQUENCE: 25

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160
```

```
Leu Asn Ile Tyr Glu Phe Gly Ser Trp Ala Arg Ala Thr Ile Val Ala
                165                 170                 175
Leu Ser Ile Val Met Ser Arg Gln Pro Val Phe Pro Leu Pro Glu Arg
            180                 185                 190
Ala Arg Val Pro Glu Leu Tyr Glu Thr Asp Val Pro Pro Arg Arg Arg
        195                 200                 205
Gly Ala Lys Gly Gly Gly Trp Ile Phe Asp Ala Leu Asp Arg Val
    210                 215                 220
Leu His Gly Tyr Gln Lys Leu Ser Val His Pro Phe Arg Arg Ala Ala
225                 230                 235                 240
Glu Ile Arg Ala Leu Asp Trp Leu Leu Glu Arg Gln Ala Gly Asp Gly
                245                 250                 255
Ser Trp Gly Gly Ile Gln Pro Pro Trp Phe Tyr Ala Leu Ile Ala Leu
            260                 265                 270
Lys Ile Leu Asp Met Thr Gln His Pro Ala Phe Ile Lys Gly Trp Glu
        275                 280                 285
Gly Leu Glu Leu Tyr Gly Val Glu Leu Asp Tyr Gly Gly Trp Met Phe
    290                 295                 300
Gln Ala Ser Ile Ser Pro Val Trp Asp Thr Gly Leu Ala Val Leu Ala
305                 310                 315                 320
Leu Arg Ala Ala Gly Leu Pro Ala Asp His Asp Arg Leu Val Lys Ala
                325                 330                 335
Gly Glu Trp Leu Leu Asp Arg Gln Ile Thr Val Pro Gly Asp Trp Ala
            340                 345                 350
Val Lys Arg Pro Asn Leu Lys Pro Gly Gly Phe Ala Phe Gln Phe Asp
        355                 360                 365
Asn Val Tyr Tyr Pro Asp Val Asp Asp Thr Ala Val Val Trp Ala
    370                 375                 380
Leu Asn Thr Leu Arg Leu Pro Asp Glu Arg Arg Arg Asp Ala Met
385                 390                 395                 400
Thr Lys Gly Phe Arg Trp Ile Val Gly Met Gln Ser Ser Asn Gly Gly
                405                 410                 415
Trp Gly Ala Tyr Asp Val Asp Asn Thr Ser Asp Leu Pro Asn His Thr
            420                 425                 430
Pro Phe Cys Asp Phe Gly Glu Val Thr Asp Pro Pro Ser Glu Asp Val
        435                 440                 445
Thr Ala His Val Leu Glu Cys Phe Gly Ser Phe Gly Tyr Asp Asp Ala
    450                 455                 460
Trp Lys Val Ile Arg Arg Ala Val Glu Tyr Leu Lys Arg Glu Gln Lys
465                 470                 475                 480
Pro Asp Gly Ser Trp Phe Gly Arg Trp Gly Val Asn Tyr Leu Tyr Gly
                485                 490                 495
Thr Gly Ala Val Val Ser Ala Leu Lys Ala Val Gly Ile Asp Thr Arg
            500                 505                 510
Glu Pro Tyr Ile Gln Lys Ala Leu Asp Trp Val Glu Gln His Gln Asn
        515                 520                 525
Pro Asp Gly Gly Trp Gly Glu Asp Cys Arg Ser Tyr Glu Asp Pro Ala
    530                 535                 540
Tyr Ala Gly Lys Gly Ala Ser Thr Pro Ser Gln Thr Ala Trp Ala Leu
545                 550                 555                 560
Met Ala Leu Ile Ala Gly Gly Arg Ala Glu Ser Glu Ala Ala Arg Arg
                565                 570                 575
```

```
Gly Val Gln Tyr Leu Val Glu Thr Gln Arg Pro Asp Gly Gly Trp Asp
                580                 585                 590

Glu Pro Tyr Tyr Thr Gly Thr Gly Phe Pro Gly Asp Phe Tyr Leu Gly
                595                 600                 605

Tyr Thr Met Tyr Arg His Val Phe Pro Thr Leu Ala Leu Gly Arg Tyr
                610                 615                 620

Lys Gln Ala Ile Glu Arg Arg
625                 630

<210> SEQ ID NO 26
<211> LENGTH: 631
<212> TYPE: PRT
<213> ORGANISM: Artificial Sequence
<220> FEATURE:
<223> OTHER INFORMATION: 215G2 SHC/HAC enzyme variant + V174I + F601Y
      mutations

<400> SEQUENCE: 26

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
                35                  40                  45

Leu Cys His Ile Leu Asp Arg Val Asp Arg Asp Arg Met Glu Lys Ile
            50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
                100                 105                 110

Ala Leu Arg Phe Ile Gln Ser Gln Gly Gly Ile Glu Ser Ser Arg Val
                115                 120                 125

Phe Thr Arg Arg Trp Leu Ala Leu Val Gly Glu Tyr Pro Trp Glu Lys
                130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Ile Val Ala
                165                 170                 175

Leu Ser Ile Val Met Ser Arg Gln Pro Val Phe Pro Leu Pro Glu Arg
                180                 185                 190

Ala Arg Val Pro Glu Leu Tyr Glu Thr Asp Val Pro Pro Arg Arg Arg
                195                 200                 205

Gly Ala Lys Gly Gly Gly Gly Trp Ile Phe Asp Ala Leu Asp Arg Val
                210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
                260                 265                 270

Lys Ile Leu Asp Met Thr Gln His Pro Ala Phe Ile Lys Gly Trp Glu
                275                 280                 285
```

```
Gly Leu Glu Leu Tyr Gly Val Glu Leu Asp Tyr Gly Gly Trp Met Phe
            290                 295                 300
Gln Ala Ser Ile Ser Pro Val Trp Asp Thr Gly Leu Ala Val Leu Ala
305                 310                 315                 320
Leu Arg Ala Ala Gly Leu Pro Ala Asp His Asp Arg Leu Val Lys Ala
                325                 330                 335
Gly Glu Trp Leu Leu Asp Arg Gln Ile Thr Val Pro Gly Asp Trp Ala
            340                 345                 350
Val Lys Arg Pro Asn Leu Lys Pro Gly Gly Phe Ala Phe Gln Phe Asp
            355                 360                 365
Asn Val Tyr Tyr Pro Asp Val Asp Asp Thr Ala Val Val Trp Ala
            370                 375                 380
Leu Asn Thr Leu Arg Leu Pro Asp Glu Arg Arg Arg Asp Ala Met
385                 390                 395                 400
Thr Lys Gly Phe Arg Trp Ile Val Gly Met Gln Ser Ser Asn Gly Gly
                405                 410                 415
Trp Gly Ala Tyr Asp Val Asp Asn Thr Ser Asp Leu Pro Asn His Thr
            420                 425                 430
Pro Phe Cys Asp Phe Gly Glu Val Thr Asp Pro Pro Ser Glu Asp Val
            435                 440                 445
Thr Ala His Val Leu Glu Cys Phe Gly Ser Phe Gly Tyr Asp Asp Ala
            450                 455                 460
Trp Lys Val Ile Arg Arg Ala Val Glu Tyr Leu Lys Arg Glu Gln Lys
465                 470                 475                 480
Pro Asp Gly Ser Trp Phe Gly Arg Trp Gly Val Asn Tyr Leu Tyr Gly
            485                 490                 495
Thr Gly Ala Val Val Ser Ala Leu Lys Ala Val Gly Ile Asp Thr Arg
            500                 505                 510
Glu Pro Tyr Ile Gln Lys Ala Leu Asp Trp Val Glu Gln His Gln Asn
            515                 520                 525
Pro Asp Gly Gly Trp Gly Glu Asp Cys Arg Ser Tyr Glu Asp Pro Ala
            530                 535                 540
Tyr Ala Gly Lys Gly Ala Ser Thr Pro Ser Gln Thr Ala Trp Ala Leu
545                 550                 555                 560
Met Ala Leu Ile Ala Gly Gly Arg Ala Glu Ser Ala Ala Arg Arg
                565                 570                 575
Gly Val Gln Tyr Leu Val Glu Thr Gln Arg Pro Asp Gly Gly Trp Asp
            580                 585                 590
Glu Pro Tyr Tyr Thr Gly Thr Gly Tyr Pro Gly Asp Phe Tyr Leu Gly
            595                 600                 605
Tyr Thr Met Tyr Arg His Val Phe Pro Thr Leu Ala Leu Gly Arg Tyr
            610                 615                 620
Lys Gln Ala Ile Glu Arg Arg
625                 630

<210> SEQ ID NO 27
<211> LENGTH: 631
<212> TYPE: PRT
<213> ORGANISM: Artificial Sequence
<220> FEATURE:
<223> OTHER INFORMATION: 215G2 SHC/HAC enzyme variant + L37Q + V174I +
      F601Y mutations
```

<400> SEQUENCE: 27

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Gln Ser Asn Val Thr Met Glu Ala Glu Tyr Val Leu
        35                  40                  45

Leu Cys His Ile Leu Asp Arg Val Asp Arg Asp Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
            115                 120                 125

Phe Thr Arg Arg Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Ile Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
            195                 200                 205

Gly Ala Lys Gly Gly Gly Gly Trp Ile Phe Asp Ala Leu Asp Arg Val
            210                 215                 220

Leu His Gly Tyr Gln Lys Leu Ser Val His Pro Phe Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
            290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Val Trp Ala
            370                 375                 380

Leu Asn Thr Leu Arg Leu Pro Asp Glu Arg Arg Arg Arg Asp Ala Met
385                 390                 395                 400

```
Thr Lys Gly Phe Arg Trp Ile Val Gly Met Gln Ser Ser Asn Gly Gly
            405                 410                 415

Trp Gly Ala Tyr Asp Val Asp Asn Thr Ser Asp Leu Pro Asn His Thr
        420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
        530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Tyr Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 28
<211> LENGTH: 625
<212> TYPE: PRT
<213> ORGANISM: Artificial sequence
<220> FEATURE:
<223> OTHER INFORMATION: Bacillus megaterium

<400> SEQUENCE: 28

Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125
```

```
Arg Trp Met Leu Ser Val Asn Gly Leu Tyr Glu Trp Pro Lys Leu Phe
        130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                    165                 170                 175

Val Ala Gly Asn Lys Lys Phe Ser Leu Thr Ser Arg His Thr Pro Ser
                180                 185                 190

Leu Ser His Leu Asp Val Arg Glu Gln Lys Gln Ser Glu Glu Thr
            195                 200                 205

Thr Gln Glu Ser Arg Ala Ser Ile Phe Leu Val Asp His Leu Lys Gln
210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
                260                 265                 270

Tyr Lys Lys Asp Ser Phe Val Ile Gln Lys Ala Ile Asp Gly Ile Cys
            275                 280                 285

Ser Leu Leu Ser Thr Cys Ser Gly His Val His Val Glu Asn Ser Thr
290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
                355                 360                 365

Pro Asp Leu Asp Asp Thr Ser Ala Ala Ile Arg Ala Leu Ser Arg Arg
370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
                420                 425                 430

Lys Asp Ala Ala Thr Asp Pro Ala Thr Ala Asp Leu Thr Gly Arg Val
            435                 440                 445

Leu Glu Cys Leu Gly Asn Phe Ala Gly Met Asn Lys Ser His Pro Ser
450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
                500                 505                 510

Ile Ile Lys Ala Ile Asn Trp Leu Lys Ser Ile Gln Gln Glu Asp Gly
            515                 520                 525

Gly Phe Gly Glu Ser Cys Tyr Ser Ala Ser Leu Lys Lys Tyr Val Pro
530                 535                 540
```

-continued

```
Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
            565                 570                 575

Phe Leu Leu Asn Pro Asn Leu Thr Glu Gln Gln Thr His Tyr Pro Thr
        580                 585                 590

Gly Ile Gly Leu Pro Gly Gln Phe Tyr Ile Gln Tyr His Ser Tyr Asn
    595                 600                 605

Asp Ile Phe Pro Leu Leu Ala Leu Ala His Tyr Ala Lys Lys His Ser
610                 615                 620

Ser
625

<210> SEQ ID NO 29
<211> LENGTH: 691
<212> TYPE: PRT
<213> ORGANISM: Artificial sequence
<220> FEATURE:
<223> OTHER INFORMATION: Streptomyces albolongus

<400> SEQUENCE: 29

Val Thr Ala Thr Ala Asp Gly Arg Leu Asp Pro Glu Tyr Asp Pro Glu
1               5                   10                  15

Pro Ala Ala Val Gly Glu Arg Pro Val Thr Asp Arg Leu Thr Gly
            20                  25                  30

Arg Gln Thr Thr Val Ala Thr Ala Pro Ala Pro Gly Ala Gly Arg Arg
            35                  40                  45

Gln Ala Glu Gly Pro Glu Arg Ser Gly Pro Leu Asp Pro Ala Gln Ala
    50                  55                  60

Leu Ala Arg Ala Thr Ala Glu Leu Leu Ser Arg Gln Ser Pro Asp Gly
65                  70                  75                  80

Trp Trp Lys Gly Asp Leu Glu Thr Asn Val Thr Met Asp Ala Glu Asp
                85                  90                  95

Leu Leu Leu Arg Gln Phe Leu Gly Ile Arg Glu Pro Glu Gln Thr Ala
            100                 105                 110

Ala Thr Ala Ala Trp Ile Arg Ser Gln Gln Arg Glu Asp Gly Thr Trp
        115                 120                 125

Ser Thr Phe Tyr Gly Gly Pro Pro Glu Leu Ser Thr Thr Val Glu Ala
    130                 135                 140

Tyr Val Ala Leu Lys Leu Ala Gly Asp Asp Pro Gly Ala Pro His Met
145                 150                 155                 160

Ala Ala Ala Ala Arg Tyr Val Arg Glu Arg Gly Gly Ile Ala Ala Ser
                165                 170                 175

Arg Val Phe Thr Arg Ile Trp Leu Ala Leu Phe Gly Trp Trp Pro Trp
            180                 185                 190

Glu Arg Leu Pro Glu Met Pro Pro Glu Ile Ile Phe Leu Pro Arg Trp
        195                 200                 205

Leu Pro Leu Asn Ile Tyr Ala Phe Gly Cys Trp Ala Arg Gln Thr Ile
    210                 215                 220

Val Pro Leu Thr Val Ser Ala His Arg Pro Val Arg Pro Ala Pro
225                 230                 235                 240

Phe Asp Leu Thr Glu Leu His Thr Asp Pro Ala Asp Pro Tyr Pro Leu
                245                 250                 255

Arg Pro Leu Ala Pro Pro Thr Gly Trp Asp Gly Val Phe Glu Arg Leu
            260                 265                 270
```

```
Asp Leu Val Leu His Ala Tyr His Lys Arg Ala Leu Arg Pro Leu Arg
            275                 280                 285

Arg Ala Ala Leu Ala Gln Ala Gly Arg Trp Ile Val Glu Arg Gln Glu
        290                 295                 300

Ala Asp Gly Cys Trp Gly Gly Ile Gln Pro Ala Val Tyr Ser Leu
305                 310                 315                 320

Ile Ala Leu His Leu Leu Gly Tyr Asp Leu Glu His Pro Val Met Arg
            325                 330                 335

Ala Gly Leu Ala Ala Phe Asp Arg Phe Thr Val His Thr Glu Asp Gly
            340                 345                 350

Arg Arg Trp Leu Glu Ala Cys Gln Ser Pro Val Trp Asp Thr Cys Leu
            355                 360                 365

Ala Thr Ile Ala Leu Arg Asp Ala Gly Leu Pro Ala Asp His Pro Ala
            370                 375                 380

Leu Val Ser Ala Ala Asp Trp Met Leu Ala Glu Glu Ile Arg Arg Pro
385                 390                 395                 400

Gly Asp Trp Ser Val Gln Arg Pro Arg Leu Ala Pro Gly Gly Trp Ala
            405                 410                 415

Phe Glu Phe Glu Asn Asp Asn Tyr Pro Asp Ile Asp Asp Thr Ala Glu
            420                 425                 430

Val Val Leu Ala Leu Lys Arg Val Ala His Pro Asp Arg Ala Arg Ile
            435                 440                 445

Asp Gly Ala Val Arg Arg Gly Val Glu Trp Asn Leu Gly Met Gln Ser
            450                 455                 460

Arg Asn Gly Ala Trp Gly Ala Phe Asp Val Asp Asn Thr Ser Thr Leu
465                 470                 475                 480

Pro Asn Lys Leu Pro Phe Cys Asp Phe Gly Glu Val Val Asp Pro Pro
            485                 490                 495

Ser Ala Asp Val Thr Ala His Val Val Glu Met Leu Ala Glu Thr Gly
            500                 505                 510

Leu Ala Gly Asp Arg Arg Thr Arg Arg Gly Ile Asp Trp Leu Leu Lys
            515                 520                 525

Asn Gln Glu Pro Asp Gly Ser Trp Phe Gly Arg Trp Gly Thr Asn Tyr
            530                 535                 540

Ile Tyr Gly Thr Gly Ser Val Leu Pro Ala Leu Val Ala Ala Gly Ile
545                 550                 555                 560

Pro Gly Ser His Pro Ala Val Arg Arg Ala Val Asp Trp Leu Ala Asp
            565                 570                 575

Arg Gln Asn Pro Asp Gly Gly Trp Gly Glu Asp Met Arg Ser Tyr Glu
            580                 585                 590

Asp Pro Val Arg Trp Ser Gly Arg Gly Asp Ser Thr Ala Ser Gln Thr
            595                 600                 605

Ala Trp Ala Leu Met Ala Leu Leu Ala Ala Gly Glu Gly Pro Asp Gly
            610                 615                 620

Ala Arg Ser Glu Val Val Glu Arg Gly Val Gln Trp Leu Cys Arg Thr
625                 630                 635                 640

Gln Leu Pro Ser Gly Ser Trp Asp Glu Pro Gln Phe Thr Gly Thr Gly
            645                 650                 655

Phe Pro Trp Asp Phe Ser Ile Asn Tyr His Leu Tyr Arg Leu Val Phe
            660                 665                 670
```

```
Pro Val Thr Ala Leu Gly Arg Tyr Leu His Gly Ser Pro Leu Thr Gly
        675                 680                 685

Gly Gly Ala
    690

<210> SEQ ID NO 30
<211> LENGTH: 656
<212> TYPE: PRT
<213> ORGANISM: Artificial sequence
<220> FEATURE:
<223> OTHER INFORMATION: Acetobacter pasteurianus

<400> SEQUENCE: 30

Met Ala Ala Asp Gly Ser Ala Leu Ser Glu Ser Arg Leu Ser Ser Glu
1               5                   10                  15

Ala Leu Asp Arg Ala Val Leu Ser Ala His Thr Ala Leu Ser Gln Ala
            20                  25                  30

Gln Gln Asp Asp Gly His Trp Val Tyr Glu Leu Glu Ala Asp Ala Thr
        35                  40                  45

Ile Pro Ala Glu Tyr Ile Leu Leu Glu His Phe Met Asp Arg Ile Asp
    50                  55                  60

Asp Ala Leu Glu Gln Lys Ile Ala Ile Tyr Leu Arg Arg Ile Gln Ser
65                  70                  75                  80

Glu Glu His Gly Gly Trp Pro Leu Tyr His Asn Gly Lys Phe Asp Leu
                85                  90                  95

Ser Ala Thr Val Lys Ala Tyr Phe Ala Leu Lys Ala Val Gly Asp Asp
            100                 105                 110

Ile Asn Ala Pro His Met Gln Arg Ala Arg Glu Ala Ile Leu Asp His
        115                 120                 125

Gly Gly Ala Glu Arg Ser Asn Val Phe Thr Arg Ser Gln Leu Ala Leu
    130                 135                 140

Phe Gly Glu Val Pro Trp Arg Ala Thr Pro Val Met Pro Val Glu Leu
145                 150                 155                 160

Met Leu Leu Pro Ala Lys Ala Phe Phe Ser Val Trp Asn Met Ser Tyr
                165                 170                 175

Trp Ser Arg Thr Val Ile Ala Pro Leu Leu Val Leu Ala Ala Leu Arg
            180                 185                 190

Pro Val Ala Ala Asn Pro Arg Gln Val His Val Arg Glu Leu Phe Val
        195                 200                 205

Thr Pro Pro Glu Lys Val Gln Asp Trp Ile Arg Gly Pro Tyr Arg Ser
    210                 215                 220

Ala Trp Gly Tyr Val Phe Lys Gly Leu Asp Ser Val Leu Arg Pro Val
225                 230                 235                 240

Val Pro Phe Ile Pro Glu Lys Thr His Lys Lys Ala Ile Gln Ala Ala
                245                 250                 255

Leu Asp Phe Ile Glu Pro Arg Leu Asn Gly Lys Asp Gly Leu Gly Ala
            260                 265                 270

Ile Tyr Pro Ala Met Ala Asn Val Val Met Met Tyr Arg Ala Met Gly
        275                 280                 285

Val Pro Asp Glu Asp Pro Arg Ala Lys Thr Ala Trp Glu Ala Val Gln
    290                 295                 300

Ala Leu Ile Val Glu Lys Asp Asp Glu Ala Tyr Cys Gln Pro Cys Val
305                 310                 315                 320

Ser Pro Ile Trp Asp Thr Gly Leu Ser Gly His Ala Met Ile Glu Ala
                325                 330                 335
```

-continued

```
Ala Ser Gly Pro Asn Gly Ile Ala Pro Glu Lys Thr Val Ala Glu Leu
            340             345             350

Lys Lys Ala Ser Ala Trp Leu Arg Ser Lys Gln Ile Leu Asn Val Lys
        355             360             365

Gly Asp Trp Ala Val Arg Asn Pro Asn Leu Ala Pro Gly Gly Trp Ala
    370             375             380

Phe Gln Tyr Gly Asn Asp Tyr Tyr Pro Asp Val Asp Thr Ala Val
385             390             395             400

Val Gly Met Leu Leu His Arg Glu Gly Asp Pro Thr Asn Ala Glu Ala
            405             410             415

Ile Glu Arg Ala Arg Thr Trp Ile Val Gly Met Gln Ser Thr Asp Gly
        420             425             430

Gly Trp Gly Ala Phe Asp Ile Asp Asn Asn Lys Asp Val Leu Asn His
        435             440             445

Ile Pro Phe Ala Asp His Gly Ala Leu Leu Asp Pro Pro Thr Ala Asp
    450             455             460

Val Thr Ala Arg Cys Ile Ser Phe Leu Ala Gln Leu Arg Asn Pro Glu
465             470             475             480

Asp Glu Pro Val Ile Gln Arg Gly Leu Glu Tyr Leu Arg Lys Glu Gln
            485             490             495

Glu Lys Asp Gly Ser Trp Phe Gly Arg Trp Gly Thr Asn Tyr Ile Tyr
            500             505             510

Gly Thr Trp Ser Ala Leu Cys Ala Leu Asn Ala Ala Gly Val Ser His
            515             520             525

Asp Asp Pro Ala Val Val Lys Ala Val Glu Trp Leu Arg Ser Val Gln
    530             535             540

Arg Ala Asp Gly Gly Trp Gly Glu Gly Cys Glu Ser Tyr Glu Gly Gly
545             550             555             560

Pro His Gly Thr Tyr Gly Glu Ser Leu Pro Ser Gln Thr Ala Trp Ala
            565             570             575

Val Leu Gly Leu Met Ala Ala Gly Arg Arg Asp Asp Pro Ala Val Thr
            580             585             590

Arg Gly Ile Ala Trp Leu Ala Asp Gln Gln Asp Ala Asn Gly Glu Trp
        595             600             605

His Glu Asp Pro Tyr Asn Ala Val Gly Phe Pro Lys Val Phe Tyr Leu
    610             615             620

Arg Tyr His Gly Tyr Lys Gln Phe Phe Pro Leu Met Ala Leu Ala Arg
625             630             635             640

Tyr Arg Asn Leu Glu Ser Ser Asn Thr Arg Arg Val Ser Phe Gly Phe
            645             650             655
```

SQUALENE HOPENE CYCLASE (SHC) VARIANTS

CROSS REFERENCE TO RELATED APPLICATIONS

This application is a national stage application of International Application No. PCT/EP2020/084491, filed 3 Dec. 2020, which claims priority from Great Britain Patent Application No. 1917688.2, filed 4 Dec. 2019, both of which applications are incorporated herein by reference.

Shc Enzymes and Enzyme Variants

TECHNICAL FIELD

The present invention relates generally to SHC/HAC enzymes and variants thereof. The present invention further relates to the various uses of the SHC/HAC enzymes and variants thereof, for example to enzymatically convert (3E, 7E)-homofarnesol (EEH) to (−)-Ambrox or to enzymatically convert E,E-bishomofarnesol (BisEEH) to Ambra oxide. The present invention also relates to the products of the enzymatic reactions, for example the (−)-Ambrox or Ambra oxide made using the SHC/HAC enzymes and variants thereof, and the various uses of said products.

BACKGROUND

Squalene Hopene Cyclases (SHCs) are membrane-bound enzymes which act as biocatalysts for the cyclisation of the linear triterpenoid squalene to hopene and hopanol.

A number of wild-type and variant SHC enzymes from a variety of bacteria have been demonstrated to be useful to convert (3E,7E)-homofarnesol to (−)-Ambrox (see, for example, WO 2016/170099; WO 2018/157021; Neumann & Simon 1986, Biol Chem Hoppe-Seyler 367, 723-729; JP2009060799; Seckler & Poralla 1986, Biochem Biophys Act 356-363; Ochs et al 1990, J Bacteriol 174, 298-302; WO 2010/139719; U.S. Pat. No. 8,759,043; WO 2012/066059; Seitz et al 2012, J Molecular Catalysis B: Enzymatic 84, 72-77; and Seitz 2012 PhD thesis, the contents of which are incorporated herein by reference). It is desirable to provide new and improved methods for making (−)-Ambrox, for example using new SHC enzymes or enzyme variants. It is also desirable to provide new and improved methods for cyclizing other substrates, for example to form compounds useful in or as fragrances.

SUMMARY

In accordance with a first aspect of the present invention there is provided a process for preparing (−)-Ambrox or a mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a SHC/HAC enzyme variant,
wherein the SHC/HAC enzyme variant has an amino acid sequence having at least about 70.0% identity to SEQ ID NO: 1,
wherein the SHC/HAC enzyme variant amino acid sequence has amino acid alterations relative to SEQ ID NO: 1 at positions corresponding to positions 132, 224 and 432 of SEQ ID NO: 1 which are M132R, A224V and I432T respectively, and
wherein the SHC/HAC enzyme variant amino acid sequence has amino acid alterations relative to SEQ ID NO: 1 at a position corresponding to position 557 of SEQ ID NO: 1 and at least one position corresponding to position 81, 431 or 613 of SEQ ID NO: 1.

In accordance with a second aspect of the present invention there is provided (−)-Ambrox obtained by or obtainable by the process of the first aspect of the present invention, including any embodiment thereof.

In accordance with a third aspect of the present invention there is provided the use of the (−)-Ambrox of the second aspect of the present invention, including any embodiment thereof, as part of a fragrance or a cosmetic or a consumer product.

In accordance with a fourth aspect of the present invention there is provided a fragrance or a cosmetic or a consumer product comprising (−)-Ambrox of the second aspect of the present invention, including any embodiment thereof.

In accordance with a fifth aspect of the present invention there is provided a SHC/HAC enzyme variant having an amino acid sequence having at least about 70.0% identity to SEQ ID NO: 1,
wherein the SHC/HAC enzyme variant amino acid sequence has amino acid alterations relative to SEQ ID NO: 1 at positions corresponding to positions 132, 224, and 432 of SEQ ID NO: 1 which are M132R, A224V and I432T respectively, and
wherein the SHC/HAC enzyme variant amino acid sequence further has amino acid alterations relative to SEQ ID NO: 1 at a position corresponding to position 557 of SEQ ID NO: 1 and at least one position corresponding to position 81, 431 or 613 of SEQ ID NO: 1.

In accordance with a sixth aspect of the present invention there is provided a nucleic acid sequence encoding the SHC/HAC enzyme variant of the fifth aspect of the present invention, including any embodiment thereof.

In accordance with a seventh aspect of the present invention there is provided a construct comprising the nucleic acid sequence of the sixth aspect of the present invention, including any embodiment thereof.

In accordance with an eighth aspect of the present invention there is provided a vector comprising the construct of the seventh aspect of the present invention, including any embodiment thereof.

In accordance with a ninth aspect of the present invention there is provided a recombinant host cell comprising the nucleic acid sequence of the sixth aspect of the present invention, the construct of the seventh aspect of the present invention, or the vector of the eighth aspect of the present invention, including any embodiment thereof.

In accordance with a tenth aspect of the present invention there is provided a process for preparing (−)-Ambrox or a mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a SHC/HAC enzyme variant, wherein the SHC/HAC enzyme variant has an amino acid sequence having at least about 70.0% identity to a wild-type SHC/HAC enzyme amino acid sequence, and wherein the SHC/HAC enzyme variant amino acid sequence has one or more amino acid alterations relative to the wild-type SHC/HAC enzyme at a position selected from positions corresponding to positions 557, 81, 431 and 613 of SEQ ID NO: 1.

In accordance with an eleventh aspect of the present invention there is provided a SHC/HAC enzyme variant, wherein the SHC/HAC enzyme variant has an amino acid sequence having at least about 70.0% identity to a wild-type SHC/HAC enzyme amino acid sequence, and wherein the SHC/HAC enzyme variant amino acid sequence has one or more amino acid alterations relative to the wild-type SHC/HAC enzyme at a position selected from positions corresponding to positions 557, 81, 431 and 613 of SEQ ID NO: 1.

In accordance with a twelfth aspect of the present invention there is provided a process for preparing (−)-Ambrox or a mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a SHC/HAC enzyme or SHC/HAC enzyme variant, wherein the SHC/HAC enzyme or SHC/HAC enzyme variant has an amino acid sequence having at least about 70.0% identity to a wild-type SHC/HAC enzyme amino acid sequence.

In accordance with a thirteenth aspect of the present invention there is provided a SHC/HAC enzyme or SHC/HAC enzyme variant, wherein the SHC/HAC enzyme or SHC/HAC enzyme variant has an amino acid sequence having at least about 70.0% identity to a wild-type SHC/HAC enzyme amino acid sequence.

In accordance with a fourteenth aspect of the present invention there is provided a process for preparing Ambra oxide, the process comprising enzymatically converting E,E-Bishomofarnesol or a mixture of isomers of bishomofarnesol comprising E,E-Bishomofarnesol to Ambra oxide or a mixture comprising Ambra oxide using a SHC/HAC enzyme or SHC/HAC enzyme variant. The SHC/HAC enzyme or SHC/HAC enzyme variant may, for example, be in accordance with any aspect of the present invention.

In accordance with a fifteenth aspect of the present invention there is provided Ambra oxide obtained by or obtainable by the process of the fourteenth aspect of the present invention, including any embodiment thereof.

In accordance with a sixteenth aspect of the present invention there is provided the use of the Ambra oxide of the fifteenth aspect of the present invention, including any embodiment thereof, as part of a fragrance or a cosmetic or a consumer product.

In accordance with a seventeenth aspect of the present invention there is provided a fragrance or a cosmetic or a consumer product comprising Ambra oxide of the fifteenth aspect of the present invention, including any embodiment thereof.

In certain embodiments of any aspect of the present invention the SHC/HAC enzyme variant has an amino acid sequence selected from SEQ ID NO: 2, SEQ ID NO: 3, SEQ ID NO: 4, SEQ ID NO: 5, SEQ ID NO: 17, SEQ ID NO: 18, SEQ ID NO: 24, SEQ ID NO: 25, SEQ ID NO: 26, SEQ ID NO: 27, SEQ ID NO: 28, SEQ ID NO: 29 and/or SEQ ID NO: 30.

In certain embodiments of any aspect of the present invention the SHC/HAC enzyme variant is encoded by a nucleic acid having a sequence selected from SEQ ID NO: 6, SEQ ID NO: 7, SEQ ID NO: 8, SEQ ID NO: 9, SEQ ID NO: 22 and SEQ ID NO: 23. Certain embodiments of the present invention may provide one or more of the following advantages:

improved EEH conversion rate, particularly in the first 12 hours or the first 6 hours;
cyclization of new substrates and/or identification of new products;
improved productivity (g/l/hour or g/l/hour/g biocatalyst);
industrial scale process for preparing end product such as (−)-Ambrox and Ambra oxide and/or isomeric mixtures thereof;
improved selectivity for EEH over other homofarnesol isomers.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

BRIEF DESCRIPTION OF THE FIGURES

Figure 7:
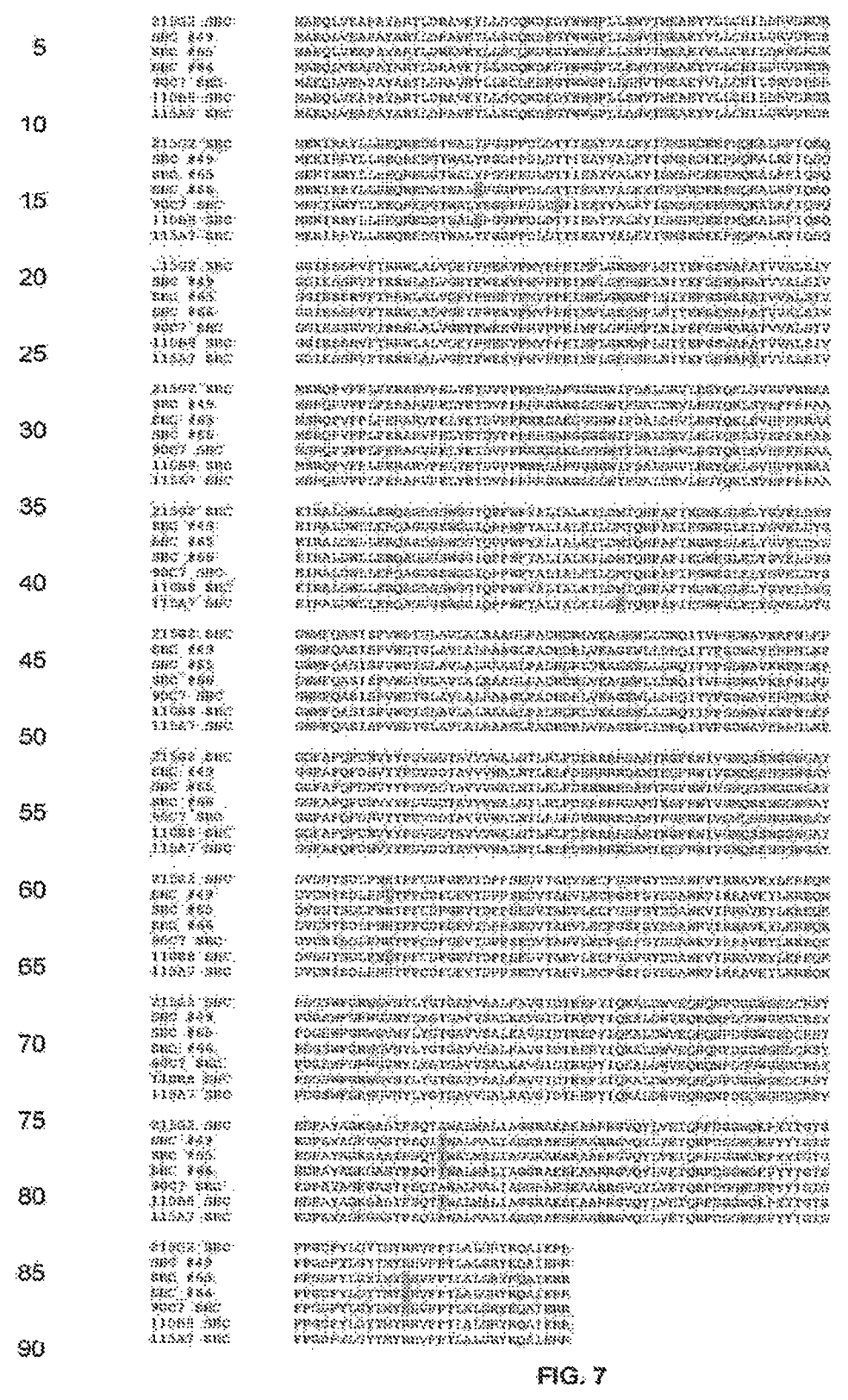

FIG. 7 shows an amino acid sequence alignment between 215G2 SHC/HAC (SEQ ID NO: 10) and SHC/HAC enzyme variants #49 (SEQ ID NO: 2), #65 (SEQ ID NO: 3), #66 (SEQ ID NO: 4), #90C7 (SEQ ID NO: 17), #110B8 (SEQ ID NO: 5) and #115A7 (SEQ ID NO: 18).

FIG. 8 shows an amino acid sequence alignment between 215G2 (SEQ ID NO: 10) and SHC/HAC enzyme variants derived from 215G2 with one of more of the substitutions V174I, F601Y and L37Q.

FIGS. 9A and 9B show an amino acid sequence alignment using CLUSTAL O (1.2.4) between wild-type AacSHC (SEQ ID NO: 1) and wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13) and wild-type GmoSHC (SEQ ID NO: 14). Amino acid positions 81, 90, 132, 224, 172, 277, 431, 432, 557 and 613 in wild-type AacSHC are highlighted with a white letter on a black background.

FIGS. 9C and 9D show an amino acid sequence alignment using CLUSTAL O (1.2.4) between wild-type AacSHC (SEQ ID NO: 1) and wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13), wild-type GmoSHC (SEQ ID NO: 14), wild-type Bme SHC (SEQ ID NO; 28), wild-type SalSHC (SEQ ID NO: 29) and wild-type ApaSHCA (SEQ ID NO: 30), Amino acid positions 81, 90, 132, 224, 172, 277, 431, 432, 557 and 613 in wild-type AacSHC are highlighted with a white letter on a black background.

SUMMARY OF THE SEQUENCES

Figure 1:
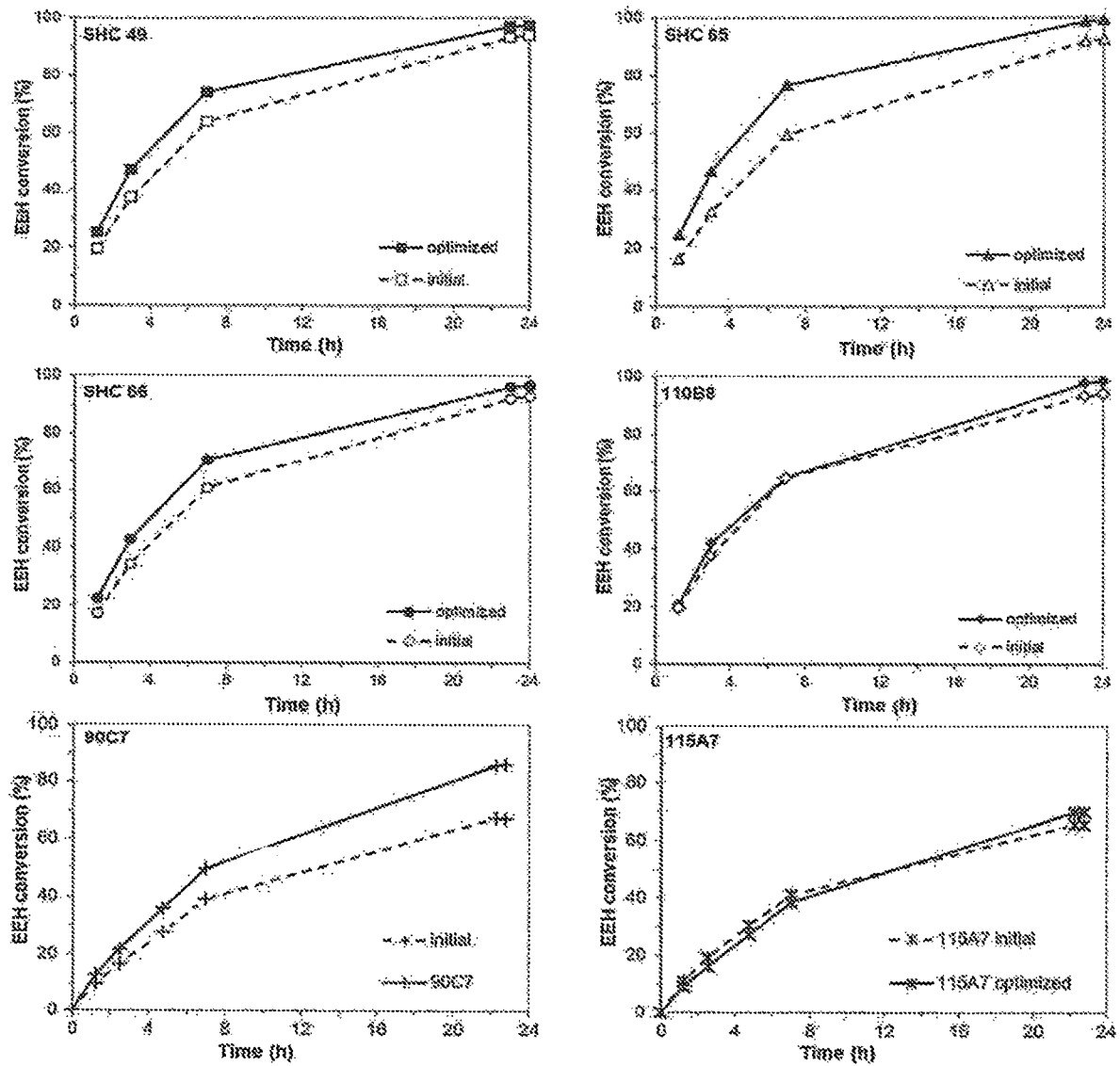
FIG. 1 shows the relative activities of SHC variants under initial and optimized reaction conditions. Reactions were run at 4 g/l EEH and biocatalyst loaded to an $OD_{650nm}$ of 10.0, either at initial conditions (35° C., pH 5.4, 0.070% SDS), or at T, pH and [SDS] set to conditions defined as optimal for each of the variants (optimised conditions).

SEQ ID NO: 1 is the wild-type *Alicyclobacillus acidocaldarius* (Aac) SHC amino acid sequence.

SEQ ID NO: 2 corresponds to SEQ ID NO: 1 with the substitutions M132R, A224V, I432T, A557T and H431L and may be referred to as SHC/HAC enzyme variant #49 herein.

SEQ ID NO: 3 corresponds to SEQ ID NO: 1 with the substitutions M132R, A224V, I432T, A557T and R613S and may be referred to as SHC/HAC enzyme variant #65 herein.

SEQ ID NO: 4 corresponds to SEQ ID NO: 1 with the substitutions M132R, A224V, I432T, Y81H, A557T and R613S and may be referred to as SHC/HAC enzyme variant #66 herein.

SEQ ID NO: 5 corresponds to SEQ ID NO: 1 with the substitutions M132R, A224V, I432T, Y81H, H431L and A557T and may be referred to as SHC/HAC enzyme variant #110B8 herein.

SEQ ID NO: 6 is the nucleic acid sequence encoding the polypeptide of SEQ ID NO: 2 (SHC/HAC enzyme variant #49).

SEQ ID NO: 7 is the nucleic acid sequence encoding the polypeptide of SEQ ID NO: 3 (SHC/HAC enzyme variant #65).

SEQ ID NO: 8 is the nucleic acid sequence encoding the polypeptide of SEQ ID NO: 4 (SHC/HAC enzyme variant #66).

SEQ ID NO: 9 is the nucleic acid sequence encoding the polypeptide of SEQ ID NO: 5 (SHC/HAC enzyme variant #110B8).

SEQ ID NO: 10 may be referred to as 215G2 and corresponds to the wild-type AacSHC amino acid sequence with the mutations M132R, A224V and I432T.

SEQ ID NO: 11 is the wild-type amino acid sequence of ZmoSHC1.

SEQ ID NO: 12 is the wild-type amino acid sequence of ZmoSHC2.

SEQ ID NO: 13 is the wild-type amino acid sequence of BjpSHC/BjaSHC.

SEQ ID NO: 14 is the wild-type amino acid sequence of GmoSHC.

SEQ ID NO: 15 is the nucleotide sequence encoding the wild-type AacSHC.

SEQ ID NO: 16 is the nucleotide sequence encoding 215G2 SHC.

SEQ ID NO: 17 corresponds to SEQ ID NO: 1 with the substitutions M132R, A224V, I432T, T90A and R613S and may be referred to as SHC/HAC enzyme variant #90C7 herein.

SEQ ID NO: 18 corresponds to SEQ ID NO: 1 with the substitutions M132R, A224V, I432T, A172T and M277K and may be referred to as SHC/HAC enzyme variant #115A7 herein.

SEQ ID NO: 19 is the wild-type amino acid sequence of TelSHC.

SEQ ID NO: 20 is the wild-type amino acid sequence of ApaSHC1.

SEQ ID NO: 21 is a GmoSHC variant.

SEQ ID NO: 22 is the nucleotide sequence encoding the polypeptide of SEQ ID NO: 17 (SHC/HAC enzyme variant #90C7).

SEQ ID NO: 23 is the nucleotide sequence encoding the polypeptide of SEQ ID NO: 18 (SHC/HAC enzyme variant #115A7).

SEQ ID NO: 24 is the amino acid sequence of the SHC/HAC variant 215G2 SHC with the additional mutation L37Q.

SEQ ID NO: 25 is the amino acid sequence of the SHC/HAC variant 215G2 SHC with the additional mutation V174I.

SEQ ID NO: 26 is the amino acid sequence of the SHC/HAC variant 215G2 SHC with the additional mutations V174I and F601Y.

SEQ ID NO: 27 is the amino acid sequence of the SHC/HAC variant 215G2 SHC with the additional mutations L37Q, V174I and F601Y.

SEQ ID NO: 28 is the wild-type amino acid sequence of BmeSHC.

SEQ ID NO: 29 is the wild-type amino acid sequence of SalSHC.

SEQ ID NO: 30 is the wild-type amino acid sequence of ApaSHCA.

DETAILED DESCRIPTION

SHC/HAC Enzymes and Variants Thereof

As used herein, the term "SHC enzyme" means a wild-type (WT) Squalene Hopene Cyclase enzyme that is naturally occurring in, for example, a thermophilic bacterium such as *Alicyclobacillus acidocaldarius*. SHCs that act in the cyclisation of homofarnesol to Ambrox may also be referred to as Homofarnesol Ambrox Cyclase (HAC) enzymes. Therefore, the term "SHC/HAC enzyme" may be used herein.

As used herein, the term "variant" is to be understood as a polypeptide which differs in comparison to the polypeptide from which it is derived by one or more changes in the amino acid sequence. The polypeptide from which a variant is derived is also known as the parent or reference polypeptide. Typically a variant is constructed artificially, preferably by gene-technological means. Typically, the polypeptide from which the variant is derived is a wild-type protein or wild-type protein domain. However, the variants usable in the present disclosure may also be derived from homologs, orthologs, or paralogs of the parent polypeptide or from artificially constructed variants, provided that the variant exhibits at least one biological activity of the parent polypeptide. The changes in the amino acid sequence may be amino acid exchanges (substitutions), insertions, deletions, N-terminal truncations, or C-terminal truncations, or any combination of these changes, which may occur at one or several sites.

As used herein, the term "SHC/HAC enzyme variant" means an enzyme that is derived from a wild-type SHC enzyme but has one or more amino acid alterations compared to the wild-type SHC enzyme and is therefore not naturally occurring in a prokaryote. The one or more amino acid alterations may, for example, modify (e.g. increase) the enzymatic activity for a substrate (e.g. EEH).

Assays for determining and quantifying SHC/HAC enzyme and/or SHC/HAC enzyme variant activity are described herein and are known in the art. By way of example, SHC/HAC enzyme and/or SHC/HAC enzyme variant activity can be determined by incubating purified SHC/HAC enzyme or enzyme variant or extracts from host cells or a complete recombinant host organism that has produced the SHC/HAC enzyme or enzyme variant with an appropriate substrate under appropriate conditions and carrying out an analysis of the reaction products (e.g. by gas chromatography (GC) or HPLC analysis). Further details on SHC/HAC enzyme and/or SHC/HAC enzyme variant activity assays and analysis of the reaction products are provided in the Examples. These assays include producing the SHC/HAC enzyme variant in recombinant host cells (e.g. *E. coli*).

As used herein, the term "activity" means the ability of an enzyme to react with a substrate to provide a desired product. The activity can be determined in what is known as an activity test for monitoring the formation of the desired product. The SHC/HAC enzyme derivatives of the present disclosure may be characterized by their ability to cyclize homofarnesol (e.g. EEH) into (−)-Ambrox and demonstrate a biological activity such as an HAC activity. The SHC/HAC enzyme derivatives of the present disclosure may be characterized by their ability to cyclize bishomofarnesol (e.g. E,E-Bishomofarnesol) into Ambra oxide.

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. It is not required that the variant exhibits such an activity to the same extent as the parent or wild-type polypeptide. A variant is regarded as a variant within the context of the present application, if it exhibits the relevant activity to a degree of at least 10% of the activity of the parent polypeptide. Likewise, a variant is regarded as a variant within the context of the present application, if it exhibits the relevant biological activity to a degree of at least 10% of the activity of the parent polypeptide (as the terms derivative and variant are used interchangeably throughout the present disclosure). In other embodiments, the SHC/HAC enzyme variants of the present disclosure show a better yield than the reference SHC protein (e.g. a wild-type SHC/HAC enzyme or a known SHC/HAC enzyme variant). The term "yield" refers to the gram of recoverable product per gram of feedstock (which can be calculated as a percent molar conversion rate). In additional embodiments, the SHC/HAC enzyme variants of the present disclosure show a modified (e.g. increased) productivity relative to the reference SHC protein (e.g. wild-type AacSHC or 215G2 AacSHC). The term "productivity" refers to the amount of recoverable product in grams per liter of reaction capacity per hour of bioconversion time (i.e. time after the substrate was added). The term "productivity" also refers to the amount of recoverable product in grams per liter of reaction capacity per hour of bioconversion time (ie time after the substrate was added) per gram of biocatalyst used in the reaction.

In further embodiments, the SHC/HAC enzyme variants of the present disclosure show a modified yield compared with the reference SHC protein (e.g. wild-type AacSHC (SEQ ID NO: 1) or 215G2 AacSHC (SEQ ID NO: 10) or wild-type ZmoSHC1 (SEQ ID NO: 11) or wild-type ZmoSHC2 (SEQ ID NO: 12) or wild-type BjpSHC (SEQ ID NO: 13) or wild-type GmoSHC (SEQ ID NO: 14) or wild-type TelSHC (SEQ ID NO: 19) or wild-type ApaSHC1 (SEQ ID NO: 20) or wild-type BmeSHC (SEQ ID NO: 28) or wild-type SalSHC (SEQ ID NO: 29) or wild-type ApaSHCA (SEQ ID NO: 30)). The term "target yield factor" refers to the ratio between the product concentration obtained and the concentration of the SHC/HAC variant enzyme (for example, purified SHC/HAC enzyme variant or an extract from the recombinant host cells producing the SHC/HAC enzyme variant) in the reaction medium. In various embodiments, the SHC/HAC enzyme variants of the present disclosure show a modified (e.g. increased) fold increase in enzymatic activity (e.g. a modified/increased homofarnesol Ambrox cyclase (HAC) activity) relative to the reference SHC protein (e.g. SEQ ID No. 1 or SEQ ID NO: 10 or SEQ ID NO: 11 or SEQ ID NO: 12 or SEQ ID NO: 13 or SEQ ID NO: 14 or SEQ ID NO: 19 or SEQ ID NO: 20 or SEQ ID NO: 28 or SEQ ID NO: 29 or SEQ ID NO: 30). This increase in activity may be at least by a factor of: 2, 3, 4, 6, 8, 10, 12, 14, 16, 18, 20, 25, 30, 35, 40, 45, 50, 55, 60, 65, 70, 75, 80, 85, 90, 95, and/or 100.

As used herein, the term "amino acid alteration" means an insertion of one or more amino acids between two amino acids, a deletion of one or more amino acids or a substitution (which may be conservative or non-conservative) of one or more amino acids with one or more different amino acids relative to the amino acid sequence of a reference amino acid sequence. Substitutions replace the amino acids of the reference sequence with the same number of amino acids in the variant sequence. Reference amino acid sequences may, for example, be a wild-type (WT) amino acid sequence (for example SEQ ID NO: 1 or SEQ ID NO: 11 or SEQ ID NO: 12 or SEQ ID NO: 13 or SEQ ID NO: 14 or SEQ ID NO: 19 or SEQ ID NO: 20 or SEQ ID NO: 28 or SEQ ID NO: 29 or SEQ ID NO: 30) or may, for example, itself be a SHC/HAC enzyme variant sequence (for example the Aac 215G2 variant-SEQ ID NO: 10).

The amino acid alterations can be easily identified by a comparison of the amino acid sequences of the SHC/HAC enzyme variant with the amino acid sequence of the reference amino acid sequence.

Conservative amino acid substitutions may be made, for instance, on the basis of similarity in polarity, charge, size, solubility, hydrophobicity, hydrophilicity, and/or the amphipathic nature of the amino acid residues involved. The 20 naturally occurring amino acids as outlined above can be grouped into the following six standard amino acid groups:

(1) hydrophobic: Met, Ala, Val, Leu, Ile;
(2) neutral hydrophilic: Cys, Ser, Thr; Asn, Gln;
(3) acidic: Asp, Glu;
(4) basic: His, Lys, Arg;
(5) residues that influence chain orientation: Gly, Pro; and
(6) aromatic: Trp, Tyr, Phe.

Accordingly, as used herein, the term "conservative substitutions" means an exchange of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt alpha-helices. Some preferred conservative substitutions within the above six groups are exchanges within the following sub-groups: (i) Ala, Val, Leu and Ile; (ii) Ser and Thr; (ii) Asn and Gln: (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) as shown above. Typically the SHC/HAC enzyme variants described herein are prepared using non-conservative substitutions which alter the biological function (e.g. HAC activity) of the disclosed SHC/HAC enzyme variants. For ease of reference, the one-letter amino acid symbols recommended by the IUPAC-IUB Biochemical Nomenclature Commission are indicated as follows. The three letter codes are also provided for reference purposes.

| One Letter Code | Three Letter Code | Amino Acid Name |
| --- | --- | --- |
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gin | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Amino acid alterations such as amino acid substitutions may be introduced using known protocols of recombinant gene technology including PCR, gene cloning, site-directed mutagenesis of cDNA, transfection of host cells, and in vitro transcription which may be used to introduce such changes to the reference sequence resulting in an SHC/HAC enzyme variant. The enzyme variants can then be screened for SHC/HAC functional activity.

Suitable sources of SHC/HAC enzymes include, for example, *Alicyclobacillus acidocaldarius* (Aac), *Zymomonas mobilis* (Zmo), *Bradyrhizobium japonicum* (Bjp), *Gluconobacter morbifer* (Gmo), *Burkholderia ambifaria*, *Bacillus anthracis*, *Methylococcus capsulatus*, *Frankia alni*, *Acetobacter pasteurianus* (Apa), *Thermosynechococcus elongatus* (Tel), *Streptomyces coelicolor* (Sco), *Rhodopseudomonas palustris* (Rpa), *Teredinibacter turnerae* (Ttu), *Pelobacter carbinolicus* (Pca), *Bacillus megaterium* (Bme), *Streptomyces albolongus* (Sal) and *Tetrahymena pyriformis* (see, for example WO 2010/139719, US 2012/01345477, WO 2012/066059, the contents of which are incorporated herein by reference).

In particular, the SHC/HAC enzyme (e.g. from which the SHC/HAC enzyme variant may be derived) may be the *Alicyclobacillus acidocaldarius* (Aac) SHC/HAC enzyme, the *Zymomonas mobilis* SHC/HAC (ZmoSHC1) enzyme the *Bradyrhizobium japonicum* (Bjp or Bja) SHC/HAC enzyme or the *Gluconobacter morbifer* (Gmo) SHC/HAC enzyme or an *Acetobacter pasteurianus* SHC/HAC (ApaSHC1) enzyme or the *Bacillus megaterium* (Bme) SHC/HAC enzyme. In particular, the SHC/HAC enzyme (e.g. from which the SHC/HAC enzyme variant may be derived) may be the *Alicyclobacillus acidocaldarius* (Aac) SHC/HAC enzyme.

For ease of reference, the designation "AacSHC" may be used to refer to the *Alicyclobacillus acidocaldarius* (Aac) SHC/HAC enzyme, "ZmoSHC" may be used to refer to the *Zymomonas mobilis* (Zmo) SHC/HAC enzymes, "BjpSHC" or "BjaSHC" may be used to refer to the *Bradyrhizobium japonicum* (Bjp) SHC/HAC enzyme, "ApaSHC" may be used to refer to the *Acetobacter pasteurianus* (Apa) SHC/HAC enzymes, "BmeSHC" may be used to refer to *Bacillus megaterium* (Bme) SHC/HAC enzyme, "SalSHC" may be used to refer to the *Streptomyces albolongus* (Sal) SHC/HAC enzyme and "GmoSHC" may be used to refer to the *Gluconobacter morbifer* (Gmo) SHC/HAC enzyme.

AacSHC, ZmoSHC and BjpSHC enzyme sequences are disclosed in BASF WO 2010/139719, US 2012/01345477A1, Seitz et al (as cited above) and Seitz (2012 PhD thesis as cited above). Two different sequences are disclosed for ZmoSHC, referred to as ZmoSHC1 and ZmoSHC2. The Gmo SHC/HAC enzyme sequence is disclosed in WO 2018/157021. The SalSHC enzyme is disclosed in Liu et al (2020): A Novel Soluble Squalene-Hopene Cyclase and Its Application in Efficient Synthesis of Hopene, Frontiers in Bioengineering and Biotechnology, vol 8, article 426.

Figure 3:
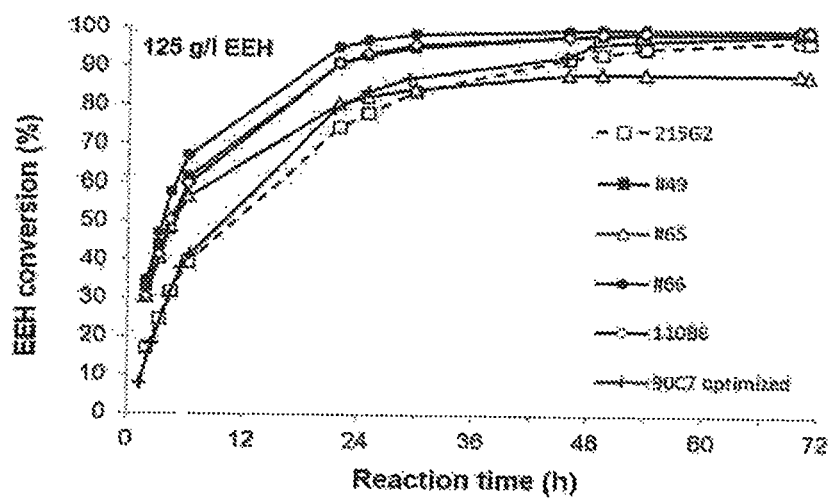
FIG. 3 shows EEH conversion to (−)-Ambrox by SHC/HAC enzyme variants under optimal conditions compared to the 215G2 parent SHC/HAC enzyme. Reactions were run at 125 g/l EEH and 250 g/l biocatalyst in the presence of 1.3% SDS, and at T and pH conditions defined as optimal for each of the variants.

Table 1 discloses sources and accession numbers of wild-type SHC enzymes.

is found six times in the SHC sequences of both *Z. mobilis* and *A. acidocaldarius* (See FIG. 3 of Reipen et al 1995, Microbiology 141, 155-161). Hoshino and Sato (2002 as cited above) report that aromatic amino acids are unusually abundant in SHCs and that two characteristic motifs were noted in the SHCs: one is a QW motif represented by specific amino acid motifs [(K/R)(G/A)X2-3(F/Y/W)(L/IV) 3X3QX2-5GXW] and the alternative is a DXDDTA motif. Wendt et al (1997, Science 277, 1811-1815 and 1999, J Mol Biol 286, 175-187) reported on the X-ray structure analysis of *A. acidocaldarius* SHC. The DXDDTA motif appears to correlate with the SHC active site.

TABLE 1

Sources and accession numbers of wild-type (WT) SHC enzymes.

| SHC Source Strain (SHC name) | Reference (and incorporated herein by reference) | Accession No. | SEQ ID No. according to WO 2010139719 US2012/0135477 (*) or to the present disclosure (**) |
|---|---|---|---|
| *Alicyclobacillus acidocaldarius* (WT AacSHC) | JP2009-060799 (Kao) Neumann et al Biol Chem (1986) 367; 723-729 | NBRC15652 | SEQ ID No: 1 ** |
| *Zymomonas mobilis* (WT ZmoSHCI) | WO2010139719 US20120135477 | ATCC31821 PF62207_2 Genpept Accession No. AAV90172 AAF12829.1 AVZ42714.1 | SEQ ID No. 1 * SEQ ID No. 2* |
| *Zymomonas mobilis* (WT ZmoSHC2) | Reipen et al (1995) Microbiology 141:155-161 | EMBL/Genbank Accession No. X80766 | SEQ ID No. 12** |
| *Bradryhizobium japonicum* (WT BjpSHC) | WO2010139719 US2012/0135477 | PF62207_5 ABQ33590.1 | SEQ ID No. 5* |
| *Burkholderia ambifaria* | WO2010139719 US2012/0135477 | | SEQ ID No. 6* |
| *Burkholderia ambifaria* | WO2010139719 US2012/0135477 | | SEQ ID No. 7* |
| *Bacillus anthracis* | WO2010139719 US2012/0135477 | | SEQ ID No. 8* |
| *Frankia alni* | WO2010139719 US2012/0135477 | | SEQ ID No. 9* |
| *Rhodopseudomonas palustris* | WO2010139719 US2012/0135477 | | SEQ ID No. 10* |
| *Gluconobacter morbifer* (WT GmoSHC) | WO2018157021 | EHH69691.1 | SEQ ID NO: 14** |
| *Thermosynechococcus elongates* (TelSHC) | | BAC09861.1 | SEQ ID NO: 19** |
| *Acetobacter pasteurianus* (ApaSHC1) | | ASC07046.1 | SEQ ID NO: 20 ** |
| *Bacillus megaterium* (WT BmeSHC) | | WP_016763969 | SEQ ID NO: 28 ** |
| *Streptomyces albolongus* (WT SalSHC) | | AZN28579 | SEQ ID NO: 29 ** |
| *Acetobacter pasteurianus* (WT ApaSHCA) | | WP_003625617 | SEQ ID NO: 30 ** |

The sequences of the wild-type AacSHC, wild-type ZmoSHC1, wild-type ZmoSHC2, wild-type BjpSHC, wild-type GmoSHC, wild-type TelSHC and wild-type ApaSHC1, wild-type BmeSHC, wild-type SalSHC and wild-type ApaSHCA, are also disclosed herein (SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 and SEQ ID NO: 30 respectively).

An alignment of WT SHC sequences prepared by Hoshino and Sato (2002 as cited above) indicates that multiple motifs were detected in all four sequences and consists of the core sequence Gln-X-X-X-Gly-X-Trp which A reference AacSHC protein as used herein may refer to the wild-type AacSHC protein as disclosed in SEQ ID NO: 1. AacSHC has the activity of a homofarnesol Ambrox cyclase (HAC) useful in the production of Ambrox derivatives through a biocatalytic reaction of SHC with a homofarnesol substrate. The main reaction of the AacSHC is the cyclisation of a linear or a non-linear substrate such as homofarnesol to produce Ambrox.

Functional homologs of the wild-type SHC/HAC enzymes or the SHC/HAC enzyme variants described herein are also suitable for use in cyclization reactions, for example for producing (−)-Ambrox, for example in a recombinant host. Thus, the recombinant host may include one or more heterologous nucleic acid(s) encoding functional homologs of the polypeptides described above and/or a heterologous nucleic acid encoding a SHC/HAC derivative enzyme as described herein.

A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild-type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional homologs described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of the nucleic acid sequences encoding the SHC derivative polypeptides and the like.

Hybridization can also be used to identify functional homologs and/or as a measure of homology between two nucleic acid sequences. A nucleic acid sequence encoding any of the proteins disclosed herein, or a portion thereof, can be used as a hybridization probe according to standard hybridization techniques. The hybridization of a probe to DNA or RNA from a test source (e.g. a mammalian cell) is an indication of the presence of the relevant DNA or RNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C. followed by a wash in 1×SSC, 0.1% SDS at 50° C. Highly stringent conditions are defined as equivalent to hybridization in 6× sodium chloride/sodium citrate (SSC) at 45° C. followed by a wash in 0.2×SSC, 0.1% SDS at 65° C. Sequence analysis to identify functional homologs can also involve BLAST, Reciprocal BLAST, or PSI-BLAST analysis of non-redundant databases using a relevant amino acid sequence as the reference sequence. Amino acid sequence is, in some instances, deduced from the nucleotide sequence. Those polypeptides in the database that have greater than 40% sequence identity are candidates for further evaluation for suitability for use in the SHC/HAC bioconversion reaction. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have for e.g. conserved functional domains.

Typically, polypeptides that exhibit at least about 30% amino acid sequence identity are useful to identify conserved regions. Conserved regions of related polypeptides exhibit at least 30%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, amino acid sequence identity. In some embodiments, a conserved region exhibits at least, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity. Sequence identity can be determined as set forth above and below.

The SHC/HAC enzymes or enzyme variants described herein and used in the methods described herein may, for example, be based on an amino acid sequence of SEQ ID NO: 1, SEQ ID NO: 10, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, SEQ ID NO: 30, or a variant, homologue, mutant, derivative or fragment thereof. The SHC/HAC enzyme or enzyme variant may, for example, have an amino acid sequence with at least 30%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO: 1, SEQ ID NO: 10, SEQ ID NO: 11, SEQ ID NO: 12, SEQ ID NO: 13, SEQ ID NO: 14 or SEQ ID NO: 19, SEQ ID NO: 20, SEQ ID NO: 28, SEQ ID NO: 29, or SEQ ID NO: 30.

In addition, the produced reference SHC may be based on an amino acid sequence produced from E. coli.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

As used herein the term "derivative" includes but is not limited to a variant. The terms "derivative" and "variant" are used interchangeably herein.

In preferred embodiments, a variant enzyme usable in the present disclosure exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes (alterations) in the amino acid sequence (i.e. exchanges, insertions, deletions, N-terminal truncations, and/or C-terminal truncations). The amino acid exchanges may be conservative and/or non-conservative. In preferred embodiments, a variant usable in the present disclosure differs from the protein or domain from which it is derived by up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acid exchanges, preferably conservative amino acid changes. Variants may additionally or alternatively comprise deletions of amino acids, which may be N-terminal truncations, C-terminal truncations or internal deletions or any combination of these. Such variants comprising N-terminal truncations, C-terminal truncations and/or internal deletions are referred to as "deletion variants" or "fragments" in the context of the present application. The terms "deletion variant" and "fragment" are used interchangeably herein. A deletion variant may be naturally occurring (e.g. splice variants) or it may be constructed artificially, preferably by gene-technological means. Typically, the protein or protein domain from which the deletion variant is derived is a wild-type protein. However, the deletion variants of the present disclosure may also be derived from homologs, orthologs, or paralogs of the parent polypeptide or from artificially constructed variants, provided that the deletion variants exhibit at least one biological activity of the parent polypeptide. Preferably, a deletion variant (or fragment) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide.

In certain embodiments, the SHC/HAC enzyme variants described herein only include substitutions and do not include any deletions or insertions.

A "variant" as used herein, can alternatively or additionally be characterised by a certain degree of sequence identity to the parent polypeptide from which it is derived. A variant of the WT/reference SHC/HAC or the SHC/HAC Derivative of the present disclosure may have a sequence identity of at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to the respective reference polypeptide or to the respective reference polynucleotide.

The expression "at least 30%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity" is used throughout the specification with regard to polypeptide and polynucleotide sequence comparisons. A polynucleotide belonging to a family of any of the enzymes disclosed herein or a protein can be identified based on its similarity to the relevant gene or protein, respectively. For example, the identification can be based on sequence identity. In certain preferred embodiments the disclosure features isolated nucleic acid molecules which are at least 30%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to (a) a nucleic acid molecule that encodes the polypeptide of a wild-type SHC/HAC enzyme (e.g. SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.) disclosed herein (b) the nucleotide sequence SEQ ID NO: 15 and (c) a nucleic acid molecule which includes a segment of at least 30 (e.g. at least 30, 40, 50, 60, 80, 100, 125, 150, 175, 200, 250, 300, 400, 500, 600, 700, 800, 850, 900, 950, 1000, or 1010) nucleotides of SEQ ID NO: 15.

Preferably, the polypeptide in question and the reference polypeptide exhibit the indicated sequence identity over a continuous stretch of 20, 30, 40, 45, 50, 60, 70, 80, 90, 100 or more amino acids. Preferably, the polynucleotide in question and the reference polynucleotide exhibit the indicated sequence identity over a continuous stretch of 60, 90, 120, 135, 150, 180, 210, 240, 270, 300 or more nucleotides. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence (e.g. SEQ ID NO: 1, SEQ ID NO: 10, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30) if not specifically indicated otherwise.

For example, a peptide sequence consisting of 130 amino acids compared to the amino acids of full length of wild-type AacSHC with 631 amino acid residues may exhibit a maximum sequence identity percentage of 20.6% (130/631× 100) while a sequence with a length of 300 amino acids may exhibit a maximum sequence identity percentage of 47.5% (300/631×100).

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) or the GAP program (mathematical algorithm of the University of Iowa) or the mathematical algorithm of Myers and Miller (1989—Cabios 4:11-17) or Clone Manager 9.

The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215, 403-410. BLAST polynucleotide searches are performed with the BLASTN program, score=100, word length=12, to obtain polynucleotide sequences that are homologous to those nucleic acids which encode the relevant protein.

BLAST protein searches are performed with the BLASTP program, score=50, word length=3, to obtain amino acid sequences homologous to the SHC polypeptide. To obtain gapped alignments for comparative purposes, Gapped BLAST is utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

Specific SHC/HAC enzymes and enzymes variants that may be used in the methods described herein are further described below.

Variants of Aac 215G2 SHC/HAC with New Mutations

It has surprisingly been found that SHC/HAC enzyme variants derived from an Aac SHC/HAC enzyme variant disclosed in WO 2016/170099 (the 215G2 SHC/HAC enzyme variant) provide improved enzymatic activity for the conversion of EEH to (−)-Ambrox. It has further surprisingly been found that the SHC/HAC enzyme variants derived from 215G2 provide improved enzymatic activity for the conversion of E,E-bishomofarnesol to Ambra oxide.

The new SHC/HAC enzyme variants have two or three amino acid alterations in addition to the amino acid substitutions already present in the 215G2 SHC/HAC enzyme variant.

There is therefore provided herein a process for making (−)-Ambrox by enzymatically converting EEH to (−)-Ambrox. There is also provided herein a process for making Ambra oxide by enzymatically converting E,E-bishomofarnesol to Ambra oxide. These processes may use any wild-type SHC/HAC enzyme or enzyme variant described herein, in particular the Aac 215G2 SHC/HAC variants described herein.

The SHC/HAC enzyme variant of Aac 215G2 SHC/HAC has an amino acid sequence having at least about 70.0% identity to SEQ ID NO: 1. For example, the SHC/HAC enzyme variant may have at least about 75.0% or at least about 80.0% or at least about 85.0% or at least about 90.0% or at least about 95.0% or at least about 95.5% or at least about 96.0% or at least about 96.5% or at least about 97.0% or at least about 97.5% or at least about 98.0% or at least about 98.5% or at least about 99.0% identity to SEQ ID NO: 1.

The enzyme variant of Aac 215G2 SHC/HAC has less than 100% identity to SEQ ID NO: 1. For example, the SHC/HAC enzyme variant may have equal to or less than about 99.5% or equal to or less than about 99.0% identity to SEQ ID NO: 1.

For example, the enzyme variant of Aac 215G2 SHC/HAC may have from about 70.0% to about 99.5% or from about 80.0% to about 99.0% or from about 85.0% to about 98.5% or from about 90.0% to about 98.0% identity to SEQ ID NO: 1.

"Percent (%) identity" with respect to a polypeptide or nucleotide sequence is defined respectively as the percentage of amino acids or nucleotides in a candidate sequence that are identical with the amino acids or nucleotides in the reference sequence, after aligning the sequence and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) or the GAP program (mathematical algorithm of the University of Iowa) or the mathematical algorithm of Myers and Miller (1989—Cabios 4:11-17).

Percentage sequence identity may be calculated using, for example, BLAST, BLAT or BlastZ (or BlastX). A similar algorithm is incorporated into the BLASTN and BLASTP programs of Altschul et al (1990) J. Mol. Biol. 215, 403-410. BLAST polynucleotide searches may be performed with the BLASTN program, score=100, word length=12, to obtain polynucleotide sequences that are homologous to those nucleic acids which encode the relevant protein. BLAST protein searches may be performed with the BLASTP program, score=50, word length=3, to obtain amino acid sequences homologous to the polypeptide.

To obtain gapped alignments for comparative purposes, Gapped BLAST may be utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

In certain embodiments, the SHC/HAC enzyme variant may have equal to or less than about 30 amino acid alterations compared to SEQ ID NO: 1. For example, the SHC/HAC enzyme variant may have equal to or less than about 25 or equal to or less than about 20 or equal to or less than about 15 or equal to or less than about 10 or equal to or less than about 9 or equal to or less than about 8 or equal to or less than about 7 or equal to or less than about 6 amino acid alterations compared to SEQ ID NO: 1. For example, the SHC/HAC enzyme variant may have at least about 5 or at least about 6 amino acid alterations compared to SEQ ID NO: 1. The amino acid alterations may, for example, be insertions, deletions and/or substitutions as described above.

In certain embodiments, the only amino acid alterations in the SHC/HAC enzyme variant compared to SEQ ID NO: 1 are substitutions (i.e. there are no insertions or deletions).

Amino acid alterations are defined relative to a reference sequence. An amino acid alteration relative to a reference sequence means that the amino acid sequence of the variant sequence is different to the reference sequence.

Amino acids in the reference sequence and the variant sequence may be assigned a number, where the numbering starts with the amino acid at the N-terminus of the polypeptide (i.e. the amino acid at the N-terminus of the polypeptide is numbered 1, the next amino acid is numbered 2 etc.). The "position" of a reference sequence refers to a specific amino acid residue present in the reference sequence as identified by the specific numbering of the amino acids in the reference sequence. The "position" of a variant sequence refers to a specific amino acid residue present in the variant sequence as identified by the specific numbering of the amino acids in the variant sequence.

Since the variant sequence may include deletions or insertions compared to the reference sequence, the amino acids in the variant sequence may be numbered differently to the same amino acids in the reference sequence. By way of example, if an amino acid is inserted between amino acids 131 and 132 of SEQ ID NO: 1, the amino acid following the insertion will have the numbering 133 in the variant sequence while it retains the numbering 132 in the reference sequence. In this example, the position of the variant sequence that corresponds to position 132 of the reference sequence is position 133. Therefore, amino acids in the variant sequence that have been retained from the reference sequence may be defined by referring to the "corresponding position" of the reference sequence. In other words, a "position" in the variant sequence may be defined by reference to a "corresponding position" in the reference sequence. In particular, substitutions in the variant sequence compared to the reference sequence may be defined by referring to the "corresponding position" of the reference sequence in spite of any insertions and/or deletions in the reference sequence. Where the amino acids of a reference sequence have been deleted, there is no "corresponding position" in the variant sequence. Where there are no insertions or deletions compared to the reference sequence (i.e. there are only substitutions), the "corresponding position" of the reference sequence will be the same as the position in the variant sequence.

The original amino acid alterations in the 215G2 SHC/HAC enzyme variant (compared to wild-type Aac SHC) are retained in the new Aac 215G2 SHC/HAC enzyme variant described herein. The original amino acid alterations in the 215G2 SHC/HAC enzyme variant compared to wild-type Aac SHC were the substitutions M132R, A224V and I432T (i.e. a substitution of the M residue at position 132 for an R residue, a substitution of the A residue at position 224 for a V residue, and a substitution of the I residue at position 432 for a T residue).

Therefore, the new Aac 215G2 SHC/HAC enzyme variants have amino acid alterations relative to SEQ ID NO: 1 at positions corresponding to positions 132, 224 and 432 of SEQ ID NO: 1 which are M132R, A224V and I432T respectively. The number "132" in "M132R", "224" in "A224V" and "432" in "I432T" refers to the numbering of SEQ ID NO: 1 and, as discussed above, does not necessarily correspond to the numbering of the variant sequence due to optional further insertions and/or deletions.

The new Aac 215G2 SHC/HAC enzyme variant amino acid sequence also has amino acid alterations relative to SEQ ID NO: 1 at a position corresponding to position 557 of SEQ ID NO: 1 and at least one position corresponding to position 81, 431 or 613 of SEQ ID NO: 1. These amino acid alterations may, for example, be substitutions, for example non-conservative substitutions.

For example, the SHC/HAC enzyme variant amino acid sequence may have amino acid alterations relative to SEQ ID NO: 1 at a position corresponding to position 557 of SEQ ID NO: 1 and one position corresponding to position 81, 431 or 613 of SEQ ID NO: 1. These amino acid alterations may, for example, be substitutions, for example non-conservative substitutions.

For example, the SHC/HAC enzyme variant amino acid sequence may have amino acid alterations relative to SEQ ID NO: 1 at a position corresponding to position 557 of SEQ ID NO: 1 and two positions selected from the positions corresponding to positions 81, 431 and 613 of SEQ ID NO: 1. These amino acid alterations may, for example, be substitutions, for example non-conservative substitutions.

For example, the SHC/HAC enzyme variant amino acid sequence may have amino acid alterations relative to SEQ ID NO: 1 at a position corresponding to position 557 of SEQ ID NO: 1 and all of the positions corresponding to positions 81, 431 and 613 of SEQ ID NO: 1. These amino acid alterations may, for example, be substitutions, for example non-conservative substitutions.

For example, the SHC/HAC enzyme variant may have amino acid alterations relative to SEQ ID NO: 1 at positions corresponding to positions 431 and 557 of SEQ ID NO: 1. These amino acid alterations may, for example, be substitutions, for example non-conservative substitutions. In certain embodiments, the SHC/HAC enzyme variant has the sequence of SEQ ID NO: 2.

For example, the SHC/HAC enzyme variant may have amino acid alterations relative to SEQ ID NO: 1 at positions corresponding to positions 557 and 613 of SEQ ID NO: 1. These amino acid alterations may, for example, be substitutions, for example non-conservative substitutions. In certain embodiments, the SHC/HAC enzyme variant has the sequence of SEQ ID NO: 3.

For example, the SHC/HAC enzyme variant may have amino acid alterations relative to SEQ ID NO: 1 at positions corresponding to positions corresponding to positions 81, 557 and 613 of SEQ ID NO: 1. These amino acid alterations may, for example, be substitutions, for example non-conservative substitutions. In certain embodiments, the SHC/HAC enzyme variant has the sequence of SEQ ID NO: 4.

For example, the SHC/HAC enzyme variant may have amino acid alterations relative to SEQ ID NO: 1 at positions corresponding to positions 81, 431 and 557 of SEQ ID NO: 1. These amino acid alterations may, for example, be substitutions, for example non-conservative substitutions. In certain embodiments, the SHC/HAC enzyme variant has the sequence of SEQ ID NO: 5.

The amino acid alteration at a position corresponding to position 557 of SEQ ID NO: 1 may, for example, be A557X. This refers to a substitution of the amino acid A at position 557 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 557.

The new amino acid (X) at a position corresponding to position 557 of SEQ ID NO: 1 may, for example, be Met, Val, Leu, Ile, Cys, Ser, Thr, Asn, Gln, Asp, Glu, His, Lys, Arg, Gly, Pro, Trp, Tyr or Phe. For example, the amino acid alteration at a position corresponding to position 557 of SEQ ID NO: 1 may substitute the amino acid of SEQ ID NO: 1 (i.e. A) for a neutral hydrophilic amino acid (i.e. Cys, Ser, Thr, Asn or Gln). For example, the amino acid alteration at a position corresponding to position 557 of SEQ ID NO: 1 may substitute the amino acid of SEQ ID NO: 1 (i.e. A) for threonine (i.e. the amino acid alteration at a position corresponding to position 557 of SEQ ID NO: 1 is A557T).

The amino acid alteration at a position corresponding to position 81 of SEQ ID NO: 1 may, for example, be Y81X. This refers to a substitution of the amino acid Y at position 81 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 81.

The new amino acid (X) at a position corresponding to position 81 of SEQ ID NO: 1 may, for example, be Met, Ala, Val, Leu, Ile, Cys, Ser, Thr, Asn, Gln, Asp, Glu, His, Lys, Arg, Gly, Pro, Trp, or Phe. For example, the amino acid alteration at a position corresponding to position 81 of SEQ ID NO: 1 may substitute the amino acid of SEQ ID NO: 1 (i.e. Y) for a basic amino acid (i.e. His, Lys or Arg). For example, the amino acid alteration at a position corresponding to position 81 of SEQ ID NO: 1 may substitute the amino acid of SEQ ID NO: 1 (i.e. Y) for histidine (i.e. the amino acid alteration at a position corresponding to position 81 of SEQ ID NO: 1 is Y81H).

The amino acid alteration at a position corresponding to position 431 of SEQ ID NO: 1 may, for example, be H431X. This refers to a substitution of the amino acid H at position 431 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 431.

The new amino acid (X) at a position corresponding to position 431 of SEQ ID NO: 1 may, for example, be Met, Ala, Val, Leu, Ile, Cys, Ser, Thr, Asn, Gln, Asp, Glu, Lys, Arg, Gly, Pro, Trp, Tyr or Phe. For example, the amino acid alteration at a position corresponding to position 431 of SEQ ID NO: 1 may substitute the amino acid of SEQ ID NO: 1 (i.e. H) for a hydrophobic amino acid (i.e. Met, Ala, Val, Leu or Ile). For example, the amino acid alteration at a position corresponding to position 431 of SEQ ID NO: 1 may substitute the amino acid of SEQ ID NO: 1 (i.e. H) for leucine (i.e. the amino acid alteration at a position corresponding to position 431 of SEQ ID NO: 1 is H431L).

The amino acid alteration at a position corresponding to position 613 of SEQ ID NO: 1 may, for example, be R613X. This refers to a substitution of the amino acid R at position 613 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 613.

The new amino acid (X) at a position corresponding to position 631 of SEQ ID NO: 1 may, for example, be Met, Ala, Val, Leu, Ile, Cys, Ser, Thr, Asn, Gln, Asp, Glu, His, Lys, Gly, Pro, Trp, Tyr or Phe. For example, the amino acid alteration at a position corresponding to position 613 of SEQ ID NO: 1 may substitute the amino acid of SEQ ID NO: 1 (i.e. R) for a neutral hydrophilic amino acid (i.e. Cys, Ser, Thr, Asn or Gln). For example, the amino acid alteration at a position corresponding to position 613 of SEQ ID NO: 1 may substitute the amino acid of SEQ ID NO: 1 (i.e. R) for serine (i.e. the amino acid alteration at a position corresponding to position 613 of SEQ ID NO: 1 is R613S).

In certain embodiments, the new Aac 215G2 SHC variant is identical to SEQ ID NO: 1 except for the following amino acid substitutions:
  (i) M132R, A224V, I432T, A557T and H431L (SEQ ID NO: 2); or
  (ii) M132R, A224V, I432T, A557T and R613S (SEQ ID NO: 3); or
  (iii) M132R, A224V, I432T, A557T, Y81H and R613S (SEQ ID NO: 4); or
  (iv) M132R, A224V, I432T, A557T, Y81H and H431L (SEQ ID NO: 5).

The SHC/HAC enzyme variant may, for example, have one or more further amino acid alterations at positions corresponding to positions 90, 172 and/or 277 of SEQ ID NO: 1. The amino acid alteration at a position corresponding to position 90 of SEQ ID NO: 1 may, for example, be T90X. This refers to a substitution of the amino acid T at position 90 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 90.

The new amino acid (X) at a position corresponding to position 90 of SEQ ID NO: 1 may, for example, be Met, Ala, Val, Leu, Ile, Cys, Ser, Asn, Gln, Asp, Glu, His, Lys, Arg, Gly, Pro, Trp, Tyr or Phe. For example, the amino acid alteration at a position corresponding to position 90 of SEQ ID NO: 1 may substitute the amino acid of SEQ ID NO: 1 (i.e. T) for a hydrophobic amino acid (i.e. Met, Ala, Val, Leu, Ile). For example, the amino acid alteration at a position corresponding to position 90 of SEQ ID NO: 1 may substitute the amino acid of SEQ ID NO: 1 (i.e. T) for alanine (i.e. the amino acid alteration at a position corresponding to position 90 of SEQ ID NO: 1 is T90A).

The amino acid alteration at a position corresponding to position 172 of SEQ ID NO: 1 may, for example, be A172X. This refers to a substitution of the amino acid T at position 172 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 172.

The new amino acid (X) at a position corresponding to position 172 of SEQ ID NO: 1 may, for example, be Met, Val, Leu, Ile, Cys, Ser, Thr, Asn, Gln, Asp, Glu, His, Lys, Arg, Gly, Pro, Trp, Tyr or Phe. For example, the amino acid alteration at a position corresponding to position 172 of SEQ ID NO: 1 may substitute the amino acid of SEQ ID NO: 1 (i.e. A) for a neutral hydrophilic amino acid (i.e. Cys, Ser, Thr, Asn, Gln). For example, the amino acid alteration at a position corresponding to position 172 of SEQ ID NO: 1 may substitute the amino acid of SEQ ID NO: 1 (i.e. A) for threonine (i.e. the amino acid alteration at a position corresponding to position 172 of SEQ ID NO: 1 is A172T).

The amino acid alteration at a position corresponding to position 277 of SEQ ID NO: 1 may, for example, be M277X. This refers to a substitution of the amino acid M at position 277 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 277.

The new amino acid (X) at a position corresponding to position 277 of SEQ ID NO: 1 may, for example, be Ala, Val, Leu, Ile, Cys, Ser, Thr, Asn, Gln, Asp, Glu, His, Lys, Arg, Gly, Pro, Trp, Tyr or Phe. For example, the amino acid alteration at a position corresponding to position 277 of SEQ ID NO: 1 may substitute the amino acid of SEQ ID NO: 1 (i.e. M) for a basic amino acid (i.e. His, Lys, Arg). For example, the amino acid alteration at a position corresponding to position 277 of SEQ ID NO: 1 may substitute the amino acid of SEQ ID NO: 1 (i.e. M) for lysine i.e. the amino acid alteration at a position corresponding to position 277 of SEQ ID NO: 1 is M277K).

The SHC/HAC enzyme variant may, for example, have one or more further amino acid alterations at positions corresponding to positions 37, 174 and/or 601 of SEQ ID NO: 1. For example, the SHC/HAC enzyme variant may have one or more amino acid substitutions (e.g. conservative or non-conservative substitutions) at positions corresponding to positions 37, 174 and/or 601 of SEQ ID NO: 1.

The amino acid alteration at a position corresponding to position 37 of SEQ ID NO: 1 may, for example, be L37X. This refers to a substitution of the amino acid L at position 37 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 37.

The new amino acid (X) at a position corresponding to position 37 of SEQ ID NO: 1 may, for example, be Met, Ala, Val, Ile, Cys, Ser, Thr, Asn, Gln, Asp, Glu, His, Lys, Arg, Gly, Pro, Trp, Tyr or Phe. For example, the amino acid alteration at a position corresponding to position 37 of SEQ ID NO: 1 may substitute the amino acid of SEQ ID NO: 1 (i.e. L) for a neutral hydrophilic amino acid (i.e. Cys, Ser, Thr, Asn or Gln). For example, the amino acid alteration at a position corresponding to position 37 of SEQ ID NO: 1 may substitute the amino acid of SEQ ID NO: 1 (i.e. L) for glutamine (i.e. the amino acid alteration at a position corresponding to position 37 of SEQ ID NO: 1 is L37Q).

The amino acid alteration at a position corresponding to position 174 of SEQ ID NO: 1 may, for example, be V174X. This refers to a substitution of the amino acid V at position 174 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 174.

The new amino acid (X) at a position corresponding to position 174 of SEQ ID NO: 1 may, for example, be Met, Ala, Leu, Ile, Cys, Ser, Thr, Asn, Gln, Asp, Glu, His, Lys, Arg, Gly, Pro, Trp, Tyr or Phe. The new amino acid (X) at a position corresponding to position 174 of SEQ ID NO: 1 may, for example, be a hydrophobic amino acid (i.e. Met, Ala, Leu or Ile). For example, the amino acid alteration at a position corresponding to position 174 of SEQ ID NO: 1 may substitute the amino acid of SEQ ID NO: 1 (i.e. V) for isoleucine (i.e. the amino acid alteration at a position corresponding to position 174 of SEQ ID NO: 1 is V174I).

The amino acid alteration at a position corresponding to position 601 of SEQ ID NO: 1 may, for example, be F601X. This refers to a substitution of the amino acid F at position 601 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 601.

The new amino acid (X) at a position corresponding to position 601 of SEQ ID NO: 1 may, for example, be Met, Ala, Val, Leu, Ile, Cys, Ser, Thr, Asn, Gln, Asp, Glu, His, Lys, Arg, Gly, Pro, Trp or Tyr. The new amino acid (X) at a position corresponding to position 601 of SEQ ID NO: 1 may, for example, be an aromatic acid (i.e. Trp, Tyr, Phe). For example, the amino acid alteration at a position corresponding to position 601 of SEQ ID NO: 1 may substitute the amino acid of SEQ ID NO: 1 (i.e. F) for tyrosine (i.e. the amino acid alteration at a position corresponding to position 601 of SEQ ID NO: 1 is F601Y).

The SHC/HAC enzyme variant may, for example, have one or more further amino acid alterations at positions corresponding to positions 77, 92, 129, 579, 601 and/or 605 of SEQ ID NO: 1. For example, the SHC/HAC enzyme variant may have one or more amino acid substitutions (e.g. conservative or non-conservative substitutions) at positions corresponding to positions 77, 92, 129, 579, 601 and/or 605 of SEQ ID NO: 1.

The amino acid alteration at a position corresponding to position 77 of SEQ ID NO: 1 may, for example, be T77X. This refers to a substitution of the amino acid T at position 77 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 77.

The new amino acid (X) at a position corresponding to position 77 of SEQ ID NO: 1 may, for example, be Met, Ala, Val, Leu, Ile, Cys, Ser, Asn, Gln, Asp, Glu, His, Lys, Arg, Gly, Pro, Trp, Tyr or Phe. For example, the amino acid alteration at a position corresponding to position 77 of SEQ ID NO: 1 may substitute the amino acid of SEQ ID NO: 1 (i.e. T) for a hydrophobic amino acid (i.e. Met, Ala, Val, Leu or Ile). For example, the amino acid alteration at a position corresponding to position 77 of SEQ ID NO: 1 may substitute the amino acid of SEQ ID NO: 1 (i.e. T) for alanine (i.e. the amino acid alteration at a position corresponding to position 77 of SEQ ID NO: 1 is T77A).

The amino acid alteration at a position corresponding to position 92 of SEQ ID NO: 1 may, for example, be I92X. This refers to a substitution of the amino acid I at position 92 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 92.

The new amino acid (X) at a position corresponding to position 92 of SEQ ID NO: 1 may, for example, be Met, Ala, Val, Leu, Cys, Ser, Thr, Asn, Gln, Asp, Glu, His, Lys, Arg, Gly, Pro, Trp, Tyr or Phe. For example, the amino acid alteration at a position corresponding to position 92 of SEQ ID NO: 1 may substitute the amino acid of SEQ ID NO: 1 (i.e. I) for a hydrophobic amino acid (i.e. Met, Ala, Val, Leu or Ile). For example, the amino acid alteration at a position corresponding to position 92 of SEQ ID NO: 1 may substitute the amino acid of SEQ ID NO: 1 (i.e. I) for valine (i.e. the amino acid alteration at a position corresponding to position 92 of SEQ ID NO: 1 is I92V).

The amino acid alteration at a position corresponding to position 129 of SEQ ID NO: 1 may, for example, be F129X. This refers to a substitution of the amino acid F at position 129 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 129.

The new amino acid (X) at a position corresponding to position 129 of SEQ ID NO: 1 may, for example, be Met, Ala, Val, Leu, Ile, Cys, Ser, Thr, Asn, Gln, Asp, Glu, His, Lys, Arg, Gly, Pro, Trp or Tyr. For example, the amino acid alteration at a position corresponding to position 129 of SEQ ID NO: 1 may substitute the amino acid of SEQ ID NO: 1 (i.e. F) for a hydrophobic amino acid (i.e. Met, Ala, Val, Leu or Ile). For example, the amino acid alteration at a position corresponding to position 129 of SEQ ID NO: 1 may substitute the amino acid of SEQ ID NO: 1 (i.e. F) for leucine (i.e. the amino acid alteration at a position corresponding to position 129 of SEQ ID NO: 1 is F129L).

The amino acid alteration at a position corresponding to position 579 of SEQ ID NO: 1 may, for example, be Q579X. This refers to a substitution of the amino acid Q at position 579 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 579.

The new amino acid (X) at a position corresponding to position 579 of SEQ ID NO: 1 may, for example, be Met, Ala, Val, Leu, Ile, Cys, Ser, Thr, Asn, Asp, Glu, His, Lys, Arg, Gly, Pro, Trp, Tyr or Phe. For example, the amino acid alteration at a position corresponding to position 579 of SEQ ID NO: 1 may substitute the amino acid of SEQ ID NO: 1 (i.e. Q) for a basic amino acid (i.e. His, Lys or Arg). For example, the amino acid alteration at a position corresponding to position 579 of SEQ ID NO: 1 may substitute the amino acid of SEQ ID NO: 1 (i.e. Q) for histidine (i.e. the amino acid alteration at a position corresponding to position 579 of SEQ ID NO: 1 is Q579H).

The amino acid alteration at a position corresponding to position 601 of SEQ ID NO: 1 may, for example, be F601X. This refers to a substitution of the amino acid F at position 601 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 601.

The new amino acid (X) at a position corresponding to position 601 of SEQ ID NO: 1 may, for example, be Met, Ala, Val, Leu, Ile, Cys, Ser, Thr, Asn, Gln, Asp, Glu, His, Lys, Arg, Gly, Pro, Trp or Tyr. The new amino acid (X) at a position corresponding to position 601 of SEQ ID NO: 1 may, for example, be an aromatic acid (i.e. Trp, Tyr, Phe). For example, the amino acid alteration at a position corresponding to position 601 of SEQ ID NO: 1 may substitute the amino acid of SEQ ID NO: 1 (i.e. F) for histidine (i.e. the amino acid alteration at a position corresponding to position 601 of SEQ ID NO: 1 is F601Y).

The amino acid alteration at a position corresponding to position 605 of SEQ ID NO: 1 may, for example, be F605X. This refers to a substitution of the amino acid F at position 605 of SEQ ID NO: 1 for any different amino acid (X). As noted above, since the SHC/HAC enzyme variants may additionally comprise insertions and/or deletions, the numbering of the new amino acid (X) in the new SHC/HAC enzyme variant may not be 605.

The new amino acid (X) at a position corresponding to position 605 of SEQ ID NO: 1 may, for example, be Met, Ala, Val, Leu, Ile, Cys, Ser, Thr, Asn, Gln, Asp, Glu, His, Lys, Arg, Gly, Pro, Trp or Tyr. The new amino acid (X) at a position corresponding to position 605 of SEQ ID NO: 1 may, for example, be an aromatic acid (i.e. Trp, Tyr, Phe). For example, the amino acid alteration at a position corresponding to position 605 of SEQ ID NO: 1 may substitute the amino acid of SEQ ID NO: 1 (i.e. F) for tryptophan (i.e. the amino acid alteration at a position corresponding to position 601 of SEQ ID NO: 1 is F605W).

For example, the SHC/HAC enzyme variant may have amino acid alterations (e.g. substitutions) at positions corresponding to positions 132 and 432 of SEQ ID NO: 1.

For example, the SHC/HAC enzyme variant may have an amino acid alteration (e.g. substitution) at a position corresponding to position 601 of SEQ ID NO: 1.

For example, the SHC/HAC enzyme variant may have amino acid alterations (e.g. substitutions) at positions corresponding to positions 77, 92 and 129 of SEQ ID NO: 1.

For example, the SHC/HAC enzyme variant may have amino acid alterations (e.g. substitutions) at positions corresponding to positions 579 and 601 of SEQ ID NO: 1.

For example, the SHC/HAC enzyme variant may have amino acid alterations (e.g. substitutions) at positions corresponding to positions 129, 132 and 432 of SEQ ID NO: 1.

For example, the SHC/HAC enzyme variant may have amino acid alterations (e.g. substitutions) at positions corresponding to positions 132, 432 and 601 of SEQ ID NO: 1.

For example, the SHC/HAC enzyme variant may have amino acid alterations (e.g. substitutions) at positions corresponding to positions 129, 132, 432 and 601 of SEQ ID NO: 1.

The new SHC/HAC enzyme variants may, for example, have increased enzymatic activity for the conversion of EEH to (−)-Ambrox or the conversion of BisEEH to Ambra oxide compared to the SHC/HAC enzyme of SEQ ID NO: 1 and/or the SHC/HAC enzyme variant of SEQ ID NO: 10. Increased enzymatic activity may refer to any aspect of the enzymatic conversion of EEH to (−)-Ambrox or enzymatic conversion of BisEEH to Ambra oxide including, for example, increased total conversion of EEH or BisEEH, increased rate of conversion of EEH or BisEEH (e.g. in the first 6 hours or in the first 12 hours of reaction), increased production of (−)-Ambrox or Ambra oxide, and decreased production of by-products. Increased enzymatic activity may be defined by increased productivity in general, which may be defined in terms of (−)-Ambrox or Ambra oxide produced per gram of biocatalyst, per hour and per liter of reaction.

The new SHC/HAC enzyme variants may, for example, provide increased EEH or E,E-bishomofarnesol (BisEEH) conversion compared to the SHC/HAC wild-type enzyme of SEQ ID NO: 1 and/or the Aac 215G2 SHC/HAC enzyme variant of SEQ ID NO: 10. Therefore, the process described herein may have an increased level of EEH or BisEEH conversion compared to the process using the SHC/HAC wild-type enzyme of SEQ ID NO: 1 and/or the SHC/HAC enzyme variant of SEQ ID NO: 10. The new SHC/HAC enzyme variants may, for example, provide increased rate of EEH or BisEEH conversion compared to the SHC/HAC wild-type enzyme of SEQ ID NO: 1 and/or the SHC/HAC enzyme variant of SEQ ID NO: 10. Therefore, the process described herein may have an increased rate of EEH or BisEEH conversion compared to the SHC/HAC wild-type enzyme of SEQ ID NO: 1 and/or the SHC/HAC enzyme variant of SEQ ID NO: 10. The new SHC/HAC enzyme variants may, for example, provide increased rate of EEH or BisEEH conversion over the first 4 hours or over the first 6 hours or over the first 8 hours or over the first 12 hours or over the first 24 hours of the reaction compared to the SHC/HAC wild-type enzyme of SEQ ID NO: 1 and/or the SHC/HAC enzyme variant of SEQ ID NO: 10. Therefore, the process described herein may have an increased rate of EEH or BisEEH conversion over the first 4 hours or over the first 6 hours or over the first 8 hours or over the first 12 hours or over the first 24 hours of the reaction compared to the SHC/HAC wild-type enzyme of SEQ ID NO: 1 and/or the SHC/HAC enzyme variant of SEQ ID NO: 10. This may be when compared to using both enzymes (i.e. the new Aac 215G2 SHC/HAC enzyme variant and the wild-type enzyme of SEQ ID NO: 1 or the 215G2 enzyme of SEQ ID NO: 10) under the same reaction conditions (e.g. same pH and temperature) or when compared to using each enzymes under their respective optimized reaction conditions (e.g. optimized pH and temperature) which may be different to each other.

For example, the new SHC/HAC enzyme variant may provide or the process may have at least about 40% EEH or BisEEH conversion in the first 12 hours of the reaction. For example, the new SHC/HAC enzyme variant may provide or the process may have at least about 45% or at least about 50% or at least about 55% or at least about 60% EEH or BisEEH conversion in the first 12 hours of the reaction. For example, the new SHC/HAC enzyme variant may provide or the process may have at least about 30% EEH or BisEEH conversion in the first 6 hours of the reaction. For example, the new SHC/HAC enzyme variant may provide or the process may have at least about 35% or at least about 45% or at least about 50% or at least about 55% EEH or BisEEH conversion in the first 12 hours of the reaction. This may be when compared to using both enzymes (i.e. the new SHC/HAC enzyme variant and the enzyme of SEQ ID NO: 1 or SEQ ID NO: 10) under the same reaction conditions (e.g. same pH and temperature) or when compared to using each enzymes under their respective optimized reaction conditions (e.g. optimized pH and temperature) which may be different to each other.

The conversion of EEH to (−)-Ambrox or the conversion of BisEEH to Ambra oxide may, for example, be determined using an activity assay as described above and may be calculated as gram of recoverable product per gram of feedstock (which can be calculated as a percent molar conversion rate).

As used herein, any reference herein to a 99%/100% conversion rate for a homofarnesol substrate to (−)-Ambrox is a reference to a 99%/100% conversion of the homofarnesol isomer (i.e. EEH) capable of conversion to (−)-Ambrox using a SHC/HAC enzyme or enzyme variant.

As used herein, any reference herein to a 99%/100% conversion rate for a bishomofarnesol substrate to Ambra oxide is a reference to a 99%/100% conversion of the bishomofarnesol isomer (i.e. BisEEH) capable of conversion to Ambra oxide using a SHC/HAC enzyme or enzyme variant.

The optimum temperature for the SHC/HAC enzyme variants of Aac 215G2 SHC/HAC may, for example, be equal to or greater than about 35° C. For example, the optimum temperature for the SHC/HAC enzyme variants of Aac 215G2 SHC/HAC may range from about 40° C. to about 50° C., for example from about 42° C. to about 48° C. or from about 44° C. to about 46° C. For example, the optimum temperature of the SHC/HAC enzyme variants of Aac 215G2 SHC/HAC may be about 45° C. The processes for making (−)-Ambrox or Ambra oxide disclosed herein may be carried out at the optimum temperature of the SHC/HAC enzyme variant.

The optimum pH for the SHC/HAC enzyme variants of Aac 215G2 SHC/HAC may, for example, be equal to or greater than about 5.4. For example, the optimum pH for the SHC/HAC enzyme variants of Aac 215G2 SHC/HAC may range from about 5.2 to about 6.0, for example from about 5.4 to about 5.8, for example from about 5.6 to about 5.8. For example, the optimum pH of the SHC/HAC enzyme variants of Aac 215G2 SHC/HAC may be about 5.6 or about 5.8. The processes for making (−)-Ambrox or Ambra oxide disclosed herein may be carried out at the optimum pH of the SHC/HAC enzyme variant.

The optimum concentration of sodium dodecyl sulfate (SDS) in the reaction medium of the process for making (−)-Ambrox or Ambra oxide disclosed herein may, for example, be from about 0.010 w/w % to about 0.10 w/w %. For example, the optimum concentration of SDS may be from about 0.040 w/w % to about 0.080 w/w %, for example about 0.050 w/w % when the substrate (e.g. EEH or BisEEH) is used at 4 g/l with cells to an $OD_{650nm}$ of 10. The optimum concentration of sodium dodecyl sulfate (SDS) in the reaction medium of the processes for making (−)-Ambrox or Ambra oxide disclosed herein may, for example, be from about 1.0 w/w % to about 1.5 w/w % when the substrate (e.g. EEH or BisEEH) is used at 125 g/l with 250 g/l of cells. For example, the optimum concentration of SDS may be from about 1.2 w/w % to about 1.4 w/w %, for example about 1.3 w/w % when the substrate (e.g. EEH or BisEEH) is used at 125 g/l with 250 g/l of cells.

The processes for making (−)-Ambrox or Ambra oxide disclosed herein may be carried out at the optimum temperature range or optimum temperature and/or the optimum pH range or optimum pH and/or the SDS optimum concentration range or optimum SDS concentration for the specific enzyme used, as set out in the Table 7 or 9 or 11 in the Examples below.

Other Variants with New Mutations at Positions Corresponding to Positions 81, 90, 172, 277, 431, 557 and/or 613 of SEQ ID NO: 1

As discussed above, it has surprisingly been found that SHC/HAC enzyme variants derived from an Aac SHC/HAC enzyme variant disclosed in WO 2016/170099 (the 215G2 SHC/HAC enzyme variant) provide improved enzymatic activity for the conversion of EEH to (−)-Ambrox and for the conversion of BisEEH to Ambra oxide. The new SHC/HAC enzyme variants have two or three amino acid alterations in addition to the amino acid substitutions already present in the 215G2 SHC/HAC enzyme variant.

It is expected that other SHC/HAC enzyme variants having one or more of the new mutations identified at positions 81, 90, 172, 277, 431, 557 and 613 of SEQ ID NO: 1 will also provide enzymatic activity (e.g. improved enzymatic activity) for the conversion of EEH to (−)-Ambrox or BisEEH to Ambra oxide.

In particular, it is expected that SHC/HAC enzyme variants derived from other non-Aac species but having one or more of the new amino acid alterations identified at positions 81, 90, 172, 277, 431, 557 and 613 of SEQ ID NO: 1 will also provide enzymatic activity for the conversion of EEH to (−)-Ambrox or BisEEH to Ambra oxide. In particular, it is expected that enzyme variants derived from ZmoSHC1, ZmoSHC2, BjpSHC, GmoSHC, TelSHC, ApaSHC1, BmeSHC, SalSHC, or ApaSHCA having one or more of the new amino acid alterations identified at positions 81, 90, 172, 277, 431, 557 and 613 of SEQ ID NO: 1 will also provide enzymatic activity for the conversion of EEH to (−)-Ambrox or BisEEH to Ambra oxide.

There is therefore provided herein a process for making (−)-Ambrox by enzymatically converting EEH to (−)-Ambrox. There is also provided herein a process for making Ambra oxide by enzymatically converting E,E-bishomofarnesol to Ambra oxide. These processes may use any wild-type SHC/HAC enzyme or enzyme variant described herein.

In addition, there is provided herein a SHC/HAC enzyme variant having at least about 70.0% identity to a wild-type SHC/HAC enzyme amino acid sequence, wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1.

In particular, there is provided herein a process for preparing (−)-Ambrox or a mixture comprising (−)-Ambrox, the process comprising enzymatically converting EEH or a mixture comprising EEH to (−)-Ambrox or a mixture comprising (−)-Ambrox using a SHC/HAC variant having at least about 70.0% identity to a wild-type SHC/HAC enzyme amino acid sequence, wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1.

In particular, there is provided herein a process for preparing Ambra oxide or a mixture comprising Ambra oxide, the process comprising enzymatically converting BisEEH or a mixture comprising BisEEH to Ambra oxide or a mixture comprising Ambra oxide using a SHC/HAC variant having at least about 70.0% identity to a wild-type SHC/HAC enzyme amino acid sequence, wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1.

The SHC/HAC enzyme variant may, for example, have an amino acid sequence having at least about 70.0% identity to a wild-type SHC/HAC enzyme amino acid sequence. For example, the SHC/HAC enzyme variant has an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to a wild-type SHC/HAC enzyme amino acid sequence.

For example, the SHC/HAC enzyme variant may, for example, have an amino acid sequence having less than 100% identity, for example equal to or less than about 99.5% or equal to or less than about 99.0% identity to a wild-type SHC/HAC enzyme amino acid sequence.

For example, the SHC/HAC enzyme variant may have from about 70.0% to about 99.5% or from about 80.0% to about 99.0% or from about 85.0% to about 98.5% or from about 90.0% to about 98.0% identity to a wild-type SHC/HAC enzyme amino acid sequence.

The wild-type SHC/HAC enzyme amino acid sequence may, for example, be that of AacSHC (SEQ ID NO: 1), ZmoSHC1 (SEQ ID NO: 11), ZmoSHC2 (SEQ ID NO: 12), BjpSHC (SEQ ID NO: 13), GmoSHC (SEQ ID NO: 14), TelSHC (SEQ ID NO: 19) or ApaSHC1 (SEQ ID NO: 20), BmeSHC (SEQ ID NO: 28), SalSHC (SEQ ID NO: 29), or ApaSHCA (SEQ ID NO: 30). In particular, the wild-type SHC/HAC enzyme amino acid sequence may be that of AacSHC (SEQ ID NO: 1).

Therefore, in certain embodiments, the SHC/HAC enzyme variant may have an amino acid sequence having at least about 70.0% identity to SEQ ID NO: 1, SEQ ID NO: 11, SEQ ID NO: 12, SEQ ID NO: 13, SEQ ID NO: 14, SEQ ID NO: 19 or SEQ ID NO: 20. For example, the SHC/HAC enzyme variant has an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.

For example, the SHC/HAC enzyme variant may, for example, have an amino acid sequence having less than 100% identity, for example equal to or less than about 99.5% or equal to or less than about 99.0% identity to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.

For example, the SHC/HAC enzyme variant may have from about 70.0% to about 99.5% or from about 80.0% to about 99.0% or from about 85.0% to about 98.5% or from about 90.0% to about 98.0% identity to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.

"Percent (%) identity" with respect to a polypeptide or nucleotide sequence is defined respectively as the percentage of amino acids or nucleotides in a candidate sequence that are identical with the amino acids or nucleotides in the reference sequence, after aligning the sequence and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) or the GAP program (mathematical algorithm of the University of Iowa) or the mathematical algorithm of Myers and Miller (1989—Cabios 4:11-17).

Percentage sequence identity may be calculated using, for example, BLAST, BLAT or BlastZ (or BlastX). A similar algorithm is incorporated into the BLASTN and BLASTP programs of Altschul et al (1990) J. Mol. Biol. 215, 403-410. BLAST polynucleotide searches may be performed with the BLASTN program, score=100, word length=12, to obtain polynucleotide sequences that are homologous to those nucleic acids which encode the relevant protein. BLAST protein searches may be performed with the BLASTP program, score=50, word length=3, to obtain amino acid sequences homologous to the polypeptide.

To obtain gapped alignments for comparative purposes, Gapped BLAST may be utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

In certain embodiments, the SHC/HAC enzyme variant may have equal to or less than about 200 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the SHC/HAC enzyme variant may have equal to or less than about 150 or equal to or less than about 120 or equal to or less than about 100 or equal to or less than about 95 or equal to or less than about 90 or equal to or less than about 85 or equal to or less than about 80 or equal to or less than about 75 or equal to or less than about 70 or equal to or less than about 65 or equal to or less than about 60 or equal to or less than about 55 or equal to or less than about 50 or equal to or less than about 45 or equal to or less than about 40 or equal to or less than about 35 or equal to or less than about 30 or equal to or less than about 25 or equal to or less than about 20 or equal to or less than about 15 or equal to or less than about 10 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.

The SHC/HAC enzyme variant may, for example, have at least about 1 or at least about 2 or at least about 3 or at least about 4 or at least about 5 or at least about 6 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.

For example, the SHC/HAC enzyme variant may have from about 1 to about 30 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19 or SEQ ID NO: 20. For example, the SHC/HAC enzyme variant may have from about 2 to about 25 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20 or SEQ ID NO: 28, SEQ ID NO: 29, or SEQ ID NO: 30. For example, the SHC/HAC enzyme variant may have from about 3 to about 20 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the SHC/HAC enzyme variant may have from about 4 to about 15 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the SHC/HAC enzyme variant may have from about 5 to about 10 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30.

The amino acid alterations may, for example, be insertions, deletions and/or substitutions as described above. For example, the amino acid alterations may be substitutions, for example, non-conservative substitutions.

In certain embodiments, the only amino acid alterations compared to the wild-type SHC/HAC enzyme (e.g. compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30) are substitutions (i.e. there are no insertions or deletions).

Amino acid alterations are defined relative to a reference sequence. An amino acid alteration relative to a reference sequence means that the amino acid sequence of the variant sequence is different to the reference sequence.

Amino acids in the reference sequence and the variant sequence may be assigned a number, where the numbering starts with the amino acid at the N-terminus of the polypeptide (i.e. the amino acid at the N-terminus of the polypeptide is numbered 1, the next amino acid is numbered 2 etc.). The "position" of a reference sequence refers to a specific amino acid residue present in the reference sequence as identified by the specific numbering of the amino acids in the reference sequence. The "position" of a variant sequence refers to a specific amino acid residue present in the variant sequence as identified by the specific numbering of the amino acids in the variant sequence.

Since the variant sequence may include deletions or insertions compared to the reference sequence, the amino acids in the variant sequence may be numbered differently to the same amino acids in the reference sequence. By way of example, if an amino acid is inserted between amino acids 131 and 132 of SEQ ID NO: 1, the amino acid following the insertion will have the numbering 133 in the variant sequence while it retains the numbering 132 in the reference sequence. In this example, the position of the variant sequence that corresponds to position 132 of the reference sequence is position 133. Therefore, amino acids in the variant sequence that have been retained from the reference sequence may be defined by referring to the "corresponding position" of the reference sequence. In other words, a "position" in the variant sequence may be defined by reference to a "corresponding position" in the reference sequence. In particular, substitutions in the variant sequence compared to the reference sequence may be defined by referring to the "corresponding position" of the reference sequence in spite of any insertions and/or deletions in the reference sequence. Where the amino acids of a reference sequence have been deleted, there is no "corresponding position" in the variant sequence. Where there are no insertions or deletions compared to the reference sequence (i.e. there are only substitutions), the "corresponding position" of the reference sequence will be the same as the position in the variant sequence.

Wild-type SHC/HAC enzymes from different species have different polypeptide lengths. The wild-type sequences may be aligned using algorithms as described above in order to identify "corresponding positions" in two different wild-type SHC/HAC enzymes. Therefore, the amino acid at a position of the variant sequence corresponding to a position in a reference sequence may, for example, be a different amino acid residue and/or may have a different number to that of the reference sequence. By way of example, the amino acid M at position 132 of AacSHC (SEQ ID NO: 1) may correspond to the amino acid Y at position 185 of ZmoSHC1 (SEQ ID NO: 11).

The amino acid alteration may therefore be defined relative to two different reference sequences. For example, the amino acid alteration may be a change compared to a first reference sequence (e.g. a wild-type SHC/HAC enzyme sequence from which the variant is derived) and the position of the amino acid alteration in the variant sequence may be defined by reference to a second reference sequence (e.g. the AacSHC (SEQ ID NO: 1)). Thus, the amino acid alteration in the SHC/HAC enzyme variant may be relative to a first wild-type SHC/HAC enzyme at a position defined by reference to a second wild-type SHC/HAC enzyme.

The SHC/HAC enzyme variant amino acid sequence has one or more amino acid alterations relative to the wild-type SHC/HAC enzyme amino acid sequence at a position selected from positions corresponding to positions 81, 90, 172, 277, 431, 557 and 613 of SEQ ID NO: 1. For example, the amino acid alterations may be at one or more positions selected from positions corresponding to positions 81, 431, 557 and 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

In certain embodiments, the SHC/HAC enzyme variant amino acid sequence has an amino acid alteration relative to the wild-type SHC/HAC enzyme amino acid sequence at a position corresponding to position 557 of SEQ ID NO: 1 and at least one position corresponding to position 81, 431 or 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

For example, the SHC/HAC enzyme variant amino acid sequence may have an amino acid alteration relative to a wild-type SHC/HAC enzyme amino acid sequence at a position corresponding to position 557 of SEQ ID NO: 1 and one position corresponding to position 81, 431 or 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

For example, the SHC/HAC enzyme variant amino acid sequence may have amino acid alterations relative to a wild-type SHC/HAC enzyme amino acid sequence at a position corresponding to position 557 of SEQ ID NO: 1 and two positions selected from positions corresponding to positions 81, 431 and 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

For example, the SHC/HAC enzyme variant amino acid sequence may have amino acid alterations relative to a wild-type SHC/HAC enzyme amino acid sequence at a position corresponding to position 557 of SEQ ID NO: 1 and all positions corresponding to positions 81, 431 and 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

For example, the SHC/HAC enzyme variant amino acid sequence has amino acid alterations relative to the wild-type SHC/HAC enzyme amino acid sequence at positions corresponding to positions 90 and 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

For example, the SHC/HAC enzyme variant amino acid sequence has amino acid alterations relative to the wild-type SHC/HAC enzyme amino acid sequence at positions corresponding to positions 172 and 277 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the wild-type sequence may be SEQ ID NO: 1.

For example, the SHC/HAC enzyme variant amino acid sequence has amino acid alterations relative to the wild-type SHC/HAC enzyme amino acid sequence at positions corresponding to positions 557 and 431 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30. For example, the wild-type sequence may be SEQ ID NO: 1.

For example, the SHC/HAC enzyme variant amino acid sequence has amino acid alterations relative to the wild-type SHC/HAC enzyme amino acid sequence at positions corresponding to positions 557 and 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the wild-type sequence may be SEQ ID NO: 1.

For example, the SHC/HAC enzyme variant amino acid sequence has amino acid alterations relative to the wild-type SHC/HAC enzyme amino acid sequence at positions corresponding to positions 81, 557 and 613 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the wild-type sequence may be SEQ ID NO: 1.

For example, the SHC/HAC enzyme variant amino acid sequence has amino acid alterations relative to the wild-type SHC/HAC enzyme amino acid sequence at positions corresponding to positions 81, 431 and 557 of SEQ ID NO: 1. The amino acid alterations may, for example, be substitutions, for example non-conservative substitutions. The wild-type SHC/HAC enzyme amino acid sequence may, for example, be SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the wild-type sequence may be SEQ ID NO: 1.

The amino acid alteration relative to the wild-type SHC/HAC enzyme amino acid sequence at a position corresponding to position 557 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 557.

The new amino acid (X) in the SHC/HAC enzyme variant amino acid sequence at a position corresponding to position 557 of SEQ ID NO: 1 may, for example, be Met, Val, Leu, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a neutral hydrophilic amino acid (i.e. Cys, Ser, Thr, Asn or Gln). For example, the new amino acid in the SHC/HAC enzyme variant may be threonine.

The amino acid alteration relative to the wild-type SHC/HAC enzyme amino acid sequence at a position corresponding to position 81 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) may not be 81.

The new amino acid (X) in the SHC/HAC enzyme variant amino acid sequence at a position corresponding to position 81 of SEQ ID NO: 1 may, for example, be Met, Ala, Val, Leu, Ile, Cys, Ser, Thr, Asn, Gln, Asp, Glu, His, Lys, Arg, Gly, Pro, Trp, or Phe. For example, the new amino acid (X) in the SHC/HAC enzyme variant may be a basic amino acid (i.e. His, Lys or Arg). For example, the new amino acid in the SHC/HAC enzyme variant may be histidine.

The amino acid alteration relative to the wild-type SHC/HAC enzyme amino acid sequence at a position corresponding to position 90 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 90.

The new amino acid (X) in the SHC/HAC enzyme variant amino acid sequence at a position corresponding to position 90 of SEQ ID NO: 1 may, for example, be Met, Ala, Val, Leu, Ile, Cys, Ser, Asn, Gln, Asp, Glu, His, Lys, Arg, Gly, Pro, Trp, Tyr or Phe. For example, the new amino acid (X) in the SHC/HAC enzyme variant may be a hydrophobic amino acid (i.e. Met, Ala, Val, Leu, Ile). For example, the new amino acid in the SHC/HAC enzyme variant may be alanine.

The amino acid alteration relative to the wild-type SHC/HAC enzyme amino acid sequence at a position corresponding to position 172 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 172.

The new amino acid (X) in the SHC/HAC enzyme variant amino acid sequence at a position corresponding to position 172 of SEQ ID NO: 1 may, for example, be Met, Val, Leu, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a neutral hydrophilic amino acid (i.e. Cys, Ser, Thr, Asn, Gln). For example, the new amino acid in the SHC/HAC enzyme variant may be threonine.

The amino acid alteration relative to the wild-type SHC/HAC enzyme amino acid sequence at a position corresponding to position 277 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 277.

The new amino acid (X) in the SHC/HAC enzyme variant amino acid sequence at a position corresponding to position 277 of SEQ ID NO: 1 may, for example, be Ala, Val, Leu, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a basic amino acid (i.e. His, Lys, Arg). For example, the new amino acid in the SHC/HAC enzyme variant may be lysine.

The amino acid alteration relative to the wild-type SHC/HAC enzyme amino acid sequence at a position corresponding to position 431 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) may not be 431.

The new amino acid (X) in the SHC/HAC enzyme variant amino acid sequence at a position corresponding to position 431 of SEQ ID NO: 1 may, for example, be Met, Ala, Val, Leu, Ile, Cys, Ser, Thr, Asn, Gin, Asp, Glu, Lys, Arg, Gly, Pro, Trp, Tyr or Phe. For example, the new amino acid (X) in the SHC/HAC enzyme variant may be a hydrophobic amino acid (i.e. Met, Ala, Val, Leu or Ile). For example, the new amino acid in the SHC/HAC enzyme variant may be leucine.

The amino acid alteration relative to the wild-type SHC/HAC enzyme amino acid sequence at a position corresponding to position 613 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) may not be 613.

The new amino acid (X) in the SHC/HAC enzyme variant amino acid sequence at a position corresponding to position 613 of SEQ ID NO: 1 may, for example, be Met, Ala, Val, Leu, Ile, Cys, Ser, Thr, Asn, Gln, Asp, Glu, His, Lys, Gly, Pro, Trp, Tyr or Phe. For example, the new amino acid (X) in the SHC/HAC enzyme variant may be a neutral hydrophilic amino acid (i.e. Cys, Ser, Thr, Asn or Gln). For example, the new amino acid in the SHC/HAC enzyme variant may be serine.

Figure 9A:
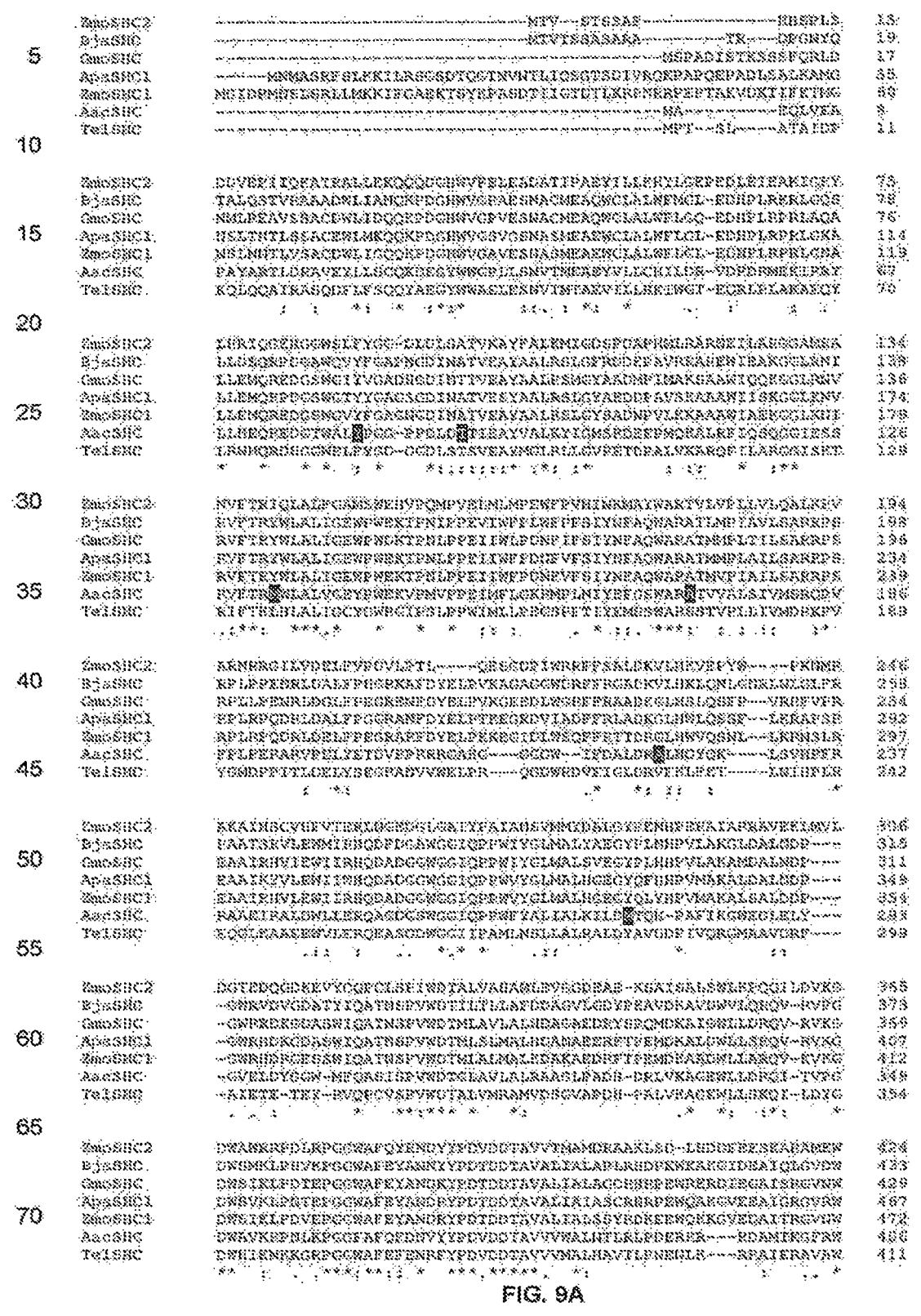
Figure 9B:
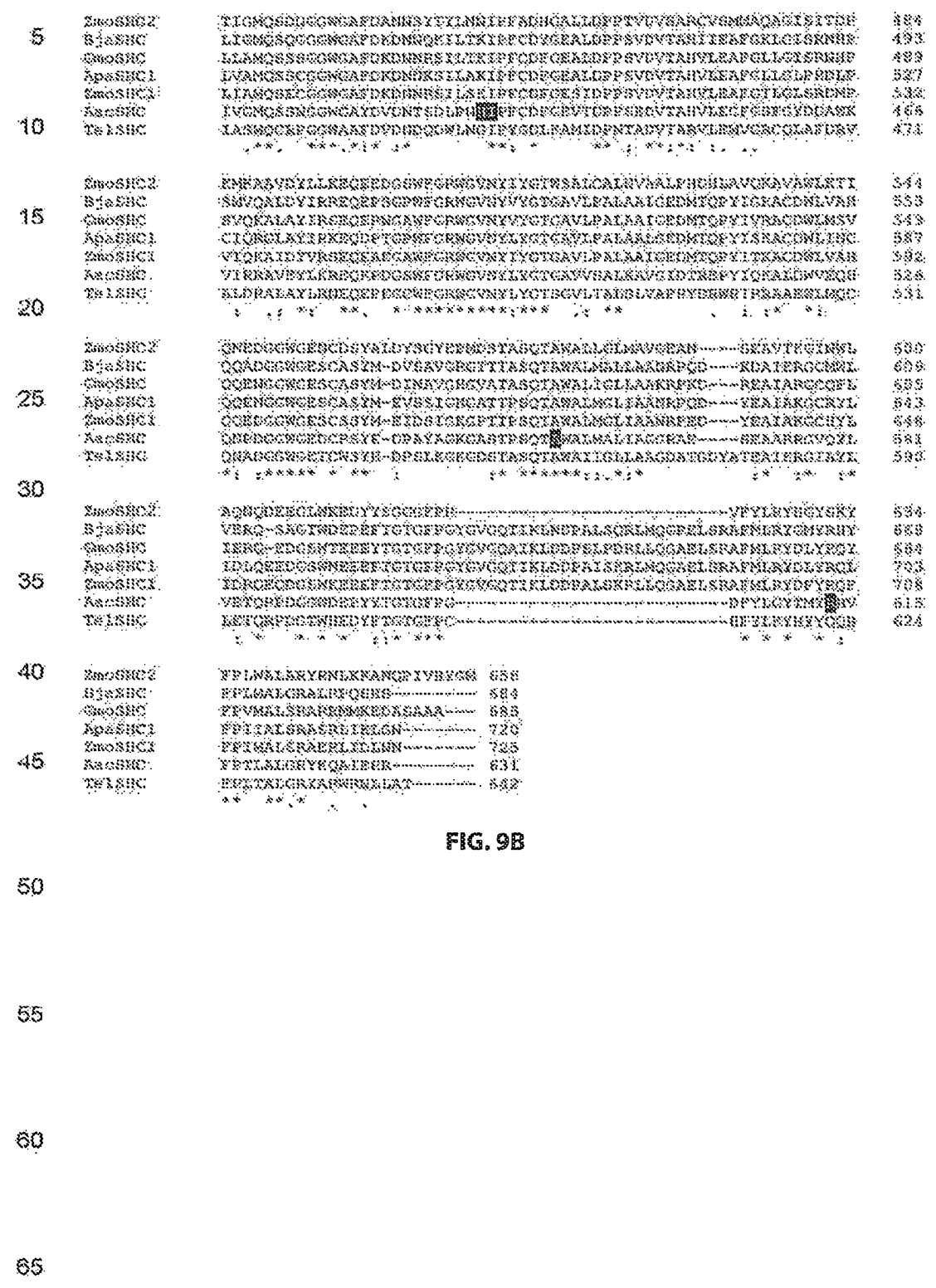
Figure 9C:
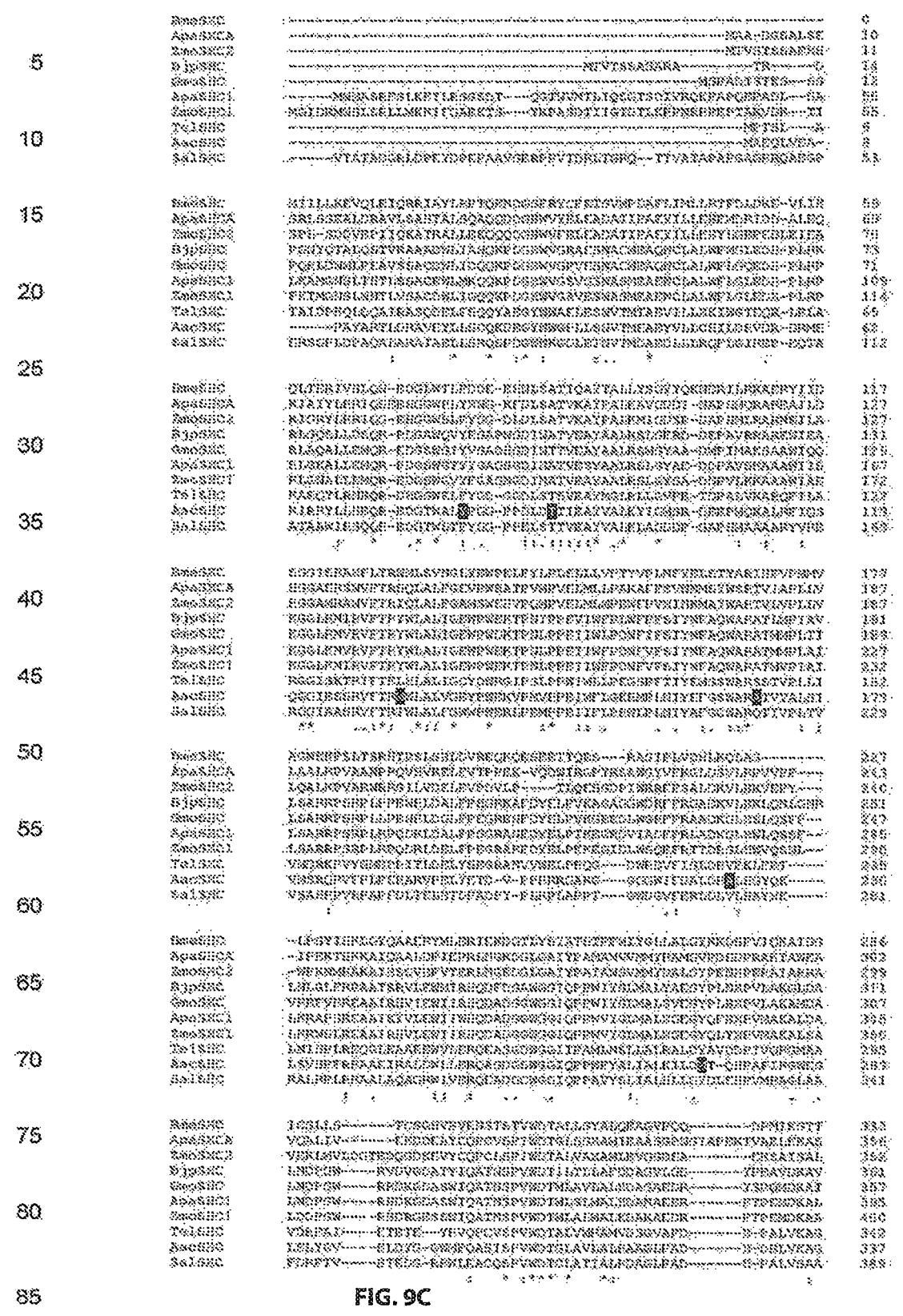
Figure 9D:
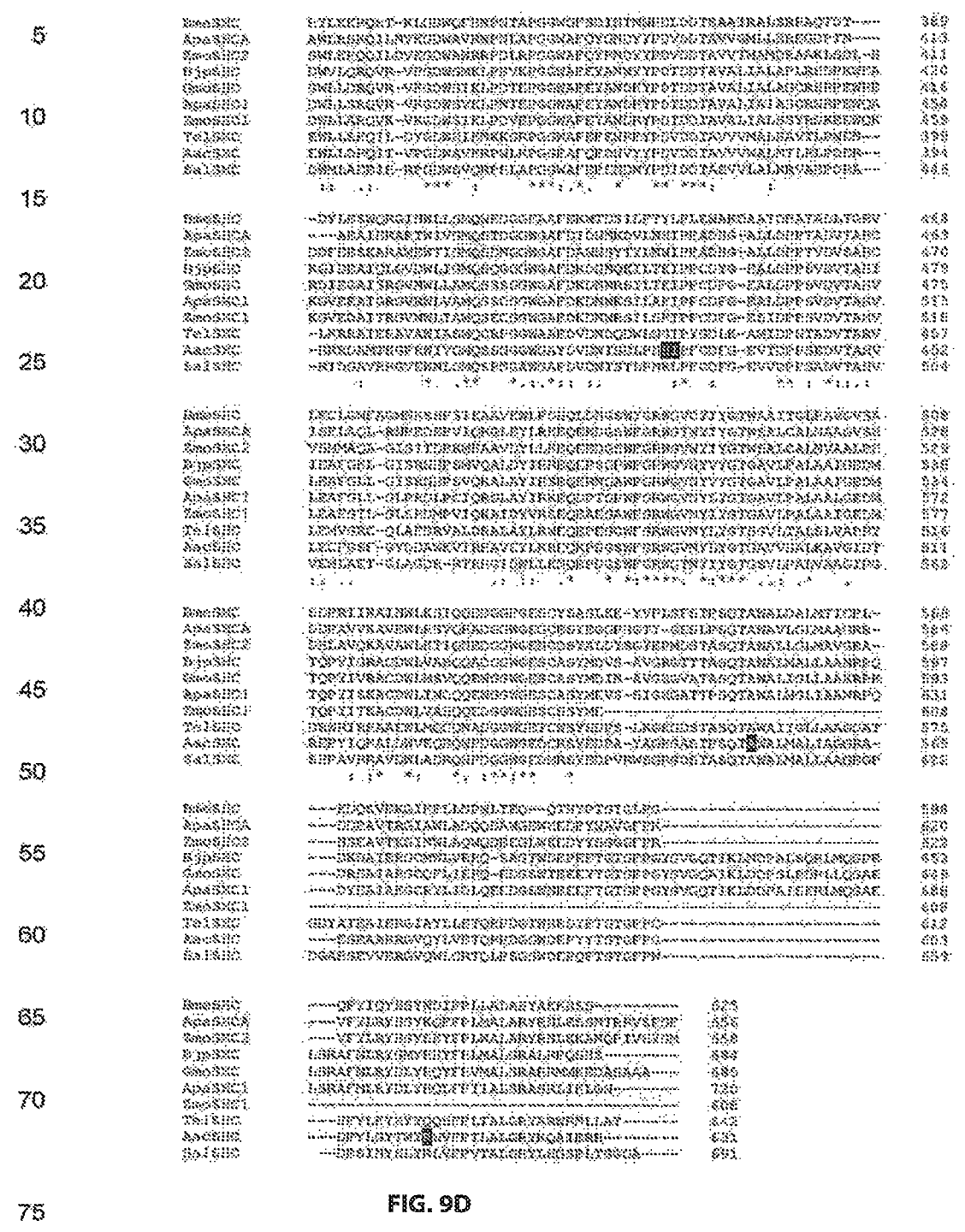

The amino acids and positions in the wild-type ZmoSHC1, ZmoSHC2, BjpSHC, GmoSHC, TelSHC and ApaSHC1 sequences (SEQ ID NOs: 11, 12, 13, 14, 19 and 20 respectively) that correspond to the amino acids of AacSHC (SEQ ID NO: 1) (e.g. the amino acids at positions 81, 431, 557 and 613 of AacSHC) are shown in FIG. 9A. The amino acids and positions in the wild-type ZmoSHC1, ZmoSHC2, BjpSHC, GmoSHC, TelSHC, ApaSHC1, BmeSHC, SalSHC and ApaSHCA sequences (SEQ ID NOs: 11, 12, 13, 14, 19, 20, 28, 29 and 30 respectively) that correspond to the amino acids of AacSHC (SEQ ID NO: 1) (e.g. the amino acids at positions 81, 431, 557 and 613 of AacSHC) are shown in FIG. 9B.

Amino acid positions 81, 90, 132, 224, 172, 277, 431, 432, 557 and 613 in wild-type AacSHC are highlighted with a white letter on a black background. The amino acids directly above or below the highlighted amino acid are therefore the amino acids and positions in ZmoSHC2, BjaSHC, GmoSHC, ApaSHC1, ApaSHC1, ZmoSHC1 and TelSHC that correspond to positions 81, 90, 132, 224, 172, 277, 431, 432, 557 and 613 of AacSHC (SEQ ID NO: 1). For example, the amino acid in BjaSHC, GmoSHC, ApaSHC1 and ZmoSHC1 that corresponds to the amino acid Y a position 81 of AacSHC (SEQ ID NO: 1) is Y. The amino acid in ZmoSHC2 and TelSHC that corresponds to the amino acid Y at position 81 of AacSHC (SEQ ID NO: 1) is F. Position 84 of TelSHC is the position of TelSHC that corresponds to position 81 of AacSHC (SEQ ID NO: 1).

In certain embodiments, one or more of the original amino acid alterations in the 215G2 SHC/HAC enzyme variant (compared to wild-type Aac SHC (SEQ ID NO: 1)) may be retained in the new SHC/HAC enzyme variants described herein. The amino acid alterations in the 215G2 SHC/HAC enzyme variant compared to wild-type Aac SHC were the substitutions M132R, A224V and I432T (i.e. a substitution of the M residue at position 132 for an R residue, a substitution of the A residue at position 224 for a V residue, and a substitution of the I residue at position 432 for a T residue).

Therefore, the SHC/HAC enzyme variant amino acid sequence may have one or more amino acid alterations relative to the wild-type SHC/HAC enzyme amino acid sequence at positions corresponding to positions 132, 224 and 432 of SEQ ID NO: 1. The amino acid alterations may, for example, be substitutions.

For example, the SHC/HAC enzyme variant amino acid sequence may have one, two, or three amino acid alterations relative to the wild-type SHC/HAC enzyme amino acid sequence at positions selected to positions corresponding to positions 132, 224 and 432 of SEQ ID NO: 1.

For example, the SHC/HAC enzyme variant amino acid sequence may have amino acid alterations relative to the wild-type SHC/HAC enzyme amino acid sequence at positions corresponding to positions 132 and 432 of SEQ ID NO: 1.

For example, the SHC/HAC enzyme variant amino acid sequence may have amino acid alterations relative to the wild-type SHC/HAC enzyme amino acid sequence at positions corresponding to positions 132, 224 and 432 of SEQ ID NO: 1.

The amino acid alteration relative to the wild-type SHC/HAC enzyme amino acid sequence at a position corresponding to position 132 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 132.

The new amino acid (X) in the SHC/HAC enzyme variant amino acid sequence at a position corresponding to position 132 of SEQ ID NO: 1 may, for example, be Ala, Val, Leu, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a basic amino acid (i.e. His, Lys or Arg). For example, the new amino acid in the SHC/HAC enzyme variant may be arginine.

The amino acid alteration relative to the wild-type SHC/HAC enzyme amino acid sequence at a position corresponding to position 224 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 224.

The new amino acid (X) in the SHC/HAC enzyme variant amino acid sequence at a position corresponding to position 224 of SEQ ID NO: 1 may, for example, be Met, Val, Leu, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a hydrophobic amino acid (i.e. Met, Val, Leu or Ile). For example, the new amino acid in the SHC/HAC enzyme variant may be valine.

The amino acid alteration relative to the wild-type SHC/HAC enzyme amino acid sequence at a position corresponding to position 432 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 432.

The new amino acid (X) in the SHC/HAC enzyme variant amino acid sequence at a position corresponding to position 432 of SEQ ID NO: 1 may, for example, be Met, Ala, Val, Leu, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a neutral hydrophilic amino acid (i.e. Cys, Ser, Thr, Asn or Gln). For example, the new amino acid in the SHC/HAC enzyme variant may be threonine.

The amino acids and positions in the wild-type ZmoSHC1, ZmoSHC2, BjpSHC, GmoSHC, TelSHC and ApaSHC1 sequences (SEQ ID NOs: 11, 12, 13, 14, 19 and 20 respectively) that correspond to the amino acids of AacSHC (SEQ ID NO: 1) (e.g. at positions 132, 224 and 432 of AacSHC) are shown in FIG. 9.

The SHC/HAC enzyme variants described herein may, for example, additionally have one or more other amino acid alterations (e.g. substitutions) at the other positions of AacSHC identified in WO 2016/170099.

Therefore, the SHC/HAC enzyme variants described herein may have one or more further amino acid alterations compare to the wild-type SHC/HAC enzyme at positions corresponding to positions 77, 92, 129, 579, 601 and/or 605 of SEQ ID NO: 1. For example, the SHC/HAC enzyme variant may have one or more amino acid substitutions relative to the wild-type SHC/HAC enzyme (e.g. conservative or non-conservative substitutions) at positions corresponding to positions 77, 92, 129, 579, 601 and/or 605 of SEQ ID NO: 1.

The amino acid alteration at a position relative to the wild-type SHC/HAC enzyme amino acid sequence at a position corresponding to position 77 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 77.

The new amino acid (X) in the SHC/HAC enzyme variant amino acid sequence at a position corresponding to position 77 of SEQ ID NO: 1 may, for example, be Met, Ala, Val, Leu, Ile, Cys, Ser, Asn, Gln, Asp, Glu, His, Lys, Arg, Gly, Pro, Trp, Tyr or Phe. For example, the new amino acid (X) in the SHC/HAC enzyme variant may be a hydrophobic amino acid (i.e. Met, Ala, Val, Leu or Ile). For example, the new amino acid in the SHC/HAC enzyme variant may be alanine.

The amino acid alteration at a position relative to the wild-type SHC/HAC enzyme amino acid sequence at a position corresponding to position 92 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 92.

The new amino acid (X) in the SHC/HAC enzyme variant amino acid sequence at a position corresponding to position 92 of SEQ ID NO: 1 may, for example, be Met, Ala, Val, Leu, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a hydrophobic amino acid (i.e. Met, Ala, Val, Leu or Ile). For example, the new amino acid in the SHC/HAC enzyme variant may be valine.

The amino acid alteration at a position relative to the wild-type SHC/HAC enzyme amino acid sequence at a position corresponding to position 129 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 129.

The new amino acid (X) in the SHC/HAC enzyme variant amino acid sequence at a position corresponding to position 129 of SEQ ID NO: 1 may, for example, be Met, Ala, Val, Leu, Ile, Cys, Ser, Thr, Asn, Gin, Asp, Glu, His, Lys, Arg, Gly, Pro, Trp, or Tyr. For example, the new amino acid (X) in the SHC/HAC enzyme variant may be a hydrophobic amino acid (i.e. Met, Ala, Val, Leu or Ile). For example, the new amino acid in the SHC/HAC enzyme variant may be leucine.

The amino acid alteration at a position relative to the wild-type SHC/HAC enzyme amino acid sequence at a position corresponding to position 579 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 579.

The new amino acid (X) in the SHC/HAC enzyme variant amino acid sequence at a position corresponding to position 579 of SEQ ID NO: 1 may, for example, be Met, Ala, Val, Leu, Ile, Cys, Ser, Thr, Asn, Asp, Glu, His, Lys, Arg, Gly, Pro, Trp, Tyr or Phe. For example, the new amino acid (X) in the SHC/HAC enzyme variant may be a basic amino acid (i.e. His, Lys, Arg). For example, the new amino acid in the SHC/HAC enzyme variant may be histidine.

The amino acid alteration at a position relative to the wild-type SHC/HAC enzyme amino acid sequence at a position corresponding to position 601 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 601.

The new amino acid (X) in the SHC/HAC enzyme variant amino acid sequence at a position corresponding to position 601 of SEQ ID NO: 1 may, for example, be Met, Ala, Val, Leu, Ile, Cys, Ser, Thr, Asn, Gln, Asp, Glu, His, Lys, Arg, Gly, Pro, Trp or Tyr. For example, the new amino acid (X) in the SHC/HAC enzyme variant may be an aromatic amino acid (i.e. Trp, Tyr, Phe). For example, the new amino acid in the SHC/HAC enzyme variant may be tyrosine.

The amino acid alteration at a position relative to the wild-type SHC/HAC enzyme amino acid sequence at a position corresponding to position 605 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 605.

The new amino acid (X) in the SHC/HAC enzyme variant amino acid sequence at a position corresponding to position 605 of SEQ ID NO: 1 may, for example, be Met, Ala, Val, Leu, Ile, Cys, Ser, Thr, Asn, Gln, Asp, Glu, His, Lys, Arg, Gly, Pro, Trp or Tyr. For example, the new amino acid (X) in the SHC/HAC enzyme variant may be an aromatic amino acid (i.e. Trp, Tyr, Phe). For example, the new amino acid in the SHC/HAC enzyme variant may be tryptophan.

The amino acid positions in wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13) and wild-type GmoSHC (SEQ ID NO: 14) sequences that correspond to the amino acid positions 81, 90, 132, 224, 172, 277, 431, 432, 557 and 613 in wild-type AacSHC are highlighted with a white letter on a black background in wild type AacSHC (SEQ ID NO: 1) in FIG. 9A.

The amino acid positions in wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13), wild-type GmoSHC (SEQ ID NO: 14), wild-type Bme SHC (SEQ ID NO: 28), wild-type SalSHC (SEQ ID NO: 29) and wild-type ApaSHCA (SEQ ID NO: 30) that correspond to amino acid positions 81, 90, 132, 224, 172, 277, 431, 432, 557 and 613 in wild-type AacSHC are highlighted with a white letter on a black background in wild type AacSHC (SEQ ID NO: 1) in FIG. 9B.

The SHC/HAC enzyme variant may, for example, have one or more further amino acid alterations relative to the wild-type SHC/HAC enzyme amino acid sequence at positions corresponding to positions 37, 174 and/or 601 of SEQ ID NO: 1. For example, the SHC/HAC enzyme variant may have one or more amino acid substitutions (e.g. conservative or non-conservative) relative to the wild-type SHC/HAC enzyme amino acid sequence at positions corresponding to positions 37, 174 and/or 601 of SEQ ID NO: 1.

The amino acid alteration relative to the wild-type SHC/HAC enzyme amino acid sequence at a position corresponding to position 37 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) may not be 37.

The new amino acid (X) in the SHC/HAC enzyme variant amino acid sequence at a position corresponding to position 37 of SEQ ID NO: 1 may, for example, be Met, Ala, Val, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a neutral hydrophilic amino acid (i.e. Cys, Ser, Thr, Asn or Gln), for example glutamine.

The amino acid alteration relative to the wild-type SHC/HAC enzyme amino acid sequence at a position corresponding to position 174 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) may not be 174.

The new amino acid (X) in the SHC/HAC enzyme variant amino acid sequence at a position corresponding to position 174 of SEQ ID NO: 1 may, for example, be Met, Ala, Leu, Ile, Cys, Ser, Thr, Asn, Gln, Asp, Glu, His, Lys, Arg, Gly, Pro, Trp, Tyr or Phe. For example, the new amino acid (X) in the SHC/HAC enzyme variant may be a hydrophobic amino acid (i.e. Met, Ala, Val, Leu or Ile), for example isoleucine.

The amino acid alteration relative to the wild-type SHC/HAC enzyme amino acid sequence at a position corresponding to position 601 of SEQ ID NO: 1 may, for example, be a substitution of the amino acid of the wild-type SHC/HAC enzyme for a different amino acid (X). As noted above, since the wild-type sequence may have a different length to SEQ ID NO: 1 and since the variant may additionally comprise insertions and/or deletions, the numbering of the new amino acid (X) may not be 601.

The new amino acid (X) in the SHC/HAC enzyme variant amino acid sequence at a position corresponding to position 601 of SEQ ID NO: 1 may, for example, be Met, Ala, Leu, Val, Ile, Cys, Ser, Thr, Asn, Gln, Asp, Glu, His, Lys, Arg, Gly, Pro, Trp or Tyr. For example, the new amino acid (X) in the SHC/HAC enzyme variant may be an aromatic amino acid (i.e. Trp, Tyr, Phe), for example tyrosine.

The amino acid positions in wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13) and wild-type GmoSHC (SEQ ID NO: 14) sequences that correspond to the amino acid positions 81, 90, 132, 224, 172, 277, 431, 432, 557 and 613 in wild-type AacSHC are highlighted with a white letter on a black background in wild type AacSHC (SEQ ID NO: 1) in FIG. 9A.

The amino acid positions in wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13), wild-type GmoSHC (SEQ ID NO: 14), wild-type Bme SHC (SEQ ID NO; 28), wild-type SalSHC (SEQ ID NO: 29) and wild-type ApaSHCA (SEQ ID NO: 30) that correspond to amino acid positions 81, 90, 132, 224, 172, 277, 431, 432, 557 and 613 in wild-type AacSHC are highlighted with a white letter on a black background in wild type AacSHC (SEQ ID NO: 1) in FIG. 9B.

Any combination of the amino acid alterations described herein is envisaged. In particular, combinations of amino acid alterations at positions corresponding to the combinations of amino acid alterations identified in AacSHC herein and in WO 2016/17009 are envisaged.

In certain embodiments, the SHC/HAC enzyme variant is identical to SEQ ID NO: 1 except for the following amino acid substitutions:

(i) M132R, A224V, I432T, A557T and H4331L (SEQ ID NO: 2); or (ii) M132R, A224V, I432T, A557T and R613S (SEQ ID NO: 3); or (iii) M132R, A224V, I432T, A557T, Y81H and R613S (SEQ ID NO: 4); or (iv) M132R, A224V, I432T, A557T, Y81H and H431L (SEQ ID NO: 5); or (v) M132R, A224V, I432T, T90A and R613S (SEQ ID NO: 17); or (vi) M132R, A224V, I432T, A172T and M277K (SEQ ID NO: 18).

The new SHC/HAC enzyme variants may, for example, have increased enzymatic activity for the conversion of EEH to (−)-Ambrox or conversion of BisEEH to Ambra oxide compared to the 215G2 SHC enzyme. Increased enzymatic activity may refer to any aspect of the enzymatic conversion of EEH to (−)-Ambrox or enzymatic conversion of BisEEH to Ambra oxide including, for example, increased total conversion of EEH or BisEEH, increased rate of conversion of EEH or BisEEH (e.g. in the first 6 hours or in the first 12 hours of reaction), increased production of (−)-Ambrox or Ambra oxide, and decreased production of by-products. Increased enzymatic activity may translate into increased productivity in general, which may be defined in terms of (−)-Ambrox or Ambra oxide produced per liter of reaction capacity and per hour of bioconversion time, or (−)-Ambrox or Ambra oxide produced per liter of reaction capacity per hour of reaction time (i.e. time after the substrate was added) and per gram of biocatalyst used in the reaction.

The new SHC/HAC enzyme variants may, for example, provide increased EEH or BisEEH conversion compared to the 215G2 SHC enzyme. Therefore, the process described herein may have an increased level of EEH or BisEEH conversion compared to the process using the 215G2 SHC enzyme. The new SHC/HAC enzyme variants may, for example, provide increased rate of EEH or BisEEH conversion compared to the 215G2 SHC enzyme. Therefore, the process described herein may have an increased rate of EEH or BisEEH conversion compared to the 215G2 SHC enzyme.

The new SHC/HAC enzyme variants may, for example, provide increased rate of EEH or BisEEH conversion over the first 4 hours or over the first 6 hours or over the first 8 hours or over the first 12 hours or over the first 24 hours of the reaction compared to the 215G2 SHC enzyme. Therefore, the process described herein may have an increased rate of EEH or BisEEH conversion over the first 4 hours or over the first 6 hours or over the first 8 hours or over the first 12 hours or over the first 24 hours of the reaction compared to the 215G2 SHC enzyme. This may be when compared to using both enzymes (i.e. the new SHC/HAC enzyme variant and the 215G2 SHC enzyme) under the same reaction conditions (e.g. same pH and temperature) or when compared to using each enzymes under their optimized reaction conditions (e.g. optimized pH and temperature) which may be different to each other.

For example, the new SHC/HAC enzyme variant may convert or the process may permit at least about 40% EEH or BisEEH conversion in the first 12 hours of the reaction. For example, the new SHC/HAC enzyme variant may convert or the process may permit at least about 45% or at least about 50% or at least about 55% or at least about 60% EEH or BisEEH conversion in the first 12 hours of the reaction. For example, the new SHC/HAC enzyme variant may convert or the process may permit at least about 30% EEH or BisEEH conversion in the first 6 hours of the reaction. For example, the new SHC/HAC enzyme variant may convert or the process may permit at least about 35% or at least about 45% or at least about 50% or at least about 55% EEH or BisEEH conversion in the first 12 hours of the reaction. This may be when compared to using both enzymes (i.e. the new SHC/HAC enzyme variant and the 215G2 SHC enzyme) under the same reaction conditions (e.g. same pH and temperature) or when compared to using each enzyme under their optimized reaction conditions (e.g. optimized pH and temperature) which may be different to each other.

The conversion of EEH to (−)-Ambrox or BisEEH to Ambra oxide may, for example, be determined using an activity assay as described above and may be calculated as gram of recoverable product per gram of feedstock (which can be calculated as a percent molar conversion rate).

As used herein, any reference herein to a 99%/100% conversion rate for a homofarnesol substrate to (−)-Ambrox or bishomofarnesol substrate to Ambra oxide is a reference to a 99%/100% conversion of the isomer capable of conversion to (−)-Ambrox or Ambra oxide using a SHC/HAC enzyme or enzyme variant.

The optimum temperature for the SHC/HAC enzyme variant may, for example, be equal to or greater than about 35° C. For example, the optimum temperature for the SHC/HAC enzyme variant may range from about 40° C. to about 50° C., for example from about 42° C. to about 48° C. or from about 44° C. to about 46° C. For example, the optimum temperature of the SHC/HAC enzyme variant may be about 45° C. The processes for making (−)-Ambrox or Ambra oxide disclosed herein may be carried out at the optimum temperature of the SHC/HAC enzyme variant.

The optimum pH for the SHC/HAC enzyme variant may, for example, be equal to or greater than about 5.4. For example, the optimum pH for the SHC/HAC enzyme variant may range from about 5.2 to about 6.0, for example from about 5.4 to about 5.8, for example from about 5.6 to about 5.8. For example, the optimum pH of the SHC/HAC enzyme variant may be about 5.6 or about 5.8. The processes for making (−)-Ambrox or Ambra oxide disclosed herein may be carried out at the optimum pH of the SHC/HAC enzyme variant.

The optimum concentration of sodium dodecyl sulfate (SDS) in the reaction medium of the processes for making (−)-Ambrox or Ambra oxide disclosed herein may, for example, be from about 0.010 w/w % to about 0.10 w/w % when the substrate (e.g. EEH or BisEEH) is used at 4 g/l with cells to an $OD_{650nm}$ of 10. For example, the optimum concentration of SDS may be from about 0.040 w/w % to about 0.080 w/w %, for example about 0.050 w/w % when the substrate (e.g. EEH or BisEEH) is used at 4 g/l with cells to an $OD_{650nm}$ of 10. The optimum concentration of sodium dodecyl sulfate (SDS) in the reaction medium of the processes for making (−)-Ambrox or Ambra oxide disclosed herein may, for example, be from about 1.0 w/w % to about 1.5 w/w % when the substrate (e.g. EEH or BisEEH) is used at 125 g/l with 250 g/l of cells. The optimum concentration of sodium dodecyl sulfate (SDS) in the reaction medium of the processes for making (−)-Ambrox or Ambra oxide disclosed herein may, for example, be from about 0.45 w/w % to about 0.85 w/w %, for example about 0.65 w/w % when the substrate (e.g. EEH or BisEEH) is used at 125 g/l with 125 g/l of cells For example, the optimum concentration of SDS may be from about 1.2 w/w % to about 1.4 w/w %, for example about 1.3 w/w % when the substrate (e.g. EEH or BisEEH) is used at 125 g/l with 250 g/l of cells.

The processes for making (−)-Ambrox or Ambra oxide disclosed herein may be carried out at the optimum temperature range or optimum temperature and/or the optimum pH range or optimum pH and/or the SDS optimum concentration range or optimum SDS concentration for the specific enzyme used, as set out in Table 7 or 9 or 11 in the Examples below.

The following numbered paragraphs define further aspects of the present disclosure.

1. A process for preparing (−)-Ambrox or a mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a SHC/HAC enzyme variant,
   wherein the SHC/HAC enzyme variant has an amino acid sequence having at least about 70.0% identity to a wild-type SHC/HAC enzyme amino acid sequence, and
   wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1.

2. A process for preparing Ambra oxide or a mixture comprising Ambra oxide, the process comprising enzymatically converting E,E-bishomofarnesol (BisEEH) or a mixture of isomers of bishomofarnesol comprising BisEEH to Ambra oxide or a mixture comprising Ambra oxide using a SHC/HAC enzyme variant,
   wherein the SHC/HAC enzyme variant has an amino acid sequence having at least about 70.0% identity to a wild-type SHC/HAC enzyme amino acid sequence, and
   wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1.

3. The process of any preceding paragraph, wherein the wild-type SHC/HAC enzyme is SEQ ID NO: 1, SEQ ID NO: 11, SEQ ID NO: 12, SEQ ID NO: 13, SEQ ID NO: 14, SEQ ID NO: 19 or SEQ ID NO: 20.

4. The process of any preceding paragraph, wherein the SHC/HAC enzyme variant has an amino acid sequence having at least about 90.0% or at least about 95.0% identity to a wild-type SHC/HAC enzyme amino acid sequence.

5. The process of any of paragraphs 1 to 4, wherein the SHC/HAC enzyme variant amino acid sequence has amino acid alterations relative to the wild-type SHC/HAC enzyme at positions corresponding to positions 90 and 613 of SEQ ID NO: 1.

6. The process of any of paragraphs 1 to 4, wherein the SHC/HAC enzyme variant amino acid sequence has amino acid alterations relative to the wild-type SHC/HAC enzyme at positions corresponding to positions 172 and 277 of SEQ ID NO: 1.

7. The process of any of paragraphs 1 to 4, wherein the SHC/HAC enzyme variant amino acid sequence has an amino acid alteration relative to the wild-type SHC/HAC enzyme at a position corresponding to position 557 of SEQ ID NO: 1 and at least one position corresponding to position 81, 431 or 613 of SEQ ID NO: 1.

8. The process of paragraph 7, wherein the SHC/HAC enzyme variant amino acid sequence has amino acid alterations relative to the wild-type SHC/HAC enzyme at positions corresponding to positions 557 and 431 of SEQ ID NO: 1.

9. The process of paragraph 7, wherein the SHC/HAC enzyme variant amino acid sequence has amino acid alterations relative to the wild-type SHC/HAC enzyme at positions corresponding to positions 557 and 613 of SEQ ID NO: 1.

10. The process of paragraph 8 or 9, wherein the SHC/HAC enzyme variant amino acid sequence has an amino acid alteration relative to the wild-type SHC/HAC enzyme at a position corresponding to position 81 of SEQ ID NO: 1.

11. The process of any preceding paragraph, wherein one or more, for example, all, of the amino acid alterations at positions 81, 90, 172, 277, 431, 557 and 613 are substitutions, for example non-conservative substitutions.

12. The process of any preceding paragraph, wherein:
the amino acid alteration at a position corresponding to position 81 of SEQ ID NO: 1 substitutes the amino acid of the wild-type SHC/HAC amino acid sequence for a basic amino acid, for example histidine; and/or
the amino acid alteration at a position corresponding to position 90 of SEQ ID NO: 1 substitutes the amino acid of the wild-type SHC/HAC amino acid sequence for a hydrophobic amino acid, for example alanine; and/or
the amino acid alteration at a position corresponding to position 172 of SEQ ID NO: 1 substitutes the amino acid of the wild-type SHC/HAC amino acid sequence for a neutral hydrophilic amino acid, for example threonine; and/or
the amino acid alteration at a position corresponding to position 277 of SEQ ID NO: 1 substitutes the amino acid of the wild-type SHC/HAC amino acid sequence for a basic amino acid, for example lysine; and/or
the amino acid alteration at a position corresponding to position 431 of SEQ ID NO: 1 substitutes the amino acid of the wild-type SHC/HAC amino acid sequence for a hydrophobic amino acid, for example leucine; and/or
the amino acid alteration at a position corresponding to position 557 of SEQ ID NO: 1 substitutes the amino acid of the wild-type SHC/HAC amino acid sequence for a neutral hydrophilic amino acid, for example threonine; and/or
the amino acid alteration at a position corresponding to position 613 of SEQ ID NO: 1 substitutes the amino acid of the wild-type SHC/HAC amino acid sequence for a neutral hydrophilic amino acid, for example serine.

13. The process of any preceding paragraph, wherein the SHC/HAC enzyme variant amino acid sequence has one or more further amino acid alterations relative to the wild-type SHC/HAC amino acid sequence selected from:
an amino acid alteration at a position corresponding to position 132 of SEQ ID NO: 1;
an amino acid alteration at a position corresponding to position 224 of SEQ ID NO: 1; and
an amino acid alteration at a position corresponding to position 432 of SEQ ID NO: 1.

14. The process of paragraph 13, wherein:
the amino acid alteration at a position corresponding to position 132 of SEQ ID NO: 1 substitutes the amino acid of the wild-type SHC/HAC enzyme amino acid sequence for a basic amino acid, for example arginine; and/or
the amino acid alteration at a position corresponding to position 224 of SEQ ID NO: 1 substitutes the amino acid of the wild-type SHC/HAC enzyme amino acid sequence for a hydrophobic amino acid, for example valine; and/or
the amino acid alteration at a position corresponding to position 432 of SEQ ID NO: 1 substitutes the amino acid of the wild-type SHC/HAC enzyme amino acid sequence for a neutral hydrophilic amino acid, for example threonine.

15. The process of any preceding paragraph, wherein the SHC/HAC enzyme variant amino acid sequence has one or more further amino acid alterations relative to the wild-type SHC/HAC amino acid sequence selected from:
an amino acid alteration at a position corresponding to position 77 of SEQ ID NO: 1; and/or
an amino acid alteration at a position corresponding to position 92 of SEQ ID NO: 1; and/or
an amino acid alteration at a position corresponding to position 129 of SEQ ID NO: 1; and/or
an amino acid alteration at a position corresponding to position 579 of SEQ ID NO: 1; and/or
an amino acid alteration at a position corresponding to position 601 of SEQ ID NO: 1; and/or
an amino acid alteration at a position corresponding to position 605 of SEQ ID NO: 1.

16. The process of paragraph 15, wherein:
the amino acid alteration at a position corresponding to position 77 of SEQ ID NO: 1 substitutes the amino acid of the wild-type SHC/HAC enzyme amino acid sequence for a hydrophobic amino acid, for example alanine; and/or
the amino acid alteration at a position corresponding to position 92 of SEQ ID NO: 1 substitutes the amino acid of the wild-type SHC/HAC enzyme amino acid sequence for a hydrophobic amino acid, for example valine; and/or
the amino acid alteration at a position corresponding to position 129 of SEQ ID NO: 1 substitutes the amino acid of the wild-type SHC/HAC enzyme amino acid sequence for a hydrophobic amino acid, for example leucine; and/or
the amino acid alteration at a position corresponding to position 579 of SEQ ID NO: 1 substitutes the amino acid of the wild-type SHC/HAC enzyme amino acid sequence for a basic amino acid, for example histidine; and/or
the amino acid alteration at a position corresponding to position 601 of SEQ ID NO: 1 substitutes the amino acid of the wild-type SHC/HAC enzyme amino acid sequence for an aromatic amino acid, for example tyrosine; and/or
the amino acid alteration at a position corresponding to position 605 of SEQ ID NO: 1 substitutes the amino acid of the wild-type SHC/HAC enzyme amino acid sequence for an aromatic amino acid, for example tryptophan.

17. The process of any preceding paragraph, wherein the SHC/HAC enzyme variant amino acid sequence has one or more further amino acid alterations relative to the wild-type SHC/HAC amino acid sequence selected from:

an amino acid alteration at a position corresponding to position 37 of SEQ ID NO: 1; and/or an amino acid alteration at a position corresponding to position 174 of SEQ ID NO: 1; and/or an amino acid alteration at a position corresponding to position 601 of SEQ ID NO: 1.

18. The process of paragraph 17, wherein:

the amino acid alteration at a position corresponding to position 37 of SEQ ID NO: 1 substitutes the amino acid of the wild-type SHC/HAC enzyme amino acid sequence for a neutral hydrophilic amino acid, for example glutamine; and/or the amino acid alteration at a position corresponding to position 174 of SEQ ID NO: 1 substitutes the amino acid of the wild-type SHC/HAC enzyme amino acid sequence for a hydrophobic amino acid, for example isoleucine; and/or the amino acid alteration at a position corresponding to position 601 of SEQ ID NO: 1 substitutes the amino acid of the wild-type SHC/HAC enzyme amino acid sequence for an aromatic amino acid, for example tyrosine.

19. The process of any preceding paragraph, wherein the SHC/HAC enzyme variant has an amino acid sequence selected from SEQ ID NO: 2, SEQ ID NO: 3, SEQ ID NO: 4, SEQ ID NO: 5, SEQ ID NO: 17 or SEQ ID NO: 18.

20. The process of any preceding paragraph, wherein the process comprises culturing recombinant host cells that produce the SHC/HAC enzyme variant.

21. The process of paragraph 20, wherein the recombinant host cell comprises a nucleic acid sequence encoding the SHC/HAC enzyme, for example selected from SEQ ID NO: 6, SEQ ID NO: 7, SEQ ID NO: 8, SEQ ID NO: 9, SEQ ID NO: 22 and SEQ ID NO: 23.

22. The process of any preceding paragraph, wherein (−)-Ambrox is produced in admixture with at least one or more of the by-products (II), (III) or (IV).

23. A process according to any preceding claim for preparing (−)-Ambrox or a reaction mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a SHC/HAC enzyme variant, wherein the SHC/HAC enzyme variant has an amino acid sequence having at least about 70.0% identity to SEQ ID NO: 1, SEQ ID NO: 11, SEQ ID NO: 12, SEQ ID NO: 13, SEQ ID NO: 14, SEQ ID NO: 19 or SEQ ID NO: 20, and wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1 wherein the mixture of isomers comprising EEH is selected from one or more of the following groups consisting of [(3E,7E) and [(3Z,7E)] and/or [(3E,7E) and (3E,7Z)] and/or [(3Z,7E), (3E,7E) and (3E,7Z)] also designated as [EE:EZ], [EE:ZE] and [EE:EZ:ZE] respectively.

24. A process according to any preceding claim for preparing Ambra oxide or a mixture comprising Ambra oxide, the process comprising enzymatically converting (E,E)-bishomofarnesol (EEH) or a mixture of isomers of bishomofarnesol comprising BisEEH to Ambra oxide or a mixture comprising Ambra oxide using a SHC/HAC enzyme variant, wherein the SHC/HAC enzyme variant has an amino acid sequence having at least about 70.0% identity to SEQ ID NO: 1, SEQ ID NO: 11, SEQ ID NO: 12, SEQ ID NO: 13, SEQ ID NO: 14, SEQ ID NO: 19 or SEQ ID NO: 20, and wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1 wherein the mixture of isomers comprising BisEEH is selected from one or more of the following groups consisting of [(E,E) and [(Z,E)] and/or [(E,E) and (E,Z)] and/or [(Z,E), (E,E) and (E,Z)] also designated as [EE:EZ], [EE:ZE] and [EE:EZ:ZE] respectively.

25. (−)-Ambrox obtained by or obtainable by the process of any preceding paragraph, for example in amorphous or crystalline form.

26. Ambra oxide obtained by or obtainable by the process of any preceding paragraph, for example in amorphous or crystalline form.

27. Use of (−)-Ambrox of paragraph 25 and/or Ambra oxide of paragraph 26 as part of a fragrance or a cosmetic or a consumer product.

28. A fragrance or a cosmetic or a consumer product comprising (−)-Ambrox of paragraph 25 and/or Ambra oxide of paragraph 26.

29. An SHC/HAC enzyme variant having an amino acid sequence having at least about 70.0% identity to a wild-type SHC/HAC enzyme amino acid sequence, wherein the SHC/HAC enzyme variant amino acid sequence has one or more amino acid alterations relative to the wild-type SHC/HAC enzyme at a position selected from positions corresponding to positions 81, 90, 172, 277, 431, 557 and 613 of SEQ ID NO: 1.

30. The SHC/HAC enzyme variant of paragraph 29, wherein the wild-type SHC/HAC enzyme is SEQ ID NO: 1, SEQ ID NO: 11, SEQ ID NO: 12, SEQ ID NO: 13, SEQ ID NO: 14, SEQ ID NO: 19 or SEQ ID NO: 20.

31. The SHC/HAC enzyme variant of paragraph 29 or 30, wherein the SHC/HAC enzyme variant has an amino acid sequence having at least about 90.0% or at least about 95.0% identity to a wild-type SHC/HAC enzyme amino acid sequence.

32. The SHC/HAC enzyme variant of any of paragraphs 29 to 31, wherein the SHC/HAC enzyme variant amino acid sequence has amino acid alterations relative to the wild-type SHC/HAC enzyme at positions corresponding to positions 90 and 613 of SEQ ID NO: 1.

33. The SHC/HAC enzyme variant of any of paragraphs 29 to 31, wherein the SHC/HAC enzyme variant amino acid sequence has amino acid alterations relative to the wild-type SHC/HAC enzyme at positions corresponding to positions 172 and 277 of SEQ ID NO: 1.

34. The SHC/HAC enzyme variant of any of paragraphs 29 to 31, wherein the SHC/HAC enzyme variant amino acid sequence has an amino acid alteration relative to the wild-type SHC/HAC enzyme at a position corresponding to position 557 of SEQ ID NO: 1 and at least one position corresponding to position 81, 431 or 613 of SEQ ID NO: 1.

35. The SHC/HAC enzyme variant of any of paragraphs 29 to 31, wherein the SHC/HAC enzyme variant amino acid sequence has an amino acid alteration relative to the wild-type SHC/HAC enzyme at positions corresponding to positions 557 and 431 of SEQ ID NO: 1.

36. The SHC/HAC enzyme variant of any of paragraphs 29 to 31, wherein the SHC/HAC enzyme variant amino acid sequence has an amino acid alteration relative to the wild-type SHC/HAC enzyme at positions corresponding to positions 557 and 613 of SEQ ID NO: 1.

37. The SHC/HAC enzyme variant of paragraph 35 or 36, wherein the SHC/HAC enzyme variant amino acid sequence has an amino acid alteration relative to the wild-type SHC/HAC enzyme at a position corresponding to position 81 of SEQ ID NO: 1.

38. The SHC/HAC enzyme variant of any of paragraphs 29 to 37, wherein one or more, for example all, of the amino acid alterations at positions 81, 90, 172, 277, 431, 557 or 613 are substitutions, for example non-conservative substitutions.

39. The SHC/HAC enzyme variant of any of paragraphs 29 to 38, wherein:
  the amino acid alteration at a position corresponding to position 81 of SEQ ID NO: 1 substitutes the amino acid of the wild-type SHC/HAC amino acid sequence for a basic amino acid, for example histidine; and/or
  the amino acid alteration at a position corresponding to position 90 of SEQ ID NO: 1 substitutes the amino acid of the wild-type SHC/HAC amino acid sequence for a hydrophobic amino acid, for example alanine; and/or
  the amino acid alteration at a position corresponding to position 172 of SEQ ID NO: 1 substitutes the amino acid of the wild-type SHC/HAC amino acid sequence for a neutral hydrophilic amino acid, for example threonine; and/or
  the amino acid alteration at a position corresponding to position 277 of SEQ ID NO: 1 substitutes the amino acid of the wild-type SHC/HAC amino acid sequence for a basic amino acid, for example lysine; and/or
  the amino acid alteration at a position corresponding to position 431 of SEQ ID NO: 1 substitutes the amino acid of the wild-type SHC/HAC amino acid sequence for a hydrophobic amino acid, for example leucine; and/or
  the amino acid alteration at a position corresponding to position 557 of SEQ ID NO: 1 substitutes the amino acid of the wild-type SHC/HAC amino acid sequence for a neutral hydrophilic amino acid, for example threonine; and/or
  the amino acid alteration at a position corresponding to position 613 of SEQ ID NO: 1 substitutes the amino acid of the wild-type SHC/HAC amino acid sequence for a neutral hydrophilic amino acid, for example serine.

40. The SHC/HAC enzyme variant of any of paragraphs 29 to 39, wherein the SHC/HAC enzyme variant amino acid sequence has one or more further amino acid alterations relative to the wild-type SHC/HAC amino acid sequence selected from:
  an amino acid alteration at a position corresponding to position 132 of SEQ ID NO: 1;
  an amino acid alteration at a position corresponding to position 224 of SEQ ID NO: 1; and
  an amino acid alteration at a position corresponding to position 432 of SEQ ID NO: 1.

41. The SHC/HAC enzyme variant of paragraph 40, wherein:
  the amino acid alteration at a position corresponding to position 132 of SEQ ID NO: 1 substitutes the amino acid of the wild-type SHC/HAC enzyme amino acid sequence for a basic amino acid, for example arginine; and/or
  the amino acid alteration at a position corresponding to position 224 of SEQ ID NO: 1 substitutes the amino acid of the wild-type SHC/HAC enzyme amino acid sequence for a hydrophobic amino acid, for example valine; and/or
  the amino acid alteration at a position corresponding to position 432 of SEQ ID NO: 1 substitutes the amino acid of the wild-type SHC/HAC enzyme amino acid sequence for a neutral hydrophilic amino acid, for example threonine.

42. The SHC/HAC enzyme variant of any of paragraphs 29 to 41, wherein the SHC/HAC enzyme variant amino acid sequence has one or more further amino acid alterations relative to the wild-type SHC/HAC amino acid sequence selected from:
  an amino acid alteration at a position corresponding to position 77 of SEQ ID NO: 1; and/or
  an amino acid alteration at a position corresponding to position 92 of SEQ ID NO: 1; and/or
  an amino acid alteration at a position corresponding to position 129 of SEQ ID NO: 1; and/or
  an amino acid alteration at a position corresponding to position 579 of SEQ ID NO: 1; and/or
  an amino acid alteration at a position corresponding to position 601 of SEQ ID NO: 1; and/or
  an amino acid alteration at a position corresponding to position 605 of SEQ ID NO: 1.

43. The SHC/HAC enzyme variant of paragraph 42, wherein:
  the amino acid alteration at a position corresponding to position 77 of SEQ ID NO: 1 substitutes the amino acid of the wild-type SHC/HAC enzyme amino acid sequence for a hydrophobic amino acid, for example alanine; and/or
  the amino acid alteration at a position corresponding to position 92 of SEQ ID NO: 1 substitutes the amino acid of the wild-type SHC/HAC enzyme amino acid sequence for a hydrophobic amino acid, for example valine; and/or
  the amino acid alteration at a position corresponding to position 129 of SEQ ID NO: 1 substitutes the amino acid of the wild-type SHC/HAC enzyme amino acid sequence for a hydrophobic amino acid, for example leucine; and/or
  the amino acid alteration at a position corresponding to position 579 of SEQ ID NO: 1 substitutes the amino acid of the wild-type SHC/HAC enzyme amino acid sequence for a basic amino acid, for example histidine; and/or
  the amino acid alteration at a position corresponding to position 601 of SEQ ID NO: 1 substitutes the amino acid of the wild-type SHC/HAC enzyme amino acid sequence for an aromatic amino acid, for example tyrosine; and/or
  the amino acid alteration at a position corresponding to position 605 of SEQ ID NO: 1 substitutes the amino acid of the wild-type SHC/HAC enzyme amino acid sequence for an aromatic amino acid, for example tryptophan.

44. The SHC/HAC enzyme variant of any of paragraphs 29 to 43, wherein the SHC/HAC enzyme variant amino acid sequence has one or more further amino acid alterations relative to the wild-type SHC/HAC amino acid sequence selected from:
  an amino acid alteration at a position corresponding to position 37 of SEQ ID NO: 1; and/or
  an amino acid alteration at a position corresponding to position 174 of SEQ ID NO: 1; and/or an amino acid alteration at a position corresponding to position 601 of SEQ ID NO: 1.

45. The SHC/HAC enzyme variant of paragraph 44, wherein:
the amino acid alteration at a position corresponding to position 37 of SEQ ID NO: 1 substitutes the amino acid of the wild-type SHC/HAC enzyme amino acid sequence for a neutral hydrophilic amino acid, for example glutamine; and/or
the amino acid alteration at a position corresponding to position 174 of SEQ ID NO: 1 substitutes the amino acid of the wild-type SHC/HAC enzyme amino acid sequence for a hydrophobic amino acid, for example isoleucine; and/or
the amino acid alteration at a position corresponding to position 601 of SEQ ID NO: 1 substitutes the amino acid of the wild-type SHC/HAC enzyme amino acid sequence for an aromatic amino acid, for example tyrosine.

46. The SHC/HAC enzyme variant of any of paragraphs 29 to 45, wherein the SHC/HAC enzyme variant has an amino acid sequence selected from SEQ ID NO: 2, SEQ ID NO: 3, SEQ ID NO: 4, SEQ ID NO: 5, SEQ ID NO: 17 and SEQ ID NO: 18.

47. A nucleic acid sequence encoding the SHC/HAC enzyme variant of any of paragraphs 29 to 46.

48. The nucleic acid sequence of paragraph 47, wherein the nucleic acid sequence is selected from SEQ ID NO: 6, SEQ ID NO: 7, SEQ ID NO: 8, SEQ ID NO: 9, SEQ ID NO: 22 and SEQ ID NO: 23.

49. A construct comprising the nucleic acid sequence of paragraph 47 or 48.

50. A vector comprising the construct of paragraph 49.

51. A recombinant host cell comprising the nucleic acid sequence of paragraph 47 or 48, the construct of paragraph 49 or the vector of paragraph 50.

52. The recombinant host cell of paragraph 51, wherein the construct is integrated into the genome of the host cell.

53. The recombinant host cell of paragraph 51 or 52, wherein the recombinant host cell is selected from prokaryotic, yeast, plant and/or insect host cells.

54. The recombinant host cell of any of paragraphs 51 to 53, wherein the recombinant host cell is a bacteria having a genus selected from *Escherichia*, *Streptomyces*, *Bacillus*, *Pseudomonas*, *Lactobacillus* and *Lactococcus*, for example wherein the recombinant host cell is *E. coli*.

55. The process according to any one of the paragraphs 1-24 wherein the mixture of isomers of homofarnesol comprising EEH comprises an EE:EZ isomer mixture.

56. The process according to paragraph 55 wherein the EE:EZ isomer mixture is in a weight ratio of: EE:EZ 90:10; EE:EZ 80:20; EE:EZ 86:14; EE:EZ 70:30; EE:EZ 69:31; or EE:EZ 66:34 or the EE:EZ isomer mixture is selected from the group consisting of: EE:EZ 90:10; EE:EZ 80:20; EE:EZ 86:14; EE:EZ 70:30; EE:EZ 69:31; and EE:EZ 66:34.

57. The process according to paragraph 56 wherein the EE:EZ isomer mixture is in a weight ratio of 80:20.

58. The process according to any one of paragraphs 1-24 or any one of paragraphs 55-57 wherein the weight ratio of SHC/HAC biocatalyst to EEH or a mixture of isomers of homofarnesol comprising EEH (preferably an EE:EZ isomer mixture in a weight ratio of 80:20) is in the range of from about 0.5-2:1 or about 0.25-2:1 or about 0.1-2:1 or about 1:1 or about 0.5:1.

59. The process according to paragraph 58 wherein the weight ratio of SHC/HAC biocatalyst to EEH or a mixture of isomers of homofarnesol comprising EEH (preferably an EE:EZ isomer mixture in a weight ratio of 80:20) is in the range of about 1:1 or about 0.5:1 or about 0.1:1.

Further SHC/HAC Enzymes and Enzyme Variants

It has further been surprisingly found that SHC/HAC enzyme variants also act on other substrates such as E,E-bishomofarnesol to make products such as Ambra oxide.

In addition, it has been surprisingly found that certain wild-type SHC enzymes provide improved (i.e. higher) selectivity for EEH over other isomers of homofarnesol compared to WT AacSHC.

It is therefore expected that further wild-type SHC/HAC enzymes and further variants of wild-type SHC/HAC enzymes will also provide enzymatic activity (e.g. improved enzymatic activity) for the conversion of EEH to (−)-Ambrox and/or for the conversion of BisEEH to Ambra oxide.

There is therefore provided herein a process for making (−)-Ambrox by enzymatically converting EEH to (−)-Ambrox. There is also provided herein a process for making Ambra oxide by enzymatically converting E,E-bishomofarnesol to Ambra oxide. These processes may use any wild-type SHC/HAC enzyme or enzyme variant described herein.

In addition, there is provided herein a SHC/HAC enzyme or a SHC/HAC enzyme variant having at least about 70.0% identity to a wild-type SHC/HAC enzyme amino acid sequence.

In particular, there provided herein a process for preparing (−)-Ambrox or a mixture comprising (−)-Ambrox, the process comprising enzymatically converting EEH or a mixture of isomers of homofarnesol comprising EEH to (−)-Ambrox or a mixture comprising (−)-Ambrox using a SHC/HAC enzyme or a SHC/HAC enzyme variant having at least about 70.0% identity to a wild-type SHC/HAC enzyme amino acid sequence.

In particular, there provided herein a process for preparing Ambra oxide or a mixture comprising Ambra oxide, the process comprising enzymatically converting BisEEH or a mixture of isomers of bishomofarnesol comprising BisEEH to Ambra oxide or a mixture comprising Ambra oxide using a SHC/HAC enzyme or a SHC/HAC enzyme variant having at least about 70.0% identity to a wild-type SHC/HAC enzyme amino acid sequence.

The "selectivity" of an enzyme or enzyme variant refers to the ability of the enzyme or enzyme variant to react with a particular substrate compared to another substrate. For example, a WT SHC enzyme or enzyme variant of WT SHC that is selective for EEH over other isomers of homofarnesol or selective for BisEEH over other isomers of bishomofarnesol means that the WT SHC enzyme or enzyme variant of WT SHC is more likely to convert EEH than other isomers of homofarnesol or to convert BisEEH than other isomers of bishomofarnesol.

For example, the wt % of total products formed as a result of the reaction of the WT SHC enzyme or enzyme variant of WT SHC with EEH may be at least about 1 percentage point greater than the wt % of total products formed as a result of the reaction of WT AacSHC with EEH. For example, the wt % of total products formed as a result of the reaction of the WT SHC enzyme or enzyme variant of WT SHC with EEH may be at least about 2 or at least about 3 or at least about 4 percentage points greater than the wt % of total products formed as a result of the reaction of WT AacSHC with EEH. For example, the wt % of total products formed as a result of the reaction of the WT SHC enzyme or enzyme variant of WT SHC with EEH may be up to about 40 or up to about 30 or up to about 20 or up to about 15 or up to about 10 percentage points greater than the wt % of total products formed as a result of the reaction of WT AacSHC with EEH. For example, the wt % of total products formed as a result of the reaction of the WT SHC enzyme or enzyme variant of WT SHC with EEH may be from about 1 to about 40 or from about 2 to about 30 or from about 3 to about 20 or from about 4 to about 10 percentage points greater than the wt % of total products formed as a result of the reaction of WT AacSHC with EEH. The total products formed as a result of the reaction of the WT SHC enzyme or enzyme variant of WT SHC or WT AacSHC or variant of WT AacSHC may, for example, comprise, consist essentially of or consist of compounds of formula (I) ((−)-Ambrox) and formula (IV) described herein when EEH is used as a substrate. The total products formed as a result of the reaction of the WT SHC enzyme or enzyme variant of WT SHC or WT AacSHC or variant of WT AacSHC may, for example, comprise, consist essentially of or consist of compounds of formula (X) and/or formula (XII) described herein when bisEEH is used as a substrate.

For example, the wt % of (−)-Ambrox formed using the WT SHC enzyme or enzyme variant of WT SHC may, for example, be at least about 1 percentage point greater than the wt % of (−)-Ambrox formed as a result of the reaction of WT AacSHC with EEH. For example, the wt % of (−)-Ambrox formed as a result of the reaction of the WT SHC enzyme or enzyme variant of WT SHC with EEH may be at least about 2 or at least about 3 or at least about 4 percentage points greater than the wt % of (−)-Ambrox formed as a result of the reaction of WT AacSHC with EEH. For example, the wt % of (−)-Ambrox formed as a result of the reaction of the WT SHC enzyme or enzyme variant of WT SHC with EEH may be up to about 40 or up to about 30 or up to about 20 or up to about 15 or up to about 10 percentage points greater than the wt % of (−)-Ambrox formed as a result of the reaction of WT AacSHC ith EEH. For example, the wt % of (−)-Ambrox formed as a result of the reaction of the WT SHC enzyme or enzyme variant of WT SHC with EEH may be from about 1 to about 40 or from about 2 to about 30 or from about 3 to about 20 or from about 4 to about 10 percentage points greater than the wt % of (−)-Ambrox formed as a result of the reaction of WT AacSHC with EEH.

Selectivity of a WT SHC enzyme or enzyme variant of WT SHC may also be compared to the selectivity of WT AacSHC or a variant of WT AacSHC by comparing the EEH:EZH conversion ratio (i.e. % conversion of EEH:% conversion of EZH) or bisEEH:bisEZH conversion ratio (i.e. % conversion of bisEEH:% conversion of bisEZH) of reactions using each enzyme. This may be determined by measuring the amount of EEH and EZH or bisEEH and bisEZH remaining in the reaction mixture when the reaction has completed. Alternatively, the selectivity of a WT SHC enzyme or enzyme variant of WT SHC may also be compared to the selectivity of WT AacSHC or a variant of WT AacSHC by comparing the ratio of the products arising from the conversion of EEH (compounds of formulae I and IV) and EZH (compounds of formulae II and III) respectively or the conversion of bisEEH (compounds of formula X and XII) and bisEZH (XI and XIII) respectively.

The SHC enzyme or enzyme variant of WT SHC may, for example, provide an EEH:EZH conversion ratio of at least about 2.0 in a process for making (−)-Ambrox from a mixture comprising EEH and EZH. For example, the WT SHC enzyme or enzyme variant of WT SHC may provide an EEH:EZH conversion ratio of at least about 2.5 or at least about 3.0 or at least about 3.5 in a process for making (−)-Ambrox from a mixture comprising EEH and EZH. For example, the WT SHC enzyme or enzyme variant of WT SHC may provide an EEH:EZH conversion ratio up to about 5.0 or up to about 4.5 or up to about 4.0 in a process for making (−)-Ambrox from a mixture comprising EEH and EZH. For example, the WT SHC enzyme or enzyme variant of WT SHC may provide an EEH:EZH conversion ratio ranging from about 2.0 to about 5.0 or from about 2.5 to about 4.5 or from about 3.0 to about 4.0 in a process for making (−)-Ambrox from a mixture comprising EEH and EZH. This may, for example, be in contrast to the conversion ratio provided by AacSHC in a process for making (−)-Ambrox from a mixture comprising EEH and EZH, which may, for example, be less than about 2.0.

The wild-type SHC/HAC enzyme (e.g. from which the SHC/HAC enzyme variant may be derived) may, for example, be a SHC obtained from *Alicyclobacillus acidocaldarius* (Aac), *Zymomonas mobilis* (Zmo), *Bradyrhizobium japonicum* (Bjp), *Gluconobacter morbifer* (Gmo), *Burkholderia ambifaria*, *Bacillus anthracis*, *Methylococcus capsulatus*, *Frankia alni*, *Acetobacter pasteurianus* (Apa), *Thermosynechococcus elongatus* (Tel), *Streptomyces coelicolor* (Sco), *Rhodopseudomonas palustris* (Rpa), *Teredinibacter turnerae* (Ttu), *Pelobacter carbinolicus* (Pca), *Tetrahymena pyriformis* (Tpy), the *Bacillus megaterium* (Bme) or *Streptomyces albolongus* (Sal) (see, for example WO 2010/139719, US 2012/01345477, WO 2012/066059, the contents of which are incorporated herein by reference).

In particular, the wild-type SHC/HAC enzyme (e.g. from which the SHC/HAC enzyme variant may be derived) may be the *Alicyclobacillus acidocaldarius* (Aac) SHC/HAC enzyme, the *Zymomonas mobilis* (Zmo) SHC/HAC enzyme, the *Bradyrhizobium japonicum* (Bjp/Bja) SHC/HAC enzyme, the *Acetobacter pasteurianus* (Apa) SHC/HAC enzyme, the *Bacillus megaterium* (Bme) SHC/HAC enzyme or the *Gluconobacter morbifer* (Gmo) SHC/HAC enzyme. In particular, the wild-type SHC/HAC enzyme (e.g. from which the SHC/HAC enzyme variant may be derived) may be the *Alicyclobacillus acidocaldarius* (Aac) SHC/HAC enzyme.

Where the WT SHC enzyme or enzyme variant of WT SHC has a higher selectivity for EEH over other isomers of homofarnesol compared to AacSHC and/or variants of AacSHC, the wild-type SHC/HAC enzyme (e.g. from which the SHC/HAC enzyme variant may be derived) is not the *Alicyclobacillus acidocaldarius* (Aac) SHC/HAC enzyme. In particular, where the WT SHC enzyme or enzyme variant of WT SHC has a higher selectivity for EEH over other isomers of homofarnesol compared to WT AacSHC and/or variants of WT AacSHC, the wild-type SHC/HAC enzyme (e.g. from which the SHC/HAC enzyme variant may be derived) may be selected from TelSHC1, ApaSHC1, ZmoSHC1, ZmoSHC2, BjaSHC, GmoSHC BmeSHC, SalSHC, ApaSHCA. For example, where the WT SHC enzyme or enzyme variant of WT SHC has a higher selectivity for EEH over other isomers of homofarnesol compared to WT AacSHC and/or variants of WT AacSHC, the wild-type SHC/HAC enzyme (e.g. from which the SHC/HAC enzyme variant may be derived) may be selected from ZmoSHC1, BjaSHC, GmoSHC, ApaSHC1 and BmeSHC.

For ease of reference, the designation "AacSHC" may be used to refer to the *Alicyclobacillus acidocaldarius* (Aac) SHC/HAC enzyme, "ZmoSHC" may be used to refer to the *Zymomonas mobilis* (Zmo) SHC/HAC enzyme, "BjpSHC" or "BjaSHC" may be used to refer to the *Bradyrhizobium japonicum* (Bjp) SHC/HAC enzyme, "GmoSHC" may be used to refer to the *Gluconobacter morbifer* (Gmo) SHC/

HAC enzyme, "BmeSHC" may be used to refer to *Bacillus megaterium* SHC/HAC enzyme.

The SHC/HAC enzyme or SHC/HAC enzyme variant may, for example, have an amino acid sequence having at least about 70.0% identity to a wild-type SHC/HAC enzyme amino acid sequence. For example, the SHC/HAC enzyme or SHC/HAC enzyme variant may have an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to a wild-type SHC/HAC enzyme amino acid sequence.

The SHC/HAC enzyme has an amino acid sequence having 100% identity to a wild-type SHC/HAC enzyme.

The SHC/HAC enzyme variant has an amino acid sequence having less than 100% identity, for example equal to or less than about 99.5% or equal to or less than about 99.0% identity to a wild-type SHC/HAC enzyme amino acid sequence.

For example, the SHC/HAC enzyme variant may have from about 70.0% to about 99.5% or from about 80.0% to about 99.0% or from about 85.0% to about 98.5% or from about 90.0% to about 98.0% identity to a wild-type SHC/HAC enzyme amino acid sequence.

The wild-type SHC/HAC enzyme amino acid sequence may, for example, be AacSHC (SEQ ID NO: 1), ZmoSHC1 (SEQ ID NO: 11), ZmoSHC2 (SEQ ID NO: 12), BjpSHC (SEQ ID NO: 13), GmoSHC (SEQ ID NO: 14), TelSHC (SEQ ID NO: 19), ApaSHC1 (SEQ ID NO: 20), BmeSHC (SEQ ID NO: 28), SalSHC (SEQ ID NO: 29) or ApaSHCA (SEQ ID NO: 30). For example, the wild-type SHC/HAC enzyme may be AacSHC (SEQ ID NO: 1).

Therefore, in certain embodiments, the SHC/HAC enzyme or SHC/HAC enzyme variant may have an amino acid sequence having at least about 70.0% identity to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the SHC/HAC enzyme or SHC/HAC enzyme variant has an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30.

For example, the SHC/HAC enzyme may have an amino acid sequence having 100% identity to SEQ ID NO: 1, SEQ ID NO: 11, SEQ ID NO: 12, SEQ ID NO: 13 SEQ ID NO: 14, SEQ ID NO: 19, SEQ ID NO: 20, SEQ ID NO: 28, SEQ ID NO: 29 or SEQ ID NO: 30.

For example, the SHC/HAC enzyme variant may, for example, have an amino acid sequence having less than 100% identity, for example equal to or less than about 99.5% or equal to or less than about 99.0% identity to SEQ ID NO: 1, SEQ ID NO: 11, SEQ ID NO: 12, SEQ ID NO: 13 SEQ ID NO: 14, SEQ ID NO: 19, SEQ ID NO: 20, SEQ ID NO: 28, SEQ ID NO: 29 or SEQ ID NO: 30.

For example, the SHC/HAC enzyme variant may have from about 70.0% to about 99.5% or from about 80.0% to about 99.0% or from about 85.0% to about 98.5% or from about 90.0% to about 98.0% identity to SEQ ID NO: 1, SEQ ID NO: 11, SEQ ID NO: 12, SEQ ID NO: 13 SEQ ID NO: 14, SEQ ID NO: 19, SEQ ID NO: 20, SEQ ID NO: 28, SEQ ID NO: 29 or SEQ ID NO: 30.

"Percent (%) identity" with respect to a polypeptide or nucleotide sequence is defined respectively as the percentage of amino acids or nucleotides in a candidate sequence that are identical with the amino acids or nucleotides in the reference sequence, after aligning the sequence and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) or the GAP program (mathematical algorithm of the University of Iowa) or the mathematical algorithm of Myers and Miller (1989—Cabios 4:11-17).

Percentage sequence identity may be calculated using, for example, BLAST, BLAT or BlastZ (or BlastX). A similar algorithm is incorporated into the BLASTN and BLASTP programs of Altschul et al (1990) J. Mol. Biol. 215, 403-410. BLAST polynucleotide searches may be performed with the BLASTN program, score=100, word length=12, to obtain polynucleotide sequences that are homologous to those nucleic acids which encode the relevant protein. BLAST protein searches may be performed with the BLASTP program, score=50, word length=3, to obtain amino acid sequences homologous to the polypeptide.

To obtain gapped alignments for comparative purposes, Gapped BLAST may be utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

In certain embodiments, the SHC/HAC enzyme variant may have equal to or less than about 200 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the SHC/HAC enzyme variant may have equal to or less than about 150 or equal to or less than about 120 or equal to or less than about 100 or equal to or less than about 95 or equal to or less than about 90 or equal to or less than about 85 or equal to or less than about 80 or equal to or less than about 75 or equal to or less than about 70 or equal to or less than about 65 or equal to or less than about 60 or equal to or less than about 55 or equal to or less than about 50 or equal to or less than about 45 or equal to or less than about 40 or equal to or less than about 35 or equal to or less than about 30 or equal to or less than about 25 or equal to or less than about 20 or equal to or less than about 15 or equal to or less than about 10 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30.

The SHC/HAC enzyme variant may, for example, have at least about 1 or at least about 2 or at least about 3 or at least about 4 or at least about 5 or at least about 6 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30.

For example, the SHC/HAC enzyme variant may have from about 1 to about 30 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the SHC/HAC enzyme variant may have from about 2 to about 25 amino acid alterations compared to the wild-type SHC/HAC enzyme, for example compared to SEQ ID NO: 1, SEQ ID NO: 11, SEQ ID NO: 12, SEQ ID NO: 1, SEQ ID NO: 14, SEQ ID NO: 19, SEQ ID NO: 20, SEQ ID NO: 28, SEQ ID NO: 29 or SEQ ID NO: 30. For example, the SHC/HAC enzyme variant may have from about 3 to about 20 amino acid alterations compared to the wild-type SHC/HAC enzyme, for example compared to SEQ ID NO: 1, SEQ ID NO: 11, SEQ ID NO: 12, SEQ ID NO: 1, SEQ ID NO: 14, SEQ ID NO: 19, SEQ ID NO: 20, SEQ ID NO: 28, SEQ ID NO: 29 or SEQ ID NO: 30. For example, the SHC/HAC enzyme variant may have from about 4 to about 15 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30. For example, the SHC/HAC enzyme variant may have from about 5 to about 10 amino acid alterations compared to the wild-type SHC/HAC enzyme, for example compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30.

The amino acid alterations may, for example, be insertions, deletions and/or substitutions as described above. For example, the amino acid alterations may be substitutions, for example, non-conservative substitutions.

In certain embodiments, the only amino acid alterations compared to the wild-type SHC/HAC enzyme (e.g. compared to SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29 or SEQ ID NO: 30) are substitutions (i.e. there are no insertions or deletions).

Amino acid alterations are defined relative to a reference sequence. An amino acid alteration relative to a reference sequence means that the amino acid sequence of the variant sequence is different to the reference sequence.

Amino acids in the reference sequence and the variant sequence may be assigned a number, where the numbering starts with the amino acid at the N-terminus of the polypeptide (i.e. the amino acid at the N-terminus of the polypeptide is numbered 1, the next amino acid is numbered 2 etc.). The "position" of a reference sequence refers to a specific amino acid residue present in the reference sequence as identified by the specific numbering of the amino acids in the reference sequence. The "position" of a variant sequence refers to a specific amino acid residue present in the variant sequence as identified by the specific numbering of the amino acids in the variant sequence.

Since the variant sequence may include deletions or insertions compared to the reference sequence, the amino acids in the variant sequence may be numbered differently to the same amino acids in the reference sequence. By way of example, if an amino acid is inserted between amino acids 131 and 132 of SEQ ID NO: 1, the amino acid following the insertion will have the numbering 133 in the variant sequence while it retains the numbering 132 in the reference sequence. In this example, the position of the variant sequence that corresponds to position 132 of the reference sequence is position 133. Therefore, amino acids in the variant sequence that have been retained from the reference sequence may be defined by referring to the "corresponding position" of the reference sequence. In other words, a "position" in the variant sequence may be defined by reference to a "corresponding position" in the reference sequence. In particular, substitutions in the variant sequence compared to the reference sequence may be defined by referring to the "corresponding position" of the reference sequence in spite of any insertions and/or deletions in the reference sequence. Where the amino acids of a reference sequence have been deleted, there is no "corresponding position" in the variant sequence. Where there are no insertions or deletions compared to the reference sequence (i.e. there are only substitutions), the "corresponding position" of the reference sequence will be the same as the position in the variant sequence.

Wild-type SHC/HAC enzymes from different species have different polypeptide lengths. The wild-type sequences may be aligned using algorithms as described above in order to identify "corresponding positions" in two different wild-type SHC/HAC enzymes. Therefore, the amino acid at a position of the variant sequence corresponding to a position in a reference sequence may, for example, be a different amino acid residue and/or may have a different number to that of the reference sequence. By way of example, the amino acid M at position 132 of AacSHC (SEQ ID NO: 1) may correspond to the amino acid Y at position 185 of ZmoSHC1 (SEQ ID NO: 11).

The amino acid alteration may therefore be defined relative to two different reference sequences. For example, the amino acid alteration may be a change compared to a first reference sequence (e.g. a wild-type SHC/HAC enzyme sequence from which the variant is derived) and the position of the amino acid alteration in the variant sequence may be defined by reference to a second reference sequence (e.g. the AacSHC (SEQ ID NO: 1)). Thus, the amino acid alteration in the SHC/HAC enzyme variant may be relative to a first wild-type SHC/HAC enzyme at a position defined by reference to a second wild-type SHC/HAC enzyme.

The SHC/HAC enzyme variant may, for example, have one or more of the specific substitutions, or combinations of substitutions, defined above with reference to SEQ ID NO: 1.

In particular, the SHC/HAC enzyme variant may have one or more of the specific substitutions, or combinations of substitutions, at one or more positions corresponding to positions 77, 81, 90, 92, 129, 132, 172, 224, 277, 431, 432, 557, 579, 601, 605 and 613 of SEQ ID NO: 1.

Each of these substitutions may, for example, independently be as defined above in the subsections titled "Variants of Aac 215G2" and "Other variants with new mutations at positions corresponding to positions 81, 90, 172, 277, 431, 557 and 613 of SEQ ID NO: 1".

In particular, the SHC/HAC enzyme variant may have one or more of the following combinations of substitutions:
(i) substitutions at positions corresponding to positions 132, 224 and 432 of SEQ ID NO: 1;
(ii) substitutions at positions corresponding to positions 132, 224, 432, 557 and 431 of SEQ ID NO: 1;
(iii) substitutions at positions corresponding to positions 132, 224, 432, 557 and 613 of SEQ ID NO: 1;
(iv) substitutions at positions corresponding to positions 132, 224, 432, 557, 81 and 613 of SEQ ID NO: 1;
(v) substitutions at positions corresponding to positions 132, 224, 432, 557, 81 and 431 of SEQ ID NO: 1;
(vi) substitutions at positions corresponding to positions 132, 224, 432, 90 and 613 of SEQ ID NO: 1;
(vii) substitutions at positions corresponding to positions 132, 224, 432, 172 and 277 of SEQ ID NO: 1;
(viii) substitutions at positions corresponding to positions 132, 224, 432 and 37 of SEQ ID NO: 1;
(ix) substitutions at positions corresponding to positions 132, 224, 432 and 174 of SEQ ID NO: 1;
(x) substitutions at positions corresponding to positions 132, 224, 432, 174 and 601 of SEQ ID NO: 1;
(xi) substitutions at positions corresponding to positions 132, 224, 432, 37, 174 and 601 of SEQ ID NO: 1.

In certain embodiments, the SHC/HAC enzyme variant is identical to SEQ ID NO: 1 except for the following amino acid substitutions:
(i) M132R, A224V, I432T, A557T and H431L (SEQ ID NO: 2); or
(ii) M132R, A224V, I432T, A557T and R613S (SEQ ID NO: 3); or
(iii) M132R, A224V, I432T, A557T, Y81H and R613S (SEQ ID NO: 4); or
(iv) M132R, A224V, I432T, A557T, Y81H and H431L (SEQ ID NO: 5); or
(v) M132R, A224V, I432T, T90A and R613S (SEQ ID NO: 17); or
(vi) M132R, A224V, I432T, A172T and M277K (SEQ ID NO: 18); or
(vii) M132R, A224V, I432T and L37Q (SEQ ID NO: 24); or
(viii) M132R, A224V, I432T, V174I (SEQ ID NO: 25); or
(ix) M132R, A224V, I432T, V174I and F601Y (SEQ ID NO: 26); or
(x) M132R, A224V, I432T, L37Q, V174I and F601Y (SEQ ID NO: 27).

The following numbered paragraphs define additional aspects of the present disclosure:
1. A process for preparing (−)-Ambrox or a mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a SHC/HAC enzyme or SHC/HAC enzyme variant,
wherein the SHC/HAC enzyme or SHC/HAC enzyme variant has an amino acid sequence having at least about 70.0% identity to a wild-type SHC/HAC enzyme amino acid sequence,
wherein the WT SHC/HAC enzyme has a higher selectivity for EEH over other isomers of homofarnesol.
2. A process for preparing Ambra oxide or a mixture comprising Ambra oxide, the process comprising enzymatically converting E,E-bishomofarnesol (BisEEH) or a mixture of isomers of bishomofarnesol comprising BisEEH to Ambra oxide or a mixture comprising Ambra oxide using a SHC/HAC enzyme or a SHC/HAC enzyme variant,
wherein the SHC/HAC enzyme or SHC/HAC enzyme variant has an amino acid sequence having at least about 70.0% identity to a wild-type SHC/HAC enzyme amino acid sequence.
3. A process for preparing (−)-Ambrox or a mixture comprising (−)-Ambrox, the process comprising enzymatically converting 3E,7E-homofarnesol (EEH) or a mixture of isomers of homofarnesol comprising EEH to (−)-Ambrox or a mixture comprising (−)-Ambrox using a SHC/HAC enzyme or a SHC/HAC enzyme variant,
wherein the SHC/HAC enzyme or SHC/HAC enzyme variant has an amino acid sequence having at least about 70.0% identity to SEQ ID NO: 1, SEQ ID NO: 11, SEQ ID NO: 12. SEQ ID NO: 13, SEQ ID NO: 14, SEQ ID NO: 19, SEQ ID NO: 20, SEQ ID NO: 28, SEQ ID NO: 29 or SEQ ID NO: 30; and
wherein the mixture of isomers comprising EEH is selected from one or more of the following groups consisting of [(3E,7E) and [(3Z,7E)] and/or [(3E,7E) and (3E,7Z)] and/or [(3Z,7E), (3E,7E) and (3E,7Z)] also designated as [EE:EZ], [EE:ZE] and [EE:EZ:ZE] respectively.
4. A process for preparing Ambra oxide or a mixture comprising Ambra oxide, the process comprising enzymatically converting E,E-bishomofarnesol (BisEEH) or a mixture of isomers of bishomofarnesol comprising BisEEH to Ambra oxide or a mixture comprising Ambra oxide using a SHC/HAC enzyme or a SHC/HAC enzyme variant,
wherein the SHC/HAC enzyme or SHC/HAC enzyme variant has an amino acid sequence having at least about 70.0% identity to SEQ ID NO: 1, SEQ ID NO: 11, SEQ ID NO: 12. SEQ ID NO: 13, SEQ ID NO: 14, SEQ ID NO: 19, SEQ ID NO: 20, SEQ ID NO: 28, SEQ ID NO: 29 or SEQ ID NO: 30; and
wherein the mixture of isomers comprising EEH is selected from one or more of the following groups consisting of [(E,E) and [(Z,E)] and/or [(E,E) and (E,Z)] and/or [(Z,E), (E,E) and (E,Z)] also designated as [EE:EZ], [EE:ZE] and [EE:EZ:ZE] respectively.
5. The process of paragraph 1 or 3, wherein the SHC/HAC enzyme has a higher selectivity for EEH over other isomers of homofarnesol compared to that of WT AacSHC.
6. The process of any of paragraphs 1, 3 or 5, wherein the wt % of total products formed as a result of the reaction of the SHC/HAC enzyme or enzyme variant with EEH is at least about 1 percentage point, for example at least about 2 percentage points or at least about 3 percentage points higher greater than the wt % of total products formed as a result of the reaction of AacSHC with EEH.
7. The process of any of paragraphs 1, 3, 5 or 6, wherein the EEH:EZH conversion ratio is at least about 2.0, for example at least about 2.5 or at least about 3.0.
8. The process of any of paragraphs 1 to 7, wherein the wild-type SHC/HAC enzyme is obtained from *Alicyclobacillus acidocaldarius* (Aac), *Zymomonas mobilis* (Zmo),

*Bradyrhizobium japonicum* (Bjp), *Gluconobacter morbifer* (Gmo), *Burkholderia ambifaria, Bacillus anthracis, Methylococcus capsulatus, Frankia alni, Acetobacter pasteurianus* (Apa), *Thermosynechococcus elongatus* (Tel), *Streptomyces coelicolor* (Sco), *Rhodopseudomonas palustris* (Rpa), *Teredinibacter turnerae* (Ttu), *Pelobacter carbinolicus* (Pca), *Tetrahymena pyriformis, Bacillus megaterium*, or *Streptomyces albolongus.*

9. The process of any of paragraphs 1 to 8, wherein the wild-type SHC/HAC enzyme is SEQ ID NO: 1, SEQ ID NO: 11, SEQ ID NO: 12, SEQ ID NO: 1, SEQ ID NO: 14, SEQ ID NO: 19, SEQ ID NO: 20, SEQ ID NO: 28, SEQ ID NO: 29 or SEQ ID NO: 30 for example wherein the wild-type SHC/HAC enzyme is SEQ ID NO: 1.

10. The process of paragraph 1, wherein the mixture of isomers of homofarnesol is selected from one or more of the following mixtures: [(3Z,7Z), (3E,7Z), (3Z,7E) and (3E,7E)], [(3Z,7E), (3E/7E) and (3E,7Z)], [(3Z,7E) and (3E,7E)], [(3Z,7E), (3E,7Z)] and/or [(3E,7E) and (3E,7Z)].

11. The process of any preceding paragraph, wherein the process uses a solubilizing agent selected from Triton X-100, Tween 80, taurodeoxycholate, Sodium taurodeoxycholate, Sodium dodecyl sulfate (SDS), and/or sodium lauryl sulfate (SLS).

12. The process of any of paragraphs 1 to 11, wherein the SHC/HAC enzyme variant has an amino acid sequence having at least about 90.0% or at least about 95.0% identity to a wild-type SHC/HAC enzyme amino acid sequence.

13. The process of any preceding paragraph, wherein the SHC/HAC enzyme variant amino acid sequence has an amino acid alteration relative to the wild-type SHC/HAC enzyme at one or more positions selected from positions corresponding to positions 81, 90, 172, 277, 431, 557 and 613 of SEQ ID NO: 1.

14. The process of any of paragraphs 1 to 13, wherein the SHC/HAC enzyme variant amino acid sequence has amino acid alterations at positions corresponding to positions 90 and 613 of SEQ ID NO: 1.

15. The process of any of paragraphs 1 to 13, wherein the SHC/HAC enzyme variant amino acid sequence has amino acid alterations at positions corresponding to positions 172 and 277 of SEQ ID NO: 1.

16. The process of any of paragraphs 1 to 13, wherein the SHC/HAC enzyme variant amino acid sequence has an amino acid alteration relative to the wild-type SHC/HAC enzyme at a position corresponding to position 557 of SEQ ID NO: 1 and at least one position corresponding to position 81, 431 or 613 of SEQ ID NO: 1.

17. The process of paragraph 16, wherein the SHC/HAC enzyme variant amino acid sequence has an amino acid alteration relative to the wild-type SHC/HAC enzyme at positions corresponding to positions 557 and 431 of SEQ ID NO: 1.

18. The process of paragraph 16, wherein the SHC/HAC enzyme variant amino acid sequence has an amino acid alteration relative to the wild-type SHC/HAC enzyme at positions corresponding to positions 557 and 613 of SEQ ID NO: 1.

19. The process of paragraph 17 or 18, wherein the SHC/HAC enzyme variant amino acid sequence has an amino acid alteration relative to the wild-type SHC/HAC enzyme at a position corresponding to position 81 of SEQ ID NO: 1.

20. The process of any preceding paragraph, wherein one or more, for example all, of the amino acid alterations at positions 81, 90, 172, 277, 431, 557 or 613 are substitutions, for example non-conservative substitutions.

21. The process of any preceding paragraph, wherein:
the amino acid alteration at a position corresponding to position 81 of SEQ ID NO: 1 substitutes the amino acid of the wild-type SHC/HAC amino acid sequence for a basic amino acid, for example histidine; and/or
the amino acid alteration at a position corresponding to position 90 of SEQ ID NO: 1 substitutes the amino acid of the wild-type SHC/HAC amino acid sequence for a hydrophobic amino acid, for example alanine; and/or
the amino acid alteration at a position corresponding to position 172 of SEQ ID NO: 1 substitutes the amino acid of the wild-type SHC/HAC amino acid sequence for a neutral hydrophilic amino acid, for example threonine; and/or
the amino acid alteration at a position corresponding to position 277 of SEQ ID NO: 1 substitutes the amino acid of the wild-type SHC/HAC amino acid sequence for a basic amino acid, for example lysine; and/or
the amino acid alteration at a position corresponding to position 431 of SEQ ID NO: 1 substitutes the amino acid of the wild-type SHC/HAC amino acid sequence for a hydrophobic amino acid, for example leucine; and/or
the amino acid alteration at a position corresponding to position 557 of SEQ ID NO: 1 substitutes the amino acid of the wild-type SHC/HAC amino acid sequence for a neutral hydrophilic amino acid, for example threonine; and/or
the amino acid alteration at a position corresponding to position 613 of SEQ ID NO: 1 substitutes the amino acid of the wild-type SHC/HAC amino acid sequence for a neutral hydrophilic amino acid, for example serine.

22. The process of any preceding paragraph, wherein the SHC/HAC enzyme variant amino acid sequence has one or more amino acid alterations relative to the wild-type SHC/HAC amino acid sequence selected from:
an amino acid alteration at a position corresponding to position 132 of SEQ ID NO: 1;
an amino acid alteration at a position corresponding to position 224 of SEQ ID NO: 1; and
an amino acid alteration at a position corresponding to position 432 of SEQ ID NO: 1.

23. The process of paragraph 22, wherein:
the amino acid alteration at a position corresponding to position 132 of SEQ ID NO: 1 substitutes the amino acid of the wild-type SHC/HAC enzyme amino acid sequence for a basic amino acid, for example arginine; and/or
the amino acid alteration at a position corresponding to position 224 of SEQ ID NO: 1 substitutes the amino acid of the wild-type SHC/HAC enzyme amino acid sequence for a hydrophobic amino acid, for example valine; and/or
the amino acid alteration at a position corresponding to position 432 of SEQ ID NO: 1 substitutes the amino acid of the wild-type SHC/HAC enzyme amino acid sequence for a neutral hydrophilic amino acid, for example threonine.

24. The process of any preceding paragraph, wherein the SHC/HAC enzyme variant amino acid sequence has one or more amino acid alterations relative to the wild-type SHC/HAC amino acid sequence selected from:
an amino acid alteration at a position corresponding to position 77 of SEQ ID NO: 1; and/or
an amino acid alteration at a position corresponding to position 92 of SEQ ID NO: 1; and/or an amino acid alteration at a position corresponding to position 129 of SEQ ID NO: 1; and/or an amino acid alteration at a position corresponding to position 579 of SEQ ID NO: 1; and/or an amino acid alteration at a position corresponding to position 601 of SEQ ID NO: 1; and/or an amino acid alteration at a position corresponding to position 605 of SEQ ID NO: 1.

25. The process of paragraph 24, wherein:

the amino acid alteration at a position corresponding to position 77 of SEQ ID NO: 1 substitutes the amino acid of the wild-type SHC/HAC enzyme amino acid sequence for a hydrophobic amino acid, for example alanine; and/or the amino acid alteration at a position corresponding to position 92 of SEQ ID NO: 1 substitutes the amino acid of the wild-type SHC/HAC enzyme amino acid sequence for a hydrophobic amino acid, for example valine; and/or the amino acid alteration at a position corresponding to position 129 of SEQ ID NO: 1 substitutes the amino acid of the wild-type SHC/HAC enzyme amino acid sequence for a hydrophobic amino acid, for example leucine; and/or the amino acid alteration at a position corresponding to position 579 of SEQ ID NO: 1 substitutes the amino acid of the wild-type SHC/HAC enzyme amino acid sequence for a basic amino acid, for example histidine; and/or the amino acid alteration at a position corresponding to position 601 of SEQ ID NO: 1 substitutes the amino acid of the wild-type SHC/HAC enzyme amino acid sequence for an aromatic amino acid, for example tyrosine; and/or the amino acid alteration at a position corresponding to position 605 of SEQ ID NO: 1 substitutes the amino acid of the wild-type SHC/HAC enzyme amino acid sequence for an aromatic amino acid, for example tryptophan.

26. The process of any preceding paragraph, wherein the SHC/HAC enzyme variant amino acid sequence has one or more further amino acid alterations relative to the wild-type SHC/HAC amino acid sequence selected from:

an amino acid alteration at a position corresponding to position 37 of SEQ ID NO: 1; and/or an amino acid alteration at a position corresponding to position 174 of SEQ ID NO: 1; and/or an amino acid alteration at a position corresponding to position 601 of SEQ ID NO: 1.

27. The process of paragraph 26, wherein:

the amino acid alteration at a position corresponding to position 37 of SEQ ID NO: 1 substitutes the amino acid of the wild-type SHC/HAC enzyme amino acid sequence for a neutral hydrophilic amino acid, for example glutamine; and/or the amino acid alteration at a position corresponding to position 174 of SEQ ID NO: 1 substitutes the amino acid of the wild-type SHC/HAC enzyme amino acid sequence for a hydrophobic amino acid, for example isoleucine; and/or the amino acid alteration at a position corresponding to position 601 of SEQ ID NO: 1 substitutes the amino acid of the wild-type SHC/HAC enzyme amino acid sequence for an aromatic amino acid, for example tyrosine.

28. The process of any preceding paragraph, wherein the SHC/HAC enzyme variant has an amino acid sequence selected from SEQ ID NO: 2, SEQ ID NO: 3, SEQ ID NO: 4, SEQ ID NO: 5, SEQ ID NO: 17, SEQ ID NO: 18, SEQ ID NO: 24, SEQ ID NO: 25, SEQ ID NO: 26 and SEQ ID NO: 27.

29. The process of any preceding paragraph, wherein the process comprising culturing recombinant host cells that produce the SHC/HAC enzyme variant.

30. The process of paragraph 29, wherein the recombinant host cell comprises a nucleic acid sequence encoding the SHC/HAC enzyme, for example selected from SEQ ID NO: 6, SEQ ID NO: 7, SEQ ID NO: 8, SEQ ID NO: 9, SEQ ID NO: 22 or SEQ ID NO: 23.

31. The process of any preceding paragraph, wherein (−)-Ambrox is produced in admixture with at least one or more of the by-products (II), (III) or (IV).

32. (−)-Ambrox obtained by or obtainable by the process of any of any preceding paragraph, for example in amorphous or crystalline form.

33. Ambra oxide obtained by or obtainable by the process of any preceding paragraph, for example in amorphous or crystalline form.

34. Use of (−)-Ambrox of paragraph 32 and/or Ambra oxide of paragraph 33 as part of a fragrance or a cosmetic or a consumer product.

35. A fragrance or a cosmetic or a consumer product comprising (−)-Ambrox of paragraph 32 and/or Ambra oxide of paragraph 33.

36. An SHC/HAC enzyme or a SHC/HAC enzyme variant having an amino acid sequence having at least about 70.0% identity to a wild-type SHC/HAC enzyme amino acid sequence.

37. The SHC/HAC enzyme or enzyme variant of paragraph 36, wherein the wild-type SHC/HAC enzyme is SEQ ID NO: 1, SEQ ID NO: 11, SEQ ID NO: 12, SEQ ID NO: 13, SEQ ID NO: 14, SEQ ID NO: 19, SEQ ID NO: 20, SEQ ID NO: 28, SEQ ID NO: 29, or SEQ ID NO: 30, for example SEQ ID NO: 1.

38. The SHC/HAC enzyme or enzyme variant of paragraph 36 or 37, wherein the SHC/HAC enzyme variant has an amino acid sequence having at least about 90.0% or at least about 95.0% identity to a wild-type SHC/HAC enzyme amino acid sequence.

39. The SHC/HAC enzyme or enzyme variant of any of paragraphs 36 to 38, wherein the SHC/HAC enzyme variant amino acid sequence has an amino acid alteration relative to the wild-type SHC/HAC enzyme at one or more positions selected from positions corresponding to positions 81, 90, 172, 277, 431, 557 and 613 of SEQ ID NO: 1.

40. The SHC/HAC enzyme or enzyme variant of any of paragraphs 36 to 39, wherein the SHC/HAC enzyme variant amino acid sequence has amino acid alterations at positions corresponding to positions 90 and 613 of SEQ ID NO: 1.

41. The SHC/HAC enzyme or enzyme variant of any of paragraphs 36 to 39, wherein the SHC/HAC enzyme variant amino acid sequence has amino acid alterations at positions corresponding to positions 172 and 277 of SEQ ID NO: 1.

42. The SHC/HAC enzyme or enzyme variant of any of paragraphs 36 to 39, wherein the SHC/HAC enzyme variant amino acid sequence has an amino acid alteration relative to the wild-type SHC/HAC enzyme at a position corresponding to position 557 of SEQ ID NO: 1 and at least one position corresponding to position 81, 431 or 613 of SEQ ID NO: 1.

43. The SHC/HAC enzyme or enzyme variant of any of paragraphs 36 to 39, wherein the SHC/HAC enzyme variant amino acid sequence has an amino acid alteration relative to the wild-type SHC/HAC enzyme at positions corresponding to positions 557 and 431 of SEQ ID NO: 1.

44. The SHC/HAC enzyme or enzyme variant of any of paragraphs 36 to 39, wherein the SHC/HAC enzyme variant amino acid sequence has an amino acid alteration relative to the wild-type SHC/HAC enzyme at positions corresponding to positions 557 and 613 of SEQ ID NO: 1.

45. The SHC/HAC enzyme or enzyme variant of paragraph 43 or 44, wherein the SHC/HAC enzyme variant amino acid sequence has an amino acid alteration relative to the wild-type SHC/HAC enzyme at a position corresponding to position 81 of SEQ ID NO: 1.

46. The SHC/HAC enzyme or enzyme variant of any of paragraphs 36 to 45, wherein one or more, for example all, of the amino acid alterations at positions 81, 90, 172, 277, 431, 557 or 613 are substitutions, for example non-conservative substitutions.

47. The SHC/HAC enzyme or enzyme variant of any of paragraphs 36 to 46, wherein:
  the amino acid alteration at a position corresponding to position 81 of SEQ ID NO: 1 substitutes the amino acid of the wild-type SHC/HAC amino acid sequence for a basic amino acid, for example histidine; and/or
  the amino acid alteration at a position corresponding to position 90 of SEQ ID NO: 1 substitutes the amino acid of the wild-type SHC/HAC amino acid sequence for a hydrophobic amino acid, for example alanine; and/or
  the amino acid alteration at a position corresponding to position 172 of SEQ ID NO: 1 substitutes the amino acid of the wild-type SHC/HAC amino acid sequence for a neutral hydrophilic amino acid, for example threonine; and/or
  the amino acid alteration at a position corresponding to position 277 of SEQ ID NO: 1 substitutes the amino acid of the wild-type SHC/HAC amino acid sequence for a basic amino acid, for example lysine; and/or
  the amino acid alteration at a position corresponding to position 431 of SEQ ID NO: 1 substitutes the amino acid of the wild-type SHC/HAC amino acid sequence for a hydrophobic amino acid, for example leucine; and/or
  the amino acid alteration at a position corresponding to position 557 of SEQ ID NO: 1 substitutes the amino acid of the wild-type SHC/HAC amino acid sequence for a neutral hydrophilic amino acid, for example threonine; and/or
  the amino acid alteration at a position corresponding to position 613 of SEQ ID NO: 1 substitutes the amino acid of the wild-type SHC/HAC amino acid sequence for a neutral hydrophilic amino acid, for example serine.

48. The SHC/HAC enzyme or enzyme variant of any of paragraphs 36 to 47, wherein the SHC/HAC enzyme variant amino acid sequence has one or more amino acid alterations relative to the wild-type SHC/HAC amino acid sequence selected from:
  an amino acid alteration at a position corresponding to position 132 of SEQ ID NO: 1;
  an amino acid alteration at a position corresponding to position 224 of SEQ ID NO: 1; and
  an amino acid alteration at a position corresponding to position 432 of SEQ ID NO: 1.

49. The SHC/HAC enzyme or enzyme variant of paragraph 48, wherein:
  the amino acid alteration at a position corresponding to position 132 of SEQ ID NO: 1 substitutes the amino acid of the wild-type SHC/HAC enzyme amino acid sequence for a basic amino acid, for example arginine; and/or
  the amino acid alteration at a position corresponding to position 224 of SEQ ID NO: 1 substitutes the amino acid of the wild-type SHC/HAC enzyme amino acid sequence for a hydrophobic amino acid, for example valine; and/or
  the amino acid alteration at a position corresponding to position 432 of SEQ ID NO: 1 substitutes the amino acid of the wild-type SHC/HAC enzyme amino acid sequence for a neutral hydrophilic amino acid, for example threonine.

50. The SHC/HAC enzyme or enzyme variant of any of paragraphs 36 to 49, wherein the SHC/HAC enzyme variant amino acid sequence has one or more amino acid alterations relative to the wild-type SHC/HAC amino acid sequence selected from:
  an amino acid alteration at a position corresponding to position 77 of SEQ ID NO: 1; and/or
  an amino acid alteration at a position corresponding to position 92 of SEQ ID NO: 1; and/or
  an amino acid alteration at a position corresponding to position 129 of SEQ ID NO: 1; and/or
  an amino acid alteration at a position corresponding to position 579 of SEQ ID NO: 1; and/or
  an amino acid alteration at a position corresponding to position 601 of SEQ ID NO: 1; and/or
  an amino acid alteration at a position corresponding to position 605 of SEQ ID NO: 1.

51. The SHC/HAC enzyme or enzyme variant of paragraph 50, wherein:
  the amino acid alteration at a position corresponding to position 77 of SEQ ID NO: 1 substitutes the amino acid of the wild-type SHC/HAC enzyme amino acid sequence for a hydrophobic amino acid, for example alanine; and/or
  the amino acid alteration at a position corresponding to position 92 of SEQ ID NO: 1 substitutes the amino acid of the wild-type SHC/HAC enzyme amino acid sequence for a hydrophobic amino acid, for example valine; and/or
  the amino acid alteration at a position corresponding to position 129 of SEQ ID NO: 1 substitutes the amino acid of the wild-type SHC/HAC enzyme amino acid sequence for a hydrophobic amino acid, for example leucine; and/or
  the amino acid alteration at a position corresponding to position 579 of SEQ ID NO: 1 substitutes the amino acid of the wild-type SHC/HAC enzyme amino acid sequence for a basic amino acid, for example histidine; and/or
  the amino acid alteration at a position corresponding to position 601 of SEQ ID NO: 1 substitutes the amino acid of the wild-type SHC/HAC enzyme amino acid sequence for an aromatic amino acid, for example tyrosine; and/or
  the amino acid alteration at a position corresponding to position 605 of SEQ ID NO: 1 substitutes the amino acid of the wild-type SHC/HAC enzyme amino acid sequence for an aromatic amino acid, for example tryptophan.

52. The SHC/HAC enzyme or enzyme variant of any of paragraphs 36 to 51, wherein the SHC/HAC enzyme variant amino acid sequence has one or more amino acid alterations relative to the wild-type SHC/HAC amino acid sequence selected from:
  an amino acid alteration at a position corresponding to position 37 of SEQ ID NO: 1; and/or an amino acid alteration at a position corresponding to position 174 of SEQ ID NO: 1; and/or an amino acid alteration at a position corresponding to position 601 of SEQ ID NO: 1.

53. The SHC/HAC enzyme or enzyme variant of paragraph 52, wherein:

the amino acid alteration at a position corresponding to position 37 of SEQ ID NO: 1 substitutes the amino acid of the wild-type SHC/HAC enzyme amino acid sequence for a neutral hydrophilic amino acid, for example glutamine; and/or the amino acid alteration at a position corresponding to position 174 of SEQ ID NO: 1 substitutes the amino acid of the wild-type SHC/HAC enzyme amino acid sequence for a hydrophobic amino acid, for example isoleucine; and/or the amino acid alteration at a position corresponding to position 601 of SEQ ID NO: 1 substitutes the amino acid of the wild-type SHC/HAC enzyme amino acid sequence for an aromatic amino acid, for example tyrosine.

54. The SHC/HAC enzyme or enzyme variant of any of paragraphs 36 to 53, wherein the SHC/HAC enzyme variant has an amino acid sequence selected from SEQ ID NO: 2, SEQ ID NO: 3, SEQ ID NO: 4, SEQ ID NO: 5, SEQ ID NO: 17, SEQ ID NO: 18, SEQ ID NO: 24, SEQ ID NO: 25, SEQ ID NO: 26 and SEQ ID NO: 27.

55. A nucleic acid sequence encoding the SHC/HAC enzyme or enzyme variant of any of paragraphs 36 to 54.

56. The nucleic acid sequence of paragraph 55, wherein the nucleic acid sequence is selected from SEQ ID NO: 2, SEQ ID NO: 3, SEQ ID NO: 4, SEQ ID NO: 5, SEQ ID NO: 22 or SEQ ID NO: 23.

57. A construct comprising the nucleic acid sequence of paragraph 55 or 56.

58. A vector comprising the construct of paragraph 57.

59. A recombinant host cell comprising the nucleic acid sequence of paragraph 52 or 53, the construct of paragraph 57 or the vector of paragraph 58.

60. The recombinant host cell of paragraph 59, wherein the construct is integrated into the genome of the host cell.

61. The recombinant host cell of paragraph 59 or 60, wherein the recombinant host cell is selected from prokaryotic, yeast, plant and/or insect host cells.

62. The recombinant host cell of any of paragraphs 59 to 61, wherein the recombinant host cell is a bacteria having a genus selected from *Escherichia, Streptomyces, Bacillus, Pseudomonas, Lactobacillus* and *Lactococcus*, for example wherein the recombinant host cell is *E. coli*.

63. The process according to any one of the paragraphs 1-31 wherein the mixture of isomers of homofarnesol comprising EEH comprises an EE:EZ isomer mixture.

64. The process according to paragraph 63 wherein the EE:EZ isomer mixture is selected from the group consisting of: EE:EZ 90:10; EE:EZ 80:20; EE:EZ 86:14; EE:EZ 70:30; EE:EZ 69:31; and EE:EZ 66:34 or wherein the EE:EZ isomer mixture is EE:EZ 90:10; EE:EZ 80:20; EE:EZ 86:14; EE:EZ 70:30; EE:EZ 69:31; or EE:EZ 66:34.

65. The process according to paragraph 64 wherein the EE:EZ isomer mixture is in a weight ratio of 80:20.

66. The process according to any one of paragraphs 1-31 or paragraphs 63-65 wherein the weight ratio of SHC/HAC enzyme to EEH or a mixture of isomers of homofarnesol comprising EEH (preferably an EE:EZ isomer mixture in a weight ratio of 80:20) is in the range of from about 0.5-2:1 or about 0.25-2:1 or about 0.1-2:1 or about 1:1 or about 0.5:1.

67. The process according to paragraph 66 wherein the weight ratio of SHC/HAC enzyme to EEH or a mixture of isomers of homofarnesol comprising EEH (preferably an EE:EZ isomer mixture in a weight ratio of 80:20) is in the range of about 1:1 or about 0.5:1 or about 0.1:1.

The following numbered paragraphs define additional aspects of the present disclosure 1. A process for preparing (−)-Ambrox or a mixture comprising (−)-Ambrox, wherein EE-homofarnesol (EEH) or a mixture of isomers comprising EE-homofarnesol (EEH) is enzymatically converted to (−)-Ambrox or a mixture comprising (−)-Ambrox wherein the enzymatic conversion is carried out using a squalene hopene cyclase/homofarnesol Ambrox cyclase (SHC/HAC) biocatalyst having a polypeptide sequence with at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO:20 (ApaSHC1), SEQ ID NO:19 (TelSHC), SEQ ID NO: 14 (GmoSHC), SEQ ID NO:28 (BmeSHC), SEQ ID NO:29 (SalSHC) and/or SEQ ID NO: 30 (ApaSHCA) under reaction conditions suitable for the production of (−)-Ambrox and wherein the mixture of isomers comprising EEH is selected from one or more of the following groups consisting of [(3E,7E) and [(3Z,7E)] and/or [(3E,7E) and (3E,7Z)] and/or [(3Z,7E), (3E,7E) and (3E,7Z)] also designated as [EE:EZ], and/or [EE:ZE] and/or [EE:EZ:ZE] respectively.

2. The process according to paragraph 1 wherein the process is carried out using an SHC/HAC biocatalyst with at least 70% at least 75%, at least 80%, at least 85%, at least 90%, at least 91%, at least 92%, at least 93%, at least 94%, at least 95%, at least 96%, at least 97%, at least 98%, at least 99% identity to SEQ ID NO:20 (ApaSHC1) or SEQ ID NO: 28 (BmeSHC).

3. The process according to paragraph 2 wherein the conversion of EEH or a mixture of isomers comprising EEH to (−)-Ambrox takes place at a temperature in the range of from about 30° C. to about 50° C., for example from about 35° C. to about 50° C. at a pH in the range of about 5 to about 7.

4. The process according to paragraph 1 or paragraph 2 wherein the process is carried out in the presence of a solubilizing agent, for example, SDS.

5. The process according to any one of paragraph 1-4 wherein the process comprises (a) culturing one or more recombinant host cells expressing the SHC/HAC enzyme under conditions which permit production of the WT SHC/HAC biocatalyst prior to the conversion of EEH or a mixture of isomers comprising EEH to (−)-Ambrox or a mixture comprising (−)-Ambrox.

6. The process according to paragraph 5 wherein the culturing step and subsequent conversion step take place optionally in the same reaction vessel under different reaction conditions.

7. The process according to paragraph 6 wherein the culturing step is at a pH range of 6 to 7 and the EEH to (−)-Ambrox step is at a pH range of 4.8-5.5.

8. The process according to any one of paragraphs 1-7 wherein the mixture of isomers comprising EEH comprises an EE:EZ isomer mixture.

9. The process according to paragraph 8 wherein the EE:EZ isomer mixture is in a weight ratio selected from the group consisting of: EE:EZ 90:10; EE:EZ 80:20; EE:EZ 86:14; EE:EZ 70:30; EE:EZ 69:31; and EE:EZ 66:34 or the EE:EZ isomer mixture in a weight ratio of: EE:EZ 90:10; EE:EZ 80:20; EE:EZ 86:14; EE:EZ 70:30; EE:EZ 69:31; and/or EE:EZ 66:34.

10. The process of paragraph 9 wherein the EE:EZ isomer mixture is in a weight ratio of 80:20.

11. The process of any one of paragraphs 1-10 wherein the weight ratio of SHC/HAC biocatalyst to EEH or a mixture of isomers comprising EEH (preferably an EE:EZ isomer mixture in a weight ratio of 80:20) is in the range of from about 0.5-2:1 or about 0.25-2:1 or about 0.1-2:1 or about 1:1 or about 0.5:1.

12. The process according to paragraph 11 wherein the weight ratio of SHC/HAC enzyme to EEH or a mixture of isomers comprising EEH (preferably an EE:EZ isomer mixture in a weight ratio of 80:20) is from about 1:1 or about 0.5:1 or about 0.1:1.

13. The process of any one of paragraph 1-12 wherein (−)-Ambrox is produced in admixture with one or more of the by-products (II), (IV) and/or (III).

14. The process of paragraph 13 wherein (−)-Ambrox is separated from the reaction medium.

15. The process of paragraph 14 wherein (−)-Ambrox is separated from the reaction medium using a filtration step, a decantation step or a combination of a filtration and a decantation step.

16. The process of paragraph 15 wherein the filtration step is a belt filtration or a rotary filtration step.

17. The process of any one of paragraphs 13-16 wherein prior to the separation step, the (−)-Ambrox is heated to a maximum temperature of 55° C.

18. The process of paragraph 17 wherein the recovered (−)-Ambrox is solubilized in a solvent.

19. The process of paragraph 18 wherein the solubilized (−)-Ambrox is filtered.

20. The process of paragraph 18 or 19 wherein the (−)-Ambrox is recovered in solid form by removing the solvent by evaporation.

21. The process of any one of paragraphs 14-20 wherein (−)-Ambrox is substantially free of the by-products (II), (IV) and/or (III).

22. A reaction product comprising the (−)-Ambrox obtainable by the process of any one of paragraphs 1-21.

23. The reaction product of paragraph 22 wherein the (−)-Ambrox is in a solid form.

24. The reaction product of paragraph 23 wherein the (−)-Ambrox is in an amorphous or crystalline form.

25. A method for making a product containing the (−)-Ambrox comprising incorporating the reaction product of any one of paragraphs 22-24 into the product.

26. The method of paragraph 25 wherein the product is a fragrance product, a cosmetic product, a cleaning product, a detergent product and/or a soap product.

27. A fragrance or cosmetic or a consumer care product comprising the reaction product of any one of paragraphs 22-24.

28. A fragrance or cosmetic or consumer care composition comprising the reaction product of any one of paragraphs 22-24 and an additional component.

29. The use of the reaction product of any one of paragraphs 22-24 as part of a fragrance or cosmetic consumer care product.

Ambrox and Uses Thereof

There is further provided herein the reaction products made by the processes described herein. The reaction products may, for example, comprise, consist essentially of consist of (−)-Ambrox and one or more further compounds, for example one or more of a compound of formula (II), a compound of formula (III) and a compound of formula (IV). As used herein, the term "Ambrox" includes (−)-Ambrox of formula (I) below as well as (−)-Ambrox in isomerically pure form or in a mixture with one or more of the following molecules of formula (II), (III), and/or (IV),

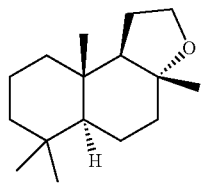
(I)

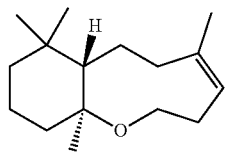
(II)

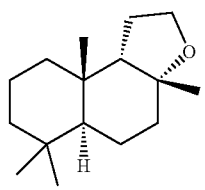
(III)

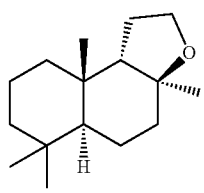
(IV)

The nomenclature for the reaction products of formulae (I), (II), (III), and (IV) is set out below.

TABLE 2

Nomenclature for the reaction products of formulae (I), (II), (III) and (IV).

| Compound | Description | Name and Structure |
|---|---|---|
| (I) | (−)-Ambrox | 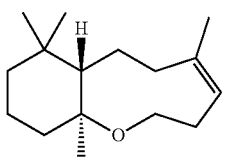 [SMILES: C/C1=C/CCO[C@@]2(C)CCCC(C)(C)[C@@H]2CC1]<br>(3aR,5aS,9aS,9bR)-3a,6,6,9a-tetramethyldodecahydronaphtho[2,1-b]furan |
| (II) | Macrocycle | (7aS,11aS,Z)-5,8,8,11a-tetramethyl-2,3,6,7,7a,8,9,10,11,11a-decahydrobenzo[b]oxonine |

TABLE 2-continued

Nomenclature for the reaction products of formulae (I), (II), (III) and (IV).

| Compound | Description | Name and Structure |
|---|---|---|
| (III) | 9b-epi-Ambrox | 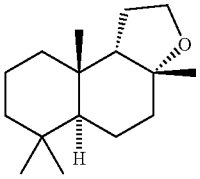 [SMILES: CC1(C)CCC[C@@]2(C)[C@H]1CC[C@@]1(C)OCC[C@@H]21]<br>(3aR,5aS,9aS,9bS)-3a,6,6,9a-tetramethyldodeca-hydronaphtho[2,1-b]furan |
| (IV) | Escher et al (1990) | 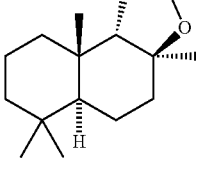<br>(3aS,5aS,9aS,9bS)-3a,6,6,9a-tetramethyldodeca-hydronaphtho[2,1-b]furan |

(−)-Ambrox is known commercially as Ambrox (Firmenich), Ambroxan (Henkel), Ambrofix (Givaudan), Amberlyn (Quest), Cetalox Laevo (Firmenich), Ambermor (Aromor) and/or Norambrenolide Ether (Pacific).

(−)-Ambrox is an industrially important aroma compound and has been used in the fragrance industry for a long time. The special desirable sensory benefits from (−)-Ambrox come from the (−) isomer rather than the (+) one. The odour of the (−) isomer is described as musk-like, woody, warm or ambery whereas the (+)-Ambrox enantiomer has a relatively weak odour note. The odour and odour thresholds for Ambrox like products are also different. While various (−)-Ambrox enriched materials are available commercially, it is desirable to produce highly enriched (−)-Ambrox materials, ideally pure (−)-Ambrox. The processes described herein may make (−)-Ambrox of formula (I) alone or in a mixture with by-products such as the compounds shown in formulae (II), (III) and/or (IV) above.

(−)-Ambrox can be produced from sclareolide according to the production process as described below. Sclareol is a product extracted from the natural plant clary sage. However, because a natural starting material is used in this process, there are potential problems in that it involves a multistage reaction, its operation is circuitous, the quantity and stability of supply of starting material may not always be satisfactory, and the reaction may not be environmentally friendly because an oxidizing agent such as chromic acid or a permanganate is used in the step of (+)-sclareol oxidative degradation.

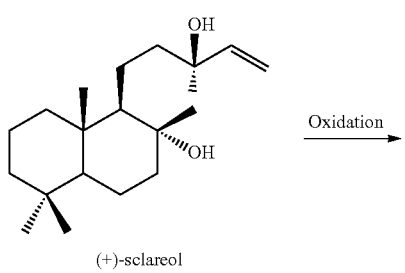

(+)-sclareol

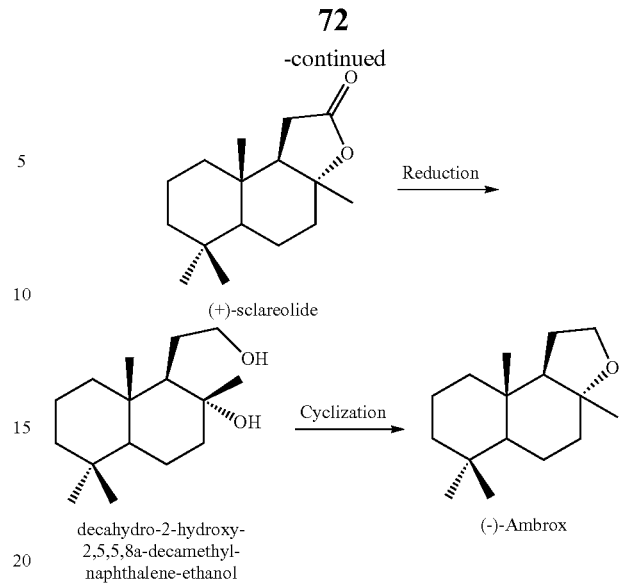

(−)-Ambrox may also be synthesized from homofarnesol using different routes. By way of example, homofarnesol can be obtained by brominating, cyanating, and hydrolysing nerolidol to give homofarnesylic acid, followed by reduction. Alternatively, homofarnesol may be obtained from farnesol, farnesylchloride, beta-farnesene or other substrates.

The processes described herein may make (−)-Ambrox of formula (I) alone or in a mixture with by-products such as the compound shown in formulae (II), (III) and/or (IV). For example, other stereoisomers of formula (I) may be made by the processes described herein.

There is therefore provided herein a compound of formula (I) or a composition comprising a compound of formula (I) obtained by or obtainable by the processes described herein, including all embodiments thereof.

In certain embodiments, not all of the homofarnesol (e.g. EEH) is converted to (−)-Ambrox or a by-product of the reaction. Therefore, the compositions described herein, for example the compositions obtained by obtainable by the processes described herein may comprise homofarnesol (e.g. EEH, for example in addition to the compound of formula (I) and/or compounds of formula (II), (III) and/or (IV)). Any remaining homofarnesol may be separated from the other reaction products such that the (−)-Ambrox product does not comprise homofarnesol. In other embodiments, all of the homofarnesol starting material is converted to (−)-Ambrox of formula (I) or a by-product of the reaction by the processes described herein.

Therefore, the compositions described herein may comprise, consist essentially of or consist of one or more of a compound of formula (I), a compound of formula (II), a compound of formula (III), a compound of formula (IV), homofarnesol starting material (e.g. EEH) and other stereoisomers of the compound of formula (I). For example, the compositions described herein may comprise, consist essentially of or consist of a compound of formula (I) and one or more of a compound of formula (II), a compound of formula (III) and a compound of formula (IV).

The compositions described herein may therefore comprise equal to or greater than about equal to or greater than about 50 wt % of the compound of formula (I) based on the total weight of the compound of formula (I), the compound of formula (II), the compound of formula (III) and the compound of formula (IV). For example, the compositions described herein may comprise equal to or greater than about 55 wt % or equal to or greater than about 60 wt % or equal to or greater than about 65 wt % or equal to or greater than about 70 wt % or equal to or greater than about 75 wt % or equal to or greater than about 80 wt % or equal to or greater than about 85 wt % or equal to or greater than about 90 wt % or equal to or greater than about 95 wt % of the compound of formula (I) based on the total weight of the compound of formula (I), the compound of formula (II), the compound of formula (III) and the compound of formula (IV). The compositions described herein may, for example, comprise equal to or less than about 100 wt % of the compound of formula (I) based on the total weight of the compound of formula (I), the compound of formula (II), the compound of formula (III) and the compound of formula (IV). For example, the mixture may comprise equal to or less than about 99 wt % or equal to or less than about 98 wt % or equal to or less than about 97 wt % of the compound of formula (I) based on the total weight of compound of formula (I), the compound of formula (II), the compound of formula (III) and the compound of formula (IV). For example, the compositions described herein may comprise from about 50 wt % to about 100 wt % or from about 60 wt % to about 99 wt % or from about 70 wt % to about 98 wt % or from about 80 wt % to about 97 wt % or from about 90 wt % to about 97 wt % of the compound of formula (I) based on the total weight of the compound of formula (I), the compound of formula (II), the compound of formula (III) and the compound of formula (IV).

The weight ratio of the compound of formula (I) to the total weight of the compound of formula (II), the compound of formula (III) and the compound of formula (IV) in the compositions described herein may, for example, range from about 60:40 to about 99:1. For example, the weight ratio of the compound of formula (I) to the total weight of the compound of formula (II), the compound of formula (III) and the compound of formula (IV) may range from about 65:35 to about 99:1 or from about 70:30 to about 99:1 or from about 75:25 to about 99:1 or from about 80:20 to about 99:1 or from about 85:15 to about 99:1 or from about 90:10 to about 99:1 or from about 95:5 to about 99:1. For example, the weight ratio of the compound of formula (I) to the total weight of the compound of formula (II), the compound of formula (III) and the compound of formula (IV) may range from about 65:35 to about 98:2 or from about 70:30 to about 97:3 or from about 75:25 to about 96:4 or from about 80:20 to about 95:5 or from about 85:15 to about 90:10.

The weight ratio of the compound of formula (I) to homofarnesol (e.g. EEH) in the compositions described herein may, for example, range from about 90:10 to about 100:0. For example, the weight ratio of the compound of formula (I) to homofarnesol (e.g. EEH) in the compositions described herein may range from about 92:8 to about 100:0 or from about 94:6 to about 100:0 or from about 95:5 to about 100:0 or from about 96:4 to about 99.5:0.5 or from about 97:3 to about 99.0:1.0 or from about 98:2 to about 99.0:1.0.

The amount of the compound of formula (I), the compound of formula (II), the compound of formula (III) and the compound of formula (IV) in a mixture of stereoisomers may, for example, be quantified by gas chromatography and/or identified by NMR spectroscopy.

(−)-Ambrox as synthesized by the processes described herein (e.g. using SHC/HAC enzymes or variants thereof and optionally recombinant host cells) may, for example, be in amorphous form or in crystalline form.

The (−)-Ambrox produced by the methods described herein (e.g. using SHC/HAC enzymes or variants thereof and optionally recombinant host cells) may be isolated by steam extraction/distillation or organic solvent extraction using a non-water miscible solvent (to separate the reaction products and unreacted substrate from the biocatalyst which stays in the aqueous phase) followed by subsequent evaporation of the solvent to obtain a crude reaction product as determined by gas chromatographic (GC) analysis. The steam extraction/distillation and organic solvent extraction methods are known to those skilled in the art.

By way of example, the resulting (−)-Ambrox may be extracted from the whole reaction mixture using an organic solvent such as a non-water miscible solvent (for example toluene). Alternatively, the resulting (−)-Ambrox may be extracted from the solid phase of the reaction mixture (obtained by, for example, centrifugation or filtration) using a water miscible solvent (for example ethanol) or a non-water miscible solvent (for example toluene). Alternatively, the resulting (−)-Ambrox may be extracted from the solid phase of the reaction mixture using a mixture of solvents. By way of further example, (−)-Ambrox is present in the solid phase as crystals or in amorphous form and can be separated from the remaining solid phase (cell material or debris thereof) and the liquid phase also by means of filtration. By way of further example, at a temperature above the melting point of (−)-Ambrox (around. 75° C.), the (−)-Ambrox may form an oil layer on top of aqueous phase, which oil layer can be removed and collected. In order to ensure a complete recovery of (−)-Ambrox after the oil layer is removed, an organic solvent may be added to the aqueous phase containing the biomass in order to extract any residual (−)-Ambrox contained in, or on or about the biomass. The organic layer can be combined with the oil layer, before the whole is further processed to isolate and purify (−)-Ambrox. The (−)-Ambrox may be further selectively crystallised to remove by-products (II), (IV) and (III) and any unreacted homofarnesol substrate from the final (−)-Ambrox product. The term "selective crystallization" refers to a process step whereby (−)-Ambrox is caused to crystallise from a solvent whilst the compounds (II), (III) and (IV) remain dissolved in the crystallising solvent to such an extent that isolated crystalline material contains only (−)-Ambrox product, or if it contains any of the other compounds (II), (III) or (IV), then they are present only in olfactory acceptable amounts. The (−)-Ambrox may, for example, be free or substantially free of by-products (II), (III) and (IV). The selective crystallisation step may use a water miscible solvent such as ethanol or the like. The selective crystallisation of (−)-Ambrox may be influenced by the presence of unreacted homofarnesol substrate and also the ratio of (−)-Ambrox to the other detectable by-products (II), (III) and/or (IV). Even if only 10% conversion of the homofarnesol substrate to (−)-Ambrox is obtained, the selective crystallisation of (−)-Ambrox is still possible.

The olfactive purity of the final (−)-Ambrox product may be determined using a 10% ethanol extract in water or by testing the crystalline material. The final (−)-Ambrox product is tested against a commercially available reference of (−)-Ambrox product for its olfactive purity, quality and its sensory profile. The (−)-Ambrox material is also tested in application studies by experts in order to determine if the material meets the specifications with respect to its organoleptic profile.

Examples of suitable water miscible and non-water miscible organic solvents suitable for use in the extraction and/or selective crystallization of (−)-Ambrox include but are not limited to aliphatic hydrocarbons, preferably those having 5 to 8 carbon atoms, such as pentane, cyclopentane, hexane, cyclohexane, heptane, octane or cyclooctane, halogenated aliphatic hydrocarbons, preferably those having one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably those having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures of these. The solvents which are especially preferably used are the abovementioned heptane, Methyl tert-butyl ether (also known as MTBE, tert-butyl methyl ether, tertiary butyl methyl ether and (BME), diisopropyl ether, tetrahydrofuran, ethyl acetate and/or mixtures thereof. Preferably, a water miscible solvent such as ethanol is used for the extraction of (−)-Ambrox from the solid phase of the reaction mixture. The use of ethanol is advantageous because it is easy to handle, it is non-toxic and it is environmentally friendly.

The term "isolated" as used herein refers to a bioconversion product such as (−)-Ambrox which has been separated or purified from components which accompany it. An entity that is produced in a cellular system different from the source from which it naturally originates is "isolated", because it will necessarily be free of components which naturally accompany it. The degree of isolation or purity can be measured by any appropriate method, e.g. gas chromatography (GC), HPLC or NMR analysis.

In some embodiments, the end product ((−)-Ambrox) is isolated and purified to homogeneity (e.g. at least 80%, 81%, 82%, 83%, 84%, 85%, 86%, 87%, 88%, 89%, or 89.5% pure or 90%, 91%, 92%, 93%, 94%, 95%, 96%, 97%, 98%, 99%, or 99.5% pure).

Desirably, the amount of (−)-Ambrox produced can be from about 1 mg/l to about 20,000 mg/l (20 g/l) or higher such as from about 20 g/l to about 200 g/l or from 100-200 g/l, preferably about 125 g/l or 150 g/l or about 188 g/l.

At least 125 g/l (−)-Ambrox may be produced in a bioconversion reaction using a recombinant *E. coli* host cell producing a SHC/HAC enzyme or enzyme variant over about 2 days. It is possible to run bioconversions at 188 g/l EEH or higher provided efficient mixing is achieved as stirring efficiency may be the only limitation of the system. In addition, a biocatalyst with improved activity (e.g. in terms of SHC variants with further improved activity or in terms of increased SHC enzyme production) may improve or maintain productivity using less biomass or increasing substrate concentration which is advantageous with respect to mixing efficiencies. For example about 1 to about 100 mg/l, about 30 to about 100 mg/l, about 50 to about 200 mg/l, about 100 to about 500 mg/l, about 100 to about 1,000 mg/l, about 250 to about 5,000 mg/l, about 1,000 (1 g/l) to about 15,000 mg/l (15 g/l), or about 2,000 (2 g/l) to about 10,000 mg/l (10 g/l) or about 2,000 (2 g/l) to about 25,000 mg/l (25 g/l) or about 2,000 (2 g/l) to about 25,000 mg/l (25 g/l), 26,000 mg/l (26 g/l), 27,000 mg/l (27 g/l), 28,000 mg/l (28 g/l), 29,000 mg/l (29 g/l), 30,000 mg/l (30 g/l), 40 g/l, 50 g/l, 60 g/l, 70 g/l, 80 g/l, 90 g/l, 100 g/l, 110 g/l, 120 g/l, 125 g/l, 130 g/l, 140 g/l, 150 g/l, 160 g/l, 170 g/l, 180 g/l, 190 g/l or 200 g/l or 300 g/l or 400 g/l or 500 g/l of (−)-Ambrox is produced.

Preferably (−)-Ambrox at a concentration of at least 100 g/l is produced within a period of time of from 48 to 72 hours.

Preferably (−)-Ambrox at a concentration of about 150 g/l is produced within a time period of from about 48 to 72 hours. Preferably (−)-Ambrox at a concentration of about 200 g/l is produced within a time period of from about 48 to 72 hours.

Preferably (−)-Ambrox at a concentration of about 250 g/l is produced within a time period of from about 48 to 72 hours.

The bioconversion of homofarnesol to (−)-Ambrox according to the present disclosure produces (−)-Ambrox as a predominant compound but may also produce compounds other than (−)-Ambrox which may or may not impart pleasant olfactive notes to the bioconversion mixture and so may contribute in a positive or negative manner to the sensory character of the (−)-Ambrox end product. Accordingly a sensory analysis is carried out using well established sensory tests utilized by trained Experts (e.g. Perfumers) so that the testing can assist in determining if a chemically relevant product is also an olfactively relevant end product relative to a reference product. The removal of one of more by-product compounds from (−)-Ambrox can improve the odor of the reaction product mixture comprising (−)-Ambrox even if the removed compounds are actually odorless compounds per se. That is, an (−)-Ambrox odor enhancement may be observed in the absence of compounds II, III and IV.

Various applications for (−)-Ambrox include but are not limited to a fine fragrance or a consumer product such as fabric care, toiletries, beauty care and cleaning products, detergent products, and soap products, including essentially all products where the currently available Ambrox ingredients are used commercially, including but not limited to: Ambrox (Firmenich), Ambroxan (Henkel), Ambrofix (Givaudan), Amberlyn (Quest), Cetalox Laevo (Firmenich), Ambermor (Aromor) and Norambrenolide Ether (Pacific) products.

Thus, there is further provided herein a use of (−)-Ambrox obtained by or obtainable by a process described herein as part of a fragrance or a cosmetic or a consumer product. There is also provided herein a product comprising (−)-Ambrox obtained by or obtainable by a process described herein. The product may, for example, be a fragrance or a cosmetic or a consumer product.

Ambra Oxide and Uses Thereof

There is further provided herein the reaction products made by the processes described herein. The reaction products may, for example, comprise, consist essentially of consist of Ambra oxide and one or more further compounds, for example one or more of a compound of formula (XI), a compound of formula (XII) and a compound of formula (XIII).

As used herein, the term "Ambra oxide" includes Ambra oxide of formula (X) below as well as Ambra oxide of formula (X) in isomerically pure form or in a mixture with one or more of the following molecules of formula (XI), (XII) and/or (XIII),

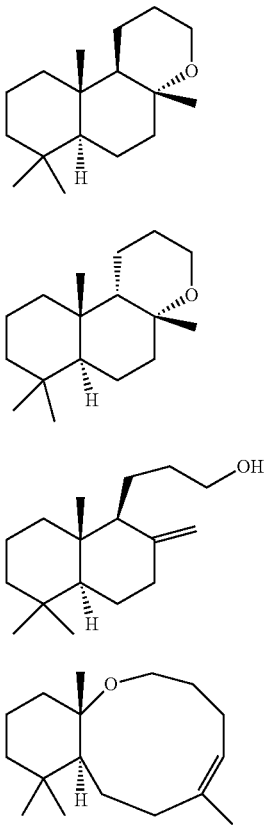

The nomenclature for the reaction products of formulae (X), (XI), (XII) and (XIII) is set out below.

TABLE 3

Nomenclature for the reaction products of formulae (X), (XI), (XII) and (XIII).

| Compound | Name and Structure |
|---|---|
| (X) | (4aR,6aS,10aS,10bR)-4a,7,7,10a-tetramethyldodecahydro-1H-benzo[f]chromene (Ambra oxide) |
| (XI) | [(4aR,6aS,10aS,10bS)-4a,7,7,10a-tetramethyldodecahydro-1H-benzo[f]chromene] |
| (XII) | [3-((1S,4aS,8aS)-5,5,8a-trimethyl-2-methylenedecahydronaphthalen-1-yl)propan-1-ol] |
| (XIII) | [(8aS,12aS,Z)-6,9,9,12a-tetramethyl-3,4,7,8,8a,9,10,11,12,12a-decahydro-2H-benzo[b]oxecine] |

Ambra oxide can be produced from (+)-Larixol as described in Bolster et al., Tetrahedron, 2002, 58(26), pages 5275-5285. However, it is desirable to provide alternative or improved methods for producing Ambra oxide.

The processes described herein may make Ambra oxide of formula (X) alone or in a mixture with by-products such as the compound shown in formulae (XI), (XII) and/or (XIII). For example, other stereoisomers of formula (X) may be made by the processes described herein.

There is therefore provided herein a compound of formula (X) or a composition comprising a compound of formula (X) obtained by or obtainable by the processes described herein, including all embodiments thereof.

In certain embodiments, not all of the bishomofarnesol (e.g. BisEEH) is converted to Ambra oxide or a by-product of the reaction. Therefore, the compositions described herein, for example the compositions obtained by obtainable by the processes described herein may comprise bishomofarnesol (e.g. bisEEH, for example in addition to the compound of formula (X) and/or compounds of formula (XI), (XII) and/or (XIII)). Any remaining homofarnesol may be separated from the other reaction products such that the Ambra oxide product does not comprise bishomofarnesol. In other embodiments, all of the bishomofarnesol starting material is converted to Ambra oxide of formula (X) or a by-product of the reaction by the processes described herein.

Therefore, the compositions described herein may comprise, consist essentially of or consist of one or more of a compound of formula (X), a compound of formula (XI), a compound of formula (XII), a compound of formula (XIII), bishomofarnesol starting material (e.g. bisEEH) and other stereoisomers of the compound of formula (X). For example, the compositions described herein may comprise, consist essentially of or consist of a compound of formula (X) and one or more of a compound of formula (XI), a compound of formula (XII) and a compound of formula (XIII).

The compositions described herein may therefore comprise equal to or greater than about equal to or greater than about 50 wt % of the compound of formula (X) based on the total weight of the compound of formula (X), the compound of formula (XI), the compound of formula (XII) and the compound of formula (XIII). For example, the compositions described herein may comprise equal to or greater than about 55 wt % or equal to or greater than about 60 wt % or equal to or greater than about 65 wt % or equal to or greater than about 70 wt % or equal to or greater than about 75 wt % or equal to or greater than about 80 wt % or equal to or greater than about 85 wt % or equal to or greater than about 90 wt % or equal to or greater than about 95 wt % of the compound of formula (X) based on the total weight of the compound of formula (X), the compound of formula (XI), the compound of formula (XII) and the compound of formula (XIII). The compositions described herein may, for example, comprise equal to or less than about 100 wt % of the compound of formula (X) based on the total weight of the compound of formula (X), the compound of formula (XI), the compound of formula (XII) and the compound of formula (XIII). For example, the mixture may comprise equal to or less than about 99 wt % or equal to or less than about 98 wt % or equal to or less than about 97 wt % of the compound of formula (X) based on the total weight of compound of formula (X), the compound of formula (XI), the compound of formula (XII) and the compound of formula (XIII). For example, the compositions described herein may comprise from about 50 wt % to about 100 wt % or from about 60 wt % to about 99 wt % or from about 70 wt % to about 98 wt % or from about 80 wt % to about 97 wt % or from about 90 wt % to about 97 wt % of the compound of formula (X) based on the total weight of the compound of formula (X), the compound of formula (XI), the compound of formula (XII) and the compound of formula (XIII).

The weight ratio of the compound of formula (X) to the total weight of the compound of formula (XI), the compound of formula (XII) and the compound of formula (XIII) in the compositions described herein may, for example, range from about 60:40 to about 99:1. For example, the weight ratio of the compound of formula (X) to the total weight of the compound of formula (XI), the compound of formula (XII) and the compound of formula (XIII) may range from about 65:35 to about 99:1 or from about 70:30 to about 99:1 or from about 75:25 to about 99:1 or from about 80:20 to about 99:1 or from about 85:15 to about 99:1 or from about 90:10 to about 99:1 or from about 95:5 to about 99:1. For example, the weight ratio of the compound of formula (X) to the total weight of the compound of formula (XI), the compound of formula (XII) and the compound of formula (XIII) may range from about 65:35 to about 98:2 or from about 70:30 to about 97:3 or from about 75:25 to about 96:4 or from about 80:20 to about 95:5 or from about 85:15 to about 90:10.

The weight ratio of the compound of formula (X) to bishomofarnesol (e.g. bisEEH) in the compositions described herein may, for example, range from about 90:10 to about 100:0. For example, the weight ratio of the compound of formula (X) to bishomofarnesol (e.g. bisEEH) in the compositions described herein may range from about 92:8 to about 100:0 or from about 94:6 to about 100:0 or from about 95:5 to about 100:0 or from about 96:4 to about 99.5:0.5 or from about 97:3 to about 99.0:1.0 or from about 98:2 to about 99.0:1.0.

The amount of the compound of formula (X), the compound of formula (XI), the compound of formula (XII) and the compound of formula (XIII) in a mixture of stereoisomers may, for example, be quantified by gas chromatography and/or identified by NMR spectroscopy.

Ambra oxide synthesized by the processes described herein (e.g. using SHC/HAC enzymes or variants thereof and optionally recombinant host cells) may, for example, be in amorphous form or crystalline form.

The Ambra oxide produced by the methods described herein (e.g. using SHC/HAC enzymes or variants thereof and recombinant host cells) may be isolated by steam extraction/distillation or organic solvent extraction using a non-water miscible solvent (to separate the reaction products and unreacted substrate from the biocatalyst which stays in the aqueous phase) followed by subsequent evaporation of the solvent to obtain a crude reaction product as determined by gas chromatographic (GC) analysis. The steam extraction/distillation and organic solvent extraction methods are known to those skilled in the art.

By way of example, the resulting Ambra oxide may be extracted from the whole reaction mixture using an organic solvent such as a non-water miscible solvent (for example toluene). Alternatively, the resulting Ambra oxide may be extracted from the solid phase of the reaction mixture (obtained by, for example, centrifugation or filtration) using a water miscible solvent (for example ethanol) or a non-water miscible solvent (for example toluene). By way of further example, Ambra oxide is present in the solid phase as crystals or in amorphous form and can be separated from the remaining solid phase (cell material or debris thereof) and the liquid phase also by means of filtration.

By way of further example, at a temperature above the melting point of Ambra oxide, the Ambra oxide may form an oil layer on top of aqueous phase, which oil layer can be removed and collected. In order to ensure a complete recovery of Ambra oxide after the oil layer is removed, an organic solvent may be added to the aqueous phase containing the biomass in order to extract any residual Ambra oxide contained in, or on or about the biomass. The organic layer can be combined with the oil layer, before the whole is further processed to isolate and purify Ambra oxide. The Ambra oxide may be further selectively crystallised to remove by-products (XI), (XII) and (XIII) and any unreacted bishomofarnesol substrate from the final Ambra oxide product. The term "selective crystallization" refers to a process step whereby Ambra oxide is caused to crystallise from a solvent whilst the compounds (XI), (XII) and (XIII) remain dissolved in the crystallising solvent to such an extent that isolated crystalline material contains only Ambra oxide product, or if it contains any of the other compounds (X), (XII) or (XIII), then they are present only in olfactory acceptable amounts. The Ambra oxide may, for example, be free or substantially free of by-products (XI), (XII) and (XIII). The selective crystallisation step may use a water miscible solvent such as ethanol or the like. The selective crystallisation of Ambra oxide may be influenced by the presence of unreacted homofarnesol substrate and also the ratio of Ambra oxide to the other detectable by-products (XI), (XII) and/or (XIII). Even if only 10% conversion of the homofarnesol substrate to Ambra oxide is obtained, the selective crystallisation of Ambra oxide is still possible.

The olfactive purity of the final Ambra oxide product may be determined using a 10% ethanol extract in water or by testing the crystalline material. The final Ambra oxide product is tested against a commercially available reference of Ambra oxide product for its olfactive purity, quality and its sensory profile. The Ambra oxide material is also tested in application studies by experts in order to determine if the material meets the specifications with respect to its organoleptic profile.

Examples of suitable water miscible and non-water miscible organic solvents suitable for use in the extraction and/or selective crystallization of Ambra oxide include but are not limited to aliphatic hydrocarbons, preferably those having 5 to 8 carbon atoms, such as pentane, cyclopentane, hexane, cyclohexane, heptane, octane or cyclooctane, halogenated aliphatic hydrocarbons, preferably those having one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably those having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures of these. The solvents which are especially preferably used are the abovementioned heptane, Methyl tert-butyl ether (also known as MTBE, tert-butyl methyl ether, tertiary butyl methyl ether and tBME), diisopropyl ether, tetrahydrofuran, ethyl acetate and/or mixtures thereof. Preferably, a water miscible solvent such as ethanol is used for the extraction of Ambra oxide from the solid phase of the reaction mixture. The use of ethanol is advantageous because it is easy to handle, it is non-toxic and it is environmentally friendly.

The term "isolated" as used herein refers to a bioconversion product such as Ambra oxide which has been separated or purified from components which accompany it. An entity that is produced in a cellular system different from the source from which it naturally originates is "isolated", because it will necessarily be free of components which naturally accompany it. The degree of isolation or purity can be measured by any appropriate method, e.g. gas chromatography (GC), HPLC or NMR analysis. In some embodiments, the end product (Ambra oxide) is isolated and purified to homogeneity (e.g. at least 80%, 81%, 82%, 83%, 84%, 85%, 86%, 87%, 88%, 89%, or 89.5% pure or 90%, 91%, 92%, 93%, 94%, 95%, 96%, 97%, 98%, 99%, or 99.5% pure).

Desirably, the amount of Ambra oxide produced can be from about 1 mg/l to about 20,000 mg/l (20 g/l) or higher such as from about 20 g/l to about 200 g/l or from 100-200 g/l, preferably about 125 g/l or 150 g/l or about 188 g/l.

For example about 1 to about 100 mg/l, about 30 to about 100 mg/l, about 50 to about 200 mg/l, about 100 to about 500 mg/l, about 100 to about 1,000 mg/l, about 250 to about 5,000 mg/l, about 1,000 (1 g/l) to about 15,000 mg/l (15 g/l), or about 2,000 (2 g/l) to about 10,000 mg/l (10 g/l) or about 2,000 (2 g/l) to about 25,000 mg/l (25 g/l) or about 2,000 (2 g/l) to about 25,000 mg/l (25 g/l), 26,000 mg/l (26 g/l), 27,000 mg/l (27 g/l), 28,000 mg/l (28 g/l), 29,000 mg/l (29 g/l), 30,000 mg/l (30 g/l), 40 g/l, 50 g/l, 60 g/l, 70 g/l, 80 g/l, 90 g/l, 100 g/l, 110 g/l, 120 g/l, 125 g/l, 130 g/l, 140 g/l, 150 g/l, 160 g/l, 170 g/l, 180 g/l, 190 g/l or 200 g/l or 300 g/l or 400 g/l or 500 g/l of Ambra oxide is produced. Preferably Ambra oxide at a concentration of at least 100 g/l is produced within a period of time from 48 to 72 hours.

Preferably Ambra oxide at a concentration of about 150 g/l is produced within a time period of from about 48 to 72 hours. Preferably Ambra oxide at a concentration of about 200 g/l is produced within a time period of from about 48 to 72 hours.

Preferably Ambra oxide at a concentration of about 250 g/l is produced within a time period of from about 48 to 72 hours.

The bioconversion of bishomofarnesol to Ambra oxide according to the present disclosure produces Ambra oxide as a predominant compound but may also produce compounds other than Ambra oxide which may or may not impart pleasant olfactive notes to the bioconversion mixture and so may contribute in a positive or negative manner to the sensory character of the Ambra oxide end product. Accordingly a sensory analysis is carried out using well established sensory tests utilized by trained Experts (e.g. Perfumers) so that the testing can assist in determining if a chemically relevant product is also an olfactively relevant end product relative to a reference product. The removal of one of more by-product compounds from Ambra oxide can improve the odor of the remaining compound (Ambra oxide) even if the removed compounds are actually odorless compounds per se. That is, an Ambra oxide odor enhancement may be observed in the absence of compounds XI, XII and XIII.

Various applications for Ambra oxide include but are not limited to a fine fragrance or a consumer product such as fabric care, toiletries, beauty care and cleaning products, detergent products, and soap products, including essentially all products where the currently available Ambra oxide ingredients are used commercially.

Thus, there is further provided herein a use of Ambra oxide obtained by or obtainable by a process described herein as part of a fragrance or a cosmetic or a consumer product. There is also provided herein a product comprising Ambra oxide obtained by or obtainable by a process described herein. The product may, for example, be a fragrance or a cosmetic or a consumer product.

Fragrance Compositions

There is further provided herein the use of the compounds and compositions described herein as or in a fragrance composition.

Thus, there is also provided herein a fragrance composition comprising one or more compounds of formula (I) or (X). A "fragrance composition" may, for example, be any composition comprising one or more compounds of formula (I) or (X) and a base material.

As used herein, the "base material" includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

Fragrance ingredients known to the art are readily available commercially from the major fragrance manufacturers. Non-limiting examples of such ingredients include:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl) pent-4-en-2-ol); eugenol (4-allyl-2-methoxyphenol); ethyl linalool ((E)-3,7- dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl) pentan-2-ol); terpineol (2-(4-methylcyclohex-3-en-1-yl) propan-2-ol); or Timberol™ (1-(2,2,6-trimethylcyclohexyl) hexan-3-ol); 2,4,7-trimethylocta-2,6-dien-1-ol, and/or [1-methyl-2 (5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl) but-3-en-2-one); 3-(4-isobutyl-2-methylphenyl) propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo [4.1.0]heptane-2,5'-[1,3]dioxane]);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

As used herein, "carrier material" means a material which is practically neutral from an odorant point of view, i.e. a material that does not significantly alter the organoleptic properties of odorants.

By "diluents" is meant any diluent conventionally used in conjunction with odorants, such as diethyl phthalate (DEP), dipropylene glycol (DPG), isopropyl myristate (IPM), triethyl citrate (TEC) and alcohol (e.g. ethanol).

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same, such as anti-oxidant adjuvant. Said anti-oxidant may be selected, for example, from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting colour or texture. It might also be an ingredient that imparts light resistance or chemical stability to one or more ingredients contained in a fragrance composition.

A detailed description of the nature and type of auxiliary agent commonly used in fragrance compositions containing same cannot be exhaustive, but it has to be mentioned that said ingredients are well known to a person skilled in the art.

There is also provided herein a consumer product comprising a compound or a composition or fragrance composition as described herein, including any embodiment thereof. The consumer product may, for example, be a cosmetic product (e.g. an eau de parfum or eau de toilette), a cleaning product, a detergent product, or a soap product.

Homofarnesol

Homofarnesol may have isomerism as shown below.

TABLE 4

Homofarnesol isomers.

| Compound | Abbreviation | Name and Structure |
| --- | --- | --- |
| E,E-Homofarnesol | EEH | 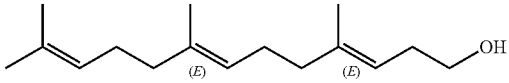 [SMILES: CC(C)=CCC/C(C)=C/CC/C(C)=C/CCO]<br>(3E,7E)-4,8,12-trimethyltrideca-3,7,11-trien-1-ol |
| E,Z-Homofarnesol | EZH | 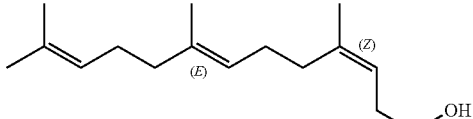<br>(3Z,7E)-4,8,12-trimethyltrideca-3,7,11-trien-1-ol |
| Z,E-Homofarnesol | ZEH | 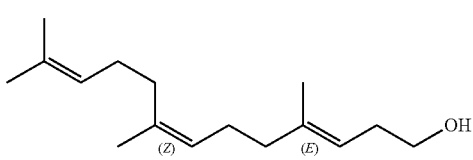 [SMILES: CC(C)=CCC/C(C)=C\CC/C(C)=C/CCO]<br>(3E,7Z)-4,8,12-trimethyltrideca-3,7,11-trien-1-ol |

TABLE 4-continued

Homofarnesol isomers.

| Compound | Abbreviation | Name and Structure |
|---|---|---|
| Z,Z-Homofarnesol | ZZH | 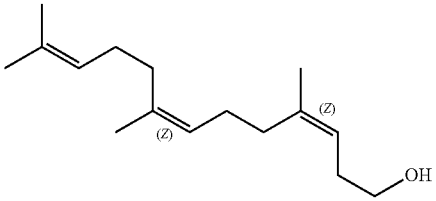 [SMILES: CC(C)=CCC/C(C)=C\CC/C(C)=C\CCO]<br>(3Z,7Z)-4,8,12-trimethyltrideca-3,7,11-trien-1-ol |

Beta-farnesene can be converted directly to E,E-homofarnesol (EEH) or indirectly to EEH via E,E-homofarnesate which is then converted to EEH. An overview on the production of (−)-Ambrox from different substrates can be found in US2012/0135477A1, WO 2010/139719, US2013.0273619A1, WO 2013/156398A1 and the Seitz PhD thesis (2012 as cited above) and Schaefer 2011 (Chemie Unserer Zeit 45, 374-388), the contents of which are incorporated herein by reference.

US2012/0135477A1 reports on the conversion of (3Z,7E) to (−)-Ambrox using ZmoSHC but according to the disclosure in Schaefer (2011) (as cited above), (7E,3Z) is only converted to 9b-epi-Ambrox (i.e. compound (III) as outlined above) and not to (−)-Ambrox. As used herein, a reference to (3Z,7E) homofarnesol is a reference to E,Z-homofarnesol which is also designated as EZH.

Whilst homofarnesol may be a mixture of four isomers, the (3Z,7Z), (3E,7Z), (3Z,7E) and (3E,7E) isomers, it seems from the literature that (−)-Ambrox is only obtained from (3E,7E) homofarnesol (see Neumann and Simon (1986) as cited above). As used herein, a reference to (3E,7E)-homofarnesol is a reference to E,E-homofarnesol which is also designated as EEH.

The starting materials for the processes described herein for preparing (−)-Ambrox may, for example, be (3E,7E)-homofarnesol or a mixture comprising (3E,7E)-homofarnesol, for example a mixture of isomers of homofarnesol comprising (3E,7E)-homofarnesol.

Preferably the homofarnesol starting material comprises a mixture of (3E,7E) and (3Z,7E), termed herein an EE:EZ isomeric mixture. An EE:EZ isomeric mixture of homofarnesol has the CAS number of 35826-67-6.

E/Z-mixture CAS 35826-67-6

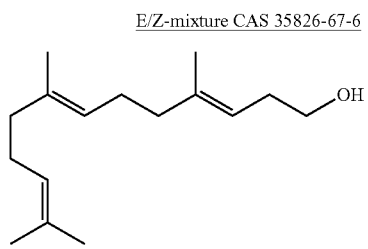

(3E,7E)-Homofarnesol
CAS; 459-89-2

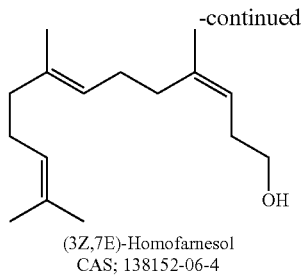

(3Z,7E)-Homofarnesol
CAS; 138152-06-4

The homofarnesol feedstock/starting material may be a mixture of isomers. Accordingly, the homofarnesol starting material may also comprise a mixture of the four isomers EE:EZ:ZZ:ZE which corresponds with (3E,7E), (3Z,7E), (3Z,7Z) and (3E,7Z). Preferably, the homofarnesol starting material is selected from one of more of the following mixture: [(3Z,7Z), (3E,7Z), (3Z,7E) and (3E,7E)], [(3Z,7E) and (3E,7E)], [(3Z,7E), (3E,7Z)] and/or [(3E,7E) and (3E,7Z)].

Preferably the homofarnesol starting material is selected from one or more of the following mixtures: [(3E,7E), (3Z,7E)] and/or [(3Z,7E), (3E/7E) and (3E,7Z)], also designated [EE:EZ] and [EE:EZ:ZE] respectively.

Accordingly, in certain embodiments, the ratio of EEH:EZH is about 100:00; 99:01; 98:02; 97:03; 96:04; 95:05; 94:06; 93:07; 92:08; 91:09; 90:10; 89:11; 88:12; 87:13; 86:14; 85:15; 84:16; 83:17; 82:18; 81:19; 80:20; 79:21; 78:22; 77:23; 76:24; 75:25; 74:26; 73:27; 72:28; 71:29; 70:30; 69:31; 68:32; 67:33; 66:34; 65:35; 64:36; 63:37; 62:38; 61:39; 60:40; 59:41; 58:42; 57:43; 56:44; 55:45: 54:46; 53:47: 52:48; 51:49; or about 50:50. For example, the ratio of EEH:EZH may range from about 50:50 to about 100:00 or from about 50:50 to about 99:01 or from about 60:40 to about 99:1 or from about 70:30 to about 95:5 or from about 80:20 to about 95:5.

In some embodiments preferably the homofarnesol starting material comprises >90% E,E-homofarnesol (EEH).

In other embodiments, the homofarnesol starting material comprises an EE:EZ weight ratio of 86:14.

In certain embodiments, the homofarnesol starting material comprises an EE:EZ weight ratio of 80:20.

In certain embodiments, the homofarnesol starting material comprises an EE:EZ weight ratio of 70:30.

In further embodiments, the homofarnesol starting material comprises an EE:EZ weight ratio of 69:31.

The number of homofarnesol isomers present may influence the speed of the reaction. A SHC/HAC enzyme or enzyme variant may be capable of converting E,E-homofarnesol to (−)-Ambrox from a complex mixture of homofarnesol isomers (e.g. EE:EZ:ZE:ZZ). However, a lower conversion rate may be observed, which is consistent with the view that homofarnesol isomers other than EEH may compete with EEH for access to the SHC/HAC derivative enzymes and thus may act as competitive inhibitors for the conversion of EEH to (−)-Ambrox and/or also act as alternative substrates (see for example, Eichhorn et al (2018) Adv. Synth. Catal. 360:2339-2351, the contents of which are incorporated here by reference). Accordingly, the homofarnesol substrate may comprise a isomeric mixture of 2-4 isomers, preferably two isomers.

Accordingly, the homofarnesol substrate may consist of or consist essentially of a isomeric mixture of 2-4 isomers, preferably two isomers.

Preferably the homofarnesol substrate comprises an EE:EZ isomeric mixture. Preferably the homofarnesol substrate consists of or consists essentially of an EE:EZ isomeric mixture.

If, for example, an EE:EZ isomer mixture is used, then compounds (eg compounds II, III and IV as set out in Table 2) other than (−)-Ambrox are in an "oily" form (rather than a sold form) which facilitates the stirring of the reaction mixture and the resulting bioconversion process.

Bishomofarnesol

Bishomofarnesol may have isomerism as shown in Table 5 below.

TABLE 5

Bishomofarnesol isomers.

| Compound | Abbreviation | Name and Structure |
|---|---|---|
| E,E-Bishomofarnesol | BisEEH | (4E,8E)-5,9,13-trimethyltetradeca-4,8,12-trien-1-ol |
| E,Z-Bishomofarnesol | BisEZH | (4Z,8E)-5,9,13-trimethyltetradeca-4,8,12-trien-1-ol |
| Z,E-Bishomofarnesol | BisZEH | (4E,8Z)-5,9,13-trimethyltetradeca-4,8,12-trien-1-ol |
| Z,Z-Bishomofarnesol | BisZZH | (4Z,8Z)-5,9,13-trimethyltetradeca-4,8,12-trien-1-ol |

Bishomofarnesol may be produced from E-Nerolidol as described in the Examples below. For example, bishomofarnesol may be produced as a mixture of two or more isomers (e.g. a mixture of E,E-bishomofarnesol and E,Z-bishomofarnesol). Whilst bishomofarnesol may present as a mixture of four isomers (the (Z,Z), (E,Z), (Z,E) and (E,E) isomers) it seems that Ambra oxide is only obtained from E,E-bishomofarnesol.

The starting materials for the processes described herein for preparing Ambra oxide may, for example, be E,E-bishomofarnesol or a mixture comprising E,E-bishomofarnesol, for example a mixture of isomers of bishomofarnesol comprising E,E-bishomofarnesol.

Preferably the bishomofarnesol starting material comprises a mixture of (BisEEH) and (BisEZH), termed herein an EE:EZ isomeric mixture.

The bishomofarnesol feedstock/starting material may be a mixture of isomers. Accordingly, the bishomofarnesol starting material may also comprise a mixture of the four isomers EE:EZ:ZZ:ZE.

Accordingly, in certain embodiments, the ratio of BisEEH:BisEZH is about 100:00; 99:01; 98:02; 97:03; 96:04; 95:05; 94:06; 93:07; 92:08; 91:09; 90:10; 89:11; 88:12; 87:13; 86:14; 85:15; 84:16; 83:17; 82:18; 81:19; 80:20; 79:21; 78:22; 77:23; 76:24; 75:25; 74:26; 73:27; 72:28; 71:29; 70:30; 69:31; 68:32; 67:33; 66:34; 65:35; 64:36; 63:37; 62:38; 61:39; 60:40; 59:41; 58:42; 57:43; 56:44; 55:45; 54:46; 53:47; 52:48; 51:49; or about 50:50. For example, the ratio of BisEEH:BisEZH may range from about 50:50 to about 100:00 or from about 50:50 to about 99:01 or from about 60:40 to about 99:1 or from about 70:30 to about 95:5 or from about 80:20 to about 95:5. In some embodiments preferably the bishomofarnesol starting material comprises >90% E,E-bishomofarnesol (EEH).

In other embodiments, the bishomofarnesol starting material comprises an BisEEH:BisEZH weight ratio of 86:14. In certain embodiments, the bishomofarnesol starting material comprises a BisEEH:BisEZH weight ratio of 80:20.

In certain embodiments, the bishomofarnesol starting material comprises a BisEEH:BisEZH weight ratio of 70:30.

In further embodiments, the bishomofarnesol starting material comprises an BisEEH:BisEZH weight ratio of 69:31.

The number of bishomofarnesol isomers present may influence the speed of the reaction. A SHC/HAC enzyme or enzyme variant may be capable of converting E,E-bishomofarnesol to Ambra oxide from a complex mixture of bishomofarnesol isomers (e.g. EE:EZ:ZE:ZZ). However, a lower conversion rate may be observed, which is consistent with the view that bishomofarnesol isomers other than BisEEH may compete with BisEEH for access to the SHC/HAC enzyme or enzyme variant and thus may act as competitive inhibitors for the conversion of BisEEH to Ambra oxide and/or also act as alternative substrates. Accordingly, the bishomofarnesol substrate may comprise a isomeric mixture of 2-4 isomers, preferably two isomers.

Accordingly, the bishomofarnesol substrate may consist of or consist essentially of a isomeric mixture of 2-4 isomers, preferably two isomers.

Preferably the bishomofarnesol substrate comprises an EE:EZ isomeric mixture.

Preferably the bishomofarnesol substrate consists of or consists essentially of an EE:EZ isomeric mixture.

Nucleic Acids and Methods of Making Nucleic Acids

There is further provided herein nucleic acids encoding a SHC/HAC enzyme or a SHC/HAC enzyme variant as described herein. The nucleic acid may, for example, be an isolated nucleic acid.

In particular, there is provided herein a construct comprising a nucleic acid sequence encoding a SHC/HAC enzyme or enzyme variant as described herein. As used herein, a "construct" is an artificially created segment of nucleic acid that is to be transfected into a target cell. The construct may comprise the nucleic acid encoding the SHC/HAC enzyme or enzyme variant and an expression controller (e.g. promoter).

There is further provided herein a vector comprising a construct as described herein. As used herein, a "vector" is a DNA molecule that is used as a vehicle to artificially carry foreign genetic material into a cell where it can be replicated and/or expressed. The vector may, for example, be a plasmid, a viral vector, a cosmid, or an artificial chromosome.

The terms "construct" and "vector" may overlap, for example where the construct is a plasmid.

In particular, there is provided herein a nucleic acid encoding an amino acid sequence of any one of SEQ ID NO: 2, SEQ ID NO: 3, SEQ ID NO: 4, SEQ ID NO: 5, SEQ ID NO: 17, SEQ ID NO: 18, SEQ ID NO: 24, SEQ ID NO: 25, SEQ ID NO: 26 and SEQ ID NO: 27.

In particular, there is provided herein a nucleic acid having the sequence of SEQ ID NO: 6, SEQ ID NO: 7, SEQ ID NO: 8, SEQ ID NO: 9, SEQ ID NO: 22 and SEQ ID NO: 23 which may, for example, be comprised in a construct or a vector as described herein.

The term "nucleic acid" or "nucleic acid molecule" as used herein shall specifically refer to polynucleotides of the disclosure which can be DNA, cDNA, genomic DNA, synthetic DNA, or RNA, and can be double-stranded or single-stranded, the sense and/or an antisense strand. The term "nucleic acid" or "nucleic acid molecule" shall particularly apply to the polynucleotide(s) as used herein, e.g. as full-length nucleotide sequence or fragments or parts thereof, which encode a polypeptide with enzymatic activity, e.g. an enzyme of a metabolic pathway, or fragments or parts thereof, respectively.

The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein (e.g. a His tag), mutein, or fragment of a given protein; and a nucleic acid which is a degenerate variant of a cDNA or a naturally occurring nucleic acid. In addition, it includes a recombinant nucleotide sequence that is part of a hybrid gene, i.e. a gene encoding a non-naturally occurring fusion protein. Fusion proteins can add one or more amino acids (such as but not limited to Histidine (His)) to a protein, usually at the N-terminus of the protein but also at the C-terminus or fused within regions of the protein. Such fusion proteins or fusion vectors encoding such proteins typically serve three purposes: (i) to increase production of recombinant proteins; (ii) to increase the solubility of the recombinant protein; and (iii) to aid in the purification of the recombinant protein by providing a ligand for affinity purification.

The term "nucleic acid" or "nucleic acid molecule" also includes codon optimised sequences suitable for expression in a particular microbial host cell (e.g. E. coli host cell). As used herein, the term "codon optimized" means a nucleic acid protein coding sequence which has been adapted for expression in a prokaryotic or a eukaryotic host cell, particularly bacterial host cells such as E. coli host cells by substitution of one or more or preferably a significant number of codons with codons that are more frequently used in bacterial (e.g. E. coli) host cell genes.

In this regard, the nucleotide sequence encoding the reference amino acid sequence (SEQ ID NO: 1 or SEQ ID NO: 10) and variants/derivatives thereof may be the original one as found in the source (e.g. SEQ ID NO: 1 found in AacSHC) or the gene can be codon-optimized for the selected host organisms, such as e.g. *E. coli*.

A ribonucleic acid (RNA) molecule can be produced by in vitro transcription. Segments of DNA molecules are also considered within the scope of the disclosure, and can be produced by, for example, the polymerase chain reaction (PCR) or generated by treatment with one or more restriction endonucleases. Segments of a nucleic acid molecule may be referred to as DNA fragments of a gene, in particular those that are partial genes. A fragment can also contain several open reading frames (ORF), either repeats of the same ORF or different ORF's. The term shall specifically refer to coding nucleotide sequences, but shall also include nucleotide sequences which are non-coding, e.g. untranscribed or untranslated sequences, or encoding polypeptides, in whole or in part. The genes as used herein, e.g. for assembly, diversification or recombination can be non-coding sequences or sequences encoding polypeptides or protein encoding sequences or parts or fragments thereof having sufficient sequence length for successful recombination events. More specifically, said genes have a minimum length of 3 bp, preferably at least 100 bp, more preferred at least 300 bp. It will be apparent from the foregoing that a reference to an isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice. An isolated nucleic acid molecule of the present disclosure encompasses segments that are not found as such in the natural state.

As used herein, the term "isolated DNA" can refer to (1) a DNA that contains sequence not identical to that of any naturally occurring sequence, a polynucleotide or nucleic acid which is not naturally occurring, (e.g. is made by the artificial combination (e.g. artificial manipulation of isolated segments of nucleic acids, e.g. by genetic engineering techniques) of two otherwise separated segments of sequences through human intervention) or (2), in the context of a DNA with a naturally-occurring sequence (e.g. a cDNA or genomic DNA), a DNA free of at least one of the genes that flank the gene containing the DNA of interest in the genome of the organism in which the gene containing the DNA of interest naturally occurs.

The term "isolated DNA" as used herein, specifically with respect to nucleic acid sequences may also refer to nucleic acids or polynucleotides produced by recombinant DNA techniques, e.g. a DNA construct comprising a polynucleotide heterologous to a host cell, which is optionally incorporated into the host cell. A chimeric nucleotide sequence may specifically be produced as a recombinant molecule. The term "recombination" shall specifically apply to assembly of polynucleotides, joining together such polynucleotides or parts thereof, with or without recombination to achieve a cross-over or a gene mosaic. For example, it is performed to join together nucleic acid segments of desired functions to generate a desired combination of functions. A recombinant gene encoding a polypeptide described herein may include the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence.

The term "recombinant" as used herein, specifically with respect to enzymes shall refer to enzymes produced by recombinant DNA techniques, i.e. produced from cells transformed by an exogenous DNA construct encoding the desired enzyme. "Synthetic" enzymes are those prepared by chemical synthesis. A chimeric enzyme may specifically be produced as recombinant molecule. The term "recombinant DNA" therefore includes a recombinant DNA incorporated into a vector into an autonomously replicating plasmid or virus, or into the genomic DNA of a prokaryote or eukaryote (or the genome of a homologous cell, at a position other than the natural chromosomal location).

In a further aspect the nucleic acid molecule(s) of the present disclosure is/are operatively linked to expression control sequences allowing expression in prokaryotic and/or eukaryotic host cells. As used herein, "operatively linked" means incorporated into a genetic construct so that expression control sequences effectively control expression of a coding sequence of interest. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression or which allow inducible expression like, for example, CUP-1 promoter, the tet-repressor as employed, for example, in the tet-on or tet-off systems, the lac system, the trp system regulatory elements. By way of example, Isopropyl β-D-1-thiogalactopyranoside (IPTG) is an effective inducer of gene expression in the concentration range of 100 μM to 1.0 mM. This compound is a molecular mimic of allolactose, a lactose metabolite that triggers transcription of the lac operon, and it is therefore used to induce gene expression when the gene is under the control of the lac operator. Another example of a regulatory element which induces gene expression is lactose. Similarly, the nucleic acid molecule(s) of the present disclosure can form part of a hybrid gene encoding additional polypeptide sequences, for example, a sequence that functions as a marker or reporter. Examples of marker and reporter genes including beta-lactamase, chloramphenicol acetyltransferase (CAT), adenosine deaminase (ADA), aminoglycoside phosphotransferase dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

In some embodiments, the present disclosure provides a recombinant polynucleotide encoding the SHC/HAC enzyme or variant thereof, which may be inserted into a vector for expression and optional purification. One type of vector is a plasmid representing a circular double stranded DNA loop into which additional DNA segments are ligated. Certain vectors can control the expression of genes to which they are functionally linked. These vectors are called "expression vectors". Usually expression vectors suitable for DNA recombination techniques are of the plasmid type. Typically, an expression vector comprises a gene such as the SHC/HAC enzyme or variant thereof as described herein. In the present description, the terms "plasmid" and "vector" may be used interchangeably since the plasmid is the vector type most often used. Such vectors can include DNA sequences which include but are not limited to DNA sequences that are not naturally present in the host cell, DNA sequences that are not normally transcribed into RNA or translated into a protein ("expressed") and other genes or DNA sequences which one desires to introduce into the non-recombinant host. It will be appreciated that typically the genome of a recombinant host described herein is augmented through the stable introduction of one or more recombinant genes. However, autonomous or replicative plasmids or vectors can also be used within the scope of this disclosure. Moreover, the present disclosure can be practiced using a low copy number, e.g. a single copy, or high copy number (as exemplified herein) plasmid or vector.

In a preferred embodiment, the vector of the present disclosure includes plasmids, phagemids, phages, cosmids, artificial bacterial and artificial yeast chromosomes, knock-out or knock-in constructs, synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

It is preferred that the proteins encoded by the introduced polynucleotide are expressed within the cell upon introduction of the vector. The diverse gene substrates may be incorporated into plasmids. The plasmids are often standard cloning vectors, e.g. bacterial multicopy plasmids. The substrates can be incorporated into the same or different plasmids. Often at least two different types of plasmid having different types of selectable markers are used to allow selection for cells containing at least two types of vectors.

Typically bacterial or yeast cells may be transformed with any one or more nucleotide sequences as is well known in the art. For in vivo recombination, the gene to be recombined with the genome or other genes is used to transform the host using standard transforming techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

Host Cells, Methods of Making Host Cells, and Methods of Making Ambrox and Ambra Oxide Using Host Cells There is further provided herein a recombinant host cell comprising a nucleic acid sequence or a construct or a vector as described herein. There is further provided herein a recombinant host cell that produces a SHC/HAC enzyme or enzyme variant as described herein.

The processes described herein for producing (–)-Ambrox or Ambra oxide may, for example, comprise culturing a recombinant host cell as described herein. As used herein, the term "culturing" refers to a process of producing living cells such that they produce a SHC/HAC enzyme or enzyme variant as described herein that can be used in a process for producing (–)-Ambrox or Ambra oxide as described herein. It is not necessary for the cells to divide and replicate themselves, although this is not excluded.

A bacterial or yeast cell may be transformed by exogenous or heterologous DNA when such DNA has been introduced inside the cell. The transforming DNA may or may not be integrated, i.e. covalently linked into the genome of the cell. In prokaryotes, and yeast, for example, the transforming DNA may be maintained on an episomal element such as a plasmid. With respect to eukaryotic cells, a stably transfected cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g. to enhance production of the product of a gene or alter the expression pattern of a gene. In some instances, the introduced DNA will modify or even replace an endogenous gene or DNA sequence, e.g. by homologous recombination or site-directed mutagenesis. Suitable recombinant hosts include microorganisms, plant cells, and plants.

The present disclosure also features recombinant hosts. The term "recombinant host", also referred to as a "genetically modified host cell" or a "transgenic cell" denotes a host cell that comprises a heterologous nucleic acid or the genome of which has been augmented by at least one incorporated DNA sequence. A host cell of the present disclosure may be genetically engineered with the polynucleotide or the vector as outlined above.

The host cells that may be used for purposes of the disclosure include but are not limited to prokaryotic cells such as bacteria (for example, *E. coli* and *B. subtilis*), which may, for example, be transformed with, for example, recombinant bacteriophage DNA, plasmid DNA, bacterial artificial chromosome, or cosmid DNA expression vectors containing the polynucleotide molecules of the disclosure; simple eukaryotic cells like yeast (for example, *Saccharomyces* and *Pichia*), which may, for example, be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondrial DNA or can be maintained extrachromosomally like, for example, episomally or can be only transiently comprised in the cells.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp, yeast host cells, such as *S. cerevisiae*, insect host cells, such as *Spodoptora frugiperda* or human host cells, such as HeLa and Jurkat.

Specifically, the cell is a eukaryotic cell, preferably a fungal, mammalian or plant cell, or a prokaryotic cell. Suitable eukaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include without limitation *E. coli*.

Preferably prokaryotes, such as *E. coli*, *Bacillus*, *Streptomyces*, or mammalian cells, like Hela cells or Jurkat cells, or plant cells, like *Arabidopsis*, may be used.

The cell may, for example, be selected from prokaryotic, yeast, plant, and/or insect host cells.

Preferably the cell is an *Aspergillus* sp. or a fungal cell, preferably, it can be selected from the group consisting of the genera *Saccharomyces*, *Candida*, *Kluyveromyces*, *Hansenula*, *Schizosaccharomyces*, *Yarrowia*, *Pichia* and *Aspergillus*.

Preferably, the cell us a bacteria cells, for example, having a genus selected from *Escherichia*, *Streptomyces*, *Bacillus*, *Pseudomonas*, *Lactobacillus* and *Lactococcus*. For example, the bacteria may be *E. coli*.

Preferably the *E. coli* host cell is an *E. coli* host cell which is recognized by the industry and regulatory authorities (including but not limited to an *E. coli* K12 host cell or an *E. coli* BL21 host cell).

One preferred host cell to use with the present disclosure is *E. coli*, which may be recombinantly prepared as described herein. Thus, the recombinant host may be a recombinant *E. coli* host cell. There are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

In one embodiment, the recombinant *E. coli* microorganism comprises nucleotide sequences encoding SHC/HAC enzyme or enzyme variant genes.

Preferably, the recombinant *E. coli* microorganism comprises a vector construct as described herein. In another preferred embodiment, the recombinant *E. coli* microorganism comprises nucleotide sequences encoding the SHC/HAC enzymes and enzyme variants disclosed herein.

Another preferred host cell to use with the present disclosure is *S. cerevisiae* which is a widely used chassis organism in synthetic biology. Thus, the recombinant host may be *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

Culturing of cells may be performed in a conventional manner. The culture medium may contain a carbon source, at least one nitrogen source and inorganic salts, and vitamins are added to it. The constituents of this medium can be the ones which are conventionally used for culturing the species of microorganism in question. Carbon sources of use in the instant method include any molecule that can be metabolized by the recombinant host cell to facilitate growth and/or production of (−)-Ambrox or Ambra oxide. Examples of suitable carbon sources include, but are not limited to, sucrose (e.g. as found in molasses), fructose, xylose, glycerol, glucose, cellulose, starch, cellobiose or other glucose containing polymer.

In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g. protein, and then provided with a source of carbon only during the fed-batch phase.

The suitability of a recombinant host cell microorganism for use in the methods of the present disclosure may be determined by simple test procedures using well known methods. For example, the microorganism to be tested may be propagated in a rich medium (e.g. LB-medium, Bactotryptone yeast extract medium, nutrient medium and the like) at a pH, temperature and under reaction conditions commonly used for propagation of the microorganism. Once recombinant microorganisms (i.e. recombinant host cells) are selected that produce the desired products of bioconversion, the products are typically produced by a production host cell line on the large scale by suitable expression systems and fermentations, e.g. by microbial production in cell culture. In one embodiment of the present disclosure, a defined minimal medium such as M9A is used for cell cultivation.

The components of M9A medium comprise: 14 g/l $KH_2PO_4$, 16 g/l $K_2HPO_4$, 1 g/l $Na_3Citrate \cdot 2H_2O$, 7.5 g/l $(NH_4)_2SO_4$, 0.25 g/l $MgSO_4 \cdot 7H_2O$, 0.015 g/l $CaCl_2 \cdot 2H_2O$, 5 g/l glucose and 1.25 g/l yeast extract).

In another embodiment of the present disclosure, nutrient rich medium such as LB was used. The components of LB medium comprise: 10 g/l tryptone, 5 g/l yeast extract, 5 g/l NaCl. Other examples of Mineral Medium and M9 Mineral Medium are disclosed, for example, in U.S. Pat. No. 6,524,831B2 and US 2003/0092143A1.

Another example of a minimal medium may be prepared as follows: for 350 ml culture: to 35 ml citric acid/phosphate stock (133 g/l $KH_2PO_4$, 40 g/l $(NH_4)_2HPO_4$, 17 g/l citric acid·$H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (see below) solution, 0.035 ml Thiamin solution and 7 ml 20% glucose were added.

Trace elements solution: 50 g/l $Na_2EDTA \cdot 2H_2O$, 20 g/l $FeSO_4 \cdot 7H_2O$, 3 g/l $H_3BO_3$, 0.9 g/l $MnSO_4 \cdot 2H_2O$, 1.1 g/l $CoCl_2$, 80 g/L $CuCl_2$, 240 g/l $NiSO_4 \cdot 7H_2O$, 100 g/l KI, 1.4 g/l $(NH_4)_6Mo_7O_{24} \cdot 4H_2O$, 1 g/l $ZnSO_4 \cdot 7H_2O$, in deionized water Thiamin solution: 2.25 g/l Thiamin·HCl in deionized water $MgSO_4$ solution: 50% (w/v) $MgSO_4 \cdot 7H_2O$ in deionized water The recombinant microorganism may be grown in a batch, fed batch or continuous process or combinations thereof. Typically, the recombinant microorganism is grown in a fermentor at a defined temperature(s) in the presence of a suitable nutrient source, e.g. a carbon source, for a desired period of time to produce sufficient enzyme to convert homofarnesol to Ambrox or to convert bishomofarnesol to Ambra oxide and to produce a desired amount of Ambrox including (−)-Ambrox or a desired amount of Ambra oxide of formula (X). The recombinant host cells may be cultivated in any suitable manner, for example by batch cultivation or fed-batch cultivation. As used herein, the term "batch cultivation" is a cultivation method in which culture medium and/or nutrients is/are neither added nor withdrawn during the cultivation.

As used herein, the term "fed-batch" means a cultivation method in which culture medium and/or nutrients is/are added during the cultivation but no culture medium is withdrawn.

One embodiment of the present disclosure provides a method of producing Ambrox or Ambra oxide in a cellular system comprising producing SHC/HAC enzymes or enzyme variants under suitable conditions in a cellular system, adding homofarnesol or bishomofarnesol to the cellular system, converting homofarnesol to Ambrox or converting bishomofarnesol to Ambra oxide using the SHC/HAC enzymes or enzyme variants produced using the cellular system, collecting Ambrox or Ambra oxide from cellular system and optionally isolating the (−)-Ambrox materials or Ambra oxide of formula (X) from the system. Expression of other nucleotide sequences may serve to enhance the method. The bioconversion method can include the additional expression of other nucleotide sequences in the cellular system. The expression of other nucleotide sequences may enhance the bioconversion pathway for making (−)-Ambrox or Ambra oxide. A further embodiment of the present disclosure is a bioconversion method of making (−)-Ambrox or Ambra oxide comprising growing host cells comprising SHC/HAC enzyme or enzyme variant genes, producing SHC/HAC enzymes or enzyme variants in the host cells, feeding homofarnesol (e.g. EEH) or bishomofarnesol (e.g. bisEEH) to the host cells, incubating the host cells under conditions of pH, temperature and solubilizing agent suitable to promote the conversion of homofarnesol to Ambrox or conversion of bishomofarnesol to Ambra oxide and collecting (−)-Ambrox or Ambra oxide of formula (X). The production of the SHC/HAC enzymes or enzyme variants in the host cells provides a method of making (−)-Ambrox or Ambra oxide of formula (X) when homofarnesol or bishomofarnesol is added to the host cells under suitable reaction conditions. Achieved conversion may be enhanced by adding more biocatalyst and SDS to the reaction mixture.

The recombinant host cell microorganism may be cultured in a number of ways in order to provide cells in suitable amounts producing the SHC/HAC enzymes or enzyme variants for the subsequent bioconversion step. Since the microorganisms applicable for the bioconversion step vary broadly (e.g. yeasts, bacteria and fungi), culturing conditions are, of course, adjusted to the specific requirements of each species and these conditions are well known and documented. Any of the art known methods for growing cells of recombinant host cell microorganisms may be used to produce the cells utilizable in the subsequent bioconversion step of the present disclosure. Typically the cells are grown to a particular density (measurable as optical density (OD)) to produce a sufficient biomass for the bioconversion reaction.

The cultivation conditions chosen influence not only the amount of cells obtained (the biomass) but the quality of the cultivation conditions also influences how the biomass becomes a biocatalyst. The recombinant host cell microorganism expressing the SHC/HAC enzyme or enzyme variant gene and producing the SHC/HAC enzyme or enzyme variant is termed a biocatalyst which is suitable for use in a bioconversion reaction. In some embodiments the biocatalyst is a recombinant whole cell producing SHC/HAC enzymes or enzyme variants or it may be in suspension or an immobilized format. In other embodiments, the biocatalyst is a membrane fraction or a liquid fraction prepared from the recombinant whole cell producing the SHC/HAC enzyme or enzyme variant (as disclosed for example in Seitz et al 2012—as cited above). The recombinant biocatalyst producing SHC/HAC enzymes or enzyme variants includes whole cells collected from the fermenter (for the bioconversion reaction) or the cells in the fermenter (which are then used in a one-pot reaction). The recombinant biocatalyst producing SHC/HAC enzymes or enzyme variants can include intact recombinant whole cell and/or cell debris. Either way, the SHC/HAC enzyme or enzyme variant is associated with a membrane (such as a cell membrane) in some way in order to receive and/or interact with a substrate (e.g. homofarnesol or bishomofarnesol), which membrane (such as a cell membrane) can be part of or comprise a whole cell (e.g. a recombinant whole cell). The SHC/HAC enzymes or enzyme variants may also be in an immobilized form (e.g. associated with an enzyme carrier) which allows the SHC/HAC enzymes or enzyme variants to interact with a substrate (e.g. homofarnesol or bishomofarnesol). The SHC/HAC enzymes or enzyme variants may also be used in a soluble form.

In one embodiment, the biocatalyst is produced in sufficient amounts (to create a sufficient biomass), harvested and washed (and optionally stored (e.g. refrigerated, frozen or lyophilized)) before starting the bioconversion step.

In a further embodiment, the cells are produced in sufficient amounts (to create a sufficient biocatalyst) and the reaction conditions are then adjusted without the need to harvest and wash the biocatalyst for the bioconversion reaction. This one step (or "one pot") method is advantageous as it simplifies the process while possibly reducing costs. The culture medium used to grow the cells is also suitable for use in the bioconversion reaction provided that the reaction conditions are adjusted to facilitate the bioconversion reaction.

The optimum pH for growing the cells is in the range of 6.0-7.0. The optimum pH for the bioconversion reaction is dependent on the type of SHC/HAC enzyme or enzyme variant used in the bioconversion reaction. The pH is regulated using techniques which are well known to the Skilled Person.

Whilst the terms "mixture" or "reaction mixture" may be used interchangeably with the term "medium" in the present disclosure (especially as it relates to a "one pot" reaction), it should be noted that growing the cells to create a sufficient biomass requires a cell culture/fermentation medium but a medium is not required for the bioconversion step as a reaction buffer will suffice at a suitable pH.

The bioconversion methods of the present disclosure are carried out under conditions of time, temperature, pH and solubilizing agent to provide for conversion of the homofarnesol or bishomofarnesol feedstock (e.g. comprising EEH or bisEEH) to (−)-Ambrox or Ambra oxide.

The pH of the reaction mixture may be in the range of 4-8, preferably, 5 to 6.5, more preferably 4.8-6.0 for the SHC/HAC enzyme variants and in the range of from about pH 5.0 to about pH 7.0 for the wild-type SHC/HAC enzymes and can be maintained by the addition of buffers to the reaction mixture. Exemplary buffers for this purpose include but are not limited to a citric acid buffer, a phosphate buffer, an acetic acid buffer and/or a succinic acid buffer.

The preferred temperature is between from about 15° C. and about 60° C., for example from about 15° C. to about 50° C. or from about 15° C. to about 45° C. or from about 30° C. to about 60° C. or from about 40° C. to about 50° C. The temperature can be kept constant or can be altered during the bioconversion process.

The Applicant has demonstrated that it may be useful to include a solubilizing agent (e.g. a surfactant, detergent, solubility enhancer, water miscible organic solvent and the like) in the bioconversion reaction.

As used herein, the term "surfactant" means a component that lowers the surface tension (or interfacial tension) between two liquids or between a liquid and a solid. Surfactants may act as detergents, wetting agents, emulsifiers, foaming agents, and dispersants. Examples of surfactants include but are not limited to Triton X-100, Tween 80, taurodeoxycholate, Sodium taurodeoxycholate, Sodium dodecyl sulfate (SDS), and/or sodium lauryl sulfate (SLS).

Whilst Triton X-100 may be used to partially purify the SHC/HAC enzyme or enzyme variant (in soluble or membrane fraction/suspension form), it may also be used in the bioconversion reaction (see for example the disclosure in Seitz (2012 PhD thesis as cited above) as well as the disclosure in Neumann and Simon (1986—as cited above) and JP2009060799. However, surprisingly, the Applicant selected and identified SDS as a particularly useful solubilizing agent from a long list of other less useful solubilizing agents. In particular, the Applicant identified SDS as a remarkably better solubilizing agent than e.g. Triton X-100 in terms of reaction velocity and yield for the homofarnesol to (−)-Ambrox bioconversion reaction (when EEH is used at both 4 g/l and 125 g/l. For at least one SHC/HAC derivative enzyme, that maximal homofarnesol to (−)-Ambrox bioconversion activity with Triton X-100 (at a concentration range of about 0.005% to 0.48%) in the reaction may be only around 20% of the activity obtained with SDS (at a concentration of about 0.07%) with EEH at 4 g/l and cells at an $OD_{650nm}$ of 10.

Without wishing to be bound by theory, the use of SDS with recombinant microbial host cells may be advantageous as the SDS may interact advantageously with the host cell membrane in order to make the SHC/HAC enzyme or enzyme variant (which is a membrane bound enzyme) more accessible to the homofarnesol substrate. In addition, the inclusion of SDS at a suitable level in the reaction mixture may improve the properties of the emulsion (homofarnesol in water) and/or improve the access of the homofarnesol substrate to the SHC enzyme within the host cell while at the same time preventing the disruption (e.g. denaturation of the SHC (WT or SHC/HAC variant) enzyme). The concentration of the solubilising agent (e.g. SDS) used in the bioconversion reaction is influenced by the biomass amount and the substrate (EEH) concentration. That is, there is a degree of interdependency between the solubilising agent (e.g. SDS) concentration, the biomass amount and the substrate (EEH) concentration. By way of example, as the concentration of homofarnesol substrate increases, sufficient amounts of biocatalyst and solubilising agent (e.g. SDS) are required for an efficient bioconversion reaction to take place. If, for example, the solubilising agent (e.g. SDS) concentration is too low, a suboptimal homofarnesol conversion may be observed. On the other hand, if, for example, the solubilising agent (e.g. SDS) concentration is too high, then there may be a risk that the biocatalyst is affected through either the disruption of the intact microbial cell and/or denaturation/inactivation of the SHC/HAC enzyme or enzyme variant. The selection of a suitable concentration of SDS in the context of the biomass amount and, substrate (EEH) concentration is within the knowledge of the Skilled Person. By way of example, a predictive model can be developed by the Skilled Person to determine the suitable SDS, substrate (EEH) and biomass concentrations. SDS in the range of 0.010-0.075% may be appropriate when 4 g/l EEH and biocatalyst to an OD of 10.0 (650 nm) are used. When 125 g/l EEH is used with 2× the wet weight of biomass, an adjusted SDS concentration (1.3%) may be appropriate. However, an investigation of the percent EEH conversion to (−)-Ambrox using different SDS/cells ratio values indicated that the correct selection of the ratio of biocatalyst, homofarnesol substrate and solubilising agent (e.g. SDS) facilitates the development of a robust bioconversion reaction system which demonstrates a degree of tolerance to a range of SDS concentrations and pH ranges.

The temperature of the bioconversion reaction for a WT SHC enzyme (eg. AacSHC) may be from about 30° C. to about 60° C., for example from about 45° C. to about 60° C., for example from about 50° C. to about 60° C., for example about 55° C.

The pH range of the bioconversion reaction for a WT SHC enzyme (eg. AacSHC) may be from about 5.0 to 7.0, more preferably from about 5.6 to about 6.2, even more preferably about 6.0.

The temperature of the bioconversion reaction for a SHC/HAC enzyme variant may be about 30° C. to about 55° C., for example from about 40° C. to about 50° C., for example about 45° C.

The pH of the bioconversion reaction for a SHC/HAC enzyme variant may be about 4.8-6.4, preferably about 5.2-6.0.

Preferably the solubilising agent used in the bioconversion reaction is SDS. The SDS concentration used in the bioconversion reaction for the WT SHC enzyme (e.g. AacSHC) may be in the range of about 0.010-0.075%, preferably about 0.030% when EEH at about 4 g/l and cells at an $OD_{650nm}$ of 10 is used.

The SDS concentration used in the bioconversion reaction for the SHC/HAC enzyme variant may be in the range of about 0.0025-0.090%, preferably about 0.050% when EEH at about 4 g/l and cells at an $OD_{650nm}$ of 10 is used.

The biocatalyst may be loaded to the reaction to an OD of about 10.0 (650 nm) when the reaction is loaded with homofarnesol at an EEH concentration of about 4 g/l EEH.

The [SDS]/[cells] ratio may be in the range of about, 10:1-20:1, preferably about 15:1-18:1, preferably about 16:1 when the ratio of biocatalyst to EEH homofarnesol is about 2:1 in the bioconversion reaction.

The SDS concentration in the bioconversion reaction for a SHC variant enzyme may be in the range of about 1-2%, preferably in the range of about 1.4-1.7%, even more preferably about 1.5% when the homofarnesol concentration is about 125 g/l EEH and the biocatalyst concentration is 250 g/l (corresponding to an OD of about 175 (650 nm)).

The ratio of biocatalyst to EEH homofarnesol substrate may be in the range of about 0.5:1-2:1, in some embodiments 2:1, preferably about 1:1 or 0.5:1.

The optimum temperature for the SHC/HAC enzyme variants may, for example, be equal to or greater than about 35° C. For example, the optimum temperature for the SHC/HAC enzyme variants may range from about 40° C. to about 50° C., for example from about 42° C. to about 48° C. or from about 44° C. to about 46° C. For example, the optimum temperature of the SHC/HAC enzyme variants may be about 45° C. The processes for making (−)-Ambrox or Ambra oxide disclosed herein may be carried out at the optimum temperature of the SHC/HAC enzyme variant.

The optimum pH for the SHC/HAC enzyme variants may, for example, be equal to or greater than about 5.4. For example, the optimum pH for the SHC/HAC enzyme variants may range from about 5.2 to about 6.0, for example from about 5.4 to about 5.8, for example from about 5.6 to about 5.8. For example, the optimum pH of the SHC/HAC enzyme variants may be about 5.6 or about 5.8. The process for making (−)-Ambrox or Ambra oxide disclosed herein may be carried out at the optimum pH of the SHC/HAC enzyme variant.

The optimum concentration of sodium dodecyl sulfate (SDS) in the reaction medium of the process for making (−)-Ambrox or Ambra oxide disclosed herein may, for example, be from about 0.010 w/w % to about 0.10 w/w %. For example, the optimum concentration of SDS may be from about 0.040 w/w % to about 0.080 w/w %, for example about 0.050 w/w % when the substrate (e.g. EEH or BisEEH) is used at 4 g/l with cells to an $OD_{650nm}$ of 10 The process for making (−)-Ambrox or Ambra oxide disclosed herein may be carried out using the optimum concentration of SDS described herein. The optimum concentration of sodium dodecyl sulfate (SDS) in the reaction medium of the processes for making (−)-Ambrox or Ambra oxide disclosed herein may, for example, be from about 1.0 w/w % to about 1.5 w/w % when the substrate (e.g. EEH or BisEEH) is used at 125 g/l with 250 g/l of cells. For example, the optimum concentration of SDS may be from about 1.2 w/w % to about 1.4 w/w %, for example about 1.3 w/w % when the substrate (e.g. EEH or BisEEH) is used at 125 g/l with 250 g/l of cells or about 0.65 w/w % when the substrate (e.g. EEH or BisEEH) is used at 125 g/l with 125 g/l of cells.

The processes for making (−)-Ambrox or Ambra oxide disclosed herein may be carried out within the optimum temperature range or at the optimum temperature and/or within the optimum pH range or at the optimum pH and/or within the SDS optimum concentration range or at the optimum SDS concentration for the specific enzyme used, as set out in Table 7 or 9 or 11 in the Examples below.

In some embodiments, Ambrox is produced using a biocatalyst to which the homofarnesol substrate is added.

In some embodiments, Ambra oxide is produced using a biocatalyst to which the bishomofarnesol substrate is added.

It is possible to add the substrate by feeding using known means (e.g. peristaltic pump, infusion syringe and the like). Homofarnesol and bishomofarnesol may be oil soluble compounds and provided in an oil format. Given that the biocatalyst (microbial cells such as intact recombinant whole cell and/or cell debris and/or immobilised enzyme) is present in an aqueous phase, the bioconversion reaction may be regarded as a three phase system (comprising an aqueous phase, a solid phase and an oil phase) when homofarnesol or bishomofarnesol is added to the bioconversion reaction mixture. This is the case even when SDS is present. By way of clarification, when a soluble WT SHC or a SHC/HAC enzyme variant is used as a biocatalyst, this is considered a two phase system.

A fermenter may be used to grow recombinant host cells expressing the SHC/HAC enzyme or enzyme variant gene and producing active SHC/HAC enzymes or enzyme variants to a sufficient biomass concentration suitable for use as a biocatalyst in the same fermenter vessel which is used to convert the homofarnesol source to (−)-Ambrox, for example in admixture with one or more of the by-products (II), (IV) and/or (III) or bishomofarnesol source to Ambra oxide, for example in admixture with one or more of the by-products (XI), (XII) and/or (XIII).

The Skilled Person will understand that higher cumulative production titers can be achieved by implementing a continuous process, such as product removal, substrate feed, and biomass addition or (partial) replacement. Preferably the bioconversion of EEH into (−)-Ambrox or BisEEH to Ambra oxide in the presence of a recombinant host cell comprising a SHC/HAC enzyme or enzyme variant generates an Ambrox or Ambra oxide yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of EEH or BisEEH employed; especially preferably, the yield is between 5 and 100, 10 and 100, and 100, 25 and 100, 30 and 100, 35 and 100, in particular between 40 and 100, 45 and 100, 50 and 100, 60 and 100, 70 and 100 mol percent.

The activity of the SHC/HAC enzyme or enzyme variant is defined via the reaction rate (amount of product/(amount of product+amount of remaining starting material))×100) in mol percent. Preferably, the bioconversion of EEH into (−)-Ambrox or BisEEH into Ambra oxide in the presence of a SHC/HAC enzyme or enzyme variant produces an (−)-Ambrox or Ambra oxide yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of EEH or BisEEH employed; especially preferably, the yield is between 5 and 100, 10 and 100, 20 and 100, 25 and 100, 30 and 100, 35 and 100, in particular between 40 and 100, 45 and 100, 50 and 100, 60 and 100, 70 and 100.

In a preferred embodiment of the invention, the yield and/or the reaction rate are determined over a defined time period of, for example, 4, 6, 8, 10, 12, 16, 20, 24, 36 or 48 hours, during which EEH is converted into (−)-Ambrox or BisEEH is converted into Ambra oxide by a recombinant host cell comprising a nucleotide sequence encoding a SHC/HAC enzyme or enzyme variant. In a further variant, the reaction is carried out under precisely defined conditions of, for example, 25° C., 30° C., 40° C., 50° C. or 60° C. In particular, the yield and/or the reaction rate are determined by carrying out the reaction of converting EEH into (−)-Ambrox or BisEEH into Ambra oxide by the SHC/HAC enzymes or enzyme variants according to the invention at 35° C. over a period of 24-72 hours.

In a further embodiment of the present invention, a recombinant host cell comprising a nucleotide sequence encoding a SHC/HAC enzyme variant is characterized in that it shows a 2-, 3-, 4-, 5-, 6-, 7-, 8-, 9-, 10-, 11-, 12-, 13-, 14-, 15-, 16-, 17-, 18-, 19- , 20-, 21-, 22-, 23-, 24-, 25-, 26-, 27-, 28-, 29-, 30-, 31-, 32-, 33-, 34-, 35-, 36-, 37-, 38- , 39-, 40-, 41-, 42-, 43-, 44-, 45-, 46-, 47-, 48-, 49-, 50-, 51-, 52-, 53-, 54-, 55-, 56-, 57- , 58-, 59-, 60-, 61-, 62-, 63-, 64-, 65-, 66-, 67-, 68-, 69-, 70-, 71-, 72-, 73-, 74-, 75-, 76- , 77-, 78-, 79-, 80-, 81-, 82-, 83-, 84-, 85-, 86-, 87-, 88-, 89-, 90-, 91-, 92-, 93-, 94-, 95- , 96-, 97-, 98-, 99-, 100-, 200-, 500-, 1000-fold or higher yield and/or reaction rates in the reaction of homofarnesol to give (−)-Ambrox or in the reaction of bishomofarnesol to give Ambra oxide in comparison with the WT SHC or SHC/HAC derivative enzyme under the same conditions. Here, the term condition relates to reaction conditions such as substrate concentration, enzyme concentration, reaction period and/or temperature. The successful development of a bioconversion process for making (−)-Ambrox from homofarnesol in a recombinant strain of E. coli comprising a nucleotide sequence encoding a WT/reference SHC or a SHC/HAC derivative can offer a low cost and industrially economical process for (−)-Ambrox production.

The successful development of a bioconversion process for making Ambra oxide from bishomofarnesol in a recombinant strain of E. coli comprising a nucleotide sequence encoding a WT/reference SHC or a SHC/HAC derivative can offer a low cost and industrially economical process for Ambra oxide production.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The term "comprising" also means "including" as well as "consisting" e.g. a composition "comprising" X may consist exclusively of X or may include something additional e.g. X+Y. It must be noted also that, as used in this specification and the appended claims, the singular forms "a", "an" and "the" include plural referents unless the content clearly dictates otherwise. By way of example, a reference to "a gene" or "an enzyme" is a reference to "one or more genes" or "one or more enzymes".

It is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by the person skilled in the art. In accordance with the present disclosure there may be conventional molecular biology, microbiology, and recombinant DNA techniques employed which are within the skill of the art.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety.

Stocks of materials for use in bioconversion reactions (125 g/l substrate or higher) were prepared either in g/l (for example a biocatalyst suspension) or w/w % (for example SDS) concentrations. Bioconversion reactions were set up by adding by weight the required amounts of individual components (for example stocks of substrate, biocatalyst suspension, SDS solution, reaction buffer) as described in, for example Example 4. For this reason the actual volume of the reaction mixture is expressed in mass units and not in volume units (see for example Example 4). Because the substrate used is an oil (density <1), a total reaction mass of e.g. 150 g (as for example in Example 4) does not translate into a reaction volume of 150 ml. Nonetheless the concentrations of the individual components in the bioconversion reaction mixtures are indicated in mass per volume (for example g/l or (w/v) %) and thus do not take into account that a total reaction mass of e.g. 150 g (as for example in. Example 4) does not correspond exactly to a reaction volume of 150 ml (as for example in Example 4).

For the avoidance of doubt, all reference to EEH in the Examples, the Figures and the legends to the Figures is a reference to the EE isomer of homofarnesol. The EEH used is taken from a homofarnesol stock comprising an EE:EZ isomer mixture in a weight ratio of 80:20.

The examples described herein are illustrative of the present disclosure and are not intended to be limitations thereon. Different embodiments of the present disclosure have been described according to the present disclosure. Many modifications and variations may be made to the techniques described and illustrated herein without departing from the spirit and scope of the disclosure. Accordingly, it should be understood that the examples are illustrative only and are not limiting upon the scope of the disclosure.

EXAMPLES

Example 1—Production and Testing of New SHC/HAC Enzyme Variants

SHC Plasmid Preparation

The gene encoding a wild-type or variant squalene hopene cyclase (SHC) enzyme was inserted into plasmid pET-28a (+), where it is under the control of an IPTG inducible T7-promotor for protein production in *Escherichia coli*. The plasmid was transformed into *E. coli* strain BL21 (DE3) using a standard heat-shock transformation protocol.

Media Preparation

The minimal medium chosen as default was prepared as follows for 350 ml culture: to 35 ml citric acid/phosphate stock (133 g/l $KH_2PO_4$, 40 g/l $(NH_4)_2HPO_4$, 17 g/l citric acid·$H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (see below), 0.035 ml Thiamin solution and 7 ml 20% glucose were added.

Trace elements solution: 50 g/l $Na_2EDTA·2H_2O$, 20 g/l $FeSO_4·7H_2O$, 3 g/l $H_3BO_3$, 0.9 g/l $MnSO_4·2H_2O$, 1.1 g/l $CoCl_2$, 80 g/L $CuCl_2$, 240 g/l $NiSO_4·7H_2O$, 100 g/l KI, 1.4 g/l $(NH_4)_6Mo_7O_{24}·4H_2O$, 1 g/l $ZnSO_4·7H_2O$, in deionized water Thiamin solution: 2.25 g/l Thiamin·HCl in deionized water $MgSO_4$ solution: 50% (w/v) $MgSO_4·7H_2O$ in deionized water Small Scale Biocatalyst Production (SHC/HAC Wild-Type Enzyme or Enzyme Variant)

350 ml culture (medium supplemented with 50 µg/ml kanamycin) were inoculated from a preculture of the *E. coli* strain BL21 (DE3) containing the SHC production plasmid. Cells were grown to an optical density of approximately 0.5 ($OD_{650nm}$) at 37° C. with constant agitation (250 rpm).

Protein production was then induced by the addition of IPTG to a concentration of 300 µM followed by incubation for a further 5-6 hours with constant shaking. The resulting biomass was finally collected by centrifugation and washed with e.g. 50 mM Tris-HCl buffer pH 7.5. The cells were stored as pellets at 4° C. or −20° C. until further use. In general 2.5 to 4 grams of cells (wet weight) were obtained from 1 liter of culture, independently of the medium used.

Biocatalyst Production in Fermenters

Fermentations were prepared and run in 750 ml InforsHT reactors. To the fermentation vessel was added 168 ml deionized water. The reaction vessel was equipped with all required probes ($pO_2$, pH, sampling, antifoam), C+N feed and sodium hydroxide bottles and autoclaved. After autoclaving is added to the reactor 20 ml 10× phosphate/citric acid buffer 14 ml 50% glucose 0.53 ml MgSO₄ solution
2 ml (NH₄)₂SO₄ solution
0.020 ml trace elements solution
0.400 ml thiamine solution
0.200 ml kanamycin stock The running parameters were set are as follows: pH=6.95, $pO_2$=40%, T=30° C., Stirring at 300 rpm. Cascade: rpm setpoint at 300, min 300, max 1000, flow (l/min) set point 0.1, min 0, max 0.6. Antifoam control: 1:9.

The fermenter was inoculated from a seed culture to an $OD_{650nm}$ of 0.4-0.5. This seed culture was grown in LB medium (+Kanamycin) at 37° C., 220 rpm for 8 h. The fermentation was run first in batch mode for 11.5 h, where after was started the C+N feed with a feed solution (sterilized glucose solution (143 ml $H_2O$+35 g glucose) to which had been added after sterilization: 17.5 ml $(NH_4)_2SO_4$ solution, 1.8 ml $MgSO_4$ solution, 0.018 ml trace elements solution, 0.360 ml Thiamine solution, 0.180 ml kanamycin stock. The feed was run at a constant flow rate of approx. 4.2 ml/h. Glucose and $NH_4^+$ measurements were done externally to evaluate availability of the C- and N-sources in the culture. Usually glucose levels stay very low.

Cultures were grown for a total of approximately 25 hours, where they reached typically an $OD_{650nm}$ of 40-45. SHC production was then started by adding IPTG to a concentration of approx. 1 mM in the fermenter (as IPTG pulse or over a period of 3-4 hours using an infusion syringe), setting the temperature to 40° C. and $pO_2$ to 20%. Induction of SHC production lasted for 16 h at 40° C. At the end of induction the cells were collected by centrifugation, washed with 0.1 M citric acid/sodium citrate buffer pH 5.4 and stored as pellets at 4° C. or −20° C. until further use.

Production and Selection of New SHC/HAC Enzyme Variants

An enzyme evolution program was carried out using the *Alicyclobacillus acidocaldarius* 215G2 SHC variant (215G2 SHC) gene previously described in WO 2016/170099 as a template. A library of about 9950 SHC variants was produced and screened for variants showing increased E,E-Homofarnesol (EEH) cyclization ability. Screening (microtiter plate set up) was run in 50 mM succinic acid/NaOH buffer pH 5.2 (0.200 ml) containing 34 g/l EEH and 0.075% sodium dodecyl sulfate (SDS). Reactions were run for 24 hours at 35° C. under constant agitation (orbital shaking, 210 rpm).

About 495 variants were chosen for confirmation in the same reaction setup. From these 495 variants, 48 were chosen for confirmation in 0.500 ml volume reactions (same conditions) with freshly produced biocatalyst (2 ml cultures).

Finally, 16 of the previous 48 variants showing improved activity on EEH were used to run EEH conversions at 34, 68, or 136 g/l in 50 mM succinic acid/NaOH buffer pH 5.2 containing EEH substrate, 0.1% SDS, and cells that had produced the SHC variants to an $OD_{600nm}$ of 40.0. The final volume was 1 ml, reactions were incubated at 35° C. and vigorously stirred on a magnetic stirrer. Reactions were sampled over time, solvent-extracted and analyzed by gas chromatography for determining EEH conversion to (−)-Ambrox) (see analytical methods below).

From this, 3 variants with improved EEH cyclization activity were selected (90C7, 110B8, and 115A7). A total of 7 mutations were identified on these 3 variants. Biocatalyst was produced from these 3 variants and EEH bioconversions run at 100 g/l EEH and 250 g/l cells in 100 mM acetic acid/sodium acetate buffer pH 4.7 in the presence of 0.975% SDS. The reaction (2 ml volume) was incubated for 72 hours at 35° C. under constant agitation (magnetic stirring) and sampled over time for GC-analysis.

A mutations study was then done to determine which of the identified single mutations or combinations of mutations were beneficial to EEH cyclization to (−)-Ambrox. 15 additional variants were constructed and biocatalyst thereof produced. The activity of these variants was tested in reactions containing either 34 g/l EEH, 77 g/l cells, and 0.4% SDS, or 34 g/l EEH, 155 g/l cells, and 0.7% SDS, or 34 g/l EEH, 250 g/l cells, and 1.0% SDS, in 50 mM succinic acid/NaOH buffer pH 4.7-5.2. Reactions (1 ml volume) were incubated at 35° C. under constant agitation (magnetic stirring), sampled over time and extracted for GC-analysis.

GC Analytics

Samples were extracted with an appropriate volume of tert-butylmethyl ether (MBTE/tBME) for quantification of their content in substrate and reaction products. The solvent fraction was separated from the water phase by centrifugation prior to analysis with gas chromatography. 1 μl of the solvent phase was injected (split ratio 10) onto a 30 m×0.32 mm×0.25 μm Zebron ZB-5 column. The column was developed at constant flow (4 ml/min H2) with the temperature gradient: 100° C., 15° C./min to 200° C., 120° C./min to 240° C., 4 min at 240° C. Inlet temperature: 250° C., detector temperature: 250° C. This resulted in separation of EEH and EZH, and of the peaks corresponding to (−)-Ambrox and 3 other reaction products resulting from Homofarnesol cyclization. It resulted as well in separation of Bis-EEH, Bis-EZH, and of the peaks corresponding to Ambra oxide and of the 3 other reaction products resulting from Bishomofarnesol cyclization.

EEH conversion was calculated from the areas of the peaks resulting from EEH cyclization and EEH with the following formula:

$$EEH\ conversion\ (\%)=100\times (Area_{Peaks\ products\ from\ EEH}/(Area_{Peaks\ products\ from\ EEH}+Area_{EEH\ Peak}))$$

BisEEH conversion was calculated in a same way from the areas of the peaks resulting from BisEEH cyclization and BisEEH in the same way as for EEH conversion.

Results

Of the 15 variants evaluated, the 6 variants listed in Table 6 below showed the best activity. Table 6 lists the new mutations identified in these variants.

TABLE 6

Mutations in selected new SHC variant enzymes.

| SHC Variant | Y81H | T90A | A172T | M277K | H431L | A557T | R613S |
|---|---|---|---|---|---|---|---|
| 110B8 (SEQ ID NO: 5) | + | | | | + | + | |
| 90C7 (SEQ ID NO: 17) | | + | | | | | + |
| 115A7 (SEQ ID NO: 18) | | | + | + | | | |

TABLE 6-continued

Mutations in selected new SHC variant enzymes.

| SHC Variant | Y81H | T90A | A172T | M277K | H431L | A557T | R613S |
|---|---|---|---|---|---|---|---|
| SHC 49 (SEQ ID NO: 2) | | | | | + | + | |
| SHC 65 (SEQ ID NO: 3) | | | | | | + | + |
| SHC 66 (SEQ ID NO: 4) | + | | | | | + | + |

Note:
these mutations appear in addition to the mutations present in 215G2 SHC: M132R, A224V, and I432T The new mutations identified in the SHC variants created are not in the vicinity of the active site of the enzyme as was observed previously when evolving wild-type *Alicyclobacillus acidocaldarius* SHC to 215G2 SHC. The majority of the new mutations identified are located again in domain 2 of the crystal structure of the enzyme (T90A, A172T, M277K and H431L). Two are located in domain 1 (A557T and R613S) and 1 at the interface between the 2 domains (Y81H).

Example 2—Optimization of Reaction Conditions for New SHC/HAC Enzyme Variants Reaction parameters investigated: temperature, SDS concentration and pH The reaction conditions for the SHC variants listed in Table 6 above in relation to Example 1 were individually optimized with regards to temperature, pH and SDS concentration.

Biocatalyst was prepared from the different variants by fermentation as described above using the *E. coli* cells transformed with the corresponding plasmid. Cells were collected by centrifugation, and stored at −20° C. until further used. The biocatalysts produced showed very similar SHC content. It could therefore be concluded that the differences in activity observed were due to the inserted mutations.

Results

Reactions of 2-5 ml volume with 4 g/l EEH and biocatalyst loaded at an $OD_{650nm}$ of 10.0 were run in 0.1 M citric acid/sodium phosphate buffer pH 5.0-6.8, in the presence of 0.0125-0.125% SDS at temperatures ranging from 28 to 50° C. and under constant agitation (Heidolph synthesis 1 Liquid device, 900 rpm).

The conditions listed in Table 7 below appeared to be the individual optimal conditions. They were confirmed in reactions run in 0.1 M succinic acid/NaOH buffer at pH around pH defined earlier as optimal.

Some deviation from the 215G2 SHC parent enzyme was noted. With only one exception the introduction of the new mutations shifted optimal temperature by 10° C. from 35° C. to about 45° C.

Example 3—Testing of New SHC/HAC Enzyme Variant Activity Under Initial and Optimized Reaction Conditions For comparing the activity of the SHC variants, biocatalysts were produced by fermentation from *E. coli* cells transformed with the appropriate plasmid. The resulting cells were used for testing EEH conversion at 4 g/l EEH with biocatalyst loaded to an $OD_{650nm}$ of 10.0, either under initial conditions (35° C., pH 5.4, 0.070% SDS), or at T, pH and [SDS] set to conditions defined as optimal for each of the variants (see Table 7 in Example 2 above). A sample of the reaction mixture was loaded onto an SDS-PAGE gel for analyzing the SHC content of the reactions. This analysis confirmed that all reactions contained identical amounts of SHC enzyme.

FIG. 1 shows the relative activities of SHC variants under initial conditions (pH 5.4, 35° C., 0.065% SDS, cells to $OD_{650nm}$ of 10), which were determined earlier as optimal reaction conditions for 215G2 SHC activity, and individually optimized reaction conditions (variable pH, T, and [SDS]).

Figure 2:
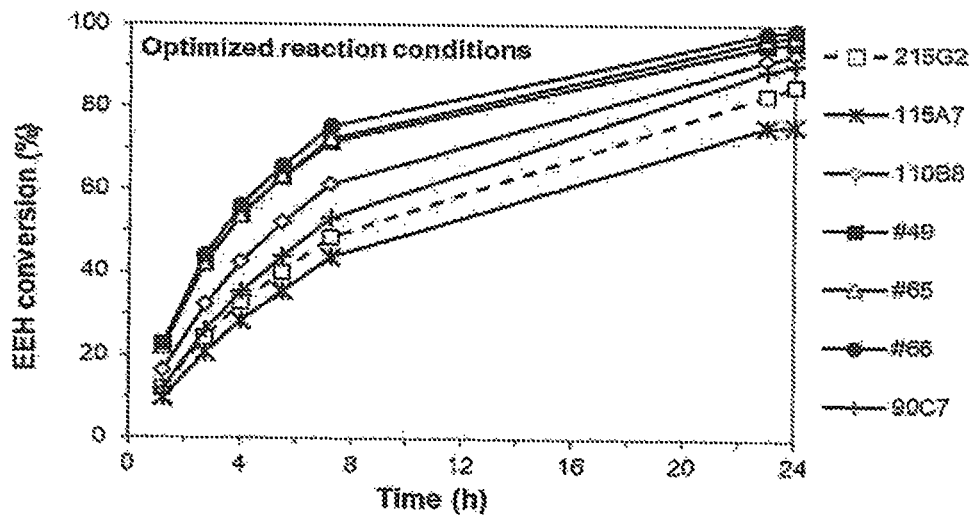
FIG. 2 shows the relative activity of SHC variants under optimized conditions compared to that of the parent 215G2 SHC enzyme. Reactions were run at 4 g/l EEH and biocatalyst loaded to an $OD_{650nm}$ of 10.0, T, pH and [SDS] set to conditions defined as optimal for each of the variants.

FIG. 2 shows the relative activities of SHC variants under optimized conditions compared to that of the parent 215G2 SHC enzyme. It was concluded that the introduction of only a few mutations in 215G2 SHC led to variants with improved or significantly improved activity (EEH cyclization to (−)-Ambrox).

Example 4—Relative Performance of SHC Variants in 125 g/l EEH Bioconversion

Biocatalysts produced by fermentation from the *E. coli* strains transformed with the plasmid carrying the gene

TABLE 7

Optimal reaction conditions for SHC variant enzymes.

| SHC Variant | Optimal Temperature (° C.) | Optimal Temperature Range (° C.) | Optimal pH | Optimal pH range | Optimal [SDS] (w/w %) | Optimal [SDS] range (w/w %) |
|---|---|---|---|---|---|---|
| 215G2 (SEQ ID NO: 10) | 35 | 32-50 | 5.4 | 5.0-6.2 | 0.060 | 0.010-0.10 |
| 110B8 (SEQ ID NO: 5) | 45 | 40-50 | 5.8 | 5.6-6.0 | 0.050 | 0.040-0.070 |
| SHC 49 (SEQ ID NO: 2) | 45 | 40-50 | 5.6 | 5.4-5.8 | 0.050 | 0.040-0.080 |
| SHC 65 (SEQ ID NO: 3) | 45 | 40-50 | 5.6 | 5.2-5.8 | 0.050 | 0.040-0.10 |
| SHC 66 (SEQ ID NO: 4) | 45 | 40-46 | 5.8 | 5.6-6.0 | 0.060 | 0.040-0.080 |
| 90C7 (SEQ ID NO: 17) | 45 | 40-46 | 5.6 | 5.2-6.0 | 0.040 | 0.025-0.050 |
| 115A7 (SEQ ID NO: 18) | 35 | 32-36 | 5.4 | 5.2-5.8 | 0.050 | 0.040-0.075 | coding for the selected new SHC variants or parent 215G2 SHC were used in 125 g/l EEH bioconversions.

A typical reaction (150 g total volume) was set up as follows in 0.75 litre Infors fermenters. The reaction vessel was loaded with an appropriate amount of Homofarnesol corresponding to 18.75 g EEH. 1.95 g SDS was added from a 31% (w/w) solution prepared in deionized water. A cell suspension is prepared from E. coli cells that had produced the SHC variant of interest by suspending the cells in 0.1 M succinic acid/NaOH buffer pH 5.1. After determination of the cell wet weight concentration of this cell suspension by centrifugation for 10 min at 10° C. and 17210 g, the appropriate volume of cells was added to the reaction vessel in order to introduce 37.5 g of cells into the reaction. The volume of the reaction was completed to 150 g with the required amount of reaction buffer pH 5.1. The reaction was run with each SHC variant at the temperature determined as optimal for its activity, and under constant stirring at 700 rpm. pH was set at the value determined as optimal for each of the SHC variant or parent 215G2 SHC using 85% $H_3PO_4$. pH regulation was done manually using 85% phosphoric acid as required. The reaction was sampled over time (1 ml), extracted with 5 volumes of MTBE/tBME (5 ml). The homofarnesol and (−)-Ambrox content of the reaction was determined by GC analysis after clarification of the solvent phase by centrifugation (table top centrifuge, 13000 rpm, 2 min), and 10- to 20-fold dilution into MTBE/tBME.

FIG. 3 shows EEH conversion to (−)-Ambrox by SHC variants and 215G2 SHC (parent enzyme) in bioconversions run at 125 g/l EEH with 250 g/l cells, and run with each SHC enzyme under optimal pH and temperature conditions.

Figure 4:
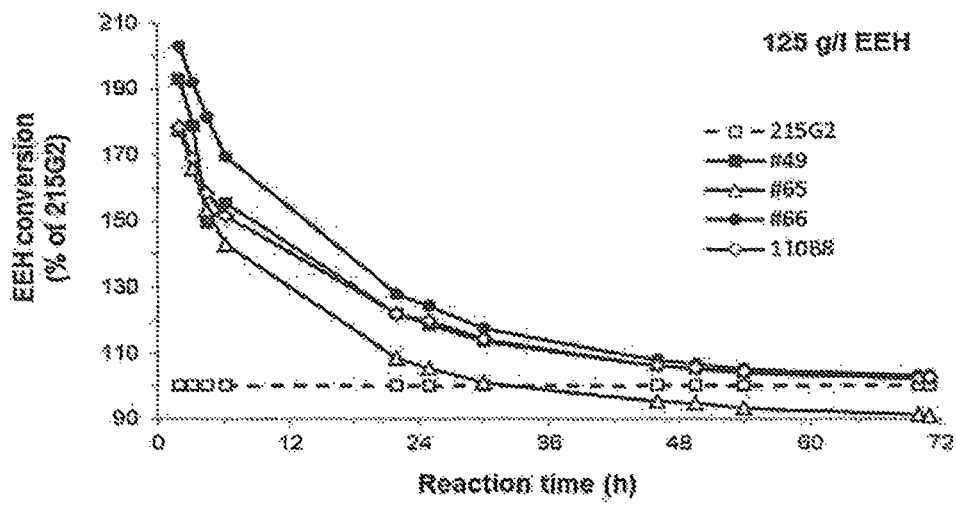
FIG. 4 shows the relative improvement of EEH conversion with the best SHC/HAC enzyme variants compared to the reference 215G2 SHC/HAC parent enzyme. Reactions were run at 125 g/l EEH and 250 g/l biocatalyst in the presence of 1.3% SDS, and at T and pH conditions defined as optimal for each of the variants. At all time points, the EEH conversion obtained with 215G2 SHC was set to 100% (reference).

FIG. 4 shows the relative improvement for the 4 best SHC variants as %-increase in EEH conversion compared to that obtained with the parent enzyme 215G2 SHC. A significant increase in initial reaction velocity, i.e. EEH conversion achieved during the first 6 to 8 hours of reaction was observed. It is anticipated that further adjustments in the reaction conditions applied in 125 g/l EEH conversion with SHC #65 would allow increasing further the activity of this variant over that of the parent SHC 215G2 SHC, and reaching full conversion as with the other SHC variants.

The data demonstrates that enzyme evolution using 215G2 SHC as the parent enzyme produced SHC enzymes with improved EEH bioconversion properties. The introduction of only a few amino acid mutations increases substantially EEH bioconversion. In this way can the conversion of EEH be reduced by approximately ⅓ or ½ in time, completion being obtained in approximately 24 h instead of 72 h depending on the SHC variant used.

Example 5—Cyclization of E,E-Bishomofarnesol to Ambra Oxide

Synthesis of Bishomofarnesol

Figure 10:
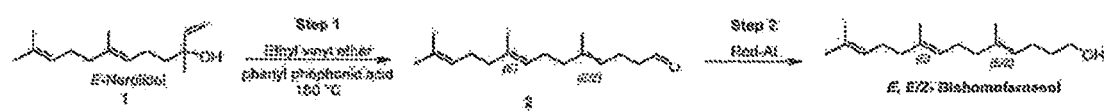
FIG. 10 is the reaction scheme used to produce a starting mixture of E,E/Z-Bishomofarnesol.

Bishomofarnesol was produced as a mixture of two isomers as outlined in FIG. 10.
Step 1:
Compound 1 of FIG. 10 (E-Nerolidol) (700.0 g, 3.148 mol, 1.0 equiv), ethyl vinyl ether (703.7 g, 9.758 mol, 3.1 equiv) and phenyl phosphonic acid (2.1 g, 0.0132 mol, 0.004 equiv) were charged to an Autoclave and the mixture was heated to 180° C. for 2.5 h. (Note: The internal pressure was raised to 14 bar). The reaction mixture was cooled to room temperature, unloaded from the autoclave and concentrated under reduced pressure to remove excess ethyl vinyl ether. The crude product was diluted with MTBE (1400 ml), washed with 2.0 M HCl (2×700 ml), water (500 ml) and brine (500 ml). The organic layer was dried over sodium sulphate, filtered and concentrated under reduced pressure. The crude product was passed through a plug of silica and then distilled to obtain compound 2 from FIG. 10 (yellow liquid, 483.0 g, 61.7%).
Step 2:
Compound 2 (420.0 g, 1.6907 mol, 1.0 equiv) in THF (5 Vol) was added to a stirred solution of Red-Al (283.26 g, 0.980 mol, 0.58 equiv, 70% in Toluene) at 0° C. over a period of 2.0 h. The reaction mixture was stirred overnight and monitored by TLC. After completion, the reaction was quenched slowly by using 10% NaOH solution (670.0 ml) 0° C. stirred at RT for 1 h. Then the reaction mixture was diluted with ice cold water (2 L) and extracted with MTBE (2×3 L). The combined organic layer was washed with water (1×2 L) and brine (1×2 L) and dried over sodium sulphate. The organic layer was concentrated under vacuum to obtain crude compound, which was purified by vacuum distillation to afford E,E/Z-Bishomofarnesol (pale-yellow liquid, 280.0 g, 66.1%).

Figure 5:
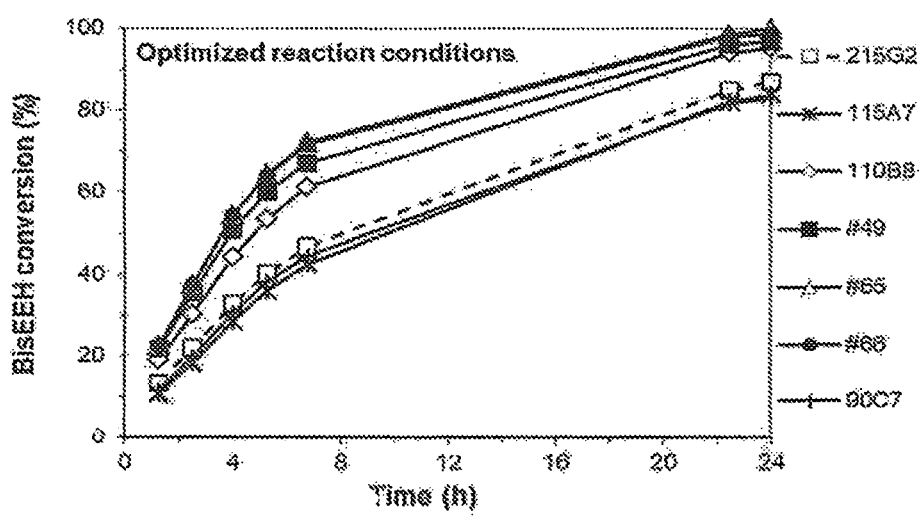
FIG. 5 shows the relative activity of SHC/HAC variants under optimal conditions compared to the parent (reference) 215G2 SHC/HAC enzyme. Reactions were run at 4 g/l BisEEH and biocatalyst loaded to an $OD_{650nm}$ of 10.0. T, pH and [SDS] were set to conditions defined as optimal for each of the variants.
Figure 6:
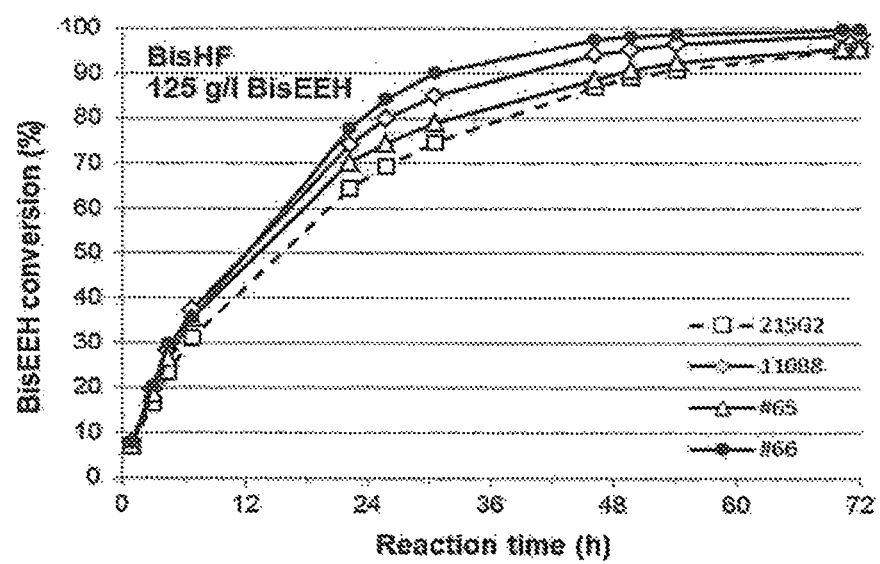
FIG. 6 shows the cyclization of Bishomofarnesol with the parent (reference) 215G2 SHC/HAC enzyme and new variant SHC/HAC enzymes. Reactions were run at 125 g/l BisEEH and 250 g/l biocatalyst in the presence of 1.3% SDS, and at 35° C. and pH 5.4 (all SHC enzymes).
Figure 11:
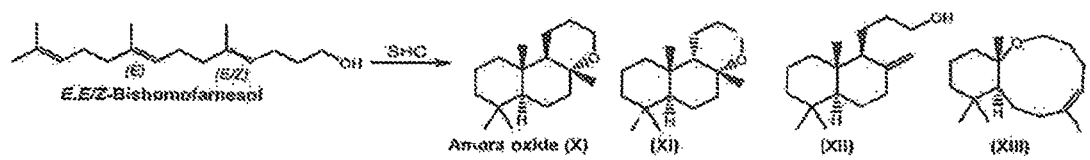
FIG. 11 is the reaction scheme showing cyclization of Bishomofarnesol with SHC enzymes. The Bishomofarnesol used consisted of a mixture of isomers.

Bishomofarnesol was produced as a mixture of isomers of E,E:E,Z ratio approx. 80:20.
Cyclization of E,E-Bishomofarnesol to Ambra Oxide
The new SHC variants produced were used in the bioconversion of Bishomofarnesol (mixture of E,E- and E,Z-Bishomofarnesol) to Ambra oxide. The reaction products in FIG. 11 were identified:
Cyclization at 4 g/l E,E-Bishomofarnesol
The activity of the variants was tested under reaction conditions individually defined as optimal and as set out in Table 7 above (temperature, pH, SDS concentration). The reactions (5 ml volume) contained 4 g/l E,E-Bishomofarnesol as the substrate. Cells that had produced the SHC variants were added to an $OD_{650nm}$ of 10.0 to start the reaction. The reactions were incubated on a Heidolph Synthesis 1 Liquid 16 device under constant agitation (900 rpm).
Bioconversion at 125 g/l E,E-Bishomofarnesol
A typical reaction (150 g total volume) was set up in 0.75 litre Infors fermenters as shown in Example 4, but loading the reactions with 125 g/l E,E-Bishomofarnesol instead of E,E-Homofarnesol. The reactions were run at 35° C. under constant agitation (700 rpm) and pH 5.4 in 0.1 M succinic acid/NaOH buffer with all SHC variants.
Results—Cyclization at 4 g/l E,E-Bishomofarnesol
A significant increase in activity was observed with SHC/HAC enzyme variants #65, #66 and #110B8 over that of the parent 215G2 SHC/HAC enzyme variant. The results are shown in FIG. 5.
Results—Bioconversion at 125 g/l E,E-Bishomofarnesol
E,E-Bishomofarnesol conversion is shown in FIG. 6. An increase in conversion was noted with each of the variants tested. At 72 hours of reaction was with all SHC variants E,E-BisHF conversion was 95% or higher. With variants SHC #66 or 110B8 SHC was 95% conversion obtained in approx. 48 hours of reaction, i.e. only ⅔ of the time required when running the bioconversion with the parent enzyme 215G2 SHC.

The reaction was extracted 5 times with 100 ml MTBE by vigorous shaking followed by phase separation by centrifugation (6000 g, 10 min, room temperature). This allowed almost full extraction of the reaction product as judged from CG analysis of the recovered solvent phases.

The variants tested with E,E-Bishomofarnesol showed improved activity over the parent 215G2 SHC enzyme although reaction conditions were not set at pH and temperature conditions defined as optimal for the new SHC variants. It is anticipated that a further increase in activity is observed when pH and temperature are set to the values determined as optimal with the individual variants as set out in the Example above.

Results—Identity of Reaction Products

Compound X, Ambra Oxide $^1$H NMR (400 MHZ, CDCl$_3$) δ 3.71-3.59 (m, 2H), 1.76 (dt, J=11.7, 3.8 Hz, 1H), 1.71-1.57 (m, 6H), 1.46-1.24 (m, 6H), 1.26 (s, 3H), 1.15 (td, J=13.2, 4.2 Hz, 1H), 0.97 (dd, J=13.2, 4.2 Hz, 1H), 0.89-0.85 (m, 1H), 0.88 (s, 3H), 0.81 (s, 3H), 0.76 (s, 3H). $^{13}$C NMR (101 MHZ, CDCl$_3$) δ ppm 74.67, 60.89, 57.81, 56.43, 42.10, 41.96, 38.97, 36.88, 33.36, 33.29, 27.68, 21.36, 19.94, 19.91, 18.60, 18.15, 15.60

Compound XI $^1$H NMR (400 MHZ, CDCl$_3$) δ ppm 3.61-3.57 (m, 2H), 2.09 (td, J=12.84, 4.40 Hz, 1 H), 1.82 (dt, J=12.23, 3.91 Hz, 1H), 1.70-1.62 (m, 2H), 1.60-1.33 (m, 7H), 1.39 (br s, 3H), 1.31-1.19 (m, 2H), 1.15-0.99 (m, 3H), 1.12 (br s, 3H), 0.87 (s, 3H), 0.80 (s, 3 H). $^{13}$C NMR (101 MHZ, CDCl$_3$) δ ppm 75.56, 60.27, 54.60, 46.99, 42.51, 38.32, 36.62, 33.45, 33.34, 31.74, 30.92, 26.64, 24.99, 21.91, 21.78, 20.96, 18.91

Compound XII $^1$H NMR (600 MHZ, BENZENE-d$_6$) δ ppm 4.94 (s, 1H), 4.64 (s, 1H), 3.38 (br t, J=5.6 Hz, 2H), 2.37 (br d, J=12.4 Hz, 1H), 1.94 (td, J=12.8, 4.1 Hz, 1H), 1.72-1.57 (m, 3 H), 1.56-1.46 (m, 3H), 1.44-1.33 (m, 3H), 1.33-1.24 (m, 2H), 1.13 (td, J=13.4, 3.4 Hz, 1H), 0.96 (br d, J=12.8 Hz, 1H), 0.89 (td, J=13.4, 2.6 Hz, 1H), 0.85 (s, 3H), 0.80 (s, 3H), 0.72 (s, 3H), 0.62 (br s, OH). $^{13}$C NMR (151 MHZ, BENZENE-d$_6$) δ ppm 148.70, 106.52, 62.78, 56.57, 55.25, 42.11, 39.90, 38.92, 38.34, 33.70, 33.44, 32.03, 24.38, 21.58, 19.64, 19.55, 14.27

Compound XIII $^1$H NMR (600 MHZ, BENZENE-d$_6$) δ ppm 5.15 (br dd, J=10.5, 4.9 Hz, 1H), 3.32 (td, J=13.2, 3.4 Hz, 1H), 3.25-3.21 (m, 1H), 3.14-3.09 (m, 1H), 2.79 (qd, J=12.3, 4.9 Hz, 1H), 1.87-1.80 (m, 2H), 1.72 (s, 3H), 1.72-1.62 (m, 6H), 1.51-1.44 (m, 1H), 1.39-1.22 (m, 5H), 1.27 (s, 3H), 1.03 (td, J=13.2, 3.0 Hz, 1H), 0.93 (s, 3H), 0.77 (s, 3H). $^{13}$C NMR (151 MHZ, BENZENE-d$_6$) δ ppm 137.10, 123.6, 78.0, 56.79, 43.05, 42.11, 37.74, 35.0 33.46, 29.20, 27.29, 24.57, 24.29, 23.48, 22.59, 22.33, 20.27

Example 6—Conversion of EEH to (−)-Ambrox Using Wild-Type SHC Enzymes

The wildtype SHC enzymes listed in Table 8 below were chosen for testing their ability to convert E,E-Homofarnesol to (−)-Ambrox.

TABLE 8

Wildtype Squalene Hopene Cyclase Enzymes.

| Squalene hopene cyclase | Origin (microorganism) | European Nucleotide Archive Number |
|---|---|---|
| AacSHC (SEQ ID NO: 1) | Alicyclobacillus acidocaldarius | ACV59449.1 |
| ApaSHC1 (SEQ ID NO: 20) | Acetobacter pasteurianus | ASC07046.1 |
| BjaSHC (SEQ ID NO: 13) | Bradyrhizobium japonicum | ABQ33590.1 |
| TelSHC (SEQ ID NO: 19) | Thermosynechococcus elongatus | BAC09861.1 |
| ZmoSHC1 (SEQ ID NO: 11) | Zymomonas mobilis | AVZ42714.1 |
| ZmoSHC2 (SEQ ID NO: 12) | Zymomonas mobilis | AAF12829.1 |
| GmoSHC (SEQ ID NO: 14) | Gluconobacter morbifer | EHH69691.1 |

Biocatalyst was produced from E. coli strains transformed with the pET-28a(+) carrying the gene for the production of the wild-type enzyme as described in Example 1 above (small scale biocatalyst production).

With each of the biocatalysts produced, it was roughly investigated the influence of pH, temperature and surfactant concentration conditions. In a first step, pH optimization was done, followed by [SDS] and temperature optimization. Confirmation of optimized reaction conditions was done in an additional set of reactions (variable pH, temperature and SDS concentration) using 0.1 M succinic acid/NaOH buffers around the pH value defined as optimal:

*pH optimization: 4 g/l EEH with 0.075% SDS, cells at an OD$_{650nm}$ of 10, in citric acid/sodiumphosphate buffer pH 5.0 to 7.0 (1 ml total volume, 40° C., 900 rpm, Heidolph Synthesis 1).

[SDS] and temperature optimization: 4 g/l EEH, cells at an OD$_{650nm}$ of 10, in citric acid/Na-phosphate buffer (1 ml total volume, 900 rpm, Heidolph Synthesis 1), varying [SDS] and temperature at optimal pH.

*confirmation of reaction conditions: 4 g/L EEH, cells at an OD$_{650nm}$ of 10, in citric acid/Na-phosphate buffer (1 ml total volume, 900 rpm, Heidolph Synthesis 1), [SDS], temperature and pH as required.

The reactions were run for 24 hours, sampled over time (t=0, t=3 h and t=22 h), extracted and analyzed for their substrate and product content, and the conversion of EEH calculated as described above. This allowed the evaluation of roughly the initial velocity of EEH conversion with each of the wildtype SHC enzymes as well as the conversion obtained after 22 hours of reaction. The reactions were run with 4 g/l EEH and biocatalyst loaded to an OD$_{650nm}$ of 10.0, at variable pH, temperature and SDS concentration.

Results

Table 9 below summarizes the conditions determined as optimal for each of the wildtype SHC enzymes tested as well as EEH conversion obtained at 22 hours of reaction when applying initial (35° C., pH 5.4, 0.070% SDS) or individually optimized reaction conditions. EEH conversion to (−)-Ambrox was observed with all of these enzymes, although at significantly varying levels. EEH conversion was highest when E. coli cells producing B. japonicum SHC and Zymomonas mobilis SHC1. Very interestingly was EEH conversion also obtained with Zymomonas mobilis SHC2, for which it was reported elsewhere that this enzyme does not cyclize EEH.

TABLE 9

Optimized reaction conditions for wildtype Squalene Hopene Cyclase enzymes.

| Squalene Hopene Cyclase | Optimized reaction conditions | | | EEH conversion at 22h (%) |
|---|---|---|---|---|
| | [SDS] (%) | T (° C.) | pH | |
| AacSHC (SEQ ID NO: 1) | 0.030 | 55 | 6.0 | 40.0 |
| ApaSHC1 (SEQ ID NO: 20) | 0.0075 | 45 | 5.2 | 9.2 |
| BjaSHC (SEQ ID NO: 13) | 0.0050 | 50 | 5.8 | 16.5 |
| TelSHC (SEQ ID NO: 19) | 0.0075 | 45 | 6.2-6.6 | 1.5 |
| ZmoSHC1 (SEQ ID NO: 11) | 0.005 | 40 | 5.0-5.4 | 70.3 |
| ZmoSHC2 (SEQ ID NO: 12) | 0.005 | 35 | 6.2-6.4 | 3.2 |
| GmoSHC (SEQ ID NO: 14) | 0.0075 | 40 | 5.6 | 12.2 |

EEH conversion obtained in reactions run at 4 g/l EEH and with biocatalyst loaded at an $OD_{650nm}$ of 10.0 applying individually optimized (T, pH, [SDS]) reaction conditions.

Example 7—Sequence Alignment of Wild-Type SHCs

The sequences of various wild-type SHCs were aligned using the parameters specified below (using Clone Manager 9 Software). The results are shown in table 10 below and FIG. 8.

Alignment: Global Protein alignment against reference molecule

Parameters: Scoring matrix: BLOSUM 62

Reference molecule: Aac SHC, Region 1 to 631

Total length of aligned sequences with gaps: 838 aas

TABLE 10

Percent SHC sequence identity relative to WT AacSHC

| Sequence | Start | End | Match | NonMatch | %Match |
|---|---|---|---|---|---|
| AacSHC (SEQ ID NO: 1) | 1 | 631 | — | — | — |
| TelSHC (SEQ ID NO: 19) | 1 | 642 | 285 | 360 | 44 |
| ApaSHC1 (SEQ ID NO: 20) | 1 | 720 | 296 | 430 | 40 |

TABLE 10-continued

Percent SHC sequence identity relative to WT AacSHC

| Sequence | Start | End | Match | NonMatch | %Match |
|---|---|---|---|---|---|
| ZmoSHC1 (SEQ ID NO: 11) | 1 | 725 | 299 | 434 | 40 |
| ZmoSHC2 (SEQ ID NO: 12) | 1 | 658 | 251 | 410 | 37 |
| BjaSHC (SEQ ID NO: 13) | 1 | 684 | 296 | 397 | 42 |
| GmoSHC (SEQ ID NO: 14) | 1 | 685 | 291 | 396 | 42 |

—: not applicable

Example 8—Optimal Reaction Conditions with SHC Variants

Methods

Figure 8:
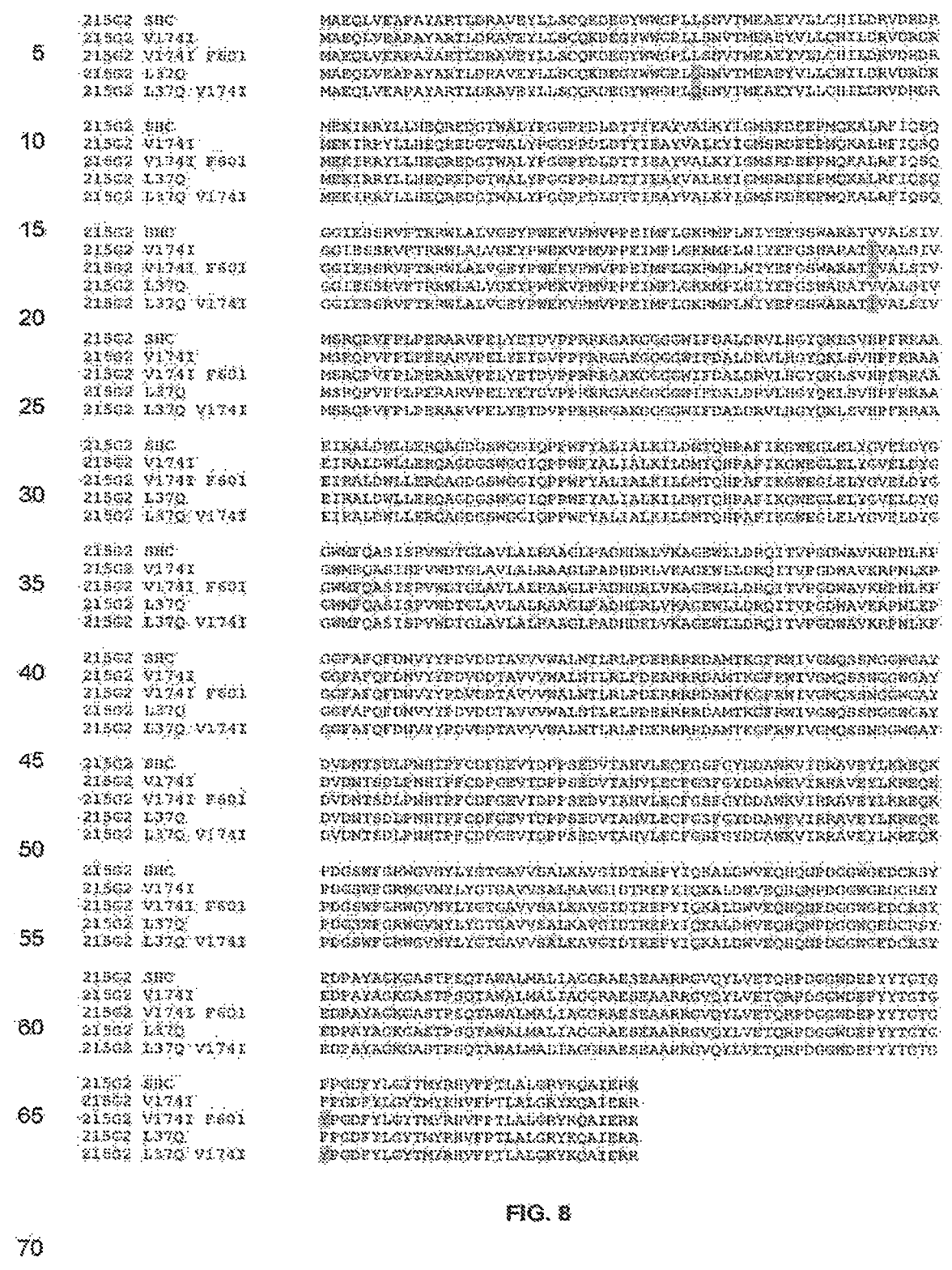

Additional mutations were introduced into 215G2 SHC producing variants [215G2+V174I], [215G2+V174I+F601], [215G2+L37Q], and [215G2+L37Q+V174I]. The sequence alignment of these variants is shown in FIG. 8.

The optimal reaction conditions for these variants were investigated as described in the Examples above. Their performance in EEH cyclization was then tested at 4 g/l substrate with cells loaded to the reaction at an $OD_{650nm}$ of 10.0.

Results

The reaction conditions (temperature, pH, SDS concentration) listed in Table 11 below appeared to be the individual optimal reaction conditions for the cyclization activity of the variants mentioned above. Variants with new mutations showed approximately the same activity as 215G2 SHC, or increased activity which may correlate to increased SHC production levels.

TABLE 11

Optimal reaction conditions for SHC variant enzymes.

| SHC/HAC Enzyme Variant | Optimal Temperature (° C.) | Optimal pH | Optimal [SDS] (weight/weight %) |
|---|---|---|---|
| 215G2 + L37Q (SEQ ID NO: 24) | 40 | 5.8 | 0.070 |
| 215G2 + V174I (SEQ ID NO: 25) | 50 | 5.2-5.4 | 0.040 |
| 215G2 + V174I + F601Y (SEQ ID NO: 26) | 40-50 | 5.2-5.6 | 0.030-0.070 |
| 215G2 + L37Q + V174I + F601Y (SEQ ID NO: 27) | 35 | 5.4-5.8 | 0.070 |

Example 9—Reaction Products

Methods

Reactions of 5 ml volume were run with 4 g/l EEH and biocatalyst loaded at an $OD_{650nm}$ of 10.0 at pH, temperature and SDS concentration defined as optimal for each enzyme and under constant agitation (Heidolph synthesis 1 Liquid device, 900 rpm).

Results

Table 12 illustrates EEH conversion after 20 h with each enzyme, and resulting distribution of reaction products. Compounds of formulae (I) ((−)-Ambrox) and (IV) result from EEH cyclization, compounds of formulae (II) (Macrocycle) and (III) (9b-epi-Ambrox) result from EZH cyclization. The Homofarnesol used was a mixture of isomers (EEH:EZH 80:20).

It is observed that all WT SHC enzymes and in particular, WT ZmoSHC1, BjaSHC, GmoSHC, ApaSHC1 at conversion levels of approximately 9% or higher show a higher selectivity towards EEH compared to WT AacSHC. This resulted in a higher proportion of compounds (I) and (IV) compared to compounds (II) and (III) in the reaction product and also translated into a higher EEH:EZH conversion ratio.

Example 4 applying temperature and pH conditions individually optimized for each variant and as set out in Example 2, with the only exception that the SDS concentration was set at 1.3 w/v % ([SDS]:[cells] ratio of 0.052) with all variants.

Results

Figure 12:
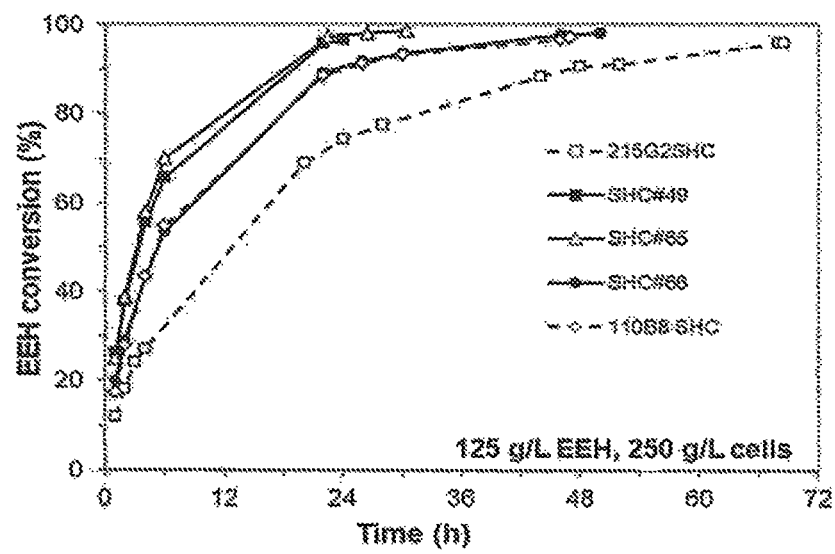
FIG. 12 shows EEH conversion to (−)-Ambrox by SHC/HAC enzyme variants under optimal conditions compared to the 215G2 parent SHC/HAC enzyme. Reactions were run at 125 g/l EEH and 250 g/l biocatalyst in the presence of 1.3% SDS, and at T and pH conditions defined as optimal for each of the variants.

Depending on the SHC/HAC variant considered, the time required for full conversion of 125 g/l of E,E-homofarnesol to (−)-Ambrox with 250 g/l of cells could be reduced by ⅓ or ⅔, full conversion being achieved in approx. 48 or 24 hours instead of approx. 72 hours with the reference SHC biocatalyst 215G2SHC (FIG. 12).

Initial reaction velocity was increased by a factor of 1.4-1.8 with the new SHC variants compared to the reference biocatalyst 215G2 SHC.

Volumetric productivity defined as Ambrox produced per litre and per hour or as Ambrox produced per litre, per hour, and per gram of biocatalyst was increased by a factor of 1.4-2.6 compared to a reference bioconversion run with 215G2SHC biocatalyst (Table 13).

TABLE 13

Volumetric productivity.

| SHC variant | [EEH] (g/l) | [cells] (g/l) | Time (h) | Conversion (%) | Productivity $(g \cdot l^{-1} \cdot h^{-1})$ | Productivity $(mg \cdot l^{-1} \cdot h^{-1} \cdot g^{-1})$ | Increase (-fold) |
|---|---|---|---|---|---|---|---|
| 215G2 | 125 | 250 | 68.5 | 95.9 | 1.75 | 7.0 | — |
| #49 | 125 | 250 | 26.5 | 98.2 | 4.65 | 18.5 | 2.6 |
| #65 | 125 | 250 | 30.5 | 98.7 | 4.10 | 16.2 | 2.3 |
| #66 | 125 | 250 | 50 | 98.1 | 2.45 | 9.8 | 1.4 |
| 110B8 | 125 | 250 | 46 | 96.8 | 2.65 | 10.5 | 1.5 |

Conversion: EEH conversion.

TABLE 12

Conversion of an EEH/EZH mixture with wild type (WT) SHC enzymes.

| SHC enzyme | EEH Conversion (%) | I | II | III | IV | I + IV | II + III |
|---|---|---|---|---|---|---|---|
| AacSHC | 40.4 | 93.5 | 1.0 | 4.8 | 0.7 | 94.2 | 5.8 |
| TelSHC1 | 1.6 | 94.8 | 2.0 | 1.7 | 1.4 | 96.2 | 3.8 |
| ApaSHC1 | 9.3 | 98.6 | 0.3 | 0.9 | 0.2 | 98.8 | 1.2 |
| ZmoSHC1 | 70.3 | 98.1 | 0.6 | 1.1 | 0.2 | 98.3 | 1.7 |
| ZmoSHC2 | 3.2 | 98.5 | 0.3 | 0.9 | 0.4 | 98.8 | 1.2 |
| BjaSHC | 16.2 | 98.0 | 0.5 | 1.0 | 0.5 | 98.5 | 1.5 |
| GmoSHC | 11.9 | 98.3 | 0.5 | 0.8 | 0.4 | 98.7 | 1.3 |

Example 10—Volumetric Productivity

New *Alicyclobacillus acidocaldarius* SHC variants were used to improve E,E-homofarnesol to (−)-Ambrox cyclization in bioconversions run at 125 g/l E,E-homofarnesol and with 250 g/l of cells as set out in Example 4. Reducing the reaction time for full EEH conversion in bioconversions run at 125 g/l with 250 g/l cells was addressed.

Methods

Biocatalysts were produced as outlined in Example 1 (fermentation). The bioconversions were run as set out in

Example 11—Volumetric Productivity

New *Alicyclobacillus acidocaldarius* SHC variants were used to improve E,E-homofarnesol to (−)-Ambrox cyclization in bioconversions run at 125 g/l E,E-homofarnesol and with 250 g/l of cells as set out in Example 4. Reducing the biocatalyst load for full EEH conversion in bioconversions run at 125 g/l substrate was addressed.

Methods

Biocatalysts were produced as outlined in Example 1 (fermentation). The bioconversions were run as set out in Example 4 applying temperature and pH conditions individually optimized for each variant and as set out in Example 2, with the only exceptions that the cell concentration was set at 125 g/l and the SDS concentration at 0.65 w/v % ([SDS]:[cells] ratio of 0.052) with all variants.

Results

Figure 13:
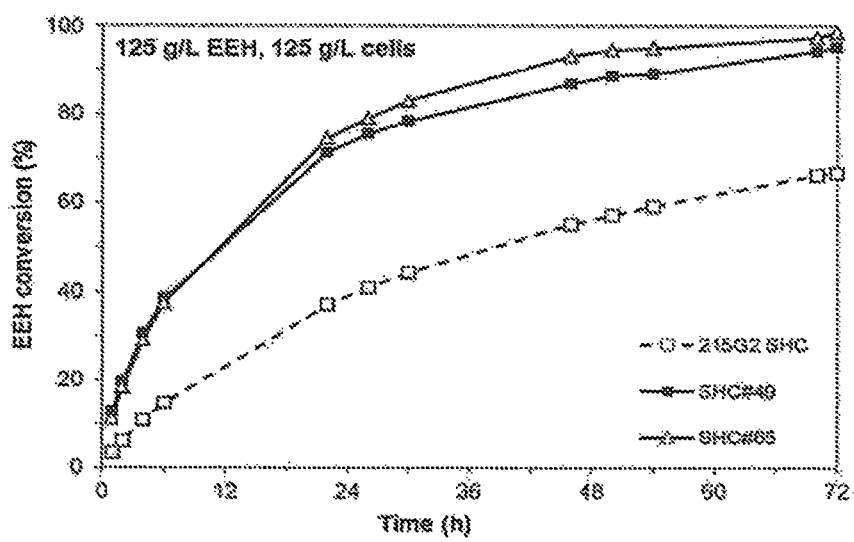
FIG. 13 shows EEH conversion to (−)-Ambrox by SHC/HAC enzyme variants under optimal conditions compared to the 215G2 parent SHC/HAC enzyme. Reactions were run at 125 g/l EEH and 125 g/l biocatalyst in the presence of 0.65% SDS, and at T and pH conditions defined as optimal for each of the variants.

With biocatalysts producing new SHC/HAC variant SHC #49 and SHC #65 it was possible to reduce the cell concentration by a factor of 2 from 250 to 125 g/l of cells for full EEH conversion in 72 hours of time (FIG. 13). EEH conversion with the reference biocatalyst 215G2 SHC was only about 67% in the same time.

Volumetric productivity defined as (−)-Ambrox produced per litre and per hour or as (−)-Ambrox produced per litre, per hour, and per gram of biocatalyst was increased by a factor of approx. 1.5 compared to the same bioconversion run with 215G2SHC biocatalyst as a reference (Table 14).

Taking a bioconversion run with 125 g/l and 250 g/l cells with the reference biocatalyst 215G2 SHC, volumetric productivity was increase by a factor of approx. 2 (Table 14).

TABLE 14

Volumetric productivity.

| SHC variant | [EEH] (g/l) | [cells] (g/l) | Time (h) | Conversion (%) | Productivity $(g \cdot l^{-1} \cdot h^{-1})$ | $(mg \cdot l^{-1} \cdot h^{-1} \cdot g^{-1})$ | Increase (-fold) | |
|---|---|---|---|---|---|---|---|---|
| 215G2 | 125 | 125 | 72 | 66.7 | 1.16 | 9.3 | — | n.a. |
| 215G2 | 125 | 250 | 68.5 | 95.9 | 1.75 | 7.0 | n.a. | — |
| #49 | 125 | 125 | 72 | 95.0 | 1.65 | 13.2 | 1.4 | 1.9 |
| #65 | 125 | 125 | 72 | 98.5 | 1.70 | 13.7 | 1.5 | 2.0 |

Conversion: EEH conversion.

n.a: not applicable.

Example 12—Volumetric Productivity

New *Alicyclobacillus acidocaldarius* SHC variants were used to improve E,E-homofarnesol to (−)-Ambrox cyclization in bioconversions run at 125 g/l E,E-homofarnesol and with 250 g/l of cells as set out in Example 4. Increasing EEH concentration in the bioconversions was addressed.

Methods

The biocatalyst was produced as outlined in Example 1 (fermentation). The bioconversions were run as set out in Example 4 but with an EEH to biocatalyst ratio of 1:1, and at constant [SDS]:[cells] ratio of 0.052. Optimized temperature and pH conditions were as defined as optimal for SHC #65 biocatalyst (Example 2).

Results

Figure 14:
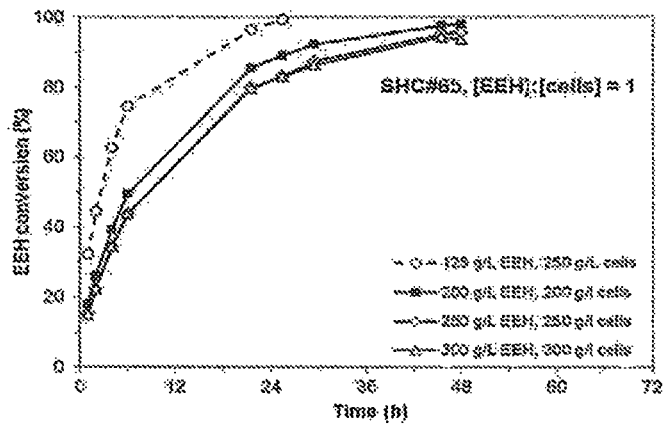
FIG. 14 shows EEH conversion to (−)-Ambrox by SHC/HAC enzyme variant SHC #65 under optimal conditions compared to the 215G2 parent SHC/HAC enzyme. Reactions were run at 125 g/l to 300 g/l EEH and either 250 g/l biocatalyst or at an [EEH]:[cells] ratio of 1. SDS was supplied at constant [SDS]:[cells] ratio of 0.052. Reactions were run at T and pH conditions defined as optimal for SHC variant #65.

With new SHC/HAC variant SHC #65 it was possible to fully convert up to 300 g/l of EEH with 300 g/l biocatalyst in 48 h (FIG. 14).

Volumetric productivity defined as Ambrox produced per litre and per hour was increase 2.3-3.4-fold. Volumetric productivity defined as Ambrox produced per litre, per hour, and per gram of biocatalyst was increased by a factor of 2.8-2.9. The fold increase refers to a reaction run at 125 g/l EEH with 250 g/l cells using 215G2SHC biocatalyst (Table 15).

Example 13—EEH Cyclization with Wt SHC Enzymes

Methods

Biocatalysts of the wild type SHC enzymes AacSHC (*Alicyclobacillus acidocaldarius* SHC, SEQ ID NO:1), GmoSHC (*Gluconobacter morbifer* SHC, SEQ ID NO:14), BjpSHC (*Bradyrhizobium japonicum* SHC, SEQ ID NO:13), ApaSHC1 and ApaSHCA (*Acetobacter pasteurianus* SHC1 and SHCA, SEQ ID NO: 20 and 30 respectively), ZmoSHC1 and ZmoSHC2 (*Zymomonas mobilis* SHC1 and SHC2, SEQ ID NO:11 and 12 respectively), SalSHC (*Streptomyces albolongus* SHC, SEQ ID NO: 29), TelSHC (*Thermosynechococcus elongates*, SEQ ID NO: 19) and of BmeSHC *Bacillus megaterium* SHC, SEQ ID NO: 28), were produced in fermentations as outlined in Example 1.

These wild-type SHC enzymes (also listed in Table 16 below) were chosen for testing their ability to convert E,E-Homofarnesol to (−)-Ambrox.

TABLE 15

Volumetric productivity.

| SHC variant | [EEH] (g/l) | [cells] (g/l) | Time (h) | Conversion (%) | Productivity $(g \cdot l^{-1} \cdot h^{-1})$ | $(mg \cdot l^{-1} \cdot h^{-1} \cdot g^{-1})$ | Increase (-fold) |
|---|---|---|---|---|---|---|---|
| 215G2 | 125 | 250 | 68.5 | 95.9 | 1.75 | 7.0 | —/— |
| #65 | 125 | 250 | 25.5 | 99.2 | 4.9 | 19.5 | 2.8/2.8 |
| #65 | 200 | 200 | 48 | 97.7 | 4.1 | 20.5 | 2.3/2.9 |
| #65 | 250 | 250 | 48 | 93.8 | 4.9 | 19.5 | 2.8/2.8 |
| #65 | 300 | 300 | 48 | 94.4 | 5.9 | 20.0 | 3.4/2.8 |

Conversion: EEH conversion

TABLE 16

Wildtype Squalene Hopene Cyclase Enzymes.

| Squalene hopene cyclase | Origin (microorganism) | European Nucleotide Archive Number or Genbank Accession Number |
|---|---|---|
| AacSHC (SEQ ID NO: 1) | Alicyclobacillus acidocaldarius | ACV59449.1 |
| ApaSHC1 (SEQ ID NO: 20) | Acetobacter pasteurianus | ASC07046.1 |
| BjaSHC (SEQ ID NO: 13) | Bradyrhizobium japonicum | ABQ33590.1 |
| TelSHC (SEQ ID NO: 19) | Thermosynechococcus elongatus | BAC09861.1 |
| ZmoSHC1 (SEQ ID NO: 11) | Zymomonas mobilis | AVZ42714.1 |
| ZmoSHC2 (SEQ ID NO: 12) | Zymomonas mobilis | AAF12829.1 |
| GmoSHC (SEQ ID NO: 14) | Gluconobacter morbifer | EHH69691.1 |
| BmeSHC (SEQ ID NO: 28) | Bacillus megaterium | WP_016763969 |
| Sal SHC (SEQ ID NO: 29) | Streptomyces albolongus | AZN28579 |
| ApaSHCA (SEQ ID NO: 30) | Acetobacter pasteurianus | WP_003625617 |

Optimal reaction conditions were investigated with BmeSHC biocatalyst as set out in Example 6 for other SHC enzymes. Optimal reaction conditions were defined as 45° C., pH 5.6 and with 0.0025 w/v % SDS for a cell load of $OD_{650nm}$ of 10 in the reaction.

Optimal reaction conditions with SalSHC were at 30° C., pH 7.0 with no surfactant addition to the reaction (Liu et al. (2020): A Novel Soluble Squalene-Hopene Cyclase and Its Application in Efficient Synthesis of Hopene, Frontiers in Bioengineering and Biotechnology, vol 8, article 426, https://doi.org/10.3389/fbioe.2020.00426).

Activity of the resulting biocatalysts was tested both at 4 g/l EEH and at 125 g/l EEH with the only exception of SalSHC where 1 g/l EEH was used instead of 4 g/l EEH.

The activity test with 4 g/l EEH (SalSHC: 1 g/l EEH) contained cells at an $OD_{650nm}$ of 10 (SalSHC biocatalyst: $OD_{650nm}$ of 40) and was otherwise run as set out in Example 6 applying individually optimized temperature and pH conditions for each SHC enzyme.

The bioconversions at 125 g/l EEH were run with 250 g/l of cells as set out in Example 4 applying temperature and pH conditions individually optimized for each SHC enzyme and as set out in Example 6. The reactions contained 1.3 w/v % SDS with AacSHC, 0.16 w/v % with BjpSHC, ZmoSHC1, ApaSHC1, 0.10 w/v % with BmeSHC, and 0.14 w/v % with GmoSHC. No bioconversions were run at 125 g/l EEH with ApaSHCA, TelSHC, SalSHC and ZmoSHC2 biocatalysts.

Results

Figure 15:
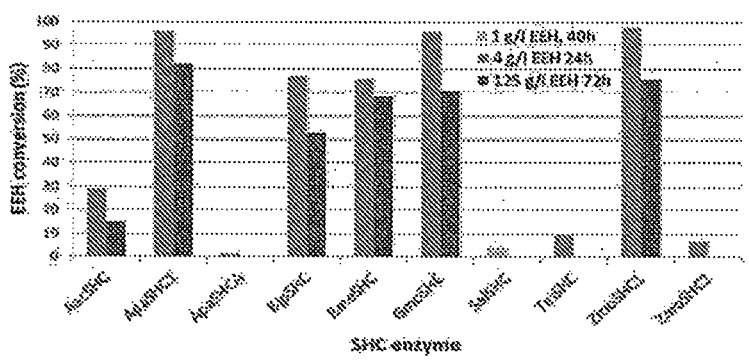
FIG. 15 shows EEH conversion to (−)-Ambrox by wild-type AacSHC (SEQ ID NO: 1), wild-type BjpSHC (SEQ ID NO: 13), wild-type Bme SHC (SEQ ID NO; 28), wild-type GmoSHC (SEQ ID NO: 14), wild-type ApaSHCA (SEQ ID NO: 30), wild-type ApaSHC1 (SEQ ID NO: 20), wild-type SalSHC (SEQ ID NO: 29), wild-type TelSHC (SEQ ID NO: 19), wild-type ZmoSHC1 (SEQ ID NO: 11) and wild-type ZmoSHC2 (SEQ ID NO: 12). Reactions were run at 4 g/l EEH for all listed wild-type SHC enzymes and at 125 g/l EEH for all listed wild-type SHC enzymes other than wild-type ApaSHCA (SEQ ID NO: 30), wild-type SalSHC (SEQ ID NO: 29), wild-type TelSHC (SEQ ID NO: 19) and wild-type ZmoSHC2 (SEQ ID NO: 12). Reactions were run at T and pH conditions and SDS concentration defined as optimal for each listed wild-type SHC enzyme. SDS concentration was adjusted in the 125 g/l EEH bioconversion to allow best biocatalyst activity.

EEH cyclization to (−)-Ambrox was observed with all SHC biocatalysts tested at low substrate concentration (1 or 4 g/l). With the wild type SHCs biocatalysts tested at 125 g/l EEH, was EEH conversion between approx. 15% and approx. 75% (FIG. 15).

Example 14—Sequence Alignment of Wild-Type SHC Enzymes

Sequence identity of SHC enzymes relative to WT AacSHC was determined either with Clone Manager 9 Software with the parameters specified below, or with blastp using default parameters. The results are summarized in Tables 17A and 17B, respectively.

Alignment: Global Protein alignment against reference molecule
Parameters: Scoring matrix: BLOSUM 62
Reference molecule: Aac SHC, Region 1 to 631
Total length of aligned sequences with gaps: 838 aas

TABLE 17A

Percent SHC sequence identity relative to WT AacSHC.

| Sequence | Start | End | Match | Non-Match | % Match |
|---|---|---|---|---|---|
| AacSHC (SEQ ID NO: 1) | 1 | 631 | — | — | — |
| TelSHC (SEQ ID NO: 19) | 1 | 642 | 285 | 360 | 44 |
| ApaSHC1 (SEQ ID NO: 20) | 1 | 720 | 296 | 430 | 40 |
| ZmoSHC1 (SEQ ID NO: 11) | 1 | 725 | 299 | 434 | 40 |
| ZmoSHC2 (SEQ ID NO: 12) | 1 | 658 | 251 | 410 | 37 |
| BjaSHC (SEQ ID NO: 13) | 1 | 684 | 296 | 397 | 42 |
| GmoSHC (SEQ ID NO: 14) | 1 | 685 | 291 | 396 | 42 |
| BmeSHC (SEQ ID NO: 28) | 1 | 625 | 194 | 443 | 30 |
| SalSHC (SEQ ID NO: 29) | 1 | 691 | 327 | 367 | 47 |
| ApaSHCA (SEQ ID NO: 30) | 1 | 656 | 259 | 403 | 39 |

—: not applicable. Sequence identitiy determined with Clone Manager 9 software.

TABLE 17B

Percent SHC sequence identity relative to WT AacSHC.

| SHC enzyme/SEQ ID | % identity |
|---|---|
| AacSHC (SEQ ID NO: 1) | — |
| TelSHC (SEQ ID NO: 19) | 45.3 |

TABLE 17B-continued

Percent SHC sequence identity relative to WT AacSHC.

| SHC enzyme/SEQ ID | % identity |
|---|---|
| ApaSHC1 (SEQ ID NO: 20) | 43.5 |
| ZmoSHC1 (SEQ ID NO: 11) | 45.3 |
| ZmoSHC2 (SEQ ID NO: 12) | 39.2 |
| BjaSHC (SEQ ID NO: 13) | 44.3 |
| GmoSHC (SEQ ID NO: 14) | 43.9 |
| BmeSHC (SEQ ID NO:28) | 31.4 |
| SalSHC (SEQ ID NO:29) | 51.8 |
| ApaSHCA (SEQ ID NO: 30) | 39.9 |

—: not applicable. Sequence identity determined with blastp.

Example 15—Sequence Alignment of Wild-Type SHCs

The wild-type SHC sequences disclosed in Tables 16-18 were aligned using Clustal O (1.2.4). The multiple sequences alignments are provided in FIGS. 9A and 9B and the percent identity between the sequences (as determined using blastp) is provided in Table 19.

TABLE 18

Sequence identity matrix calculated with blastp.

| % identity | AacSHC | BjpSHC | BmeSHC | GmoSHC | ApaSHCA | ApaSHC1 | SalSHC | TelSHC | ZmoSHC1 | ZmoSHC2 |
|---|---|---|---|---|---|---|---|---|---|---|
| AacSHC | 100 | | | | | | | | | |
| BjpSHC | 44.3 | 100 | | | | | | | | |
| BmeSHC | 31.4 | 28.1 | 100 | | | | | | | |
| GmoSHC | 43.9 | 71.6 | 30.5 | 100 | | | | | | |
| ApaSHCA | 39.9 | 36.8 | 30.7 | 37.1 | 100 | | | | | |
| ApaSHC1 | 43.5 | 69.4 | 29.7 | 75.8 | 37.2 | 100 | | | | |
| SalSHC | 51.8 | 43.4 | 31.3 | 42.6 | 39.3 | 42.4 | 100 | | | |
| TelSHC | 45.3 | 39.3 | 30.4 | 39.1 | 40.5 | 39.2 | 44.4 | 100 | | |
| ZmoSHC1 | 45.3 | 69.6 | 30.8 | 76.7 | 36.8 | 76.8 | 45 | 39.5 | 100 | |
| ZmoSHC2 | 39.2 | 36.8 | 32.1 | 35.3 | 55.1 | 35.2 | 42 | 41.4 | 36.8 | 100 |

Example 16—Influence of Cultivation Conditions on Biocatalyst Specific Activity Methods As an alternative to the biocatalyst production methods outlined in Example 1 (shake flask cultivation and fermentation) the production of biocatalyst using auto-inducing medium (AIM) was tested. The medium was prepared using AIM-TB broth base including trace elements (Formedium). 25 ml AIM-TB in 100 ml baffled shake flask was enriched with 1% glycerol. The culture was inoculated at an $OD_{650nm}$ of 2E-07; cultivation lasted for 18±1 h at 37° C. under constant shaking (220 rpm).

The activity of the collected biocatalysts was tested in the standard activity test at 4 g/l E,E-homofarnesol, cells to an $OD_{650nm}$ of 10 as set out in Example 2, and applying otherwise optimal temperature, pH and [SDS] as outlined in Examples 2 and 6 depending on the SHC enzyme considered.

Results

The activity of the SHC biocatalyst considered varied strongly depending on the cultivation medium and conditions for biocatalyst production (Table 19). In a same way it is expected that biocatalyst production using alternative or modified fermentation protocols will result in biocatalysts with lower or higher specific activity than when produced applying the fermentation protocol outlined in Example 1.

TABLE 19

Influence of cultivation method on EEH conversion.

| | EEH conversion at 24 h (%) | | |
|---|---|---|---|
| SHC biocatalyst | AIM-TB Shake flask | Minimal medium Shake flask | Minimal medium Fermenter |
| SHC 65 | 41-70 | n.d. | 100 |
| ZmoSHC1 | 47-57 | 60-70 | 91 |
| BjpSHC | 11-26 | 14-17 | 90 |
| ApaSHC1 | 24-35 | 4-9 | 94 | n.d.: not determined.

Example 17—Influence of [SDS]:[Cells] Ratio on EEH Conversion

Methods

Biocatalyst was produced as outlined in Example 1 (fermentation) from the E. coli strain producing the SHC variant enzyme SHC #65. EEH bioconversions were run as set out in Example 4 but with 125 g/l EEH and 150 g/l cells. Reactions were run at pH 5.6 and 45° C. defined as optimal for SHC #65. SDS in the reactions varied from 0.060, 0.066, 0.072, 0.078, 0.084, and 0.090% resulting into [SDS]:[cells] ratio of: 0.040, 0.044, 0.048, 0.052, 0.056, and 0.060, respectively.

Results

Figure 16:
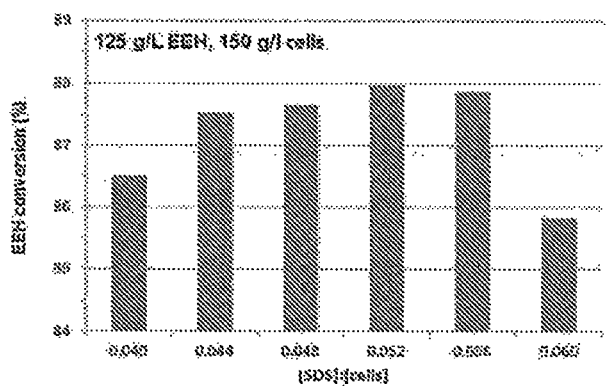
FIG. 16 shows EEH conversion to (−)-Ambrox by SHC/HAC. Bioconversions were run with the SHC #65 biocatalyst. Reactions were run at 125 g/l EEH with 150 g/l cells, at 45° C. and pH 5.6, and in the presence of 0.060 to 0.090% SDS corresponding to a [SDS]:[cells] ratio ranging from 0.040 to 0.060. EEH conversion values at 72 h of reaction are indicated.

EEH conversion was in all reactions >85%, maximal conversion being obtained at an [SDS]:[cells] ratio ranging from 0.044-0.056. At an [SDS]:[cells] ratio of 0.040 and 0.060 was conversion lightly lower (FIG. 16).

The foregoing broadly describes certain embodiments of the present invention without limitation. Variations and modifications as will be readily apparent to those skilled in the art are intended to be within the scope of the present invention as defined in and by the appended claims.

The invention claimed is:

1. A process for preparing (−)-Ambrox or a mixture comprising (−)-Ambrox, the process comprising enzymatically converting (3E,7E)-homofarnesol (EEH) or a mixture of isomers of homofarnesol comprising EEH to (−)-Ambrox or a mixture comprising (−)-Ambrox using a squalene hopene cyclase/homofarnesol Ambrox cyclase (SHC/HAC) enzyme variant,
   wherein the SHC/HAC enzyme variant has an amino acid sequence having at least 70.0% identity to SEQ ID NO: 1,
   wherein the SHC/HAC enzyme variant amino acid sequence has amino acid alterations relative to SEQ ID NO: 1 at positions corresponding to positions 132, 224 and 432 of SEQ ID NO: 1 which are M132R, A224V and I432T respectively, and
   wherein the SHC/HAC enzyme variant amino acid sequence has amino acid alterations relative to SEQ ID NO: 1 at a position corresponding to position 557 of SEQ ID NO: 1 and at least one position corresponding to position 81, 431 or 613 of SEQ ID NO: 1.

2. The process according to claim 1, wherein the SHC/HAC enzyme variant has an amino acid sequence having at least 90.0% identity to SEQ ID NO: 1.

3. The process according to claim 1, wherein the SHC/HAC enzyme variant amino acid sequence has amino acid alterations relative to SEQ ID NO: 1 at positions corresponding to positions 557 and 431 of SEQ ID NO: 1.

4. The process according to claim 1, wherein the SHC/HAC enzyme variant amino acid sequence has amino acid alterations relative to SEQ ID NO: 1 at positions corresponding to positions 557 and 613 of SEQ ID NO: 1.

5. The process according to claim 3, wherein the SHC/HAC enzyme variant amino acid sequence has a further amino acid alteration relative to SEQ ID NO: 1 at a position corresponding to position 81 of SEQ ID NO: 1.

6. The process according to claim 1, wherein one or more of the amino acid alterations at positions 81, 431, 557, or 613 are substitutions.

7. The process according to claim 1, wherein:
the amino acid alteration at a position corresponding to position 557 of SEQ ID NO: 1 substitutes the amino acid of SEQ ID NO: 1 for a neutral hydrophilic amino acid; and/or
the amino acid alteration at a position corresponding to position 81 of SEQ ID NO: 1 substitutes the amino acid of SEQ ID NO: 1 for a basic amino acid; and/or
the amino acid alteration at a position corresponding to position 431 of SEQ ID NO: 1 substitutes the amino acid of SEQ ID NO: 1 for a hydrophobic amino acid; and/or
the amino acid alteration at a position corresponding to position 613 of SEQ ID NO: 1 substitutes the amino acid of SEQ ID NO: 1 for a neutral hydrophilic amino acid.

8. The process according to claim 1, wherein the SHC/HAC enzyme variant has an amino acid sequence selected from SEQ ID NO: 2, SEQ ID NO: 3, SEQ ID NO: 4, and SEQ ID NO: 5.

9. The process according to claim 1, wherein the enzymatic conversion takes place at a temperature in the range of about 30° C. to about 50° C., and/or at a pH in the range of about 5 to about 6.

10. The process according to claim 1, wherein the process comprises culturing recombinant host cells that produce the SHC/HAC enzyme variant.

11. The process of claim 10, wherein the recombinant host cells comprise the nucleic acid sequence selected from SEQ ID NO: 7.

12. The process according to claim 1, wherein (−)-Ambrox is produced in an admixture with at least one or more of the by-products (II), (III), and (IV),

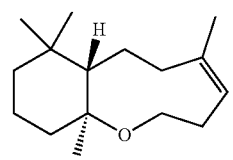
(II)

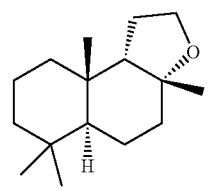
(III)

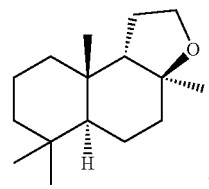
(IV)

13. The process according to claim 1, wherein the SHC/HAC enzyme variant has an increased enzymatic activity relative to SEQ ID NO: 1 or wherein the SHC/HAC enzyme variant provides an increased rate of EEH conversion over the first 6 hours, 8 hours, or 12 hours of the reaction compared to SEQ ID NO: 1 and/or SEQ ID NO: 10.

* * * * *